US012712052B2

(12) United States Patent
Behsaz et al.

(10) Patent No.: US 12,712,052 B2
(45) Date of Patent: Aug. 18, 2026

(54) METHOD AND SYSTEM TO IDENTIFY NATURAL PRODUCTS FROM MASS SPECTROMETRY AND GENOMICS DATA

(71) Applicant: Carnegie Mellon University, Pittsburgh, PA (US)

(72) Inventors: Bahar Behsaz, Pasadena, CA (US); Liu Cao, Pittsburgh, PA (US); Mustafa Guler, Pittsburgh, PA (US); Yi-Yuan Lee, Ithaca, NY (US); Hosein Mohimani, Pittsburgh, PA (US); Mihir Mongia, Pittsburg, PA (US); Donghui Yan, Pittburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 753 days.

(21) Appl. No.: 18/076,280

(22) Filed: Dec. 6, 2022

(65) Prior Publication Data

US 2023/0282311 A1 Sep. 7, 2023

Related U.S. Application Data

(60) Provisional application No. 63/286,333, filed on Dec. 6, 2021.

(51) Int. Cl.
*G16B 40/10* (2019.01)

(52) U.S. Cl.
CPC .................................... *G16B 40/10* (2019.02)

(58) Field of Classification Search
None
See application file for complete search history.

(56) References Cited

U.S. PATENT DOCUMENTS

2018/0373833 A1 12/2018 Merwin et al.
2019/0130999 A1 5/2019 Oppenheim et al.
2021/0257056 A1 8/2021 Liu et al.
2022/0208540 A1 6/2022 Behsaz et al.

FOREIGN PATENT DOCUMENTS

WO WO 2020123387 6/2020
WO WO 2021092456 5/2021

OTHER PUBLICATIONS

August et al., "Biosynthesis of the ansamycin antibiotic rifamycin: deductions from the molecular analysis of the rif biosynthetic gene cluster of *Amycolatopsis mediterranei* S699," Chemistry & Biology, Feb. 1, 1998, 5(2):69-79.

(Continued)

*Primary Examiner* — Walter L Lindsay, Jr.
*Assistant Examiner* — Geoffrey T Evans
(74) *Attorney, Agent, or Firm* — Fish & Richardson P.C.

(57) ABSTRACT

A method and system is for receiving data representing gene clusters, the gene clusters including one or more genes configured to encode one or more polypeptides or other small molecules; accessing a machine learning model, the machine learning model being trained with a training dataset that associates the gene clusters to structures of one or more small molecules represented in the data; applying the machine learning model to the data representing the gene clusters; identifying, based on applying the machine learning model, one or more monomers associated with at least one gene cluster represented in the data; and determining a structure for a natural product including the one or more monomers.

25 Claims, 62 Drawing Sheets

Specification includes a Sequence Listing.

(56) References Cited

OTHER PUBLICATIONS

Blin et al., "antiSmash 5.0: updates to the secondary metabolite genome mining pipeline," Nucleic Acids Research, Jul. 2, 2019, 47(W1): W81-7.
Blin et al., "antiSmash 6.0: improving cluster detection and comparison capabilities," Nucleic Acids Research, Jul. 2, 2021, 49(W1): W29-35.
Blin et al., "The antiSmash database version 3: increased taxonomic coverage and new query features for modular enzymes," Nucleic Acids Research, Jan. 8, 2021, 49(D1): D639-43.
Campelo et al., "The candicidin gene cluster from *Streptomyces griseus* imru 3570," Microbiology, Jan. 1, 2002, 148(1):51-9.
Cortes et al., "An unusually large multifunctional polypeptide in the erythromycin-producing polyketide synthase of saccharopolyspora erythraea," Nature, Nov. 8, 1990, 348:176-8(abstract only).
Duverger et al., "The anticancer drug mithramycin a sensitises tumour cells to apoptosis induced by tumour necrosis factor (tnf)," British Journal of Cancer, May 17, 2004, 90(10):2025-31.
Efstratiou et al., "Waterborne transmission of protozoan parasites: review of worldwide outbreaks—an update 2011-2016," Water Research, May 1, 2017, 114:14-22(abstract only).
Flahault et al., "Influenza pandemics: past, present and future challenges," Public Health Reviews, May 29, 2010, 32(1):319-40.
Gokhale et al., "Role of linkers in communication between protein modules," Current Opinion in Chemical Biology, Feb. 1, 2000, 4(1):22-7(abstract only).
Gottardi et al., "Abyssomicin Biosynthesis: Formation of an Unusual Polyketide, Antibiotic-Feeding Studies and Genetic Analysis," ChemBioChem, Jun. 14, 2011, 12(9):1401-10.
Graybill et al., "Interaction of Rifampin with Other Antifungal Agents in Experimental Murine Candidiasis," Reviews of Infectious Diseases, Jul. 1, 1983, 5(3): S620-5.
Grimm et al., "Characterization of the *Streptomyces peucetius* atcc 29050 genes encoding doxorubicin polyketide synthase," Gene, Dec. 30, 1994, 151(1-2):1-10(abstract only).
Gurevich et al., "Increased diversity of peptidic natural products revealed by modification-tolerant database search of mass spectra," Nature Microbiology, Mar. 3, 2018, 3(3):319-27.
Helfrich et al., "Automated structure prediction of trans-acyltransferase polyketide synthase products," Nature Chemical Biology, Jul. 15, 2019, 15(8):813-21.
Ikeda et al., "Organization of the biosynthetic gene cluster for the polyketide anthelmintic macrolide avermectin in streptomyces avermitilis," Proceedings of the National Academy of Sciences of the United States of America, Aug. 17, 1999, 96(17):9509-9514.
Kautsar et al., "MIBiG 2.0: a repository for biosynthetic gene clusters of known function," Nucleic Acids Research, Jan. 8, 2020, 48(D1): D454-8.
Kim et al., "PubChem 2023 update," Nucleic Acids Research, Jan. 6, 2023, 51(D1):D1373-80.
Li et al., "DDAP: docking domain affinity and biosynthetic pathway prediction tool for type I polyketide synthases," Bioinformatics, Feb. 1, 2020, 36(3):942-4.
Marshall et al., "D-Ala-D-Ala ligases from glycopeptide antibiotic-producing organisms are highly homologous to the enterococcal vancomycin-resistance ligases VanA and VanB," Proceedings of the National Academy of Sciences of the United States of America, Jun. 10, 1997, 94(12):6480-3.
Mohimani et al., "Dereplication of microbial metabolites through database search of mass spectra," Nature Communications, Oct. 2, 2018, 9(1):4035.
Newman et al., "Natural Products as Sources of New Drugs from 1981 to 2014," Journal of Natural Products, Mar. 25, 2016, 79(3):629-661.
nfs.gov [online], "Computational methods for nonribosomal peptide discovery," Jul. 16, 2021, retrieved on Mar. 10, 2023, retrieved from URL<https://www.nsf.gov/awardsearch/showAward?AWD_ID=2117640&HistoricalAwards=false>, 3 pages.
Potter et al., "HMMER web server: 2018 update," Nucleic Acids Research, Jul. 2, 2018, 46(W1): W200-4.
Pyta et al., "Specific interactions between rifamycin antibiotics and water influencing ability to overcome natural cell barriers and the range of antibacterial potency," ACS Infectious Diseases, Aug. 28, 2019, 5(10):1754-1763(abstract only).
Schwecke et al., "The biosynthetic gene cluster for the polyketide immunosuppressant rapamycin," Proceedings of the National Academy of Sciences of the United States of America, Aug. 15, 1995, 92(17):7839-7843.
Shushni et al., "Balticolid: A New 12-Membered Macrolide with Antiviral Activity from an Ascomycetous Fungus of Marine Origin," Marine Drugs, May 13, 2011, 9(5): 844-851.
Staunton et al., "Polyketide biosynthesis: a millennium review," Natural Product Reports, Aug. 2001, 18(4):380-416(abstract only).
Ullmann, "An algorithm for subgraph isomorphism," Journal of the ACM (JACM), Jan. 1, 1976, 23(1):31-42.
Yadav et al., "Computational approach for prediction of domain organization and substrate specificity of modular polyketide synthases," Journal of Molecular Biology, Apr. 25, 2003, 328(2):335-63(abstract only).
International Search Report and Written Opinion in International Appln. No. PCT/US2022/052046 mailed on Dec. 21, 2023, 14 pages.
International Preliminary Report on Patentability in International Appln. No. PCT/US2022/052046, mailed on Jun. 20, 2024, 13 pages.
Aanandhalakshmi et al., Bioactive Oligosaccharides Production, Characterization, and Applications, John Wiley & Sons, Ltd, 2021, pp. 165-199.
Abramova et al., "Assessing the significance of peptide spectrum match scores," 17th International Workshop on Algorithms in Bioinformatics (WABI 2017), Aug. 2017, 88:14:1-14:11.
Agrawal et al., "RiPPMiner: a bioinformatics resource for deciphering chemical structures of RiPPs based on prediction of cleavage and cross-links," Nucleic Acids Research, May 12, 2017, 45:W80-W88.
Allgaier et al., "Epidermin: sequencing of a heterodetic tetracyclic 21-peptide amide antibiotic," Eur J Biochem., Oct. 1986, 160(1):9-22.
Almaliti et al., "Sharing and community curation of mass spectrometry data with global natural products social molecular networking," Nat Biotechnol., Aug. 9, 2016, 34(8):828-837.
Altschul et al., "Basic local alignment search tool," Journal of Molecular Biology, Oct. 1990, 215(3):403-410.
Arnison et al., "Ribosomally synthesized and post-translationally modified peptide natural products: overview and recommendations for a universal nomenclature," Natural Product Reports, Jan. 2013, 30(1):108-160, 100 pages (author manuscript).
Aron et al., "Reproducible molecular networking of untargeted mass spectrometry data using GNPS," Nature Protocols, May 2020, 15:1954-1991.
Ashby, "The value and limitations of short-term genotoxicity assays and the inadequacy of current cancer bioassay chemical selection criteria," Ann. N. Y. Acad. Sci., Jun. 1988, 534(1):133-138.
Atanasov et al., "Natural products in drug discovery: advances and opportunities," Nature Reviews Drug Discovery, Mar. 2021, 20:200-216.
Baldassarre et al., "Explainability techniques for graph convolutional networks," CoRR, Submitted on May 31, 2019, arXiv:1905.13686v1, 21 pages.
Bandeira et al., "Protein identification by spectral networks analysis," Proceedings of the National Academy of Sciences, Apr. 2007, 104(15):6140-6145.
Bankevich et al., "SPAdes: a new genome assembly algorithm and its applications to single-cell sequencing," Journal of Computational Biology, May 2012, 19(5):455-477.
Baptista et al., "Natural products with preservative properties for enhancing the microbiological safety and extending the shelf-life of seafood: A review," Food Research International, Jan. 2020, 127:108762, 23 pages.
Behsaz et al., "De Novo Peptide Sequencing Reveals Many Cyclopeptides in the Human Gut and Other Environments," Cell Systems, Jan. 2020, 10:99-108.

(56) References Cited

OTHER PUBLICATIONS

Behsaz et al., "Integrating genomics and metabolomics for scalable non-ribosomal peptide discovery," Nature Communications, May 2021, 12(3225):1-17.
Behsaz et al., "Platform for large-scale natural product discovery identifies novel antifungal targeting drug-resistant candidiasis," Paper, Presented at the ASMS Conference on Mass Spectrometry and Allied Topics, Houston TX, Jun. 4-8, 2023, 36 pages.
Bholowalia et al., "EBK-means: A clustering technique based on elbow method and k-means in WSN," International Journal of Computer Applications, Nov. 2014, 105(9):17-24.
Bittremieux et al., "Open Access Repository-Scale Propagated Nearest Neighbor Suspect Spectral Library for Untargeted Metabolomics," BioRxiv, Sep. 3, 2023, 38 pages.
Blaskovich et al., "Helping chemists discover new antibiotics," ACS Infect. Dis., May 13, 2015, 1(7):285-287.
Blin et al., "antiSmash 4.0—improvements in chemistry prediction and gene cluster boundary identification," Nucleic Acids Research, Apr. 28, 2017, 45(W1):W36-W41.
Blin et al., "The antiSmash database, a comprehensive database of microbial secondary metabolite biosynthetic gene clusters," Nucleic Acids Research, Oct. 24, 2016, 45(D1):D555-D559.
Borisova et al., "Biosynthesis of Desosamine: Construction of a New Macrolide Carrying a Genetically Designed Sugar Moiety.," Organic Letters, Apr. 1999, 1:133-136.
Bronstein et al., "Geometric deep learning: Going beyond Euclidean data," IEEE Signal Processing Magazine, Jul. 2017, 34(4):18-42.
Caesar et al., "Metabolomics and Genomics in Natural Products Research: Complementary Tools for Targeting New Chemical Entities," Nat. Prod. Rep., Nov. 2022, 38(11):2041-2065 (author manuscript).
Cao et al., "MetaMiner: A Scalable Peptidogenomics Approach for Discovery of Ribosomal Peptide Natural Products with Blind Modifications from Microbial Communities," Cell Systems, Dec. 18, 2019, 9:600-608.
Cao et al., "MolDiscovery: Learning Mass Spectrometry Fragmentation of Small Molecules," bioRxiv, Nov. 2020, 19 pages.
Cao et al., "MolDiscovery: learning mass spectrometry fragmentation of small molecules," Nature Communications, 2021, 12(3718):1-13.
Challis et al., "Coelichelin, a new peptide siderophore encoded by the *Streptomyces coelicolor* genome: structure prediction from the sequence of its non-ribosomal peptide synthetase," FEMS Microbiology Letters, 2000, 187(2):111-114.
Chang et al., "shiny: Web Application Framework for R," Jan. 2021, retrieved on Apr. 8, 2025, retrieved from URL <https://cran.r-project.org/web/packages/shiny/shiny.pdf>, 227 pages.
Chen et al., "Enhanced recursive feature elimination," Paper, Presented at the Sixth International Conference on Machine Learning and Applications (ICMLA 2007), Cincinnati, Ohio, Dec. 13-15, 2007, pp. 429-435.
Chevrette et aL "Sand Puma: ensemble predictions of nonribosomal peptide chemistry reveal biosynthetic diversity across Actinobacteria," Bioinformatics, Jun. 19, 2017, 33(20):3202-3210.
Chigumba et al., "Discovery and biosynthesis of cyclic plant peptides via autocatalytic cyclases," Nature Chemical Biology, Jan. 2022, 18:18-28.
Cho et al., "Beta-lactam antibiotics induce a lethal malfunctioning of the bacterial cell wall synthesis machinery," Cell, Dec. 4, 2014, 159(6):1300-1311.
Chu et al., "Discovery of MRSA active antibiotics using primary sequence from the human microbiome," Nature Chemical Biology, Oct. 2016, 12:1004-1006.
Cimermancic et al., "Insights into secondary metabolism from a global analysis of prokaryotic biosynthetic gene clusters," Cell, Jul. 2014, 158:412-421.
Claesen et al., "Biosynthesis and Regulation of Grisemycin, a New Member of the Linaridin Family of Ribosomally Synthesized Peptides Produced by Streptomyces griseus IFO 13350," J. Bacteriol., May 2011, 193(10):2510-2516.
Claesen et al., "Genome mining and genetic analysis of cypemycin biosynthesis reveal an unusual class of posttranslationally modified peptides," Proceedings of the National Academy of Sciences, Sep. 2010, 107(37):16297-16302.
Clevenger et al., "A scalable platform to identify fungal secondary metabolites and their gene clusters," Nature Chemical Biology, Jun. 2017, 13:895-901.
Condie et al., "The biosynthesis of Caryophyllaceae-like cyclic peptides in *Saponaria vaccaria* L. from DNA-encoded precursors," The Plant Journal, Jun. 2011, 67(4):682-690.
Conti et al., "Structural basis for the activation of phenylalanine in the non-ribosomal biosynthesis of gramicidin S," The EMBO Journal, Jul. 1997, 16(14):4174-4183.
Coo-Add, "Open-access Antimicrobial Screening Database," available on or before Dec. 6, 2021, via Internet Archive: Wayback Machine URL <https://web.archive.org/web/20250114144300/https://db.co-add.org/>, retrieved on Apr. 8, 2025, retrieved from URL <https://db.co-add.org>, 1 page.
Corsello et al., "The Drug Repurposing Hub: A next-generation drug library and information resource," Nature Medicine, Apr. 2017, 23(4):405-408.
Courraud et al., "Studying autism using untargeted metabolomics in newborn screening samples," Journal of Molecular Neuroscience, Jan. 30, 2021, 71:1378-1393.
Da Silva et al., "Illuminating the dark matter in metabolomics," Proceedings of the National Academy of Sciences, Oct. 13, 2015, 112(41):12549-12550.
Dai et al., "Discriminative embeddings of latent variable models for structured data," Paper, Presented at the Proceedings of the 33rd International Conference on Machine Learning, New York City, New York, Jun. 19-24, 2016; Proceedings of Machine Learning Research, 2016, 48:2702-2711.
Daly et al., "The N-terminal pro-domain of the kalata B1 cyclotide precursor is intrinsically unstructured," Peptide Science, Aug. 2016, 106:825-833.
Daly et al., "The role of the cyclic peptide backbone in the anti-HIV activity of the cyclotide kalata B1," FEBS letters, Aug. 13, 2004, 574:69-72.
De et al., "Design, Synthesis, and Structure—Activity Relationship of Substrate Competitive, Selective, and in Vivo Active Triazole and Thiadiazole Inhibitors of the c-Jun N-Terminal Kinase," J. Med. Chem., Mar. 2009, 52(7):1943-1952.
De los Santos, "NeuRiPP: Neural network identification of RiPP precursor peptides," Scientific Reports, Sep. 2019, 9(13406):1-9.
Depke et al., "Untargeted LC-MS metabolomics differentiates between virulent and avirulent clinical strains of Pseudomonas aeruginosa," Biomolecules, Jul. 13, 2020, 10(1041):1-21.
Donia et al., "A global assembly line for cyanobactins," Nature Chemical Biology, Jun. 2008, 4(6):341-343.
Dührkop et al., "Systematic classification of unknown metabolites using high-resolution fragmentation mass spectra," Nature Biotechnology, Nov. 2020, 39:462-471.
Eberhard et al., "Metabolites as predictive biomarkers for Trypanosoma cruzi exposure in triatomine bugs," Computational and Structural Biotechnology Journal, May 21, 2021, 19:3051-3057.
Eddy, "Profile hidden Markov models," Bioinformatics, Jan. 1998, 14(9):755-763.
Elias et al., "Target-decoy search strategy for increased confidence in large-scale protein identifications by mass spectrometry," Nature Methods, Feb. 2007, 4(3):207-214.
Ernst et al., "Gestational age-dependent development of the neonatal metabolome," Pediatric Research, Sep. 17, 2020, 89(6):1396-1404.
Fenyo et al., "A method for assessing the statis-tical significance of mass spectrometry-based protein identifications using general scoring schemes," Analytical Chemistry, Feb. 2003, 75(4):768-774.
Férir et al., "The lantibiotic peptide labyrinthopeptin A1 demonstrates broad anti-HIV and anti-HSV activity with potential for microbicidal applications," PloS One, May 2013, 8(5):1-16.
Finn et al., "HMMER web server: interactive sequence similarity searching," Nucleic Acids Research, May 18, 2011, 39(suppl 2):W29-W37.

(56) References Cited

OTHER PUBLICATIONS

Flatt et al., "Biosynthesis of aminocyclitol-aminoglycoside antibiotics and related compounds.," Nat. Prod. Rep., Dec. 21, 2006, 24:358-392.
Fleeman et al., "Combinatorial libraries as a tool for the discovery of novel, broad-spectrum antibacterial agents targeting the ESKAPE pathogens," J. Med. Chem., Mar. 17, 2015, 58(8):3340-3355.
Frank et al., "Clustering millions of tandem mass spectra," Journal of Proteome Research, Jun. 2007, 7(01):113-122.
Frank et al., "PepNovo: de novo peptide sequencing via probabilistic network modeling," Analytical Chemistry, Feb. 15, 2005, 77(4):964-973.
Frank et al., "Spectral archives: extending spectral libraries to analyze both identified and unidentified spectra," Nature Methods, May 2011, 8:587-591 (author manuscript).
Geurts et al., "Extremely randomized trees," Machine Learning, Mar. 2006, 63(1):3-42.
github.com [online], "HypoRiPPAtlas Server," Dec. 6, 2022, retrieved on Mar. 20, 2025, retrieved from URL <https://github.com/mohimanilab/seq2ripp>, 6 pages.
Goering et al., "Metabologenomics: Correlation of microbial gene clusters with metabolites drives discovery of a nonribosomal peptide with an unusual amino acid monomer," ACS Central Science, Jan. 20, 2016, 2:118-127.
Gómez-Rodríguez et al., "Adipostatins E-J, New Potent Antimicrobials Identified as Inhibitors of Coenzyme-A Biosynthesis," Tetrahedron Lett., Jan. 30, 2020, 61(5):1-15 (Author Manuscript).
Gupta et al., "Target-decoy approach and false discovery rate: when things may go wrong," Journal of the American Society for Mass Spectrometry, May 2011, 22(7):1111-1120.
Hadjithomas et al., "IMG-ABC: A Knowledge Base To Fuel Discovery of Biosynthetic Gene Clusters and Novel Secondary Metabolites.," MBio., Jul. 14, 2015, 6(4):1-10.
Hadjithomas et al., "IMG-ABC: new features for bacterial secondary metabolism analysis and targeted biosynthetic gene cluster discovery in thousands of microbial genomes," Nucleic Acids Research, Nov. 28, 2016, 45(D1):D560-D565.
Hamill, "Amphotericin B formulations: A comparative review of efficacy and toxicity," Drugs, Jun. 2013, 73:919-934.
Hannigan et al., "A deep learning genome-mining strategy for biosynthetic gene cluster prediction," Nucleic Acids Research, Aug. 10, 2019, 47(18):1-13.
Harvey et al., "HEx: A heterologous expression platform for the discovery of fungal natural products," Science Advances, Apr. 2018, 4:1-14.
Harvey et al., "The re-emergence of natural products for drug discovery in the genomics era," Nature Reviews Drug Discovery, Jan. 2015, 14(2):111-129 (author manuscript).
Hirst et al., "Quantitative structure-activity relationships by neural networks and inductive logic programming. I. The inhibition of dihydrofolate reductase by pyrimidines," Journal of Computer-Aided Molecular Design, Aug. 1994, 8(4):405-420.
Hojati et al., "Structure, biosynthetic origin, and engineered biosynthesis of calcium-dependent antibiotics from *Streptomyces coelicolor*," Chemistry & Biology, Nov. 2002, 9:1175-1187.
Hong et al., "Molecular cloning and sequence analysis of the sisomicin biosynthetic gene cluster from *Micromonospora inyoensis*," Biotechnology Letters, Nov. 2008, 31:449-455.
Howarth et al., "DP4-AI automated NMR data analysis: straight from spectrometer to structure," Chem. Sci., Mar. 2020, 11:4351-4359.
Procop et al., "M27M44s-Ed3: Performance Standards for Antifungal Susceptibility Testing of Yeasts," Clinical And Laboratory Standards Institute, Aug. 2022, retrieved on Jul. 22, 2025, retrieved from URL <https://clsi.org/media/1895/m60ed1_sample.pdf>, 10 pages.
Hu et al., "Retrospective Analysis of the Clinical Characteristics of Candida auris Infection Worldwide From 2009 to 2020," Frontiers in Microbiology, May 20, 2021, 12(658329):1-9.
Iorio et al., "A glycosylated, labionin-containing lanthipeptide with marked antinociceptive activity," ACS Chemical Biology, Nov. 2013, 9:398-404.
Irwin et al., "Zinc—A free database of commercially available compounds for virtual screening," Journal of Chemical Information and Modeling, Dec. 2004, 45(1):177-182.
Jarmusch et al., "ReDU: a framework to find and reanalyze public mass spectrometry data," Nature Methods, Aug. 2020, 17:901-904.
Jennings et al., "Biosynthesis and insecticidal properties of plant cyclotides: The cyclic knotted proteins from *Oldenlandia affinis*," Proceedings of the National Academy of Sciences, Sep. 11, 2001, 98(19):10614-10619.
Ji et al., "In vivo activation of the p53 tumor suppressor pathway by an engineered cyclotide," Journal of the American Chemical Society, Jul. 2013, 135(31):11623-11633.
Jumper et al., "Highly accurate protein structure prediction with alphafold," Nature, Jul. 15, 2021, 596(7873):583-589.
Kahn et al., "Estimation of particle transmission by random sampling," National Bureau of Standards Applied Mathematics Series, 1951, 12:27-30.
Kale et al., "MetaboLights: An Open-Access Database Repository for Metabolomics Data," Current Protocols in Bioinformatics, Mar. 2016, Supplement 53:14.13.1-14.13.18.
Kalinski et al., "Molecular networking reveals two distinct chemotypes in pyrroloiminoquinone-producing Tsitsikamma favus sponges," Marine Drugs, Jan. 2019, 17(60):1-16.
Källberg et al., "Template-based protein structure modeling using the raptorx web server," Nature Protocols, Jul. 2012, 7(8):1511-1522.
Kang et al., "Recent advances in heterologous expression of natural product biosynthetic gene clusters in Streptomyces hosts," Current Opinion in Biotechnology, Jun. 2021, 69:118-127.
Kautsar et al., "BiG-SLiCE: A highly scalable tool maps the diversity of 1.2 million biosynthetic gene clusters," GigaScience, Jan. 2021, 10(1):1-17.
Kautsar et al., "Mibig 2.0: a repository for biosynthetic gene clusters of known function," Nucleic Acids Research, Oct. 2019, 48:D454-458.
Kaweewan et al., "Isolation and structure determination of a new thiopeptide globimycin from *Streptomyces globisporus* subsp. globisporus based on genome mining," Tetrahedron Letters, Jan. 2018, 59(4):409-414 (author manuscript).
Kersten et al., "A mass spectrometry-guided genome mining approach for natural product peptidogenomics," Nature Chemical Biology, Oct. 2011, 7:794-802 (author manuscript).
Kersten et al., "Gene-guided discovery and engineering of branched cyclic peptides in plants, " PNAS, Oct. 29, 2018, 115(46):E10961-E10969.
Kijima et al., "Subgraph isomorphism in graph classes," Discrete Mathematics, Jul. 28, 2012, 312:3164-3173.
Kim et al., "PubChem in 2021: new data content and improved web interfaces," Nucleic Acids Research, Nov. 5, 2020, 49(D1):D1388-D1395.
Kim et al., "Pubchem substance and compound databases," Nucl. Acids Res., Sep. 22, 2015, 44(D1):D1202-D1213.
Kim et al., "Spectral probabilities and generating functions of tandem mass spectra: a strike against decoy databases," Journal of Proteome Research, Jul. 2008, 7(8):3354-3363.
Kim et al., "The Generating Function of CID, ETD, and CID/ETD Pairs of Tandem Mass Spectra: Applications to Database Search," Molecular & Cellular Proteomics, Dec. 2010, 9(12):2840-2852.
King et al., "Drug design by machine learning: The use of inductive logic programming to model the structure-activity relationships of trimethoprim analogues binding to dihydrofolate reductase," Proc. Natl. Acad. Sci., Dec. 1992, 89(23):11322-11326.
Kodani et al., "SapT, a lanthionine-containing peptide involved in aerial hyphae formation in the streptomycetes," Molecular Microbiology, Oct. 18, 2005, 58(5):1368-1380.
Kojima et al., "kgcn: A graph-based deep learning framework for chemical structures," Journal of Cheminformatics, May 2020, 12(1):1-10.
Krause et al., "Aminoglycosides: An overview," Cold Spring Harb. Perspect. Med., 2016, 6(a027029):1-18.

(56) References Cited

OTHER PUBLICATIONS

Kroeze et al., "PRESTO-Tango as an open-source resource for interrogation of the druggable human gpcrome," Nature Structural & Molecular Biology, Apr. 2015, 22(5):362-369.
Kuo et al., "Nematode-Trapping Fungi Produce Diverse Metabolites during Predator-Prey Interaction," Metabolites, Mar. 20, 2020, 10(117):1-24.
Kursa et al., "Feature selection with the Boruta package," J. Stat. Softw., Sep. 2010, 36(11):1-13.
Kwon et al., "Sulfated polysaccharides effectively inhibit SARS-CoV-2 in vitro," Cell Discovery, Jul. 2020, 6(50):2-4.
Lakey et al., "A new channel-forming antibiotic from Streptomyces coelicolor A3 (2) which requires calcium for its activity," Journal of General Microbiology, Dec. 1983, 129:3565-3573.
Landrum et al., "Sep. 4, 2016 (Q3 2016) Release," github.com, Feb. 5, 2017, retrieved on Apr. 8, 2025, retrieved from URL <https://github.com/rdkit/rdkit/releases/tag/Release_2016_09_4/>, 2 pages.
Lee et al., "HypoNPAtlas: an Atlas of hypothetical natural product for mass spectrometry database search," Nature Communications, Jul. 14, 2023, 14(4219):1-17, and Supplementary Information, 59 pages.
Li et al., "Automated genome mining for natural products," BMC Bioinformatics, Jun. 16, 2009, 10(185):1-10.
Liu et al., "Constrained graph variational autoencoders for molecule design," Paper, Presented at the Thirty-Second Annual Conference on Neural Information Processing Systems (NIPS), Montreal, Canada, Dec. 2-8, 2018; Advances in Neural Information Processing Systems 31 (NeurIPS 2018), 2018, 31:7795-7804.
Longo et al., "Chapter Eighteen—Transient Mammalian Cell Transfection with Polyethylenimine (PEI)," Methods in Enzymology, 2013, 529:227-240.
Ludwig et al., "De Novo Molecular Formula Annotation and Structure Elucidation Using SIRIUS 4," Computational Methods and Data Analysis for Metabolomics, Jan. 2020, 2104:185-207.
Lv et al., "A new antifungal agent (4-phenyl-1, 3-thiazol-2-yl) hydrazine induces oxidative damage in Candida albicans," Front. Cell. Infect. Microbiol., Oct. 7, 2020, 10(557):1-9.
Lybbert et al., "Mining public mass spectrometry data to characterize the diversity and ubiquity of P. aeruginosa specialized metabolites," Metabolites, Nov. 5, 2020, 10(445):1-13.
Ma et al., "A conditional neural fields model for protein threading," Bioinformatics, Jun. 2012, 28(12):i59-i66.
Magarvey et al., "Biosynthetic pathway for mannopeptimycins, lipoglycopeptide antibiotics active against drug-resistant gram-positive pathogens," Antimicrobial Agents and Chemotherapy, Jun. 2006, 50(6):1175-1187.
Martínez-Núñez et al., "Nonribosomal peptides synthetases and their applications in industry," Sustainable Chemical Processes, Aug. 2016, 4(13):1-8.
Matasci et al., "Data access for the 1,000 Plants (1KP) project," GigaScience, Dec. 2014, 3(1):1-10.
McCranie et al., "Bioactive Oligosaccharide Natural Products," Natural Product Reports, Jun. 2014, 31:1026-1042.
McDonald et al., "American Gut: an Open Platform for Citizen-Science Microbiome Research," mSystems, May 15, 2018, 3(3):1-28.
McGivern, "Ziconotide: a review of its pharmacology and use in the treatment of pain," Neuropsychiatric Disease and Treatment, 2007, 3(1):69-85.
Medema et al., "Minimum Information about a Biosynthetic Gene cluster," Nature Chemical Biology, Sep. 2015, 11(9):625-631.
Merwin et al., "DeepRiPP integrates multiomics data to automate discovery of novel ribosomally synthesized natural products," Proceedings of the National Academy of Sciences, Jan. 7, 2020, 117(1):371-380.
Miller et al., "Structural Biology of Nonribosomal Peptide Synthetases," Methods in Molecular Biology, Feb. 2016, 1401:3-29.
Milshteyn et al., "Accessing Bioactive Natural Products from the Human Microbiome," Cell Host and Microbe, Jun. 13, 2018, 23:725-736.
Minowa et al., "Comprehensive Analysis of Distinctive Polyketide and Nonribosomal Peptide Structural Motifs Encoded in Microbial Genomes," Journal of Molecular Biology, May 2007, 368(5):1500-1517.
Mohimani et al., "A new approach to evaluating statistical significance of spectral identifications," Journal of Proteome Research, Jan. 23, 2013, 12(4):1560-1568.
Mohimani et al., "Automated genome mining of ribosomal peptide natural products," ACS Chem Biol., May 6, 2014, 9(7):1545-1551.
Mohimani et al., "Cycloquest: identification of cyclopeptides via database search of their mass spectra against genome databases," Journal of Proteome Research, Aug. 19, 2011, 10(10):4505-4512.
Mohimani et al., "Dereplication of peptidic natural products through database search of mass spectra," Nature Chemical Biology, Jan. 2017, 13(1):30-37.
Mohimani et al., "Dereplication, Sequencing and Identification of Peptidic Natural Products: from Genome Mining to Peptidogenomics to Spectral Networks," Nat. Prod. Rep., Oct. 2015, 33:73-86.
Mohimani et al., "Moldiscovery: Learning mass spectrometry fragmentation of small molecules," Research Square, Sep. 11, 2020, 30 pages.
Mohimani et al., "Multiplex De Novo Sequencing of Peptide Antibiotics," Journal of Computational Biology, Nov. 2011, 18(11):1371-1381.
Mohimani et al., "NRPquest: Coupling mass spectrometry and genome mining for nonribosomal peptide discovery," Journal of Natural Products, Aug. 12, 2014, 77:1902-1909.
Mohimani et al., "Sequencing cyclic peptides by multistage mass spectrometry," Proteomics, Jul. 2011, 11(18):3642-3650.
Mohr et al., "Pinensins: the first antifungal lantibiotics," Angewandte Chemie International Edition, Sep. 2015, 54(38):11254-11258.
Mongia et al., "AdenPredictor: Accurate prediction of the adenylation domain specificity of nonribosomal peptide Biosynthetic Gene Clusters in Microbial Genomes," Bioinformatics, Jun. 2023, 39:i40-i46; Supplementary Information, May 2022, 9 pages.
Mongia et al., "AdenPredictor: Accurate prediction of the adenylation domain specificity in nonribosomal peptides Biosynthetic Gene Clusters in Microbial Genomes," Bioinformatics, 2023, 39:i40-i46.
Mongia et al., "An interpretable machine learning approach to identify mechanism of action of antibiotics," Scientific Reports, Jun. 20, 2022, 12(10342):1-11.
Mongia et al., "Fast Mass Spectrometry Search and Clustering of Untargeted Metabolomics Data," Nature Biotechnology, Jan. 2024, 42:1672-1677.
Montavon et al., "Explaining nonlinear classification decisions with deep Taylor decomposition," Pattern Recognition, May 2017, 65:211-222.
Moss et al., "Loss of co-linearity by modular polyketide synthases: A mechanism for the evolution of chemical diversity," Natural Product Reports, Sep. 13, 2004, 21:575-593.
Navarro-Munoz et al., "A computational framework to explore large-scale biosynthetic diversity," Nature Chemical Biology, Jan. 2020, 16:60-68.
Nesvizhskii, "A survey of computational methods and error rate estimation procedures for peptide and protein identification in shotgun proteomics," Journal of Proteomics, Oct. 2010, 73(11):2092-2123.
Newman et al., "Natural products as sources of new drugs from 1981 to 2014," Journal of Natural Products, Feb. 7, 2016, 79:629-661.
Newman et al., "Natural products as sources of new drugs over the 30 years from 1981 to 2010," Journal of Natural Products, Feb. 8, 2012, 75(3):311-335.
Newman et al., "Natural Products as Sources of New Drugs over the Nearly Four Decades from Jan. 1981 to Sep. 2019," Journal of Natural Products, Mar. 12, 2020, 83:770-803.
Nguyen et al., "Indexing the Pseudomonas specialized metabolome enabled the discovery of poaeamide B and the bananamides," Nature Microbiology, Oct. 2016, 2:1-10 (author manuscript).
Nguyen et al., "MS/MS networking guided analysis of molecule and gene cluster families," Proceedings of the National Academy of Sciences of the United States of America, Jun. 24, 2013, 110:E2611-E2620.

(56) References Cited

OTHER PUBLICATIONS

Nothias et al., "Feature-based molecular networking in the GNPS analysis environment," Nature Methods, Sep. 2020, 17:905-908.
Olender et al., "Multidirectional efficacy of biologically active nitro compounds included in medicines," Pharmaceuticals, May 29, 2018, 11(54):1-29.
O'Neill, "Antimicrobial resistance: tackling a crisis for the health and wealth of nations the review on antimicrobial resistance chaired. In Review Paper—Tackling a Crisis for the Health and Wealth of Nations," The Review on Antimicrobial Resistance, Dec. 2014, 20 pages.
Pagano et al., "Thiostrepton, a New Antibiotic. I. In Vitro Studies," Antibiotics Annual, 1955-1956, 3:554-559.
Painter et al., "Concanamycin A counteracts HIV-1 Nef to enhance immune clearance of infected primary cells by cytotoxic T lymphocytes," Proceedings of the National Academy of Sciences, Sep. 22, 2020, 117(38):23835-23846.
Palaniappan et al., "IMG-ABC v.5.0: an update to the IMG/Atlas of Biosynthetic Gene Clusters Knowledgebase," Nucleic Acids Research, Oct. 29, 2019, 48:D422-D430.
Park et al., "Discovery of cahuitamycins as biofilm inhibitors derived from a convergent biosynthetic pathway," Nat. Commun., Feb. 16, 2016, 7(10710):1-11.
Pearson et al., "Mitogen-activated protein (MAP) kinase pathways: Regulation and physiological functions," Endocrine Reviews, Apr. 2001, 22(2):153-183.
Pence et al., "Chemspider: an online chemical information resource," Chemical Education Today, Nov. 2010, 87(11):1123-1124.
Petras et al., "Non-Targeted Metabolomics Enables the Prioritization and Tracking of Anthropogenic Pollutants in Coastal Seawater," ChemRxiv, Sep. 13, 2019, 22 pages.
Pham et al., "Quinolone antibiotics," MedChemComm, Jun. 2019, 10(10):1719-1739.
Piepersberg et al., "The Biochemistry and Genetics of Aminoglycoside Producers," Aminoglycoside Antibiotics: From Chemical Biology to Drug Discovery, Jan. 2007, pp. 15-118.
Pope et al., "Explainability Methods for Graph Convolutional Neural Networks," Paper, Presented at the Proceedings of the IEEE/CVF Conference on Computer Vision and Pattern Recognition, Long Beach, California, Jun. 16-20, 2019, pp. 10772-10781.
Pye et al., "Retrospective analysis of natural products provides insights for future discovery trends," Proceedings of the National Academy of Sciences U.S.A., May 30, 2017, 114(22):5601-5606.
Qian et al., "Modified guanidine polymers: Synthesis and antimicrobial mechanism revealed by AFM," Polymer, Mar. 29, 2008, 49(10):2471-2475.
Quinn et al., "Global chemical effects of the microbiome include new bile-acid conjugations," Nature, Feb. 26, 2020, 579(7797):123-129.
Raheem et al., "Application of metabolomics and molecular networking in investigating the chemical profile and antitrypanosomal activity of British bluebells (Hyacinthoides non-scripta)," Scientific Reports, Feb. 22, 2019, 9(2547):1-13.
Ramos et al., "Natural products targeting strategies involving molecular networking: different manners, one goal," Natural Product Reports, Jul. 2019, 36(7):960-980.
Rausch et al., "Specificity prediction of adenylation domains in nonribosomal peptide synthetases (nrps) using transductive support vector machines (tsvms)," Nucleic Acids Research, Oct. 12, 2005, 33(18):5799-5808.
Reeve et al., "Understanding the structural mechanisms of antibiotic resistance sets the platform for new discovery," Future Microbiol., Oct. 2015, 10(11):1727-1733.
Reginaldo et al., "Molecular Networking Discloses the Chemical Diversity of Flavonoids and Selaginellins in Selaginella convoluta," Planta Medica, Dec. 9, 2020, 87:113-123.
Rhodes et al., "Global epidemiology of emerging Candida auris," Current Opinion in Microbiology, Jul. 3, 2019, 52:84-89.
Rice et al., "EMBOSS: The European Molecular Biology Open Software Suite," Trends in Genetics, Jun. 2000, 16(6):276-277.
Rince et al., "Characterization of the lacticin 481 operon: the *Lactococcus lactis* genes 1ctF, lctE, and lctG encode a putative ABC transporter involved in bacteriocin immunity," Applied and Environmental Microbiology, Nov. 1997, 63(11):4252-4260.
Rince et al., "Cloning, expression, and nucleotide sequence of genes involved in production of lactococcin DR, a bacteriocin from *Lactococcus lactis* subsp. *lactis*.," Appl Environ Microbiol., May 1994, 60(5):1652-1657.
Robertson et al., "Discovery of Surfactins as Inhibitors of MicroRNA Processing Using Cat-ELCCA.," ACS Med. Chem. Lett., Apr. 2, 2021, 12:878-886.
Rodriguez et al., "Radamycin, a novel thiopeptide produced by *streptomyces* sp. Rsp9," The Journal of Antibiotics, Apr. 2002, 55(4):383-390.
Röttig et al., "NRPSpredictor2—a web server for predicting NRPS adenylation domain specificity," Nucleic Acids Research, May 9, 2011, 39:W362-W367.
Sainsbury et al., "pEAQ: versatile expression vectors for easy and quick transient expression of heterologous proteins in plants," Plant Biotechnology Journal, Sep. 2009, 7(7):682-693.
Scheubert et al., "Significance estimation for large scale metabolomics an-notations by spectral matching," Nature Communications, Nov. 2017, 8(1494):1-10.
Schnell et al., "Prepeptide sequence of epidermin, a ribosomally synthesized antibiotic with four sulphide-rings," Nature, May 19, 1988, 333:276-278.
Schorn et al., "A community resource for paired genomic and metabolomic data mining," Nature Chemical Biology, Apr. 2021, 17:363-368.
Schultz et al., "Biosynthesis and Structures of Cyclomarins and Cyclomarazines, Prenylated Cyclic Peptides of Marine Actinobacterial Origin," Journal of the American Chemical Society, Mar. 2008, 130(13):4507-4516.
Sidhu et al., "Borrelidin Induces the Unfolded Protein Response in Oral Cancer Cells and Chop-Dependent Apoptosis," ACS Med Chem Lett., Sep. 8, 2015, 6:1122-1127.
Skinnider et al., "Comprehensive prediction of secondary metabolite structure and biological activity from microbial genome sequences," Nature Communications, Nov. 2020, 11(6058):1-14.
Skinnider et al., "Genomic charting of ribosomally synthesized natural product chemical space facilitates targeted mining," Proceedings of the National Academy of Sciences, Oct. 3, 2016, 113(42):E6343-E6351.
Srivastava et al., "Monosaccharide biosynthesis pathways database," Glycobiology, Apr. 28, 2021, 31(12):1636-1644.
Stachelhaus et al., "The specificity-conferring code of adenylation domains in nonribosomal peptide synthetases," Chemistry & Biology, Jun. 29, 1999, 6:493-505.
Stokes et al., "A deep learning approach to antibiotic discovery," Cell, Feb. 20, 2020, 180(4):688-702.
Subramanian, et al., "Gene set enrichment analysis: A knowledge-based approach for interpreting genome-wide expression profiles," PNAS, Oct. 25, 2005, 102(43):15545-15550.
Sud et al., "Metabolomics Workbench: An international repository for metabolomics data and metadata, metabolite standards, protocols, tutorials and training, and analysis tools," Nucleic Acids Research, Oct. 13, 2015, 44:D463-D470.
The Integrative HMP (iHMP) Research Network Consortium, "The Integrative Human Microbiome Project: Dynamic Analysis of Microbiome-Host Omics Profiles during Periods of Human Health and Disease," Cell Host & Microbe, Sep. 10, 2014, 16:276-289.
Thompson et al., "A communal catalogue reveals Earth's multiscale microbial diversity," Nature, Nov. 23, 2017, 551:457-463.
Tibshirani et al., "Regression shrinkage and selection via the lasso," Journal of the Royal Statistical Society Series B: Statistical Methodology, Jan. 1996, 58(1):267-288.
Trautman et al., "Domain-targeted metabolomics delineates the heterocycle assembly steps of colibactin biosynthesis," Journal of the American Chemical Society, Feb. 27, 2017, 139:4195-4201.
Tripathi et al., "Baulamycins A and B, broad-spectrum antibiotics identified as inhibitors of siderophore biosynthesis in *Staphylococcus aureus* and Bacillus anthracis," Journal of the American Chemical Society, Jan. 8, 2014, 136:1579-1586.

(56) References Cited

OTHER PUBLICATIONS

Ueda et al., "AmfS, an extracellular peptidic morphogen in Streptomyces griseus," Journal of Bacteriology, Mar. 2002, 184(5):1488-1492.
Van Der Hooft et al., "Linking genomics and metabolomics to chart specialized metabolic diversity," Chemical Society Reviews, May 2020, 49:3297-3314.
Van der Maaten et al., "Visualizing data using t-SNE," Journal of Machine Learning Research, Nov. 2008, 9(86):2579-2605.
Van der Velden et al., "Autocatalytic backbone N-methylation in a family of ribosomal peptide natural products," Nature Chemical Biology, Jun. 5, 2017, 13(8):833-835.
Van Santen et al., "The natural products atlas: An open access knowledge base for microbial natural products discovery," ACS Central Science, Nov. 14, 2019, 5(11):1824-1833.
Villen-Altamirano et al., "Restart: A method for accelerating rare event simulations," Queueing, performance and Control in ATM, 1991, pp. 71-76.
Vizcaino et al., "Comparative metabolomics and structural characterizations illuminate colibactin pathway-dependent small molecules," Journal of the American Chemical Society, Jun. 16, 2014, 136:9244-9247.
Walker et al., "A Machine Learning Bioinformatics Method to Predict Biological Activity from Biosynthetic Gene Clusters," Journal of Chemical Information and Modeling, May 2021, 61(6):2560-2571.
Walker et al., "Precursor peptide-targeted mining of more than one hundred thousand genomes expands the lanthipeptide natural product family," BMC Genomics, Jun. 2020, 21(387):1-17.
Wang et al., "Antibacterial diamines targeting bacterial membranes," J. Med. Chem., Mar. 10, 2016, 59(7):3140-3151.
Wang et al., "Bioinformatic prospecting and synthesis of a bifunctional lipopeptide antibiotic that evades resistance," Science, May 27, 2022, 376:991-996.
Wang et al., "Mass spectrometry searches using MASST," Nature Biotechnology, Jan. 2020, 38:23-26.
Wang et al., "Protein secondary structure prediction using deep convolutional neural fields," Scientific Reports, Jan. 11, 2016, 6(18962):1-11.
Wang et al., "Raptorx-property: a web server for protein structure property prediction," Nucleic Acids Research, Apr. 25, 2016, 44:W430-W435.
Wang et al., "Sharing and community curation of mass spectrometry data with Global Natural Products Social Molecular Networking," Nature Biotechnology, Aug. 2016, 34(8):828-837.
Waterman et al., "Rapid and accurate estimates of statistical significance for sequence data base searches," Proceedings of the National Academy of Sciences, May 1994, 91(11):4625-4628.
Watrous et al., "Mass spectral molecular networking of living microbial colonies," Proceedings of the National Academy of Sciences, May 14, 2012, 109:E1743-E1752.
Wehmeier et al., "Enzymology of aminoglycoside biosynthesis-deduction from gene clusters," Methods in Enzymology, 2009, 459:459-491.
Weininger, "Smiles, a chemical language and information system. 1. Introduction to methodology and encoding rules," Journal of Chemical Information and Computer Sciences, Feb. 1988, 28(1):31-36.
Whitt et al., "Synthesis of hydrazone derivatives of 4-[4-formyl-3-(2-oxochromen-3-yl) pyrazol-1-yl] benzoic acid as potent growth inhibitors of antibiotic-resistant *Staphylococcus aureus* and Acinetobacter baumannii," Molecules, May 29, 2019, 24(2051):2-16.
who.int [online], "Lack of new antibiotics threatens global efforts to contain drug-resistant infections," Jan. 17, 2020, retrieved on Mar. 20, 2025, retrieved from URL <https://www.who.int/news/item/17-01-2020-lack-of-new-antibiotics-threatens-global-efforts-to-contain-drug-resistant-infections>, 3 pages.
Woo et al., "Molecular Networking Reveals the Chemical Diversity of Selaginellin Derivatives, Natural Phosphodiesterase-4 Inhibitors from *Selaginella tamariscina*," Journal of Natural Products, Jun. 2019, 82(7):1820-1830.
Wu et al., "MoleculeNet: A Benchmark for Molecular Machine Learning," CoRR, Submitted on Oct. 26, 2018, arXiv:1703.00564v3, 65 pages.
Yahara et al., "Structures of anti-ace and-renin peptides from lycii radicis cortex," Tetrahedron letters, 1989, 30(44):6041-6042.
Yang et al., "Analyzing learned molecular representations for property prediction," J. Chem. Inf. Model., 2019, 59(8):3370-3388.
Yang et al., "Molecular networking as a dereplication strategy," Journal of Natural Products, Sep. 11, 2013, 76:1686-1699.
Ying et al., "Gnn explainer: A tool for post-hoc explanation of graph neural networks," CoRR, Submitted on Mar. 10, 2019, arXiv:1903.03894v1, 10 pages.
You et al., "Design Space for Graph Neural Networks," CoRR, Submitted on Jul. 23, 2021, arXiv:2011.08843v2, 19 pages.
Zhang et al., "Small molecule accurate recognition technology (smart) to enhance natural products research," Scientific Reports, Oct. 27, 2017, 7(14243):1-17.
Zhou et al., "Structure and Biosynthesis of Xenoamicins from Entomopathogenic *Xenorhabdus*," Chemistry—A European Journal, Nov. 2013, 19:16772-16779.
Ziemert et al., "Ribosomal synthesis of tricyclic depsipeptides in bloom-forming cyanobacteria," Angewandte Chemie, Sep. 2008, 120(40):7870-7873.
Zuegg et al., "How to Stimulate and Facilitate Early Stage Antibiotic Discovery," ACS Infectious Diseases, Jun. 2020, 6(6):1302-1304.

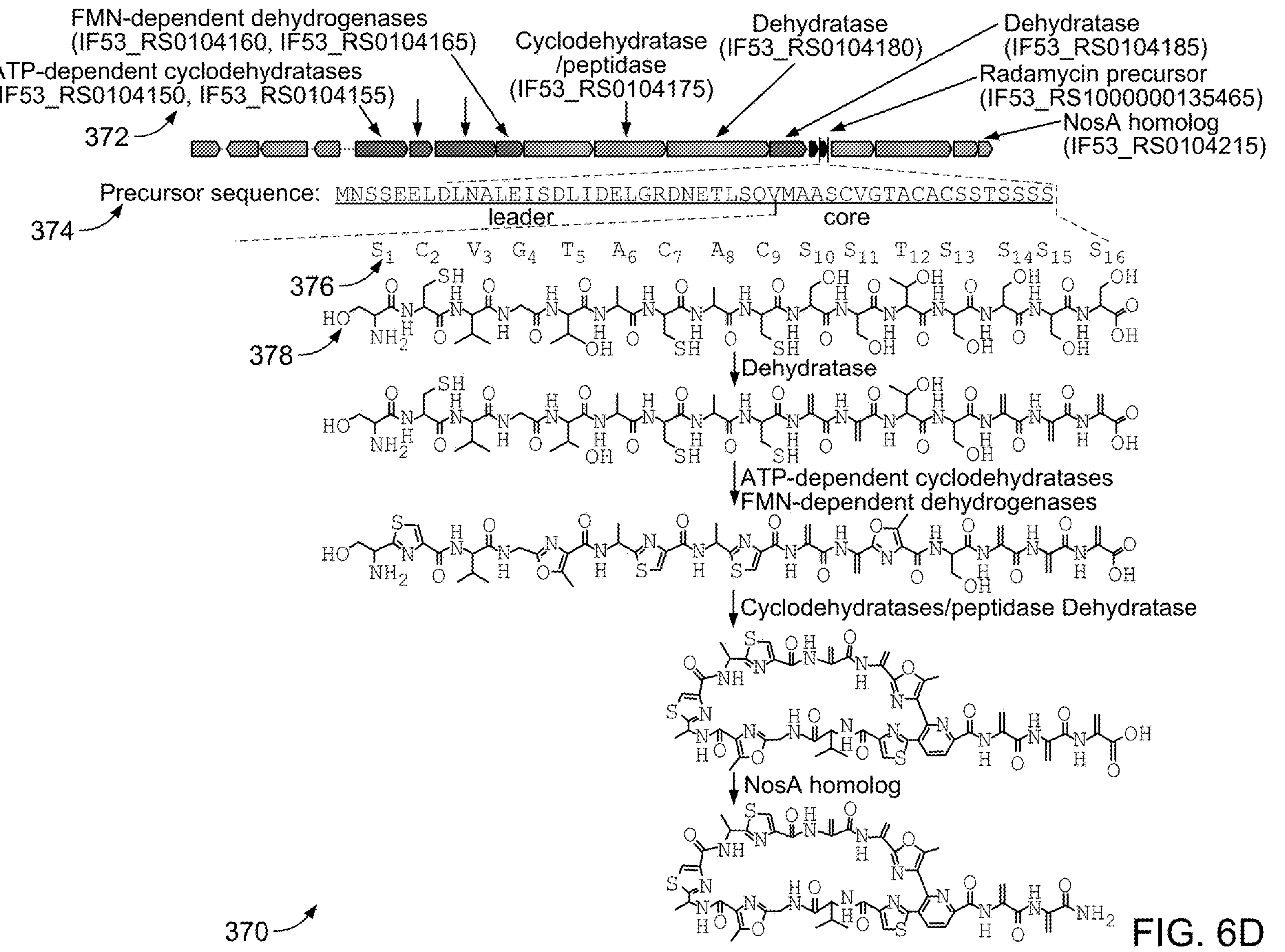
FMN-dependent dehydrogenases
(IF53_RS0104160, IF53_RS0104165)
ATP-dependent cyclodehydratases
(IF53_RS0104150, IF53_RS0104155)
Cyclodehydratase
/peptidase
(IF53_RS0104175)
Dehydratase
(IF53_RS0104180)
Dehydratase
(IF53_RS0104185)
Radamycin precursor
(IF53_RS1000000135465)
NosA homolog
(IF53_RS0104215)
372
Precursor sequence: MNSSEELDLNALEISDLIDELGRDNETLSQVMAASCVGTACACSSTSSSS
374
leader
core
$S_1$ $C_2$ $V_3$ $G_4$ $T_5$ $A_6$ $C_7$ $A_8$ $C_9$ $S_{10}$ $S_{11}$ $T_{12}$ $S_{13}$ $S_{14}$ $S_{15}$ $S_{16}$
376
378
Dehydratase
ATP-dependent cyclodehydratases
FMN-dependent dehydrogenases
Cyclodehydratases/peptidase Dehydratase
NosA homolog
370
FIG. 6D

| | C1 | C2 | C3 |
|---|---|---|---|
| C1 | 0 | 1 | 0 |
| C2 | 1 | 0 | 1 |
| O3 | 0 | 1 | 0 |

| | N1 | C2 | C3 | O4 | O5 |
|---|---|---|---|---|---|
| N1 | 0 | 1 | 0 | 0 | 0 |
| C2 | 1 | 0 | 1 | 0 | 0 |
| C3 | 0 | 1 | 0 | 1 | 1 |
| O4 | 0 | 0 | 1 | 0 | 0 |
| O5 | 0 | 0 | 1 | 0 | 0 |

| | N1 | C2 | C3 | O4 | O5 |
|---|---|---|---|---|---|
| C1 | 0 | 1 | 0 | 0 | 0 |
| C2 | 0 | 0 | 1 | 0 | 0 |
| O3 | 0 | 0 | 0 | 1 | 0 |

| | N1 | C2 | C3 | O4 | O5 |
|---|---|---|---|---|---|
| C1 | 0 | 1 | 0 | 0 | 0 |
| C2 | 0 | 0 | 1 | 0 | 0 |
| O3 | 0 | 0 | 0 | 0 | 1 |

| | N1 | C2 | C3 | O4 | O5 |
|---|---|---|---|---|---|
| C1 | 0 | 0 | 1 | 0 | 0 |
| C2 | 0 | 1 | 0 | 0 | 0 |
| O3 | 0 | 0 | 0 | 0 | 1 |

| | N1 | C2 | C3 | O4 | O5 |
|---|---|---|---|---|---|
| C1 | 0 | 0 | 1 | 0 | 0 |
| C2 | 0 | 1 | 0 | 0 | 0 |
| O3 | 0 | 0 | 0 | 1 | 0 |

| Ion | m/z | Mass error | Sequence |
|---|---|---|---|
| b3 | 361.151 | 0.00051 | YS*Q |
| b5 | 562.222 | 0.00035 | YS*QVC |
| b6 | 631.244 | 0.00053 | YS*QVCS* |
| b7 | 745.335 | 0.00067 | YS*QVCS*I |
| b8 | 844.406 | -0.00177 | YS*QVCS*IV |
| b10 | 1046.49 | -0.00449 | YS*QVCS*IVVC |
| b11 | 1160.53 | -0.00161 | YS*QVCS*IVVCN |
| b12 | 1243.56 | 0.00078 | YS*QVCS*IVVCNT* |
| b12 (+2) | 622.284 | 0.00018 | YS*QVCS*IVVCNT* |
| b13 | 1046.49 | 0.00047 | YS*QVCS*IVVCNT*V |
| b13 (+2) | 671.819 | -0.00021 | YS*QVCS*IVVCNT*V |
| y2 | 179.049 | -0.00074 | CG |
| y3 | 292.133 | -0.00056 | ICG |
| y4 | 391.202 | -0.00123 | VICG |
| y6 | 573.304 | 0.00274 | T*VVICG |
| y7 | 687.352 | -0.00291 | NT*VVICG |
| y8 | 790.359 | -0.00026 | CNT*VVICG |
| y9 | 889.426 | 0.00131 | VCNT*VVICG |
| y10 | 988.5 | -0.00418 | VVCNT*VVICG |

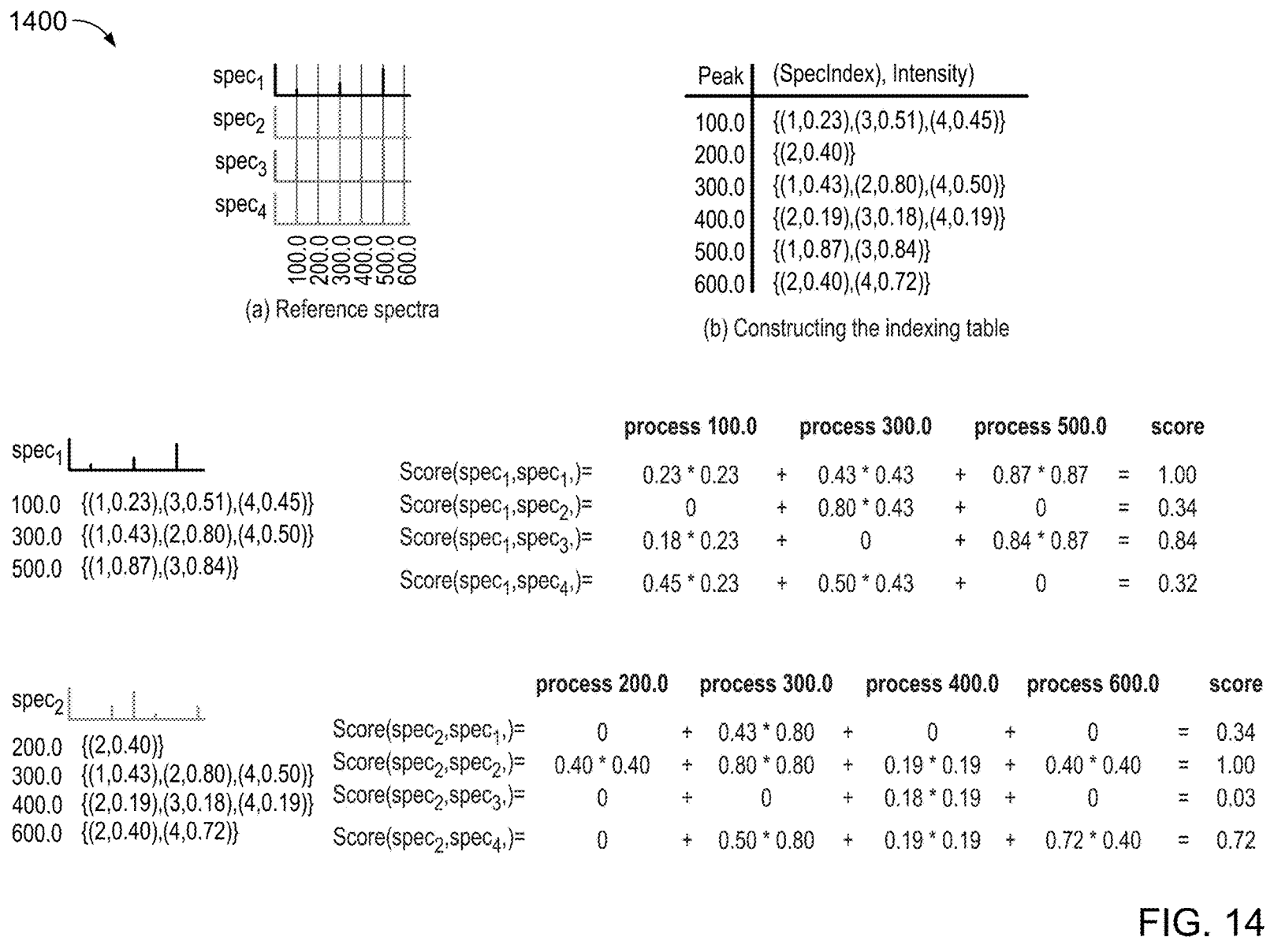

1400 spec$_1$
spec$_2$
spec$_3$
spec$_4$
100.0 200.0 300.0 400.0 500.0 600.0

(a) Reference spectra

| Peak | (SpecIndex), Intensity) |
|---|---|
| 100.0 | {(1,0.23),(3,0.51),(4,0.45)} |
| 200.0 | {(2,0.40)} |
| 300.0 | {(1,0.43),(2,0.80),(4,0.50)} |
| 400.0 | {(2,0.19),(3,0.18),(4,0.19)} |
| 500.0 | {(1,0.87),(3,0.84)} |
| 600.0 | {(2,0.40),(4,0.72)} |

(b) Constructing the indexing table spec$_1$

| | |
|---|---|
| 100.0 | {(1,0.23),(3,0.51),(4,0.45)} |
| 300.0 | {(1,0.43),(2,0.80),(4,0.50)} |
| 500.0 | {(1,0.87),(3,0.84)} |

| | process 100.0 | | process 300.0 | | process 500.0 | | score |
|---|---|---|---|---|---|---|---|
| Score(spec$_1$,spec$_1$,)= | 0.23 * 0.23 | + | 0.43 * 0.43 | + | 0.87 * 0.87 | = | 1.00 |
| Score(spec$_1$,spec$_2$,)= | 0 | + | 0.80 * 0.43 | + | 0 | = | 0.34 |
| Score(spec$_1$,spec$_3$,)= | 0.18 * 0.23 | + | 0 | + | 0.84 * 0.87 | = | 0.84 |
| Score(spec$_1$,spec$_4$,)= | 0.45 * 0.23 | + | 0.50 * 0.43 | + | 0 | = | 0.32 |

spec$_2$

| | |
|---|---|
| 200.0 | {(2,0.40)} |
| 300.0 | {(1,0.43),(2,0.80),(4,0.50)} |
| 400.0 | {(2,0.19),(3,0.18),(4,0.19)} |
| 600.0 | {(2,0.40),(4,0.72)} |

| | process 200.0 | | process 300.0 | | process 400.0 | | process 600.0 | | score |
|---|---|---|---|---|---|---|---|---|---|
| Score(spec$_2$,spec$_1$,)= | 0 | + | 0.43 * 0.80 | + | 0 | + | 0 | = | 0.34 |
| Score(spec$_2$,spec$_2$,)= | 0.40 * 0.40 | + | 0.80 * 0.80 | + | 0.19 * 0.19 | + | 0.40 * 0.40 | = | 1.00 |
| Score(spec$_2$,spec$_3$,)= | 0 | + | 0 | + | 0.18 * 0.19 | + | 0 | = | 0.03 |
| Score(spec$_2$,spec$_4$,)= | 0 | + | 0.50 * 0.80 | + | 0.19 * 0.19 | + | 0.72 * 0.40 | = | 0.72 |

FIG. 14

$spec_3$

| | |
|---|---|
| 100.0 | {(1,0.23),(3,0.51),(4,0.45)} |
| 400.0 | {(2,0.19),(3,0.18),(4,0.19)} |
| 500.0 | {(1,0.87),(3,0.84)} |

$spec_4$

| | |
|---|---|
| 100.0 | {(1,0.23),(3,0.51),(4,0.45)} |
| 300.0 | {(1,0.43),(2,0.80),(4,0.50)} |
| 400.0 | {(2,0.19),(3,0.18),(4,0.19)} |
| 600.0 | {(2,0.40),(4,0.72)} |

(c) Retrieiving the lists corresponding to each peak

| | process 100.0 | | process 400.0 | | process 500.0 | | score |
|---|---|---|---|---|---|---|---|
| Score($spec_3$,$spec_1$,)= | 10.6 * 0.51 | + | 0 | + | 40.2 * 0.84 | = | 0.84 |
| Score($spec_3$,$spec_2$,)= | 0 | + | 10.3 * 0.18 | + | 0 | = | 0.03 |
| Score($spec_3$,$spec_3$,)= | 31.4 * 0.51 | + | 0 | + | 52.4 * 0.84 | = | 1.00 |
| Score($spec_3$,$spec_4$,)= | 22.4 * 0.51 | + | 9.2 * 0.18 | + | 0 | = | 0.26 |

| | process 100.0 | | process 300.0 | | process 400.0 | | process 600.0 | | score |
|---|---|---|---|---|---|---|---|---|---|
| Score($spec_4$,$spec_1$,)= | 0.23 * 0.45 | + | 0.43 * 0.80 | + | 0 | + | 0 | = | 0.32 |
| Score($spec_4$,$spec_2$,)= | 0 | + | 0.80 * 0.50 | + | 0.19 * 0.19 | + | 0.40 * 0.72 | = | 0.72 |
| Score($spec_4$,$spec_3$,)= | 0.51 * 0.45 | + | 0 | + | 0.18 * 0.19 | + | 0 | = | 0.26 |
| Score($spec_4$,$spec_4$,)= | 0.45 * 0.45 | + | 0.50 * 0.50 | + | 0.19 * 0.19 | + | 0.72 * 0.72 | = | 1.00 |

(d) Calculating SharedScore

| | $spec_1$ | $spec_2$ | $spec_3$ | $spec_4$ |
|---|---|---|---|---|
| $spec_1$ | 1.00 | 0.34 | 0.84 | 0.31 |
| $spec_2$ | 0.34 | 1.00 | 0.03 | 0.72 |
| $spec_3$ | 0.84 | 0.03 | 1.00 | 0.26 |
| $spec_4$ | 0.32 | 0.72 | 0.26 | 1.00 |

(e) Forming the score matrix

| | $spec_1$ | $spec_2$ | $spec_3$ | $spec_4$ |
|---|---|---|---|---|
| $spec_1$ | 1.00 | 0.34 | 0.84 | 0.31 |
| $spec_2$ | 0.34 | 1.00 | 0.03 | 0.72 |
| $spec_3$ | 0.84 | 0.03 | 1.00 | 0.26 |
| $spec_4$ | 0.32 | 0.72 | 0.26 | 1.00 |

(f) Forming Molecular Network

| △- 1200.0 - 1100.0 | △- 1100.0 - 1100.0 | △- 1000.0 - 1100.0 |
|---|---|---|
| 100.0+ △ {(2,21.6)} | 100.0+ △ {(5,31.4),(6,31.4),(7,10.3)} | 200.0+ △ {(9,20.4)} |
| 200.0+ △ {(1,20.1),(2,42.7),(4,24.0)} | 200.0+ △ {(5,10.2),(6,29.4),(8,38.1)} | 500.0+ △ {(9,12.3),(10,49.2),(12,35.3)} |
| 500.0+ △ {(2,21.6),(4,35.4)} | 500.0+ △ {(6,20.1),(7,10.3),(8,18.8)} | 600.0+ △ {(11,36.4)} |
| | 600.0+ △ {(8,10.3)} | |

(c) retrieve rows from indexing table corresponding to shared and shifted peaks of query spectrum (only shifted peaks shown)

| | process 100.0+ △ | | process 200.0+ △ | | process 500.0+ △ | | process 600.0+ △ | | score |
|---|---|---|---|---|---|---|---|---|---|
| ShiftedScore(query,$spec_1$)= | | + | 20.1 * 20.7 | + | | + | | = | 416.07 |
| ShiftedScore(query,$spec_2$)= | 21.6 * 10.3 | + | 42.7 * 20.7 | + | 21.6 * 14.6 | + | | = | 1419.57 |
| ShiftedScore(query,$spec_3$)= | | + | | + | | + | | = | 0 |
| ShiftedScore(query,$spec_4$)= | | + | 24.6 * 20.7 | + | 35.4 * 14.6 | + | | = | 1025.06 |

| | process 100.0+ △ | | process 200.0+ △ | | process 500.0+ △ | | process 600.0+ △ | | |
|---|---|---|---|---|---|---|---|---|---|
| ShiftedScore(query,$spec_6$)= | 31.4 * 10.3 | + | 29.4 * 20.7 | + | 20.1 * 14.6 | + | | = | 1225.46 |
| ShiftedScore(query,$spec_5$)= | 31.4 * 10.3 | + | 10.2 * 20.7 | + | | + | | = | 543.56 |
| ShiftedScore(query,$spec_7$)= | 10.3 * 10.3 | + | | + | 10.3 * 14.6 | + | | = | 256.47 |
| ShiftedScore(query,$spec_8$)= | | + | 38.1 * 20.7 | + | 10.3 * 14.6 | + | 10.3 * 40.1 | = | 1352.08 |

| | | process 200.0+ △ | | process 500.0+ △ | | process 600.0+ △ | | |
|---|---|---|---|---|---|---|---|---|
| ShiftedScore(query,$spec_9$)= | + | 20.4 * 20.7 | + | 12.3 * 14.6 | + | 0 | = | 601.86 |
| ShiftedScore(query,$spec_{10}$)= | + | 0 | + | 49.2 * 14.6 | + | 0 | = | 718.32 |
| ShiftedScore(query,$spec_{11}$)= | + | 0 | + | 0 | + | 36.4 * 40.1 | = | 1459.64 |
| ShiftedScore(query,$spec_{12}$)= | + | 0 | + | 35.3 * 14.6 | + | 0 | = | 515.38 |

(d) Computing shared and shifted scores (only shifted scores shown)

Hydroxylation

Marcolactonization

FIG. 21

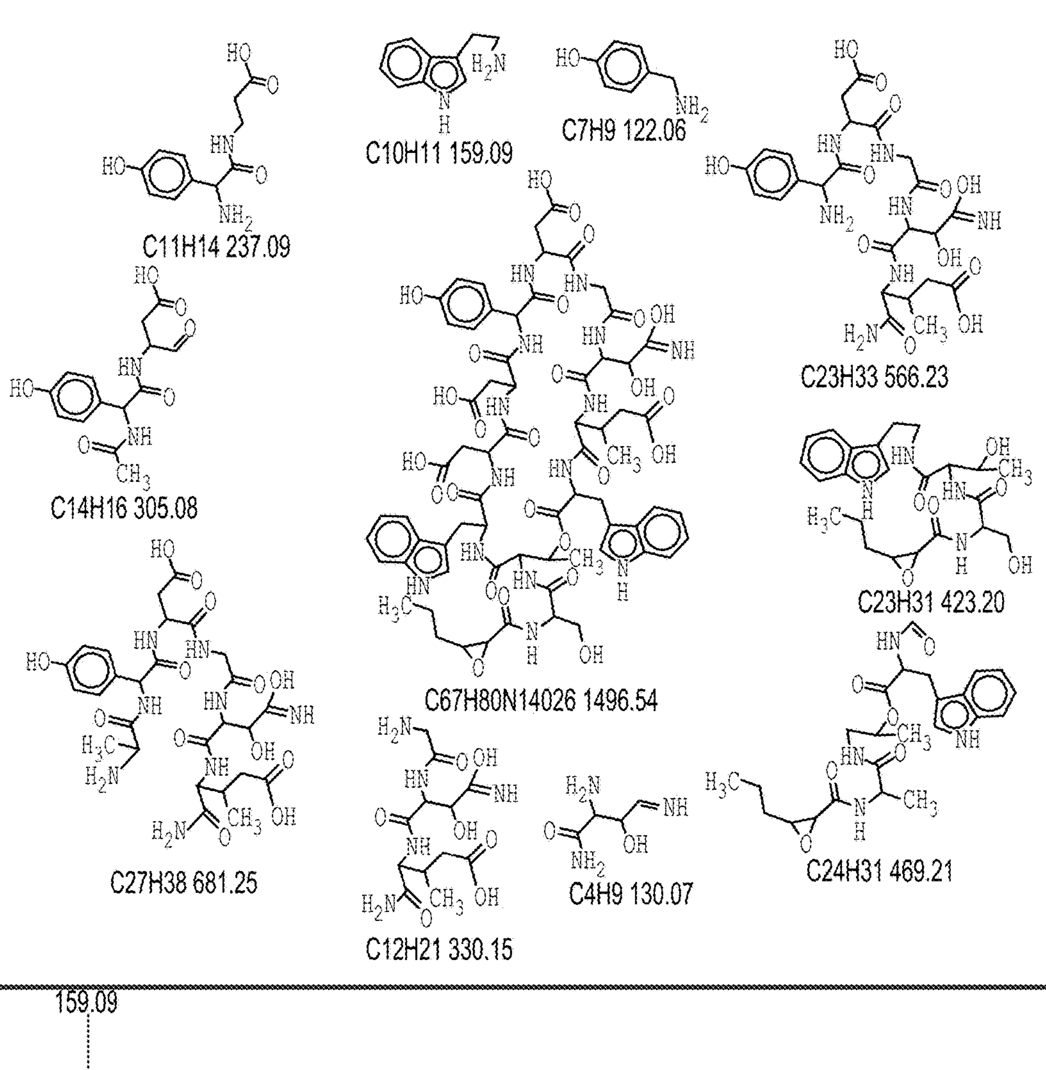
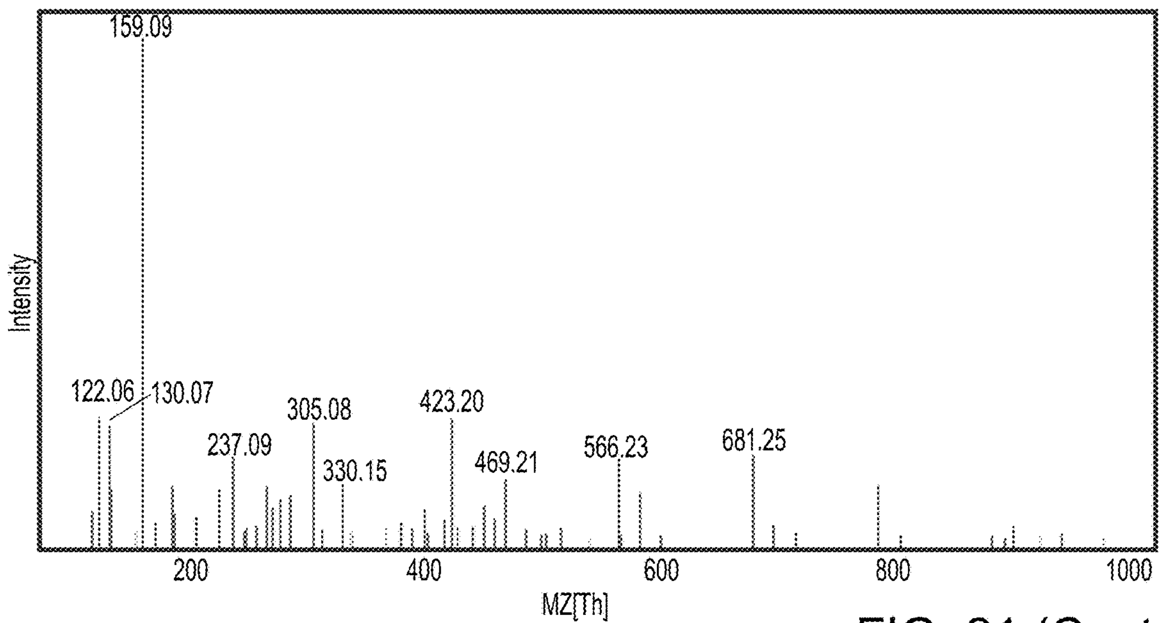
FIG. 21 (Cont.)

2500
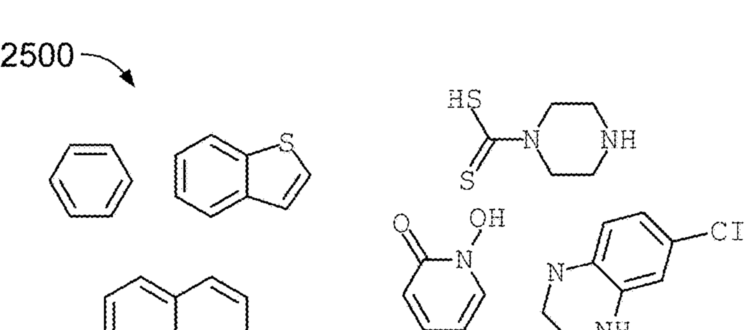
a) training data consisting of active and inactive molecules
d) query molecule
Br Br
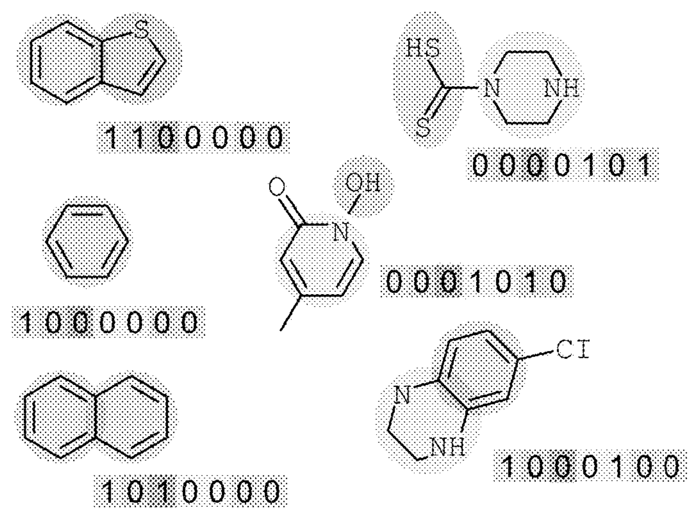
Br Br
1000000
b) identifying unique rings/functional groups and extract features
e) extracting query feature vector
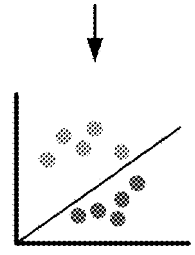
c) training machine learing model to classify active from inactive
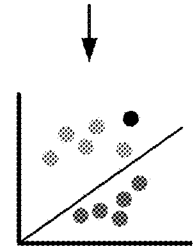
f) predicting the activity
FIG. 25

2800

| | Staphylococcus aureus | Pseudomonas aeruginosa | Acinetobacter baumannii | Klebsiella pneumoniae | Cryptococcus neoformans | Escheria coli | Candida albicans |
|---|---|---|---|---|---|---|---|
| nitro | X | | X | | | | |
| C1-NNCN1 | X | | | | | | |
| C1-CNCN1 | X | | | | | | |
| amidine | X | | | | | | |
| carbonyl | X | | | | | X | |
| haloalkane | X | X | | | | X | |
| hydroxyl | X | | | | | | X |
| C1=CNC=CC1 | X | X | X | X | X | | |
| guanidine | | X | X | X | X | | |
| C1=COCC1 | | X | X | | | | |
| C1=CNCCC1 | | X | X | X | X | | |
| C1CNCCN1 | | X | | | | | |
| amine | | X | | X | | | |
| C1=CCCC=C1 | | X | | | | | |
| hydrazine | | | X | | | | X |
| C1=CCC=CC1 | | | X | | | | |
| C1CCCCC1 | | | X | | | | |
| C1CC[N+]CC1 | | | | X | | | |
| C1=CNCSC1 | | | | X | X | | |
| C1CCNC1 | | | | X | | X | |
| C1CCCC1 | | | | X | | | |
| C1CNC1 | | | | | X | | |
| C1-CCCCC1 | | | | | X | | |
| C1-CCCC-C1 | | | | | X | | |
| imide | | | | | | X | X |
| imine | | | | | | X | X |
| C1=CCOC1 | | | | | | X | X |
| C1CCNCC1 | | | | | | X | X |
| C1COCCNI1 | | | | | | X | |
| C1COCO1 | | | | | | | X |
| ester | | | | | | | X |

(a)
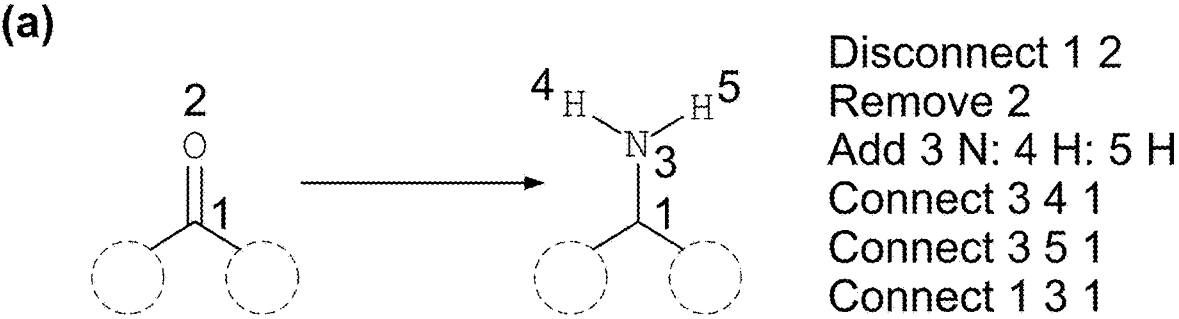
(b)
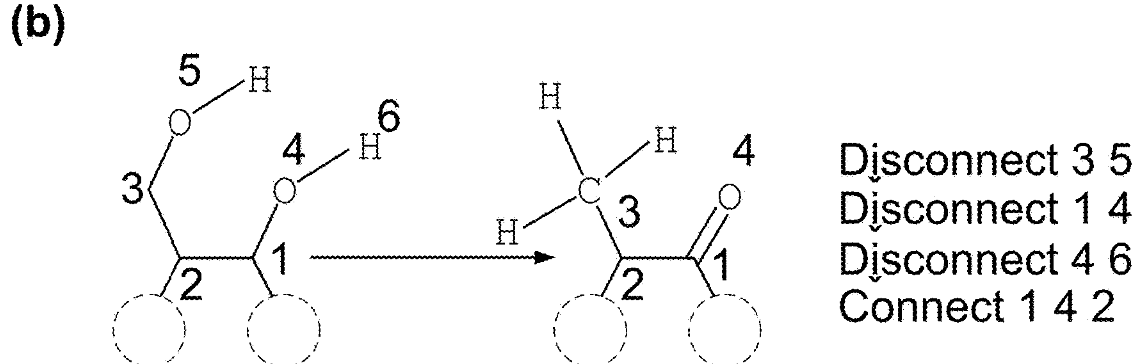
FIG. 35

FIG. 37

SEQUENCE LISTING

```
Sequence total quantity: 49
SEQ ID NO: 1            moltype = AA  length = 7
FEATURE                 Location/Qualifiers
source                  1..7
                        mol_type = protein
                        organism = synthetic construct
SEQUENCE: 1
ILLYPSY                                                                7

SEQ ID NO: 2            moltype = AA  length = 7
FEATURE                 Location/Qualifiers
source                  1..7
                        mol_type = protein
                        organism = synthetic construct
SEQUENCE: 2
VLFYRSY                                                                7

SEQ ID NO: 3            moltype = AA  length = 6
FEATURE                 Location/Qualifiers
source                  1..6
                        mol_type = protein
                        organism = synthetic construct
SEQUENCE: 3
FLLYPY                                                                 6

SEQ ID NO: 4            moltype = AA  length = 7
FEATURE                 Location/Qualifiers
source                  1..7
                        mol_type = protein
                        organism = synthetic construct
SEQUENCE: 4
FLLYPSY                                                                7

SEQ ID NO: 5            moltype = AA  length = 4
FEATURE                 Location/Qualifiers
source                  1..4
                        mol_type = protein
                        organism = synthetic construct
SEQUENCE: 5
ILLY                                                                   4

SEQ ID NO: 6            moltype = AA  length = 8
FEATURE                 Location/Qualifiers
source                  1..8
                        mol_type = protein
                        organism = synthetic construct
SEQUENCE: 6
QPFGVFAW                                                               8

SEQ ID NO: 7            moltype = AA  length = 8
FEATURE                 Location/Qualifiers
source                  1..8
                        mol_type = protein
                        organism = synthetic construct
SEQUENCE: 7
QPFGVFSW                                                               8

SEQ ID NO: 8            moltype = AA  length = 5
FEATURE                 Location/Qualifiers
source                  1..5
                        mol_type = protein
                        organism = synthetic construct
SEQUENCE: 8
QLKVW                                                                  5

SEQ ID NO: 9            moltype = AA  length = 19
FEATURE                 Location/Qualifiers
source                  1..19
                        mol_type = protein
                        organism = Streptomyces rimosus
SEQUENCE: 9
DTGHCSGVCT VLVCTVAVC                                                   19

SEQ ID NO: 10           moltype = AA  length = 17
FEATURE                 Location/Qualifiers
source                  1..17
                        mol_type = protein
                        organism = Streptomyces albus
```

```
SEQUENCE: 10
YSQVCSIVVC NTVVICG                                                    17

SEQ ID NO: 11           moltype = AA  length = 21
FEATURE                 Location/Qualifiers
source                  1..21
                        mol_type = protein
                        organism = Streptomyces lavenduligriseus
SEQUENCE: 11
YTQGCSGLCT IVICATVVIC G                                               21

SEQ ID NO: 12           moltype = AA  length = 21
FEATURE                 Location/Qualifiers
source                  1..21
                        mol_type = protein
                        organism = Streptomyces sp.
SEQUENCE: 12
STAGCSGLCT IIVCATVVIC A                                               21

SEQ ID NO: 13           moltype = AA  length = 24
FEATURE                 Location/Qualifiers
source                  1..24
                        mol_type = protein
                        organism = Streptomyces pathocidini
SEQUENCE: 13
ITSISYCTPG CTSDGGGSGC SHCC                                            24

SEQ ID NO: 14           moltype = AA  length = 24
FEATURE                 Location/Qualifiers
source                  1..24
                        mol_type = protein
                        note = Streptomyces moroccanus
                        organism = Streptomyces sp.
SEQUENCE: 14
ITSISYCTPG CTSEGGGSGC SHCC                                            24

SEQ ID NO: 15           moltype = AA  length = 20
FEATURE                 Location/Qualifiers
source                  1..20
                        mol_type = protein
                        organism = Streptomyces cinerochromogenes
SEQUENCE: 15
YTEGCSGLCT ILVCATVVIC                                                 20

SEQ ID NO: 16           moltype = AA  length = 12
FEATURE                 Location/Qualifiers
source                  1..12
                        mol_type = protein
                        organism = Streptomyces hygroscopicus
SEQUENCE: 16
MTQVCPVTSW HC                                                         12

SEQ ID NO: 17           moltype = AA  length = 20
FEATURE                 Location/Qualifiers
source                  1..20
                        mol_type = protein
                        organism = Streptomyces rimosus
SEQUENCE: 17
PSRSSSPGSF PPGSTPSAPS                                                 20

SEQ ID NO: 18           moltype = AA  length = 17
FEATURE                 Location/Qualifiers
source                  1..17
                        mol_type = protein
                        organism = Streptomyces albus
SEQUENCE: 18
YSQVCSIVIC NTVVICS                                                    17

SEQ ID NO: 19           moltype = AA  length = 17
FEATURE                 Location/Qualifiers
source                  1..17
                        mol_type = protein
                        organism = Streptomyces kanamyceticus
SEQUENCE: 19
ISGEESCFRT CTTCSLC                                                    17

SEQ ID NO: 20           moltype = AA  length = 25
FEATURE                 Location/Qualifiers
source                  1..25
```

```
                        mol_type = protein
                        organism = Streptomyces sulphureus
SEQUENCE: 20
TEGGGGDSSG CSGVCTIVVC TVIVC                                          25

SEQ ID NO: 21           moltype = AA  length = 22
FEATURE                 Location/Qualifiers
source                  1..22
                        mol_type = protein
                        organism = Streptomyces anulatus
SEQUENCE: 21
TGSQVSLLVC EYSSLSVVLC TP                                             22

SEQ ID NO: 22           moltype = AA  length = 16
FEATURE                 Location/Qualifiers
source                  1..16
                        mol_type = protein
                        organism = Streptomyces anulatus
SEQUENCE: 22
CLPEPFPTAT TRVGCD                                                    16

SEQ ID NO: 23           moltype = AA  length = 16
FEATURE                 Location/Qualifiers
source                  1..16
                        mol_type = protein
                        note = Streptomyces paludis
                        organism = Streptomyces sp.
SEQUENCE: 23
SGEESCFRTC TTCSLC                                                    16

SEQ ID NO: 24           moltype = AA  length = 23
FEATURE                 Location/Qualifiers
source                  1..23
                        mol_type = protein
                        organism = Streptomyces anulatus
SEQUENCE: 24
CRPPSASLCI TSDRSSTGRY LSM                                            23

SEQ ID NO: 25           moltype = AA  length = 22
FEATURE                 Location/Qualifiers
source                  1..22
                        mol_type = protein
                        organism = Streptomyces brasiliensis
SEQUENCE: 25
TGSQVSVLVC EYSSLSVVLC TP                                             22

SEQ ID NO: 26           moltype = AA  length = 11
FEATURE                 Location/Qualifiers
source                  1..11
                        mol_type = protein
                        organism = synthetic construct
SEQUENCE: 26
MAASCVCSST S                                                         11

SEQ ID NO: 27           moltype = AA  length = 15
FEATURE                 Location/Qualifiers
source                  1..15
                        mol_type = protein
                        organism = synthetic construct
SEQUENCE: 27
MTLGPPGDRI ELDRD                                                     15

SEQ ID NO: 28           moltype = AA  length = 53
FEATURE                 Location/Qualifiers
source                  1..53
                        mol_type = protein
                        organism = synthetic construct
SEQUENCE: 28
MNSAGGTEAS CTIGCAFDGE GGSTEASCIG CMAFDCAGEA SCITGCAFDG SWG           53

SEQ ID NO: 29           moltype = AA  length = 50
FEATURE                 Location/Qualifiers
source                  1..50
                        mol_type = protein
                        organism = synthetic construct
SEQUENCE: 29
MNSSEELDLN ALEISDLIDE LGRDNETLSQ VMAASCVGTA CACSSTSSSS               50

SEQ ID NO: 30           moltype = AA  length = 35
```

```
FEATURE                Location/Qualifiers
source                 1..35
                       mol_type = protein
                       organism = synthetic construct
SEQUENCE: 30
MTYERPTLTR AGGFRKVTGV KNTGPKDVLG GKQLL                        35

SEQ ID NO: 31          moltype = AA  length = 53
FEATURE                Location/Qualifiers
source                 1..53
                       mol_type = protein
                       organism = synthetic construct
SEQUENCE: 31
MSDTMERTEL TDLDELIGDL ETRITETELT ETEADTGHCS GVCTVLVCTV AVC    53

SEQ ID NO: 32          moltype = AA  length = 55
FEATURE                Location/Qualifiers
source                 1..55
                       mol_type = protein
                       organism = synthetic construct
SEQUENCE: 32
MRRTSLRCRL DRRRKVTTMR LRYTPPKVVR IGRVEKLTGQ LRHGTPDLLG HGNIW  55

SEQ ID NO: 33          moltype = AA  length = 505
FEATURE                Location/Qualifiers
source                 1..505
                       mol_type = protein
                       organism = synthetic construct
SEQUENCE: 33
MELRLLFLFF LVILHLAGVS SQFDDSHNLH NEGEEAFPNV DKLPTQPAGG VPEKFGKDLL  60
NHMAQSGLFS GGVSEKFGKN LLNHMAQPDI LPIIYGGGAH ENFGKDLLNH MAQPDLLPII  120
YGGGAPEKIE KDLLNHKAQS DLFSGGASEK FGKDLLNHMA QPDMLPIIYG GGAHENFGKD  180
LLNHMAQPDL LPIIYGGGAP EKIEKDLLNH KAQSDLFSGG ASEKFGKNLL NHMAQPNMLP  240
IIYGGGAHEN FGKNLLNHMA QPDMLPIIYG GGAPMKDSKL MKGNVASFFL ENDLLLGKTM  300
KLHFTNPITG AKFLPLDIAK SIPFASNKLP EILNRFNIEP KSSDVEIVKQ TISLCEGQKS  360
IETEHKYCAT SLESLIDFSR SKLGEDIKIY STEVDEEIKQ DYKIIKESIV KLGDKSVVCH  420
KLNYMYAVYY CHHVHATKVY MATLEGENGV KENAIAACHA DTKGWNPKHL AFQLLNIKPG  480
TDTICHFLSS DTLVLVPQKD KDVSY                                    505

SEQ ID NO: 34          moltype = AA  length = 51
FEATURE                Location/Qualifiers
source                 1..51
                       mol_type = protein
                       organism = synthetic construct
SEQUENCE: 34
MPNGKTEFEL DALIDDLDAR VTESELAVSE NTGAYSQVCS IVVCNTVVIC G      51

SEQ ID NO: 35          moltype = AA  length = 9
FEATURE                Location/Qualifiers
source                 1..9
                       mol_type = protein
                       organism = synthetic construct
SEQUENCE: 35
MNWTGLNAI                                                     9

SEQ ID NO: 36          moltype = AA  length = 5
FEATURE                Location/Qualifiers
source                 1..5
                       mol_type = protein
                       organism = synthetic construct
SEQUENCE: 36
YSQVC                                                         5

SEQ ID NO: 37          moltype = AA  length = 6
FEATURE                Location/Qualifiers
source                 1..6
                       mol_type = protein
                       organism = synthetic construct
SEQUENCE: 37
YSQVCS                                                        6

SEQ ID NO: 38          moltype = AA  length = 7
FEATURE                Location/Qualifiers
source                 1..7
                       mol_type = protein
                       organism = synthetic construct
SEQUENCE: 38
YSQVCSI                                                       7
```

```
SEQ ID NO: 39              moltype = AA  length = 8
FEATURE                    Location/Qualifiers
source                     1..8
                           mol_type = protein
                           organism = synthetic construct
SEQUENCE: 39
YSQVCSIV                                                           8

SEQ ID NO: 40              moltype = AA  length = 10
FEATURE                    Location/Qualifiers
source                     1..10
                           mol_type = protein
                           organism = synthetic construct
SEQUENCE: 40
YSQVCSIVVC                                                         10

SEQ ID NO: 41              moltype = AA  length = 11
FEATURE                    Location/Qualifiers
source                     1..11
                           mol_type = protein
                           organism = synthetic construct
SEQUENCE: 41
YSQVCSIVVC N                                                       11

SEQ ID NO: 42              moltype = AA  length = 12
FEATURE                    Location/Qualifiers
source                     1..12
                           mol_type = protein
                           organism = synthetic construct
SEQUENCE: 42
YSQVCSIVVC NT                                                      12

SEQ ID NO: 43              moltype = AA  length = 13
FEATURE                    Location/Qualifiers
source                     1..13
                           mol_type = protein
                           organism = synthetic construct
SEQUENCE: 43
YSQVCSIVVC NTV                                                     13

SEQ ID NO: 44              moltype = AA  length = 4
FEATURE                    Location/Qualifiers
source                     1..4
                           mol_type = protein
                           organism = synthetic construct
SEQUENCE: 44
VICG                                                               4

SEQ ID NO: 45              moltype = AA  length = 6
FEATURE                    Location/Qualifiers
source                     1..6
                           mol_type = protein
                           organism = synthetic construct
SEQUENCE: 45
TVVICG                                                             6

SEQ ID NO: 46              moltype = AA  length = 7
FEATURE                    Location/Qualifiers
source                     1..7
                           mol_type = protein
                           organism = synthetic construct
SEQUENCE: 46
NTVVICG                                                            7

SEQ ID NO: 47              moltype = AA  length = 8
FEATURE                    Location/Qualifiers
source                     1..8
                           mol_type = protein
                           organism = synthetic construct
SEQUENCE: 47
CNTVVICG                                                           8

SEQ ID NO: 48              moltype = AA  length = 9
FEATURE                    Location/Qualifiers
source                     1..9
                           mol_type = protein
                           organism = synthetic construct
SEQUENCE: 48
VCNTVVICG                                                          9
```

-continued

```
SEQ ID NO: 49          moltype = AA  length = 10
FEATURE                Location/Qualifiers
source                 1..10
                       mol_type = protein
                       organism = synthetic construct
SEQUENCE: 49
VVCNTVVICG                                                  10
```

METHOD AND SYSTEM TO IDENTIFY NATURAL PRODUCTS FROM MASS SPECTROMETRY AND GENOMICS DATA

CLAIM OF PRIORITY

This application claims priority under 35 U.S.C. § 119(e) to U.S. Patent Application Ser. No. 63/286,333, filed on Dec. 6, 2021, the entire contents of which are hereby incorporated by reference.

GOVERNMENT SUPPORT CLAUSE

This invention was made with United States government support under grant number GM137413, awarded by the National Institutes of Health, under grant 2117640, awarded by the National Science Foundation, and under grant DE-SC0021340, awarded by the Department of Energy. The U.S. Government has certain rights in the invention.

TECHNICAL FIELD

This disclosure relates to drug discovery. More specifically, this disclosure relates to machine learning models configured for determining molecular structures of compounds based on gene clusters.

SEQUENCE LISTING

The instant application contains a Sequence Listing which has been submitted via Patent Center and is hereby incorporated by reference in its entirety. Said .xml copy, created on Feb. 18, 2026, is named 26100-0143001, and is 44,835 bytes in size.

BACKGROUND

Identification of small molecule compounds, including natural products and other compounds, is a process used for drug discovery. Recent advances in mass spectrometry have enabled the collection of tandem mass spectra (MS/MS) of small molecules from hundreds of thousands of environments. To identify which molecules are present in a sample, one can search mass spectra collected from the sample against millions of molecular structures in databases of such fragments, which is a spectral library search. This is a challenging task as currently it is not clear how small molecules are fragmented in mass spectrometry. The existing approaches, including in-silico search of small molecule structure databases, use the domain knowledge from chemistry to predict fragmentation of molecules, however these rule-based methods fail to explain many of the peaks in mass spectra of small molecules.

SUMMARY

This disclosure describes systems and methods for determining a structure of compounds from mass spectrometry data. The system is configured to determine a two-dimensional (2D) structure that indicates the bond structure between molecules of a compound by analysis and classification of mass spectra of the compound. Generally, samples of natural products or other materials are received. The system is configured to generate genomics data from the samples of those natural products or other materials. The genomics data indicate genetic data for which microbes are in the sample and the potential for generating therapeutic small-molecule compounds (e.g., drugs). From the same samples, metabolomics data are obtained. This includes performing mass spectrometry of the samples to determine the chemistry of the metabolites in the samples.

The systems and methods described in this specification are configured to relate the genomics data and the metabolomics spectra data from the samples. From this relationship, machine learning models are trained to predict the natural product of the sample and determine which microbes present in the sample are responsible for generating the natural product. The data processing pipeline can be as follows. Microbial samples are obtained. From the microbial samples, the system performs multi-omics sequencing to generate the genomics data as previously described. The system is configured for data mining to develop the relationship between the genomics data and the metabolomics data. From the relationship, one or more compounds are identified (e.g., small molecule compounds). The system can then purify the identified compounds. The purified compounds are then tested for different bacteria (e.g., simulating bacterial infections). The final result is that new chemical entities and their efficacies are identified for use as drugs.

The one or more advantages previously described can be enabled by one or more embodiments. The processes described in this specification enable drug discovery using mass spectra. The accuracy and scalability of determining the structure of the compounds is improved relative to conventional methods for drug discovery from natural products, such as those subsequently described, and for structure analysis of compounds. For example, the traditional approaches are labor intensive, expensive, and inaccurate as they tend to miss viable drug candidates. The methods presented here are eight times more sensitive in detection of small molecules from mass spectra.

Existing models for metabolomics are inaccurate because there is no good model to predict a molecular structure from a mass spectra. Currently, a molecular structure is divided into fragments, and mass spectra of these fragments are measured. This disclosure describes a model is trained with fragments from mass spectrometry to predict the chemical structure.

The data processing system is configured to determine which known small molecules are present or absent in a specific sample (e.g., a microbial sample). For example, the data processing system is configured to identify small molecule biomarkers in plasma/oral/urinal/fecal/tissue samples from a patient for disease diagnosis or prognosis. Epidemiologists are interested in identifying small molecule disease risk factors from diet and the environment. Ecologists are interested in characterizing the molecules produced by microbes in various microbial communities. Natural product researchers are trained to identify all known molecules in their sample, clearing the path towards the discovery of novel antimicrobial or antitumor molecules.

Advances in high-throughput mass spectrometry have enabled collection of billions of mass spectra from hundreds of thousands of host-oriented/environmental samples. A mass spectrum is the fingerprint of a small molecule, which can be represented by a set of mass peaks. To identify small molecules in a sample with tens of thousands of spectra, one can either de novo predict small molecule structure corresponding to mass spectra, search these mass spectra against tens of thousands of reference spectra in spectral libraries, or search these mass spectra against millions of molecular structures in small molecule databases. De novo prediction can potentially identify both known and novel small molecules. However, de novo prediction is rarely used in practice because of an intrinsic complexity of small molecule structures and a low signal-to-noise ratio of mass spectral data. While spectral library search is generally the most reliable mass spectral annotation method, current reference spectral libraries are limited to tens of thousands of molecules, and the majority of known small molecules are not represented in any reference spectral library. Furthermore, associating mass spectra of all known small molecules individually is expensive and time-consuming. The most frequently used strategy for small molecule identification is in-silico search of small molecule structure databases, this approach enables small molecule identification in known databases. Moreover, in-silico database search also applies to discovery of novel small molecules through genome mining.

The majority of in-silico database search methods are rule-based models that incorporate domain knowledge, such as bond types, hydrogen rearrangement, and dissociation energy to predict fragmentations of small molecules and score small molecule-spectrum pairs. However, due to the complex rules involved in small molecule fragmentation, these methods are computationally inefficient for heavy small molecules. Moreover, these predictions, which are based on expert knowledge, do not explain many of the peaks in mass spectra.

As previously described, the efficiency and accuracy of small molecule identification is achieved by the data processing system by (i) designing an efficient algorithm to generate mass spectrometry fragmentations and (ii) developing a probabilistic model to identify small molecules from their mass spectra.

The methods described herein enable a lower false discovery rate (FDR) having an eight-fold improvement compared to existing methods. For example, on a subset of the GNPS repository with known genomes, the data processing system described in this specification correctly linked 20 known and three novel biosynthetic gene clusters to their molecular products.

The method and system described herein each provide scalable, efficient and accurate in-silico predictions and identification of varying classes of compounds with an expanded range of up to 5000 Daltons (Da) of molecular weight. Furthermore, the systems described herein are more efficient than existing methods in terms of run-time and memory consumption. For example, run-time can be reduced by a factor of 60 and memory consumption can be reduced by a factor of 1000.

The method and system for searching databases of mass spectrometry (MS) data, improve the efficiency and accuracy of compound identification from MS data, such as from MS/MS fragmentation data. In some embodiments, the present invention can identify compounds in complex mixtures. The system includes an efficient algorithm to construct fragmentation graphs of compounds, including hypothetical molecules, enabling in-silico database search for molecules up to 5000 Da. The data processing system is configured to construct a metabolite graph for a compound structure and then generate a fragmentation graph from the metabolite graph.

In some implementations, the metabolite graph for hypothetical molecules is made by applying hypothetical modifications of known molecules.

In some implementations, a machine learning model is used by the data processing system to match compounds with their mass spectra and improves the accuracy of the database searching. In some implementations, the machine learning models can include a probabilistic learning model to match compounds with their mass spectra and improve the accuracy of database searching.

The data processing system is configured to determine molecules predicted as the products of biosynthetic gene clusters, including non-ribosomal peptide biosynthetic gene clusters, ribosomally synthesized and post-translationally modified peptide biosynthetic gene clusters, polyketide biosynthetic gene clusters, carbohydrate biosynthetic gene clusters, aminoglycoside biosynthetic gene clusters, and polysaccharide biosynthetic gene clusters.

Additional examples of compounds identified by the data processing system include small molecules, small molecule natural products (including from the class of non-ribosomal peptides, polyketides, ribosomally synthesized and post-translationally modified peptides, carbohydrates, aminoglycosides, and polysaccharides.

In a general aspect, a process includes receiving data representing gene clusters, the gene clusters including one or more genes configured to encode one or more polypeptides or other small molecules. The process includes accessing a machine learning model, the machine learning model being trained with a training dataset that associates the gene clusters to structures of one or more small molecules represented in the data. The process includes applying the machine learning model to the data representing the gene clusters. The process includes identifying, based on applying the machine learning model, one or more monomers associated with at least one gene cluster represented in the data. The process includes determining a structure for a natural product including the one or more monomers.

In some implementations, the machine learning model is trained by performing operations comprising: accessing a set of hypothetical structures for natural products including the structure for the natural product; generating a set of random structures of molecules, the random structures including small molecules; testing, using mass spectrometry data representing known structures and the set of random structures, the set of hypothetical structures for the natural products including the structure for the natural product; generating a score for the structure, the score indicating a match between the structure and a known structure represented in the mass spectrometry data; filtering, based on the score, one or more hypothetical structures from the set of hypothetical structures to generate a filtered set of hypothetical structures that includes the structure for the natural product; and generating the training dataset for training the machine learning model, the training dataset including the filtered set of hypothetical structures.

In some implementations, the process includes determining a class associated with the gene clusters; and accessing, based on the class, a set of training data that is specific to the class associated with the gene clusters.

In some implementations, the process includes predicting a biological activity of an identified natural product based on the machine learning model that is trained with the training dataset. In some implementations, the process includes generating, based on predicting the activity, a data library comprising data that associates a gene cluster with a respective biological activity. In some implementations, the process includes purifying the natural product based on the determined structure.

In some implementations, determining the structure for the natural product including the one or more monomers comprises: predicting, based on the one or more monomers that are identified, a core molecule that is assembled by combining a group of monomers; determining one or more particular gene clusters represented in the data that cause a change of a structure of the core molecule; and identifying an enzyme associated with one or more particular gene clusters that cause the change to the structure of the core molecule.

In some implementations, the core molecule includes a peptide, and wherein the change comprises an addition of an amino acid.

In some implementations, the change comprises an addition of a lipid tail to the core molecule.

In some implementations, the change comprises an addition of a monomer to the core molecule.

In some implementations, the data representing the gene clusters comprises one or more data signatures, wherein data signatures comprise a location of a gene cluster with respect to one or more other gene clusters; and wherein determining the structure for a natural product including the one or more monomers is based on the data signatures.

In some implementations, the core molecule includes a peptide, and wherein the change comprises an addition of an amino acid.

In some implementations, the core molecule includes a non-ribosomal peptide.

In some implementations, the core molecule includes a ribosomally synthesized and post-translationally modified peptide.

In some implementations, the core molecule includes a polyketide.

In some implementations, the core molecule includes a saccharide or aminoglycoside.

In some implementations, the change comprises an addition of a lipid tail to the core molecule.

In some implementations, the core molecule includes a hybrid of non-ribosomal peptide and/or ribosomally synthesized and post-translationally modified peptide and/or a polyketide and/or a saccharide or aminoglycoside, and wherein the change comprises an addition of a monomer.

In some implementations, the data representing the gene clusters comprises one or more data signatures, wherein data signatures comprise a location of a gene cluster with respect to one or more other gene clusters; and wherein determining the structure for a natural product including the one or more monomers is based on the data signatures.

In some implementations, structures of predicted molecules are stored in a computer format that allows for accelerated search against mass spectra.

In a general aspect, a system for searching a database to identify structures of molecular compounds from mass spectrometry data includes at least one processor; and a memory storing instructions that, when executed by the at least one processor, cause the at least one processor to perform operations previously described.

In a general aspect, one or more non-transitory computer readable media store instructions for searching a database to identify structures of molecular compounds from mass spectrometry data, the instructions, when executed by at least one processor, being configured to cause the at least one processor to perform the operations previously described.

The details of one or more implementations are set forth in the accompanying drawings and the description below. Other features and advantages will be apparent from the description and drawings, and from the claims.

BRIEF DESCRIPTION OF DRAWINGS

FIG. 6D (SEQ ID NO: 29) shows an example process for determining a molecular structure based on genomic data in case of Ribosomally Synthesized and post-translationally modified peptides.

FIG. 14 shows a process

FIG. 16 shows graphs

FIGS. 21, 22 and 23 illustrate the NPDiscover processes.

FIG. 25 shows a process for predicting bioactivity of small molecules.

FIG. 31 shows the top 31 ring/functional group features predicted to govern the mechanism of action of molecules along with pathogens they inhibit.

FIG. 34 shows a list of saccharide post-assembly modifications

FIG. 35 shows enzymatic modifications are stored in a computer readable format

FIG. 37 shows identifying neomcyin by searching the spectral dataset.

Like reference symbols in the various drawings indicate like elements.

DETAILED DESCRIPTION

Figure 1:
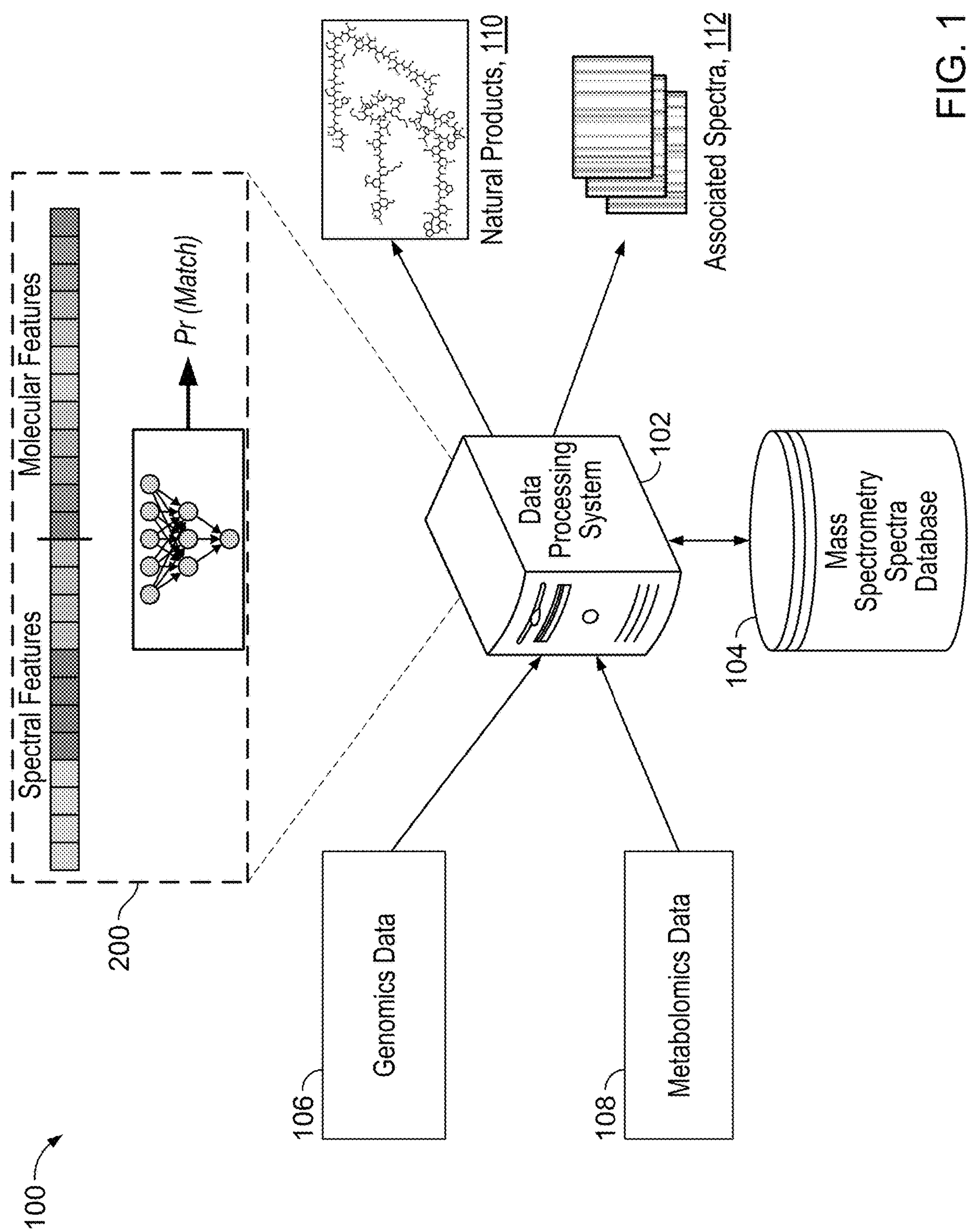
FIG. 1 shows an example system for identifying the structures of molecular compounds from mass spectrometry data.

FIG. 1 shows an example environment 100 of a data processing system 102 for identifying the structures of molecular compounds from mass spectrometry data. The data processing system 102 includes a computing system that is configured to execute one or more machine learning models. The machine learning models receive genomics data 106 and metabolomics data 108. In this specification, genomics data 106 includes gene sequences. In this specification, metabolomics data 108 include data describing the metabolome. The metabolome includes a set of small-molecule (<5 kDa) metabolites, such as metabolic intermediates, hormones and other signaling molecules, and secondary metabolites, that are found within a biological sample, such as a single organism (e.g., a microbe). The data processing system 102 receives spectra data from a mass spectrometry spectra database 104 (database 104). The data processing system 102 processes the genomics data 106 and the metabolomics data 108 to identify natural products from spectra of the metabolomics data and pair these natural products with their respective spectra. The data processing system 102 is configured to output one or more identified natural products data 110 from the received samples (e.g., in the metabolomics data 108) associated with a given spectra. The natural products data 110 include a representation of small molecule structures (e.g., two dimensional structures) represented by the spectra of the samples. In some implementations, the output includes a ranked list of natural products in the natural products data 110. The data processing system 102 generally outputs data linking or associating the identified natural products of the natural products data 110 with each spectra of the spectra data 112. The spectra data 112 include results of performing mass spectrometry on a sample. In some implementations, the spectra data 112 are included in the metabolomics data 108. In some implementations, the spectra data 112 are generated as part of the processes described herein.

The data processing system 102, described in further detail below, is configured to receive the genomics data 106 and the metabolomics data 108 and generate associations between identified natural products of the natural products data 110 and the extracted spectra of the spectra data 112. More specifically, the data processing system 102 is configured to generate metabolite graphs and generate fragmentation graphs. These processes are described in greater detail in relation to FIGS. 3A-3B.

To generate the fragmentation graphs, in some embodiments the data processing system 102 uses a machine learning model configured to determine bridges and 2-cuts in the metabolite graphs that are more probable than other possible bridges or 2-cuts in the fragmentation graph. As described in relation to FIG. 2, a process 200 including machine learning models, such as a probabilistic model, is executed by the data processing system 102 for matching fragmentation graphs of the metabolomics data and mass spectra. The matches or pairs of fragments and mass spectra are scored by the data processing system 102. The scoring process is further described in relation to FIG. 1B.

The data processing system 102 is configured to identify one or more natural products based on the scoring. In some implementations, the data processing system 102 outputs a ranked list of potential natural products. Once the natural product(s) of the sample are identified, the sample can be purified and tested against various infections to complete the process of drug discovery, described in relation to FIG. 41.

Figure 2:
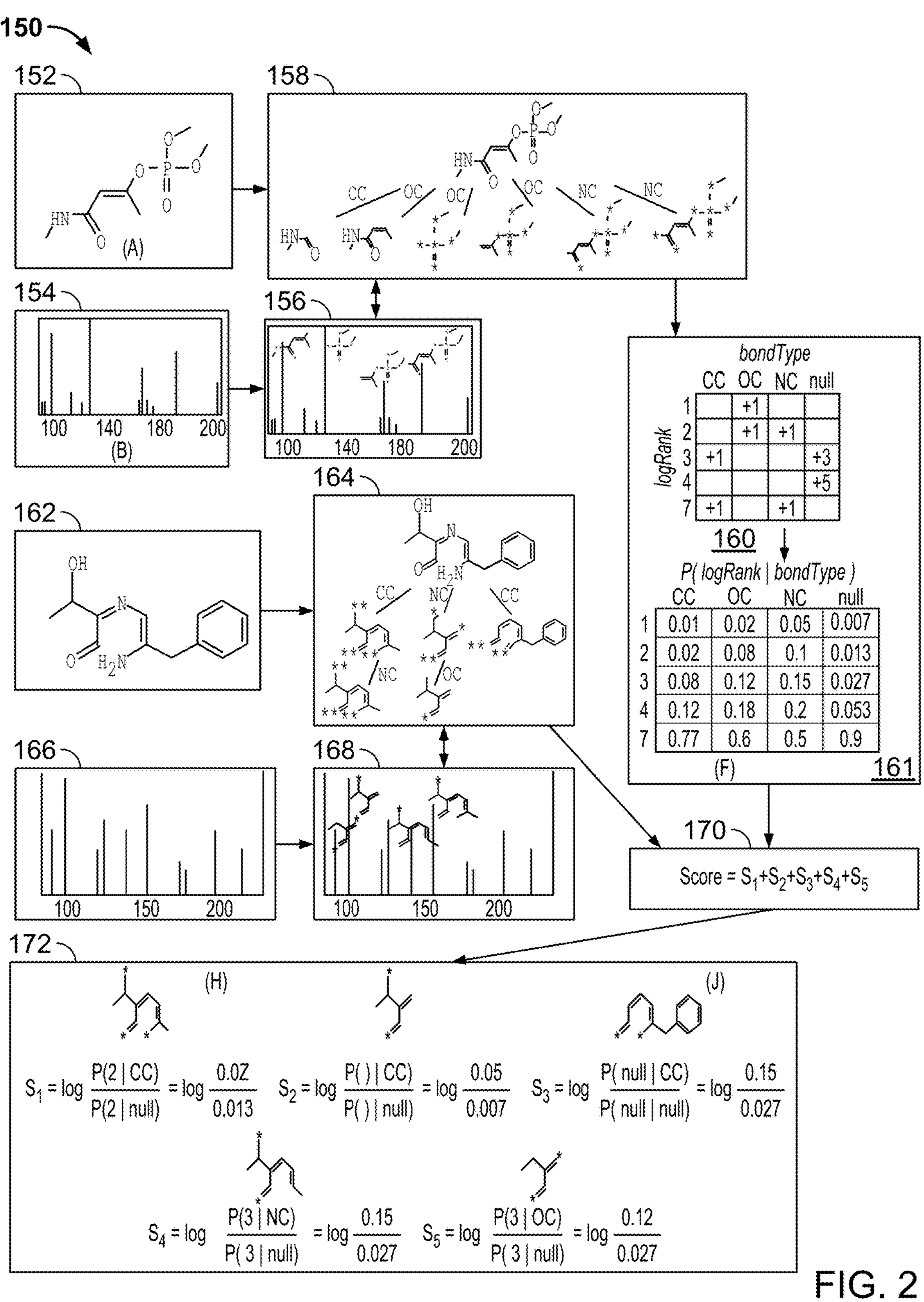
FIG. 2 shows an example process 150 performed by the data processing system 102 for identifying the structures of molecular compounds from mass spectrometry data using the system of FIG. 1.

FIG. 2 shows an example process 150 performed by the data processing system 102 for identifying the structures of molecular compounds from mass spectrometry data using the system of FIG. 1. Steps 152, 154, 156, 158, 160 and 161 show a training procedures for training the probabilistic model of the data processing system 102. Steps 162, 164, 166, 168, 170 and 172 are the scoring procedures based on the pre-trained probabilistic model. At step 152, a reference molecule R in the spectra is identified. At step 154, a reference spectrum of R is obtained. At step 158, the fragmentation graph of R is generated. A root node represents whole molecule, while the other nodes are fragments of it. The edges are annotated with the type of bonds where the fragmentation occurs. A fragment is annotated if it corresponds to a mass peak in the reference spectrum with a logrank of 1, 2, 3, or 4 respectively.

At step 156, an annotation of the reference spectrum of R is shown. A mass peak is annotated with a fragment if its mass is identical to the mass of the fragment plus charge, within a tolerance. As step 160, a table is generated that counts the number of fragments observed in training data with a specific bond type and an associated logrank. This table is called a count matrix. Because the number of peaks is small, the peaks have logranks of 1-4. The absent ones are shown with the lowest possible logrank=7. Logranks between 1-6 are allowed corresponding to peaks with ranks between 1-64. The null column corresponds to the experimental peaks which cannot be explained by the fragmentation graph. At step 161, the probabilistic model P(logrank|bondtype) is shown, which is determined by normalizing the count matrix.

At step 162, a molecule Q in a chemical structure database is obtained. At step 164, a query spectrum is obtained. At step 166, a fragmentation graph of Q is generated. At step 168, an annotation of the query spectrum with the fragmentation graph of Q is generated. At steps 170 and 172, a computation of the query spectrum match score is generated. This is the sum of scores of all the fragments in the annotated fragmentation graph. The P(Logrank=i|bondtype) is represented by P(i|bondtype).

Constructing Fragmentation Graphs of Small Molecules

The data processing system 102 constructs a metabolite graph for a small molecule structure and then generates a fragmentation graph from the metabolite graph. To simplify the modelling of small molecule fragmentation, mass spectrometry is assumed to break only N—C, O—C and C—C bonds.

To construct a metabolite graph, the data processing system 102 disconnects N—C, O—C and C—C bonds. The resulting connected components form the nodes of the metabolite graph. Edges in the metabolite graph correspond to bonds between the connected components.

The fragmentation graph of a molecule is a directed acyclic graph with a single source (the metabolite graph) where nodes are fragments of the molecule and directed edges between the nodes represent bridge or 2-cut fragmentations. To construct a fragmentation graph, the data processing system 102 searches for all the bridges and 2-cuts of the metabolite graph to obtain depth one fragments of the molecule (e.g., using Hopcroft and Tarjan's algorithm). Each fragment of the molecule is represented by a fixed length binary vector that indicates the presence or absence of metabolite graph nodes in the fragment. Depth-two fragments are formed by a bitwise AND operation between their parent fragments and depth one fragments. This generalizes to computing fragments at depth n>−1 by intersecting their parents (fragments at depth n−1) with fragments at depth 1. The final fragmentation graph is constructed by connecting the source node to all depth one fragment nodes and then iteratively connecting depth n−1 fragment nodes to the corresponding fragments at depth n.

Learning a Probabilistic Model to Match Mass Spectra and Small Molecules.

The data processing system 102 uses a naive scoring scheme which ignores that (i) fragmentation probability of different bonds are different, (ii) bridges have a higher chance of fragmentation than 2-cuts, (iii) peaks with higher intensity have higher chances of corresponding to a fragmentation than lower intensity peaks, (iv) matches are biased towards molecules, with large fragmentation graph size, and (v) matches are biased towards spectra with a large number of peaks. A probabilistic model is developed to overcome these issues for matching spectra with small molecules. Given a molecule-spectrum pair in the training data, a fragmentation graph of the molecule is constructed using the fragmentation graph construction algorithm previously described. Each fragment in the fragmentation graph is assigned a (bond type, logRank) label.

BondType represents the bond(s) disconnected in the parent fragment to produce the current fragment. BondType can either be one bond (bridge) or two bonds (2-cut). Bridges can be OC, NC, CC, while 2-cuts can be their pairwise combinations.

LogRank represents the intensity of the mass peak corresponding to the fragment. Intensity rank is an abundance measure of mass peaks in a spectrum. The better the intensity rank is (closer to rank 1), the more abundant the corresponding fragment. To reduce the number of parameters and avoid overfitting, peaks are grouped according to their log Rank instead of directly using intensity rank. A fragment is annotated with a logRank between 1-6 if there is a peak with a rank between 1-64 in the spectrum that is also within 0.01 Da of the mass of the fragment. If there is no such mass peak, the fragment is annotated with logRank=7.

In the annotated fragmentation graph, the logRank of each fragment depends only on its bondType and the logRank of its parent. The direct parent is considered. Considering grandparents of the fragments increases the number of parameters by an order of magnitude, resulting in overfitting. Additionally, a logRank of each mass peak is independent from the logRank of other peaks. This assumption simplifies the probabilistic model. Finally, the root node has logRank 0.

Scoring a Spectrum Against a Small Molecule

Given a query tandem mass spectrum and a small molecule in a chemical structure database, if the spectrum precursor mass is within 0.02 Dalton of the mass of the small molecule and the user-specified adduct, these become a candidate pair for scoring. The data processing system 102 generates the fragmentation graph of the molecule and annotates the query spectrum against the fragmentation graph. Based on the described probabilistic model, a log-likelihood ratio model is used to score the spectrum against the small molecule:

Computing FDR

Target-decoy analysis is used to estimate FDR. The data processing system 102 randomly shuffles the fragmentation graph of target molecules to create decoy fragmentation graphs. The data processing system 102 searches tandem mass spectra against the target and the decoy fragmentation graph databases respectively. At each score cutoff, there are target matches to the target database and $N_{decoy}$ matches to the decoy database, and the ·FDR is estimated as $N_{decoy}/N_{target}$.

FIG. 2 shows an example process 200 for executing a trained machine learning model to identify the structures of molecular compounds from mass spectrometry data using machine learning models. The model is configured for learning a fragmentation pattern of small molecules in mass spectrometry based on a message-passing neural network (MPNN) framework for graph-structured data. The data processing system 102 is therefore an efficient database search tool for de-replication of small molecules based on corresponding associated mass spectra.

The process 200 is executed by the data processing system 102. As shown in the process 200, an input mass spectrum 202 is converted to a feature set 204 using either the dense or sparse representational method. In the machine learning model, the spectra is represented using the peak masses and their intensities. This spectral representation is then encoded into a continuous latent space via a neural network 206. The*denotes convolution. An input molecule 208 is converted into a molecular graph with node and edge labels 210. The data processing system 102 encodes the molecular graph into a continuous latent space by a message passing neural network 212. The data processing system 102 uses a concatenation of spectral 206 and molecular 212 embeddings as input an into a machine learning model. The machine learning model includes a sigmoid activation configured to generate outputs as scalar scores representative of a probability of the input spectrum and the chosen small molecule being a true match 214. The probability analysis is described in greater detail U.S. Pub. 2022/0208540, filed Dec. 17, 2021, titled "System for Identifying Structures of Molecular Compounds from Mass Spectrometry Data," the entire contents of which are incorporated by reference herein.

Accurate Prediction of the Adenylation Domain Specificity of Nonribosomal Peptide Biosynthetic Gene Clusters in Microbial Genomes Nonribosomal peptides (NRPs) are a class of natural products with diverse applications in medicine and agriculture. NRPs are synthesized by non-ribosomal peptide synthetase (NRPS), which are modular assembly lines at minimum consisting of an adenylation domains (A-domains), peptidyl carrier domains (PCP-domains), and condensation domains (C-domains). Usually, each NRPS module is responsible for the recruitment of a single amino acid into the backbone of NRP, which is specified by the A-domain. This section of this specification describes a machine learning model that provides substrate binding predictions and unsupervised clustering for A-domains. By utilizing the extra trees machine learning model, the machine learning model described in this section improves prediction accuracy over the state of the art by eight percent. Moreover, by clustering A-domains using the k-means algorithm, the machine learning model described in this section identifies A-domains corresponding to previously unreported amino acids.

The results associated with the machine learning model described in this section shows that while the existing methods are accurate in case of A-domains that are very similar to domains with known substrates (present in the original training data), their accuracy drops significantly in case of novel A-domains (domains that are distinct from any domain in the training data). In fact, this is a common shortcoming of machine learning methods with string or graph inputs. To alleviate this problem, the machine learning model is applied with various learning techniques (e.g. logistic regression, decision trees, random forests, probabilistic learning and graph neural networks) across different features. These features include amino acids in the binding pocket, their physiochemical properties, and their three-dimensional properties predicted by RaptorX and Alphafold. These results show that tree-based machine learning models outperform the existing approaches in overall accuracy by 8%. In case of A-domains that are significantly different from training data, tree-based methods improve state of the art methods by ~30%. These results show that in contrast to the previous reports, using physiochemical features does not improve the performance of machine learning algorithms in comparison to more basic amino acid features.

This section describes execution of an unsupervised clustering of 453,560 A-domains extracted from 689,227 microbial genomes available at National Center for Biotechnology Information GenBank repository. Information visualization of the results show that labelled A-domains (with known specificity) are not uniformly distributed in the space of all A-domains: 148 out of 200 largest clusters do not contain any known A-domains. We hypothesize that these domains are likely to represent novel amino acids with novel chemistry and bioactivities, making them potential leads for drug discovery.

Figure 3A:
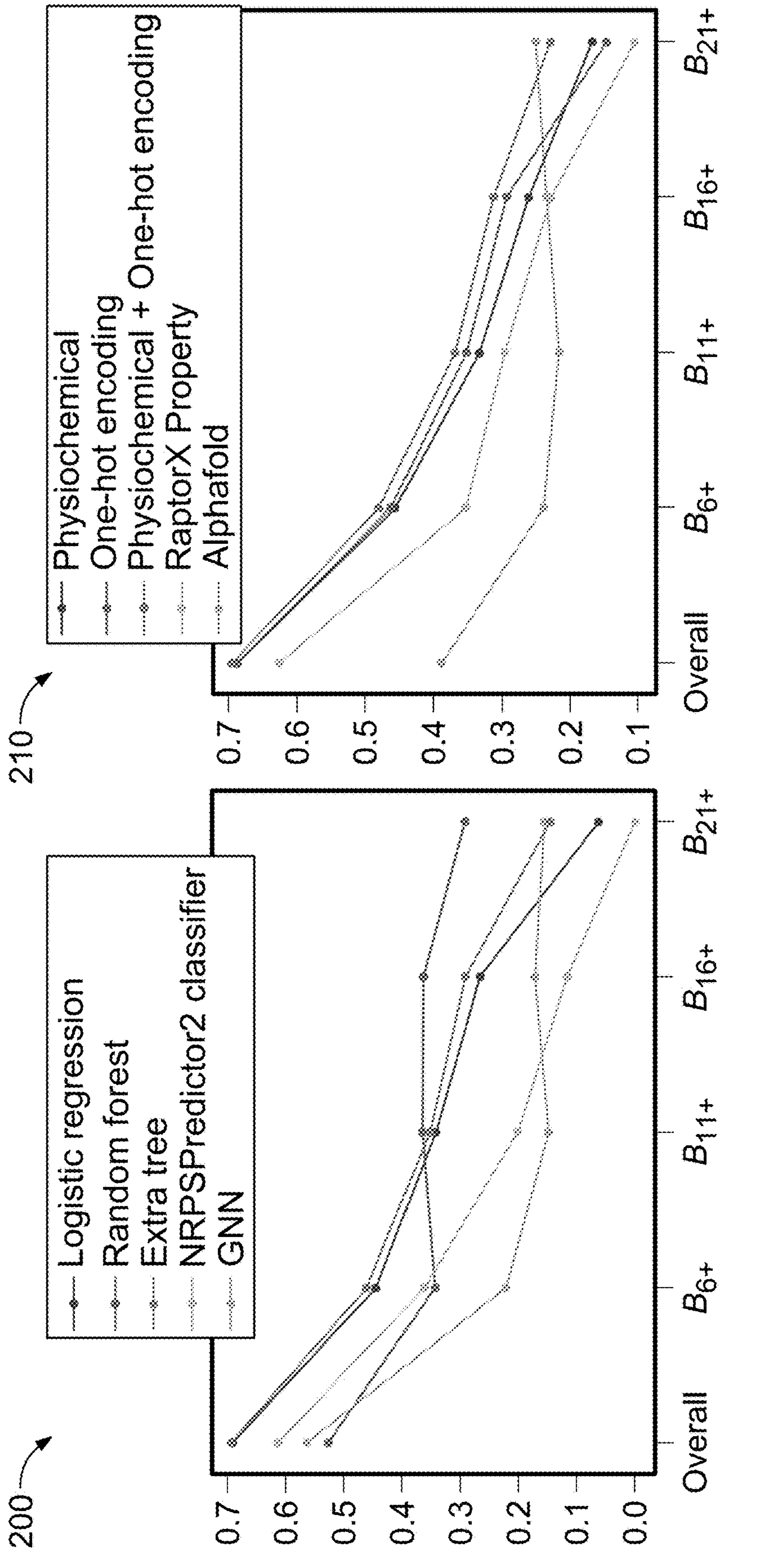
FIGS. 3A-3B shows graphs representing results of the machine learning models.

FIG. 3A shows graphs 200, 210 representing results of the machine learning models described in this section. Graph 200 shows accuracy outcomes of logistic regression, Random forest, Extra tree, NRPSpredictor2 and graph neural network classifiers using one-hot encoding scheme. Graph 210 show accuracy outcomes of extra tree classifier using different encoding schemes.

Graph 200 shows a comparison of accuracy of various machine learning models using one-hot encoding features. In order to evaluate the generalization ability of these models, each model's accuracy is shown for various test datasets differing in the degree of dissimilarity with the training data. The test data points are split into buckets. For every given positive number k, Bk is defined to be the bucket containing data points with minimum hamming distance k from any training data point. Thus, buckets with higher k represent the test sets containing data points that are more distinct from the training set. Moreover, Bk+ is defined as the portion of the test data for which the minimum hamming distance to any training data point is at least k. Various methods are benchmarked on different buckets. The results in graph 200 show that the extra tree method achieves 69% overall accuracy, in comparison to 61% overall accuracy for NRPSpredictor2. In case of B21+ bucket (novel A-domains with less similarity to known A-domains), extra tree achieves 15% accuracy in comparison to 0% for NRPSpredictor2.

Figure 3B:
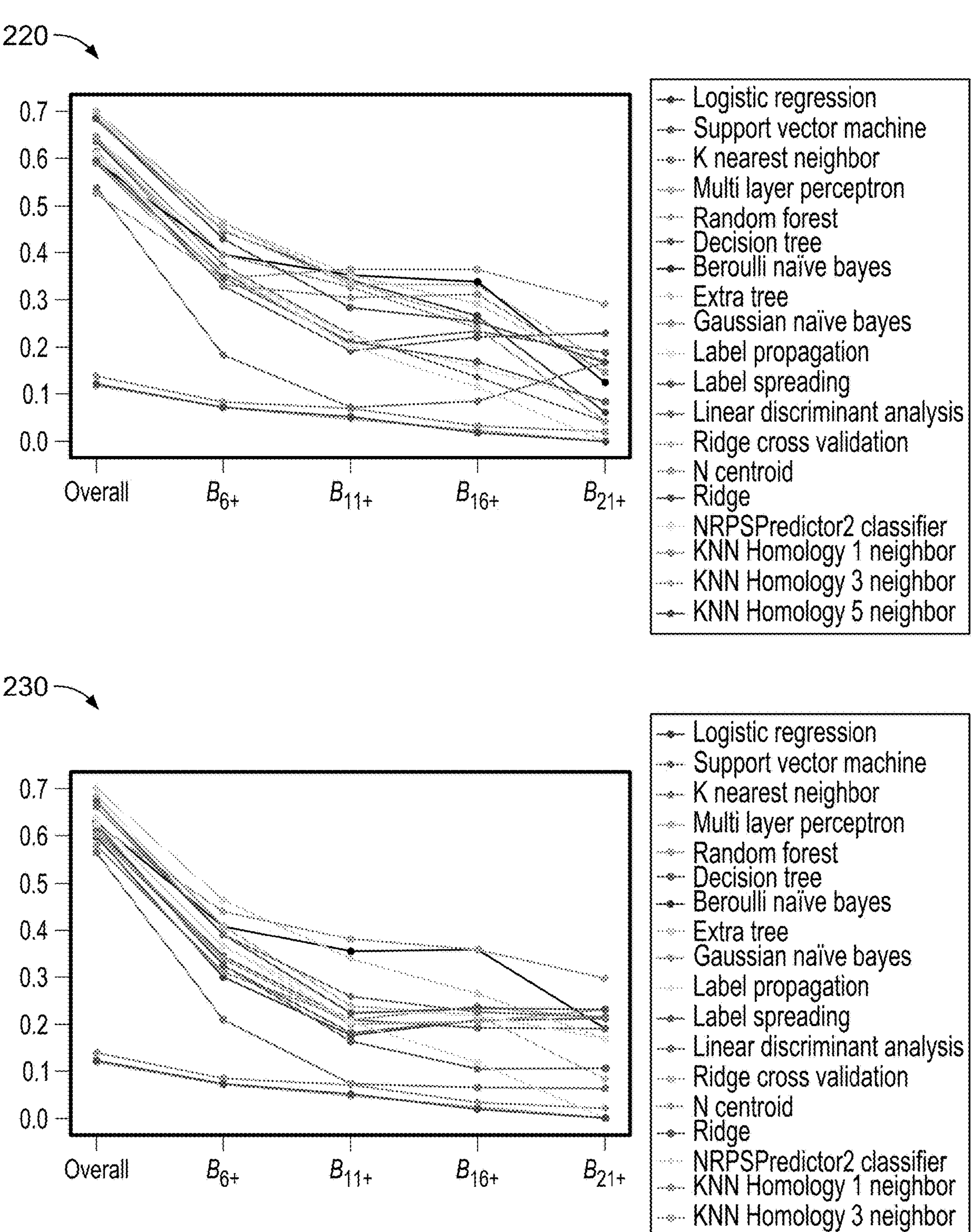

FIG. 3B shows comparison of various methods based on physiochemical and RaptorX features. Accuracy of different classifiers is shown in graph 220 using one-hot encoding. Graph 230 shows accuracy of different classifiers based on physiochemical features. In KNN Homology 'x' neighbor classifier, label of each test data point is denoted by the label with maximum vote from x closest neighbors from training data points. Distance measure is edit distance computed with respect to full sequences of A-domains.

Figure 3C:
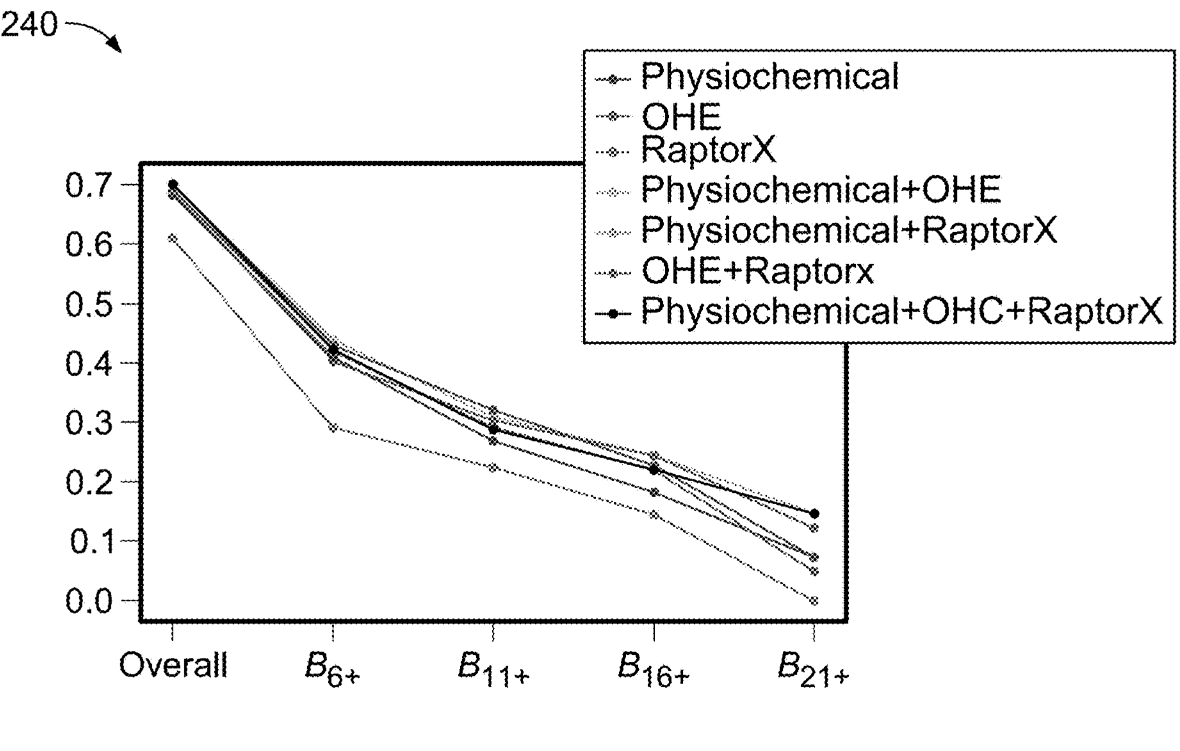
FIG. 3C shows a graph that illustrates a comparison of various encoding techniques.

Turning back to FIG. 3A, graph 210 shows a comparison of accuracy of extra tree method using one-hot encoding (OHE), physiochemical (used for NRPSPredictor2), and RaptorX features. The results in graph 210 show that physiochemical features are not improving the accuracy of learning. FIG. 3C shows a graph 240 that illustrates a comparison of various encoding techniques with an extra tree classifier. OHE stands for one-hot encoding.

A significant portion (10.9%) of training data is from phenylalanine residues. This results in a bias towards predicting phenylalanine, as shown in graphs 400, 410, 420, 440, 460, and 480 of and FIGS. 4A, 4B, and 4C.

Figure 4A:
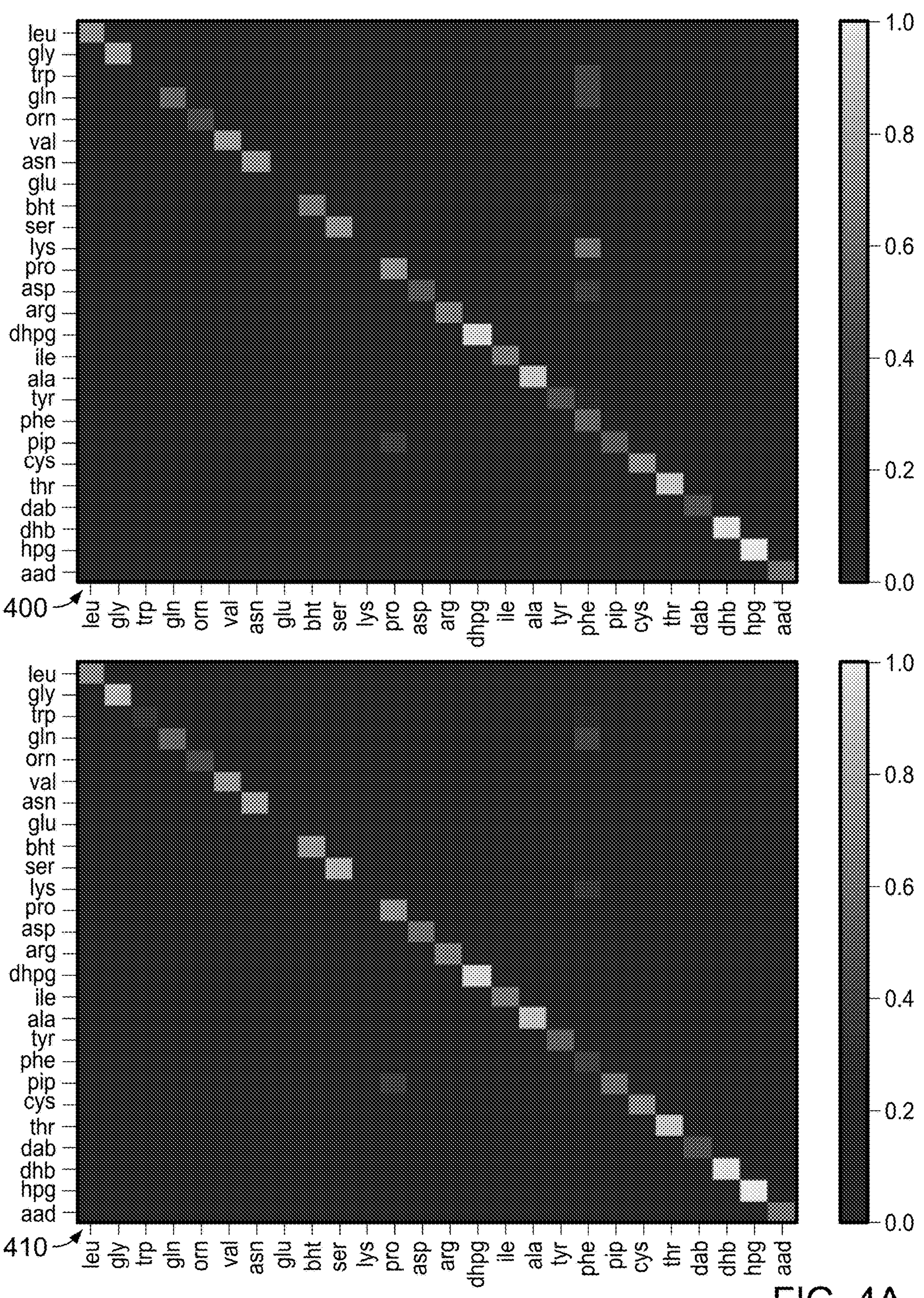
FIGS. 4A-4C show confusion matrices.
Figure 4B:
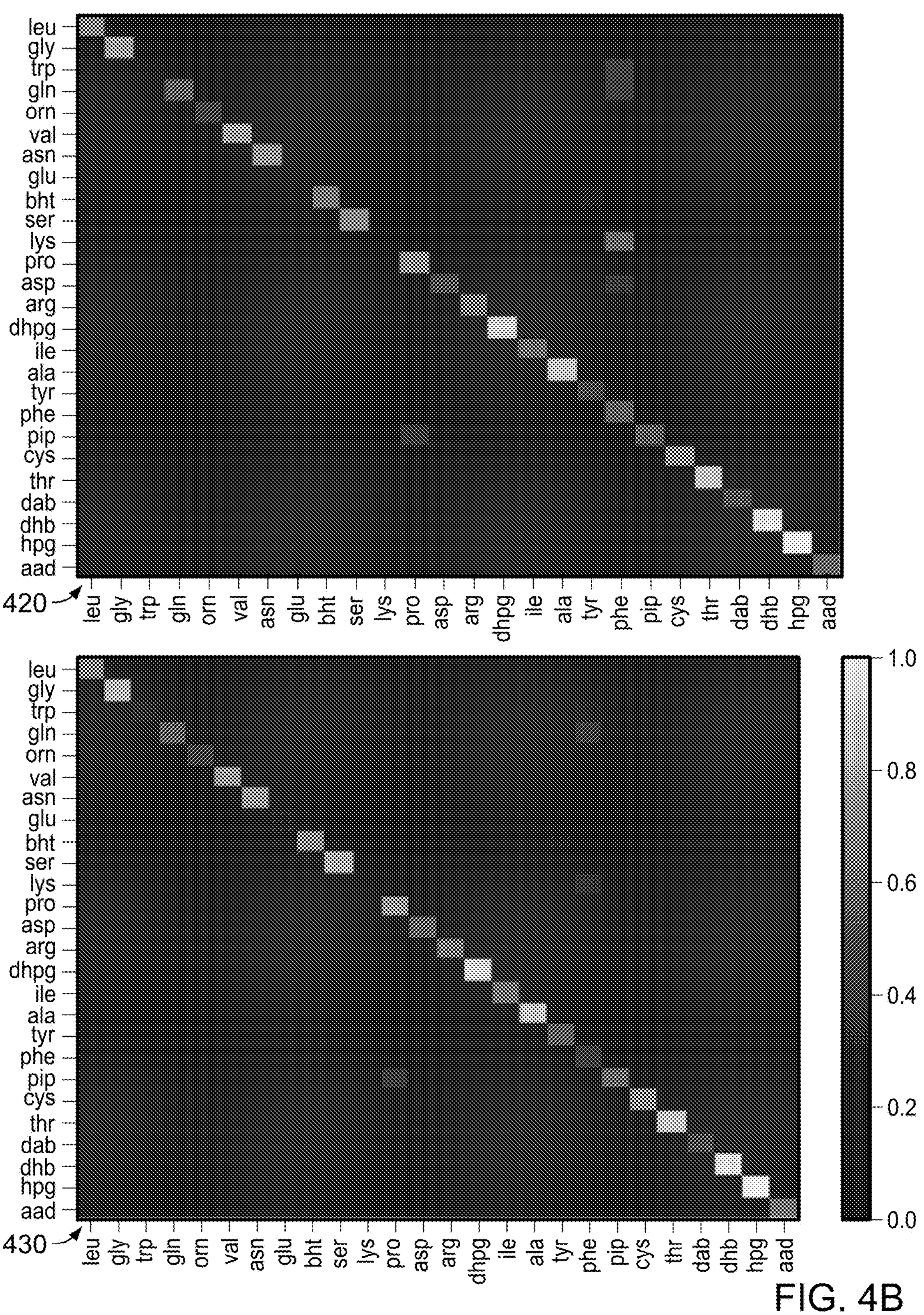
Figure 4B:
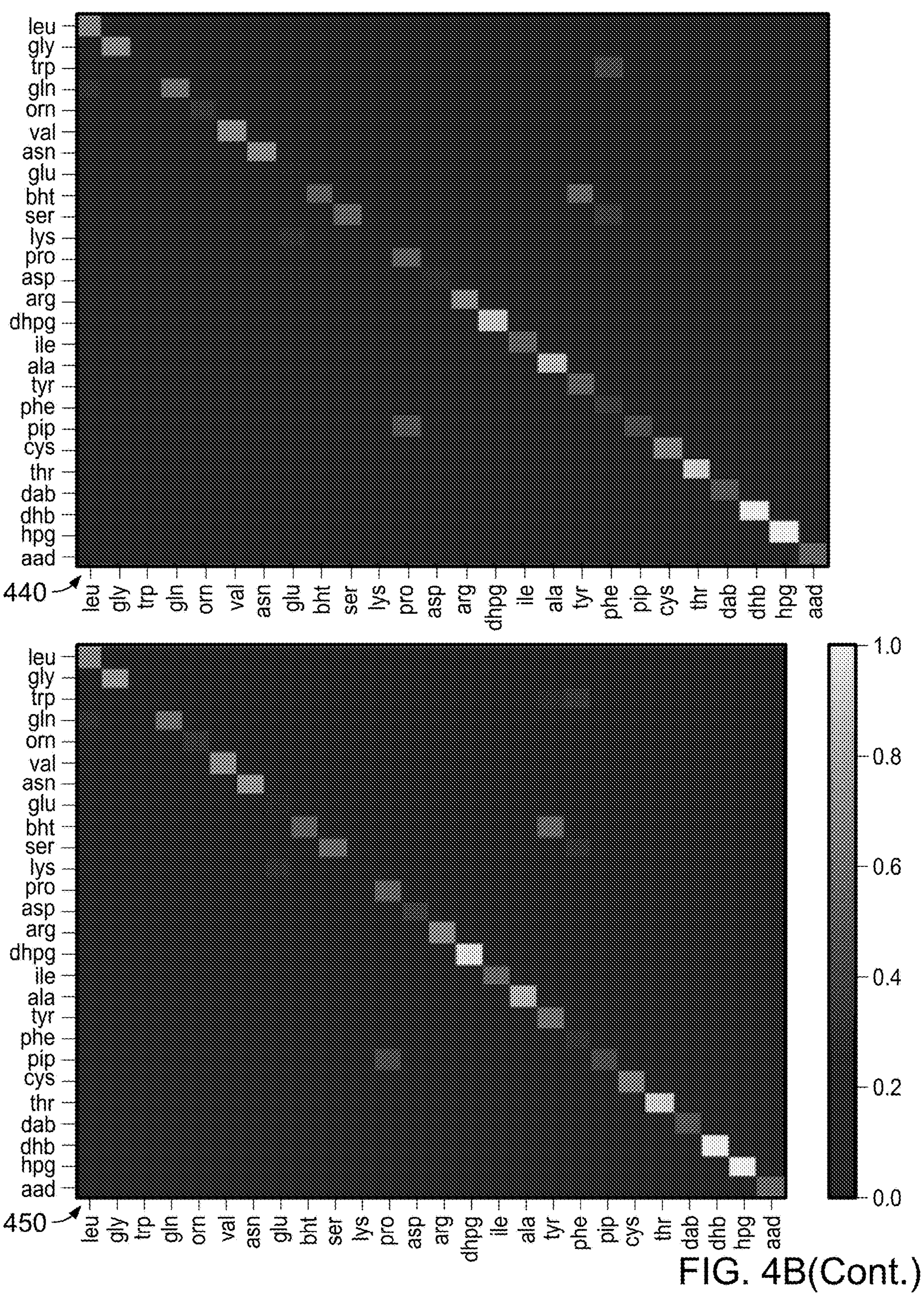
Figure 4C:
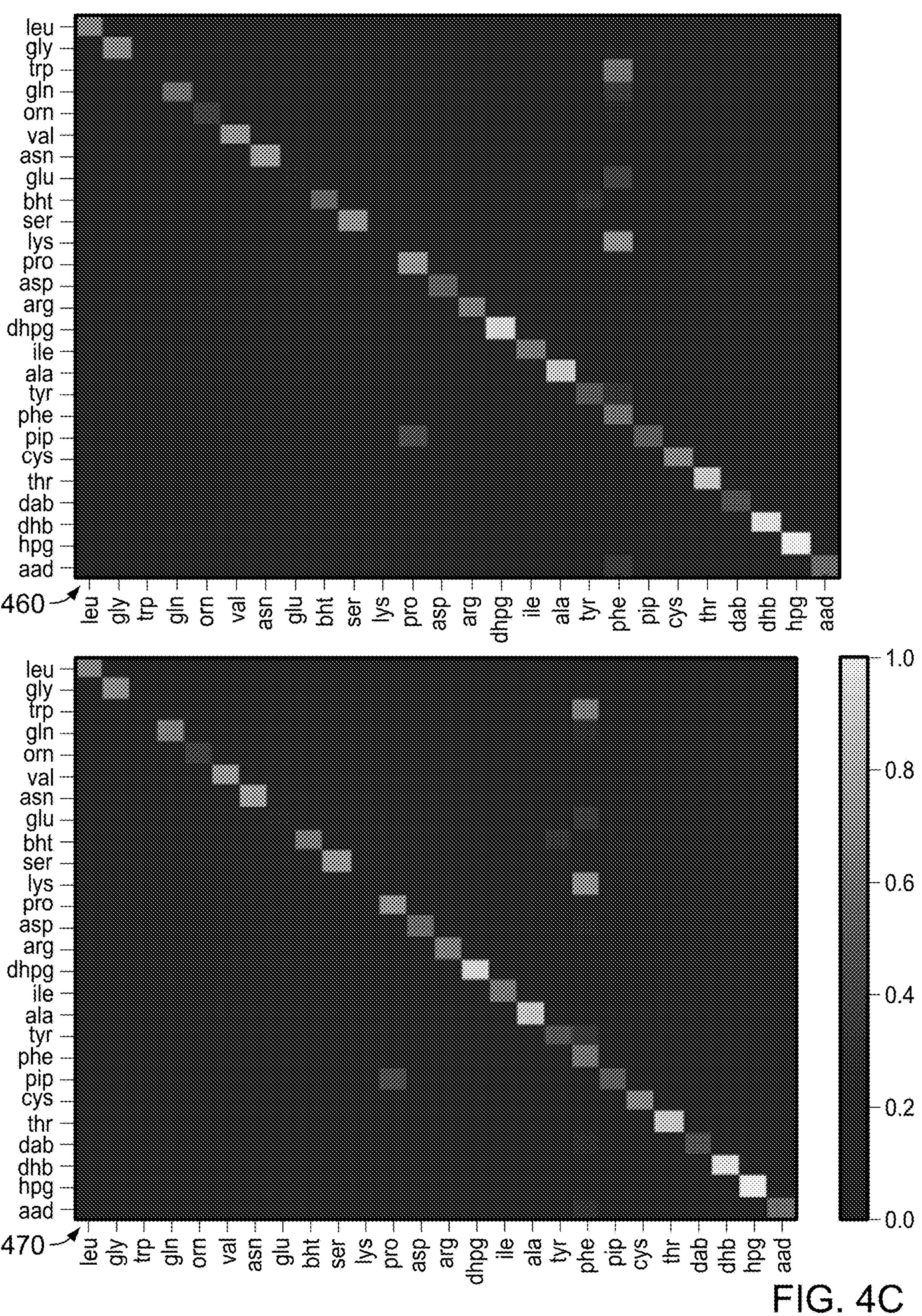
Figure 4C:
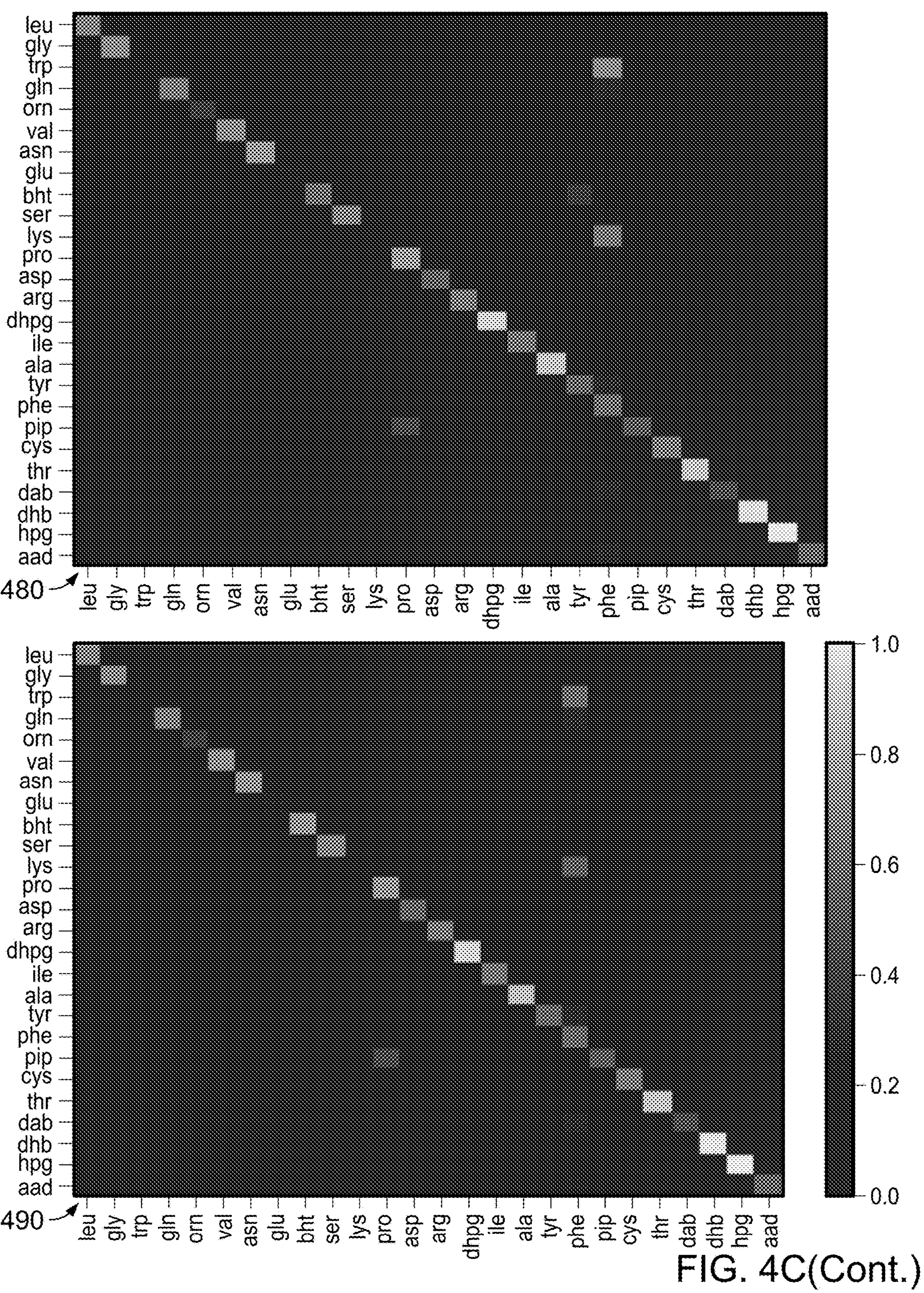

FIG. 4A shows confusion matrices 400, 410 obtained by using logistic regression on OHE scheme before (matrix 400) and after (matrix 410) applying weight balancing. FIGS. 4B-C show confusion matrices 420, 430, 440, 450, 460, 470, 480 and 490. A confusion matrix is shown for logistic regression with OHE (matrix 420), logistic regression with physiochemical encoding (matrix 440), extra tree with OHE (matrix 460), extra tree with physiochemical encoding (480), and confusion matrices after weight balancing in respective order (matrices 430, 450, 470, and 490).

To alleviate the issue of data bias, weight balancing is applied. Weight balancing improves the accuracy of prediction for some classifiers. Table 1 shows the change in test accuracy using physiochemical encoding style or one-hot encoding style when weight balancing is applied to four classifiers. Graph 410 and matrices show confusion matrix 430, 450, 470, and 490 represent the updated matrices after application of weight balancing.

TABLE 1

Accuracy of different classifiers using physiochemical encoding [15]/OHE scheme before and after applying weight balancing

| | before weight balancing | | after weight balancing | |
|---|---|---|---|---|
| Classifier | Physiochemical | OHE | Physiochemical | OHE |
| logistic regression | 0.588 | 0.692 | 0.594 | 0.685 |
| random forest | 0.612 | 0.527 | 0.667 | 0.634 |
| decision tree | 0.615 | 0.614 | 0.608 | 0.603 |
| extra tree | 0,688 | 0.693 | 0.691 | 0.699 |
| svm | 0.609 | 0.637 | 0.611 | 0.637 |

For unsupervised clustering of A-domains from microbial genomes, 453,560 A-domains were identified by mining 689,227 microbial genome available from NCBI GenBank. After clustering the 34 amino acid binding pocket of these A-domains using K-means clustering based on hamming distance, the elbow method revealed 200 clusters.

Figure 5A:
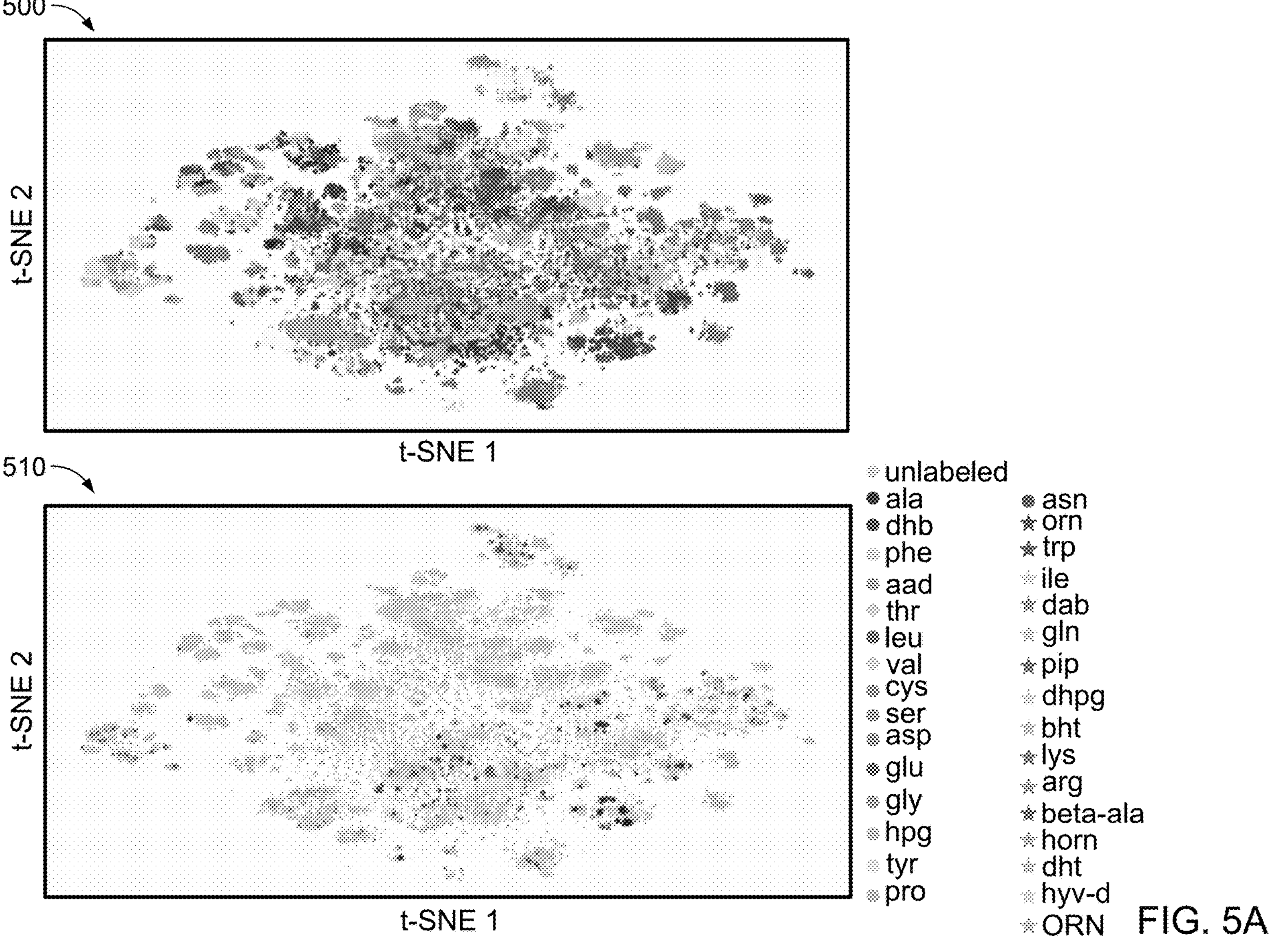
FIGS. 5A-5B shows visualizations of clusters.
Figure 5B:
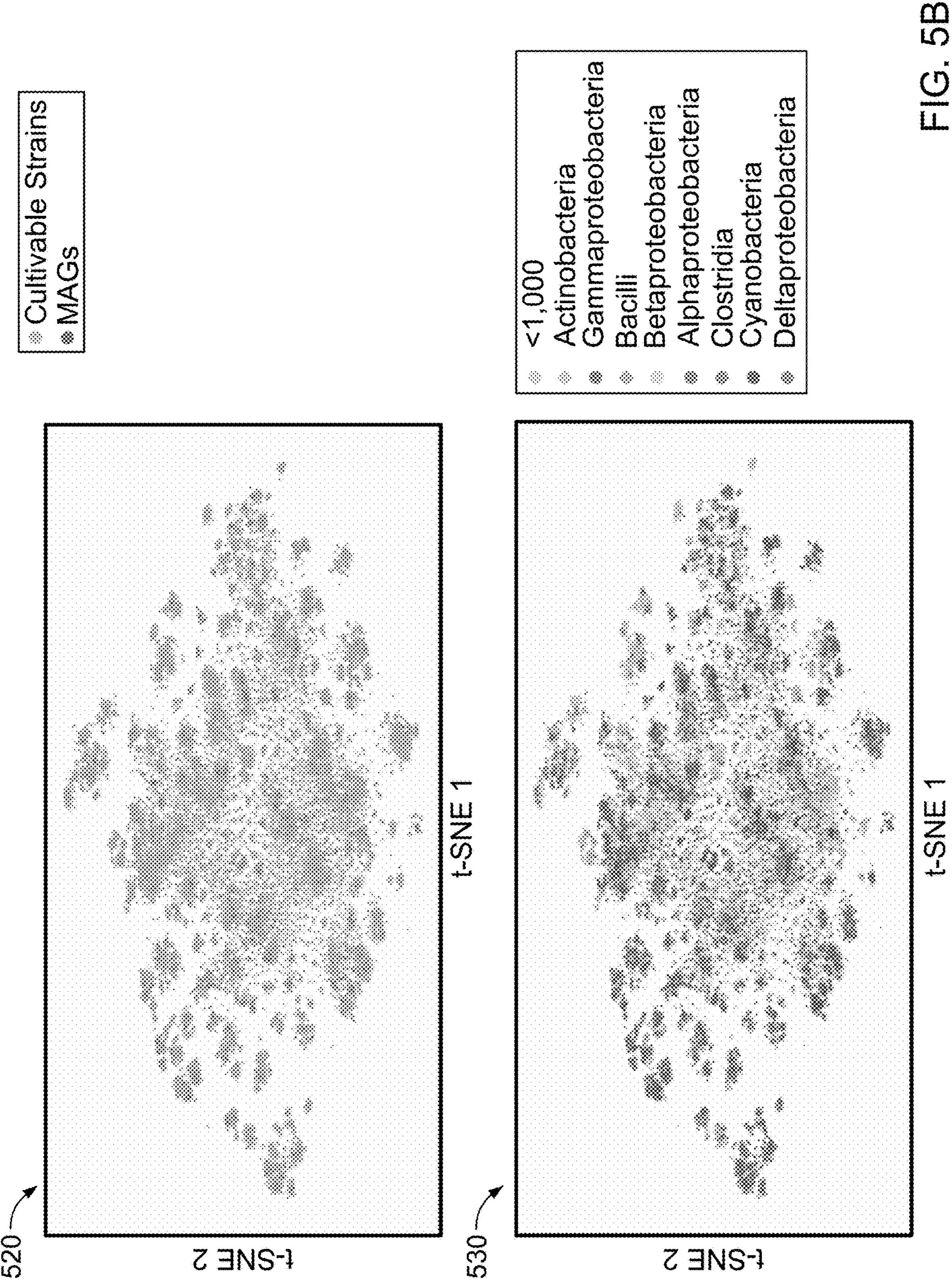

FIG. 5A shows visualizations of clusters. Image 500 shows a t-SNE visualization of 200 clusters constructed by applying k-means on physiochemical encoding of A-domains. All A-domains belonging to a specific cluster are given the same shaded color. Image 510 shows a t-SNE visualization of all labeled (dark) and unlabeled (light) A-domains. Labeled A-domains are shaded-coded by substrates. The images 500 shows two-dimensional embedding of all the A-domains using the t-SNE method. Among the 200 clusters, only 52 clusters included A-domains with known labels. Image 510 shows labeled and unlabeled A-domains. FIG. 5B shows image 520 that indicates that A-domains are not separable based on cultivability. Image 530 shows that A-domains are not separable based on their phylum.

In case of novel substrate specificities (e.g. novel amino acids), classification techniques are unable to provide information about the specificity. In these cases, instead of the identity of the suspects, their properties can be predicted. Table 2 shows the accuracy of various machine learning techniques in predicting different physiochemical properties of the substrate, including hydrophobicity, polarity, charge, aromaticity, presence of carboxyl and hydroxyl groups, and the number of atoms in the side chain. These results show that the extra tree method achieves high accuracy in all these predictions. Currently NRPSpredictor2 can predict hydrophobicity. Table 3 compares the F1 scores of hydrophobicity classification for three different types of substrates: hydrophobic, hydrophilic aliphatic and hydrophilic aromatic amino acids. We observed that almost all classifiers produced similarly accurate results for hydrophilic substrates, whereas NRPSPredictor2 is around 6% and 18% less accurate in case of hydrophobic aliphatic and aromatic substrates, respectively.

pockets of A-domains to predict of their substrate specificity. However, it remained unclear whether these features improve the accuracy of classification. In these data, it is shown that that these features are not essential for accurate specificity prediction and simpler features that encode the identity of amino acids resulted in similar or better accuracies.

The accuracy of existing methods dropped for test A-domains that are further away (in terms of hamming distance) from the training A-domains. The current evaluation metrics that measure the overall accuracy based on the training A-domains are unable to capture such deficiencies. Therefore, the machine learning models shown in this section of the specification include an evaluation metric to measure robustness of various machine learning techniques for the test data that is dissimilar to the training data. Generally, random forest and extra trees have the highest robustness in comparison to the other methods. The machine learning model identified 168 clusters of A-domains that could potentially correspond to novel amino acids. These A-domains belong to cultivable microbes, making them a source for future discovery of non-ribosomal peptides with novel modes of action. The machine learning model described herein further predicted various properties of their substrates including hydrophobicity, polarity, charge, aromaticity, presence of carboxyl and hydroxyl groups, and the number of atoms in the side chain.

The machine learning model described in this section significantly improves the prediction accuracy of the speci-

TABLE 2

Accuracy of different classifiers in predicting categorical amino acid attributes using OHE. The attributes from left to right are substrate polarity, substrate charge, substrate aromaticity, whether substrate contains a carboxyl group, whether substrate contains a hydroxyl group, and whether the substrate side chain contains more than four atoms.

| Accuracy | Polarity | Charge | Aromaticity | Carboxyl | Hydroxyl | side chain |
|---|---|---|---|---|---|---|
| logistic regression | 0.86 | 0.88 | 0.85 | 0.92 | 0.92 | 0.84 |
| k-nearest neighbor | 0.87 | 0.89 | 0.84 | 0.92 | 0.9 | 0.84 |
| multilayer perceptron | 0.84 | 0.88 | 0.85 | 0.93 | 0.93 | 0.83 |
| ridge cross validation | 0.80 | 0.87 | 0.87 | 0.93 | 0.93 | 0.85 |
| ridge | 0.85 | 0.87 | 0.84 | 0.91 | 0.9 | 0.82 |
| extra tree | 0.86 | 0.89 | 0.84 | 0.93 | 0.93 | 0.85 |

Table 3 shows F1 scores of different classifiers in predicting hydrophobic characteristics.

| Accuracy | Hydrophobic | Hydrophobic Aliphatic | Hydrophobic Aromatic |
|---|---|---|---|
| logistic regression. | 0.68 | 0.86 | 0.78 |
| k nearest neighbor | 0.72 | 0.85 | 0.78 |
| multi layer perceptron | 0.67 | 0.84 | 0.78 |
| ridge cross validation | 0.71 | 0.87 | 0.79 |
| ridge | 0.69 | 0.85 | 0.77 |
| extra tree | 0.70 | 0.87 | 0.79 |
| NRPSPredictor2 | 0.60 | 0.8 | 0.60 |

Currently, hundreds of thousands of NRP BGCs have been identified from microbial genomes. However, the molecular structure of the NRPs encoded by the majority of these BGCs have not yet been determined. During the past two decades various machine learning approaches have been developed to predict the amino acids present in the molecular products of these BGCs based on the amino acid sequence of their A-domains. These methods use physiochemical properties of the amino acids in the binding ficity of adenylation domains in nonribosomal peptides. Integration of AdenPredictor with mass spectrometry search techniques, e.g. NRPquest and NRPminer, and can accelerate the automated discovery of novel nonribosomal peptides.

Machine learning methods are trained on a portion of 1,546 labeled A-domains (A-domains with known substrate specificity). A-domains are mapped to their signatures, and 658 unique signatures are selected. Unsupervised clustering is conducted on 453,560 A-domains extracted from 689,227 microbial genomes from the National Center for Biotechnology Information GenBank repository, using antiSMASH. Previously, physiochemical descriptors of amino acids in the binding pocket of A-domains are used as features for learning substrate specificities. In addition to these descriptors, one-hot encoding (OHE) features, RaptorX structural and property features, and AlphaFold structural features are considered. In one-hot encoding, each amino acid is mapped to a binary vector of length 20, where one entry (corresponding to the amino acid) is one, and the rest are zero. RaptorX and AlphaFold structural features are three dimensional locations of the amino acids in the binding pocket as predicted by the CNFpred and AlphaFold neural networks, after aligning with GrsA. RaptorX property features include fifteen structural and chemical properties of amino acids, including secondary structure type, disordered state, and solvent accessibility predicted by DeepCNF neural network.

Several machine learning classifiers were applied, including logistic regression, support vector machine, k nearest neighbor, multilayer perceptron, random forest, decision tree, Bernoulli naive Bayes, Gaussian naive Bayes, extremely randomized trees, and graph neural networks. To obtain consistent estimates of the test set accuracy, data were shuffled and applied the machine learning classifiers 20 times. In each shuffle, the data is split randomly into training and test sets in 80:20 ratio. The test accuracy was averaged over 20 shuffles.

The parameter details for scikit-learn based classifiers are given as follows. Logistic regression: random state=0, max iter=400, multi class="multinomial", solver="newton-cg"; support vector machine: random state=0, multi class="crammer singer", tol=1e-9, max iter-2000 K nearest neighbor: weights="distance"; multilayer perceptron: random state=1, max iter=400, early stopping=false; random forest: max depth=4, criterion="entropy"; decision tree: random state=0, criterion="entropy"; Bernoulli naive Bayes: default parameters; extra tree: n estimators=100, random state=0, criterion="gini"; Gaussian naive Bayes: default parameters; label propagation: kernel="knn"; label spreading: kernel="knn"; linear discriminant analysis: default parameters; ridge cross validation: default parameters; N centroid: default parameters; ridge: default parameters.

In many of learning tasks, it is common to see that the prediction accuracy drops for test data that are more distinct from training data. To evaluate the generalizability of machine learning classifiers, the test data points are split into buckets. For every given positive number k, Bk is defined as to be the bucket containing data points with minimum hamming distance k from any training data point. Thus, buckets with higher k represent the test sets including data points that are more distinct from the training set. Moreover, Bk+ is defined as the portion of the test data for which the minimum hamming distance to any training data point is at least k. Various methods are benchmarked on different buckets.

In order to remove bias induced by the imbalanced data set, we apply weight balancing. For each machine learning model, the loss function has the form $$\min \sum_{t=1}^{T} L(f(x^t), y^t) \tag{1}$$

where t is the index of each training point, $y^t$ represents the true label of each training point, $x^t$ represents the features of each training point, $f$ is the classification function, and L refers to a loss function that is low when $f(x^t)$ is similar to $y^t$ and high otherwise. In weight balancing the loss function is modified to be $$\min \sum_{t=1}^{T} \frac{L(f(x^t), y^t)}{b^t} \tag{2}$$

where $b^t$ is the number of training points with label $y^t$. Bias toward frequent residues is avoided. Each label contributes the same amount to the loss function that is being minimized.

Unlabeled A-domains are clustered using K-means clustering based on the hamming distance of their binding pockets, and visualized using t-distributed stochastic neighbor embedding (t-SNE). Classification algorithms that represent the substrate prediction as an output vector with each position in the vector corresponding to the probability that a given amino acid is the substrate for the A-domain, will be unable to make predictions for novel substrates. In order to account for these novel substrates, we have also explored various learning techniques to predict chemical properties of the final amino acid monomer, including polarity, hydrophobicity, charge, and the presence of aromatic ring, carboxyl, or hydroxyl groups. Such methods enable a user to narrow down the identity of the amino acid.

Atlas of Hypothetical Natural Products for Mass Spectrometry Database Search

Figure 6A:
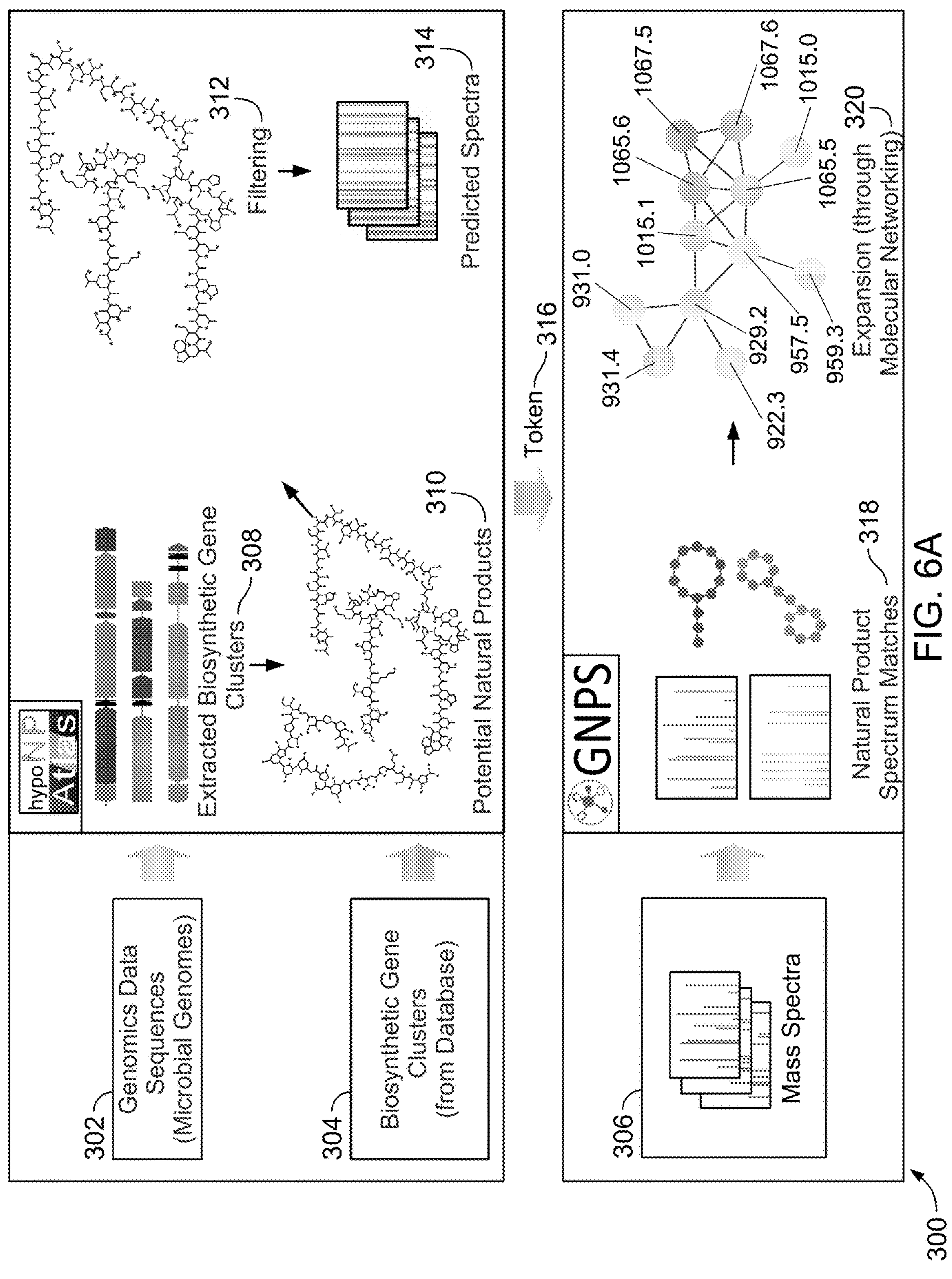
FIG. 6A shows an example process for training and executing a machine learning model to identify the structures of molecular compounds from mass spectrometry data and sequenced genomes.

FIG. 6A shows an example process 300 for training the machine learning model identify the structures of molecular compounds from mass spectrometry data. The process 300 can be executed by data processing system 102 of FIG. 1 and is an example of the process described in FIG. 2. In this example, the compounds include ribosomally synthesized and post-translationally modified peptides (RiPPs), or ribosomal natural products. For this example, the process 300 is configured for novel RiPP discovery. At step 308, the data processing system 102 extracts biosynthetic gene clusters (BGCs) from available metabolomics data 302, 304. A BGC includes a locally clustered group of two or more genes that together encode a biosynthetic pathway for the production of a secondary metabolite from microbial examples. At step 310, the data processing system 102 builds associations between structures and spectra by predicting hypothetical molecule structures from the BGCs. At step 312, the potential natural products are filtered to specific taxonomies or gene clusters based on the taxa- or meta-genomic data available from the samples of interest. At step 314, the data processing system 102 predicts mass spectrometry fragmentation of the hypothetical natural products, along with known RiPPs the data 304.

The data processing system 102 generates 316 a token representing the predicted spectra and natural products pairs. The data processing system 102 collects mass spectra data 306 for the environmental samples or the microbial isolates. At step 318, the data processing system 102 searches the mass spectra 306 against the predicted spectra data from step 314 of hypothetical molecules. The data processing system 102 outputs high-scoring RiPP-spectrum matches. Here, high scoring matches include matches above a threshold correlation score or a list of the most likely candidates, regardless of score. The identifications are further expanded at step 320 by the data processing system 102 through propagation in the molecular network. In an example, steps 308, 310, 312, and 314 performed once to prepare the machine learning models. The data processing system 102 stores the relationships stored in a repository (such as database 104). Steps 306, 318, and 320 are repeated for every new mass spectral dataset.

Overall, the process of generating hypothetical RiPPs from genomes includes four steps. The data processing system 102 extracts BGCs from the input genome by searching RiPP related genes. The data processing system 102 then extracts all ORFs from each BGC and identifies the RiPP precursor ORFs. The data processing system 102 then identifies the potential cleavage site within the ORFs and produces cores. The data processing system 102 generates hypothetical chemical structures of the RiPP from the core and the enzymes in the BGC. More specifically, the data processing system 102 identifies RiPP BGCs based on the biosynthetic enzymes from a microbial genome sequence. The data processing system 102 identifies RiPP precursor ORFs from a BGC. The data processing system 102 identifies RiPP core peptides from an ORF. The data processing system 102 generates a combinatorial list of feasible mature RiPPs for each core peptide based on the tailoring enzymes present in the BGC. These steps are now described in greater detail.

The data processing system 102 extracts RiPP BGCs in the following steps. The data processing system 102 translates the genome sequence is translated in six frames. The data processing system 102 identifies RiPP related proteins through a search. The data processing system 102 defines contigs by extracting genome sequence from the middle of the protein to 10,000 bp upstream and downstream. Contigs include a series of overlapping DNA sequences used to make a physical map that reconstructs the original DNA sequence of a chromosome or a region of a chromosome. The data processing system 102 identifies BGCs after merging overlapping contigs.

The data processing system 102 identifies RiPP precursor ORFs in the following steps. The data processing system 102 translates the DNA sequence of the BGC in six frames. The data processing system 102 identifies RiPP biosynthetic enzymes using a search. The data processing system 102 extracts ORFs in the vicinity of the biosynthetic enzymes (default 10,000 base pairs). The data processing system 102 identifies candidate RiPP precursors are identified using ORF prediction tools. The data processing system 102 filters this list of candidate ORFs using a deep neural network, shown in FIG. 3B.

The data processing system 102 predicts RiPP core peptides from their ORFs in the following steps. The data processing system 102 identifies top k N-terminal and C-terminal cleavage sites from each ORF using a deep neural network (k is a user-defined threshold). The data processing system 102 generates a combinatorial list of putative core sequences (up to k2 cases). When the precursor contains repetitive patterns (e.g. cyanobactins and plant RiPPs), the data processing system 102 uses a repeat-specific core finding strategy to identify core sequences from repeated prefix and suffix patterns FIG. 6B shops a process of generating hypothetical RiPPs from genomes in seq2ripp involves four steps: genome2bgc, bgc2orf, orf2core and core2ripp. Genome2bgc extracts BGCs from the input genome by searching RiPP related genes. Bgc2orf extracts all ORFs from each BGC and identifies the RiPP precursor ORFs. Orf2core identifies the potential cleavage site within the ORFs and produces cores. Core2ripp generates hypothetical chemical structures of the RiPP from the core and the enzymes in the BGC. For example, the colored region in each compound indicates the modification introduced by the enzyme with corresponding color in the BGC.

Figure 6B:
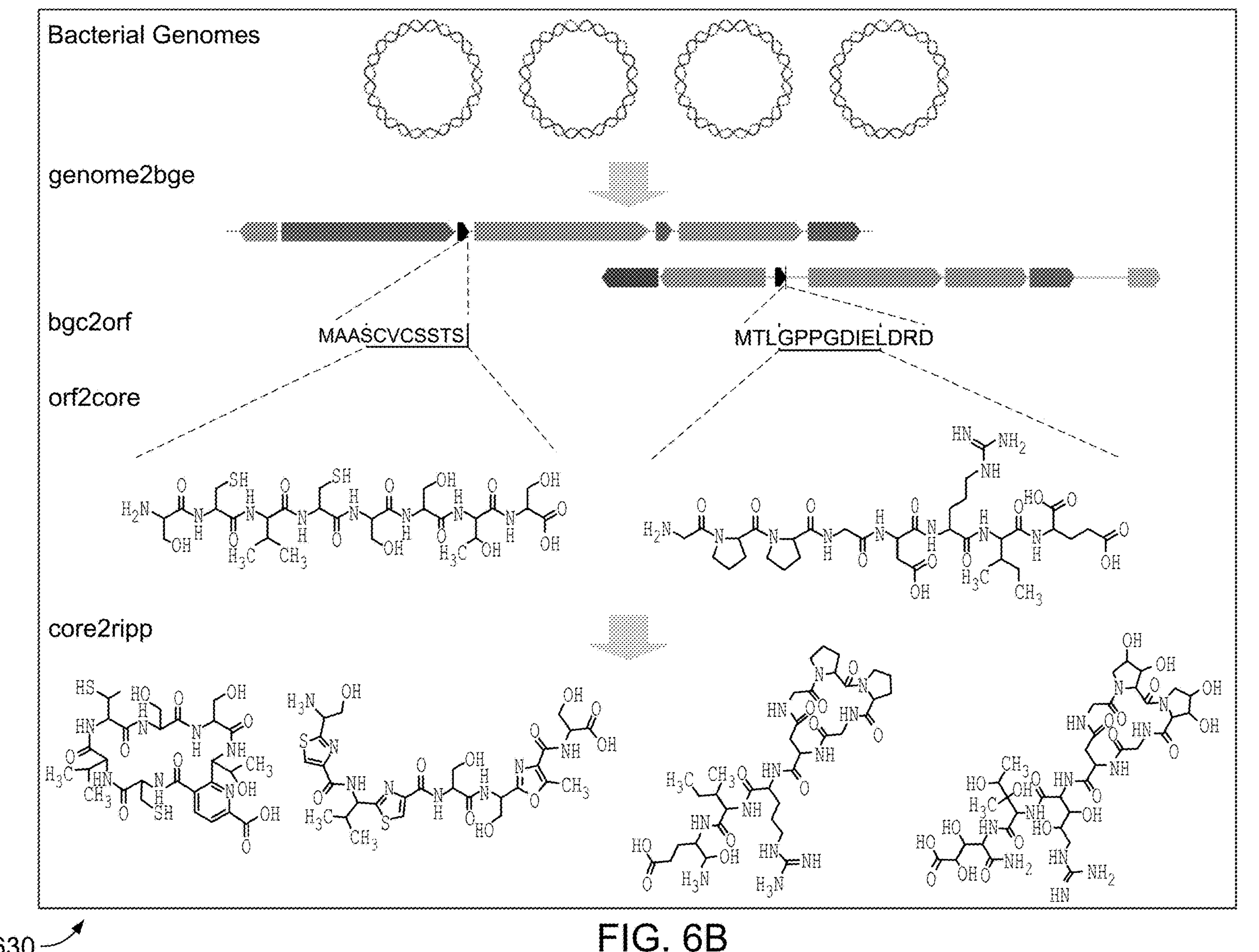
FIG. 6B (SEQ ID Nos: 26-27) illustrates a process.

FIG. 6B illustrates the seq2ripp pipeline 630 that includes the following steps described in the Methods section: (i) genome2bgc identifies RiPP BGCs based on the biosynthetic enzymes from a microbial genome sequence, (ii) bgc2orf identifies RiPP precursor ORFs from a BGC, (iii) orf2core identifies RiPP core peptides from an ORF, and (iv) core2ripp generates a combinatorial list of feasible mature RiPPs for each core peptide based on the tailoring enzymes present in the BGC.

A genome2bgc algorithm extracts RiPP BGCs in the following steps: (i) the genome sequence is translated in six frames, (ii) RiPP related proteins are identified using hmmsearch, (iii) contigs are defined by extracting genome sequence from the middle of the protein to 10,000 bp upstream and downstream, (iv) BGCs are identified after merging overlapping contigs.

Figure 6C:
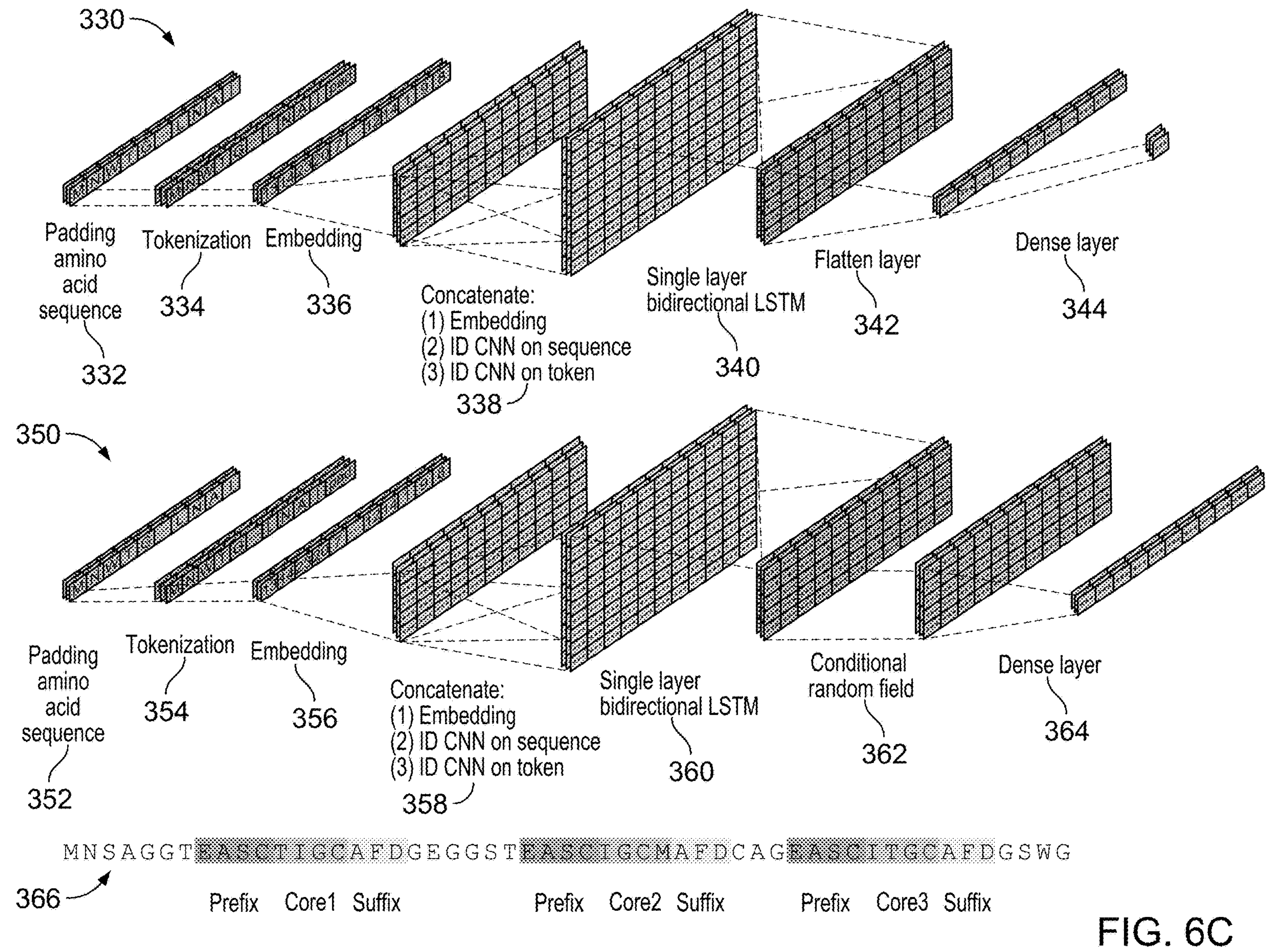
FIG. 6C (SEQ ID Nos: 28 and 35) shows an example of a machine learning model for predicting the structure of natural products from genome sequence in case of ribosomally synthesized and post-translationally modified peptides.

A bgc2orf algorithm identifies RiPP precursor ORFs in the following steps: (i) the DNA sequence of the BGC is translated in six frames, (ii) RiPP biosynthetic enzymes are identified using hmmsearch, (iii) ORFs in the vicinity of the biosynthetic enzymes are extracted (default 10,000 bp), (iv) candidate RiPP precursors are identified using ORF prediction tools, and (v) bgc2orf filters this list of candidate ORFs using a deep neural network, as shown in FIG. 6C.

Orf2core is an algorithm that predicts RiPP core peptides from their ORFs in the following steps: (i) top k N-terminal and C-terminal cleavage sites from each ORF are identified using a deep neural network (k is a user-defined threshold), (ii) a combinatorial list of putative core sequences (up to k2 cases) are generated, and (iii) when the precursor contains repetitive patterns (e.g. cyanobactins and plant RiPPs), a repeat-specific core finding strategy is used to identify core sequences from repeated prefix and suffix patterns.

Datasets. 22,671 complete microbial genomes from RefSeq and 2,002 draft *Streptomyces* microbial genomes were used for constructing the Atlas. The 46 paired datasets of spectra and genomic data fare analyzed from the Paired Omics Data Platform (PoDP) (917 strains, 7,604,198 MS/MS scans), and a paired dataset of *Actinomyces* (119 strains, 409,245 MS/MS scans, MSV000083738.)

A performance of seq2ripp pipeline is shown on radamycin, grisemycin, and lacticin 481. Radamycin is a thipeptide from *Streptomyces globisporus* isolated from tomato flowers. Grisemycin is a linaridin from *Streptomyces griseus* IFO 13350, and lacticin 481 is a lanthipeptide from *Lactococcus lactis* subsp. *lactis*, respectively. Radamycin acts as a signaling peptide to regulate the gene expression in *Streptomyces lividans*. There is no antimicrobial activity detected in grisemycin, whereas Lacticin 481 shows antibacterial activity. Genome2bgc identifies 20 RiPP BGCs in *Streptomyces globisporus* NRRL B-2709, including the radamycin BGC. Bgc2orf further finds 48 ORFs in these BGCs, and orf2core identifies 273 cores in these ORFs. Finally, core2ripp discovers 120,701 hypothetical mature RiPPs in this strain, including the correct radamycin RiPP. Searching mass spectra collected on the extracts of *Streptomyces globisporus* against these 120,701 RiPPs using Dereplicator+ results in a top scoring match with score 25 and p-value 3.0×10-46 that corresponds to the correct radamycin structure (FIG. 4 and FIG. 5). MetaMiner, which ignores fragmentations between O—C and C—C bonds and higher fragmentation depths, assigns a score of 9 and p-value of 3.0×10-17 to the correct radamycin. NeuRiPP and DeepRiPP are both able to identify the correct radamycin ORF. However, DeepRiPP cannot identify the correct core sequence (NeuRiPP currently does not contain a core-finding module). Similarly, for grisemycin and lacticin 481, seq2ripp identifies the correct structure among top predictions, and Dereplicator+ correctly picks the correct structure as the most significant match to their mass spectra.

FIG. 6C shows examples of a machine learning models 330, 350, for identifying natural products from genomic sequences 366. More specifically, FIG. 6C shows deep neural networks (DNNs) used to identify candidate ORFs from genomic sequences. The model 330 includes a padding process 332, a tokenization 334, an embedding layer 336, two 1D convolutional neural networks (CNNs) 338, a single layer bidirectional long short-term memory (LSTM) network 340, a flatten layer 342, and a dense layer 344. This model 330 takes an ORF peptide sequence as input, and classifies the peptide as RiPP or non-RiPP ORF.

An example of model 330 is now described. In an example, all input sequences are padded to a length of 200 amino acids. Each amino acid, including the padding symbol, is tokenized and embedded into a vector of size 100. The model 330 includes two 1D CNNs. One CNN convolves the input sequence in terms of its topology, the other CNN convolves the tokenized vectors. The convolution on the sequence helps the model to detect the RiPP features on amino acids; the convolution on the token vector summarizes the embedded character information in high dimensional space. The outputs from the two CNNs and the input embeddings are concatenated and fed into a single layer bidirectional LSTM. The LSTM learns and summarizes the sequential features from the amino acid chain. The output of the LSTM is flattened and converted to a binary output with a flattened layer and a dense layer. The prediction loss is calculated by cross entropy loss during the training of the model. The learning rate begins with 1e-3 and decreases 10% every 40 epochs.

The model 350 includes a padding process 352, a tokenization 354, an embedding layer 356, two 1D CNNs 358, a single layer bidirectional LSTM 360, a conditional random field layer 362 and a dense layer 364. This model 350 takes an ORF as input, and identifies k N-terminal and k C-terminal cleavage sites, where k is a user-defined value. Sequence 366 represents an alternative core finder used to search repeated (at least twice) prefix-suffix patterns and identify the core sequence in the patterns.

An example of model 350 is now described. A discriminatory deep learning model predicts core and non-core frames of sequences given the amino acid sequence of an ORF as the continuous input. All input sequences are padded to a length of 200 amino acids. Each amino acid is tokenized and embedded into a vector of size 25. The model 350 includes two 1D CNNs. One CNN convolves the input sequence in terms of its topology, and the other CNN convolves the tokenized vectors. The convolution on the sequence helps the model to detect amino acids surrounding the enzymatic cleavage site. The convolution on the token vector summarizes the embedded character information in high dimensional space. The outputs from the two CNNs, and the input embeddings are concatenated and fed into a single layer bidirectional LSTM. The LSTM learns the translation from the amino acid chain to core and non-core frames of sequences. The prediction loss is calculated by a conditional random forest layer, which calculates the negative log-likelihood during the training of the model, and performs the Viterbi algorithm to optimize labels during prediction.

Genome2bgc found 328,676 RiPP BGCs in 22,671 microbial genomes. Bgc2orf found 55,100 ORFs in these BGCs. Orf2core found 1,207,991 cores in these ORFs. Table 4 summarizes the number of BGCs, ORFs and cores retrieved by different seq2ripp modules.

TABLE 4

The result of different methods for finding ORFs and cores. PoDP, Streptomyces, RefSeq and MIBiG datasets have 17,505, 48,542, 328,676 and 140 BGCs respectively.

| RefSeq complete genome sequences | | | |
|---|---|---|---|
| ORF finding method | # of ORFs | Core finding method | # of cores |
| bgc2orf-default | 1,462,190 | orf2core-default | 28,104,725 |
| | | DeepRiPP | 1,399,584 |
| | | BLAST | 47,297 |
| | | Exhaustive | 1,935,244,230 |
| | | Hybrid | 67,702,377 |
| DeepRiPP | 4,245,672 | orf2core-default | 83,127,610 |
| | | DeepRiPP | 4,245,672 |
| | | BLAST | 53,994 |
| | | Exhaustive | 417,344,918 |
| | | Hybrid | 156,098,686 |
| NeuRiPP | 590,130 | orf2core-default | 11,135,261 |
| | | DeepRiPP | 590,130 |
| | | BLAST | 22,045 |
| | | Exhaustive | 815,140,696 |
| | | Hybrid | 26,387,236 |
| MetaMiner | 77,048,129 | orf2core-default | 1,414,233,849 |
| | | DeepRiPP | 77,048,129 |
| | | BLAST | 143,373 |
| | | Exhaustive | 64,816,509,805 |
| | | Hybrid | 2,527,814,682 |
| MetaMiner-BLAST | 58,873 | orf2core-default | 1,072,400 |
| | | DeepRiPP | 57,997 |
| | | BLAST | 135,628 |
| | | Exhaustive | 155,232,201 |
| | | Hybrid | 4,174,482 |
| **PoDP genome sequences** | | | |
| ORF finding method | # of ORFs | core finding method | # of cores |
| bgc2orf-default | 55,100 | orf2core-default | 1,207,991 |
| | | DeepRiPP | 55,100 |
| | | BLAST | 9,079 |
| | | Exhaustive | 78,318,885 |
| | | Hybrid | 2,795,957 |
| DeepRiPP | 262,304 | orf2core-default | 6,675,702 |
| | | DeepRiPP | 262,304 |
| | | BLAST | 9,714 |
| | | Exhaustive | 348,578,525 |
| | | Hybrid | 11,606,959 |
| NeuRiPP | 48,510 | orf2core-default | 1,013,664 |
| | | DeepRiPP | 48,510 |
| | | BLAST | 8,630 |
| | | Exhaustive | 77,590,389 |
| | | Hybrid | 2,396,326 |
| MetaMiner | 2,648,558 | orf2core-default | 55,255,123 |
| | | DeepRiPP | 2,648,564 |
| | | BLAST | 12,349 |
| | | Exhaustive | 2,607,192,135 |
| | | Hybrid | 95,069,866 |
| MetaMiner-BLAST | 4042 | orf2core-default | 93,339 |
| | | DeepRiPP | 4,034 |
| | | BLAST | 11,915 |
| | | Exhaustive | 10,134,054 |
| | | Hybrid | 287,276 |

TABLE 4-continued

The result of different methods for finding ORFs and cores. PoDP, Streptomyces, RefSeq and MIBiG datasets have 17,505, 48,542, 328,676 and 140 BGCs respectively.

| ORF finding method | # of ORFs | Core finding method | # of cores |
|---|---|---|---|
| *Streptomyces* genome sequences | | | |
| bgc2orf-default | 86,562 | orf2core-default | 2,159,946 |
| | | DeepRiPP | 86,562 |
| | | BLAST | 29,294 |
| | | Exhaustive | 152,470,849 |
| | | Hybrid | 4,898,675 |
| DeepRiPP | 915,480 | orf2core-default | 23,446,615 |
| | | DeepRiPP | 915,480 |
| | | BLAST | 32,117 |
| | | Exhaustive | 1,428,141,300 |
| | | Hybrid | 45,040,561 |
| NeuRiPP | 84,170 | orf2core-default | 2,036,843 |
| | | DeepRiPP | 84,170 |
| | | BLAST | 30,664 |
| | | Exhaustive | 194,396,190 |
| | | Hybrid | 5,448,996 |
| MetaMiner | 4,311,660 | orf2core-default | 102,056,584 |
| | | DeepRiPP | 4,311,660 |
| | | BLAST | 37,715 |
| | | Exhaustive | 6,564,777,642 |
| | | Hybrid | 204,848,764 |
| MetaMiner-BLAST | 14,191 | orf2core-default | 338,741 |
| | | DeepRiPP | 14,046 |
| | | BLAST | 36,284 |
| | | Exhaustive | 36,040,489 |
| | | Hybrid | 993,380 |
| MIBIG BGCs | | | |
| bgc2orf-default | 401 | orf2core-default | 10,667 |
| | | DeepRiPP | 401 |
| | | BLAST | 2,678 |
| | | Exhaustive | 599,728 |
| | | Hybrid | 23,256 |
| DeepRiPP | 1,161 | orf2core-default | 36,569 |
| | | DeepRiPP | 1,161 |
| | | BLAST | 2,595 |
| | | Exhaustive | 1,360,751 |
| | | Hybrid | 54,689 |
| NeuRiPP | 415 | orf2core-default | 10,510 |
| | | DeepRiPP | 415 |
| | | BLAST | 2,792 |
| | | Exhaustive | 553,988 |
| | | Hybrid | 21,914 |
| MetaMiner | 13,005 | orf2core-default | 297,628 |
| | | DeepRiPP | 13,005 |
| | | BLAST | 2,974 |
| | | Exhaustive | 10,551,662 |
| | | Hybrid | 417,949 |
| MetaMiner-BLAST | 508 | orf2core-default | 13,653 |
| | | DeepRiPP | 464 |
| | | BLAST | 4,574 |
| | | Exhaustive | 1,031,441 |
| | | Hybrid | 35,130 |

DeepRiPP extracts more ORFs than bgc2orf, while NeuRiPP extracts fewer ORFs. DeepRiPP extracts fewer cores than orf2core leading to a larger number of predicted core peptides by seq2ripp modules compared to DeepRiPP across the sampled genomes. The BLAST method, which finds regions of local similarity between potential and known ORFs, extracts fewest number of ORFs and cores, while the exhaustive method, which extracts all the substrings of the ORFs with length ranging from 3 to 30 amino acids, results in the largest amount of ORFs and cores.

Figure 6E:
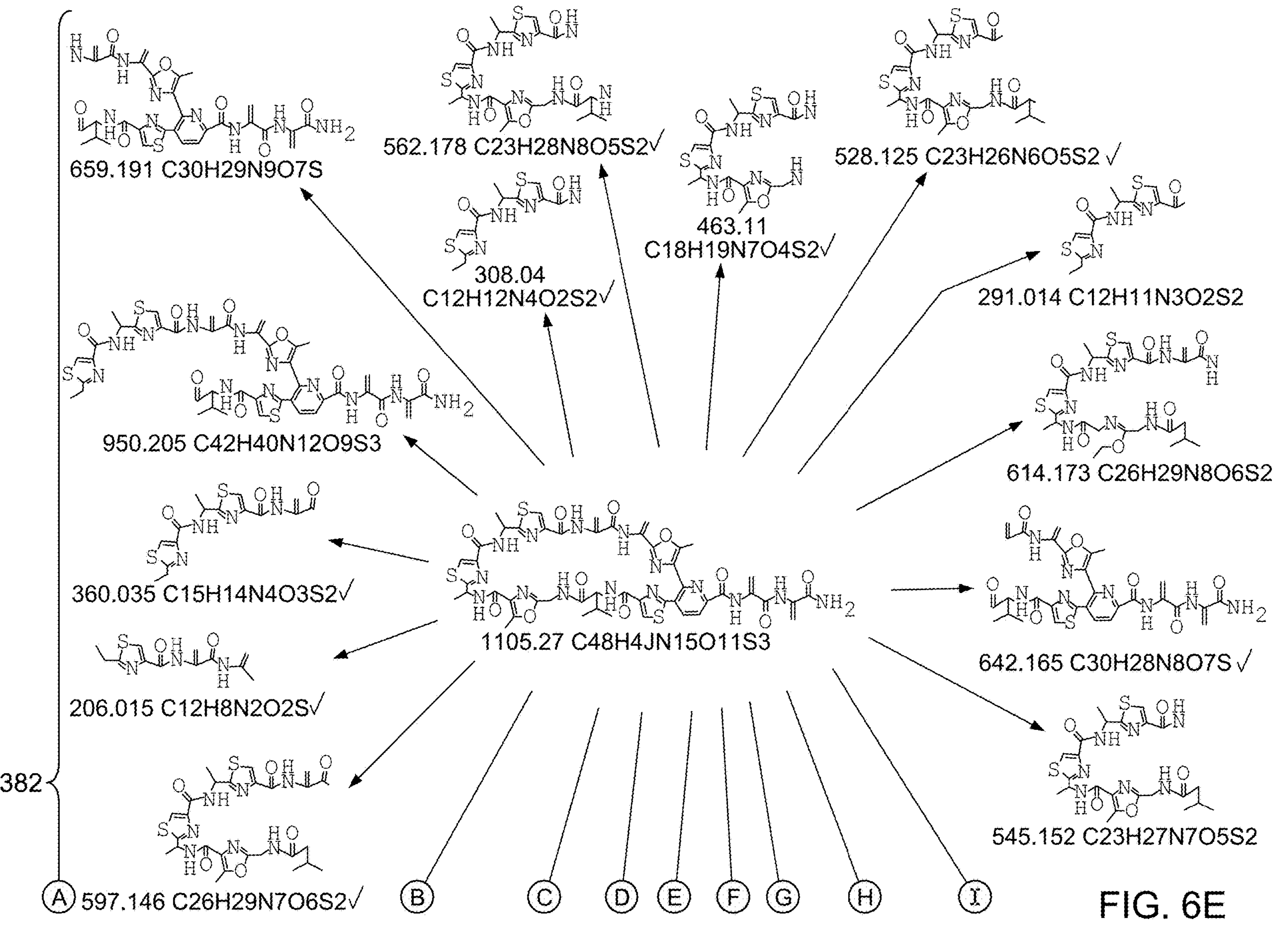
FIG. 6E shows an example process for mapping structures of molecules to spectra data.
Figure 6E:
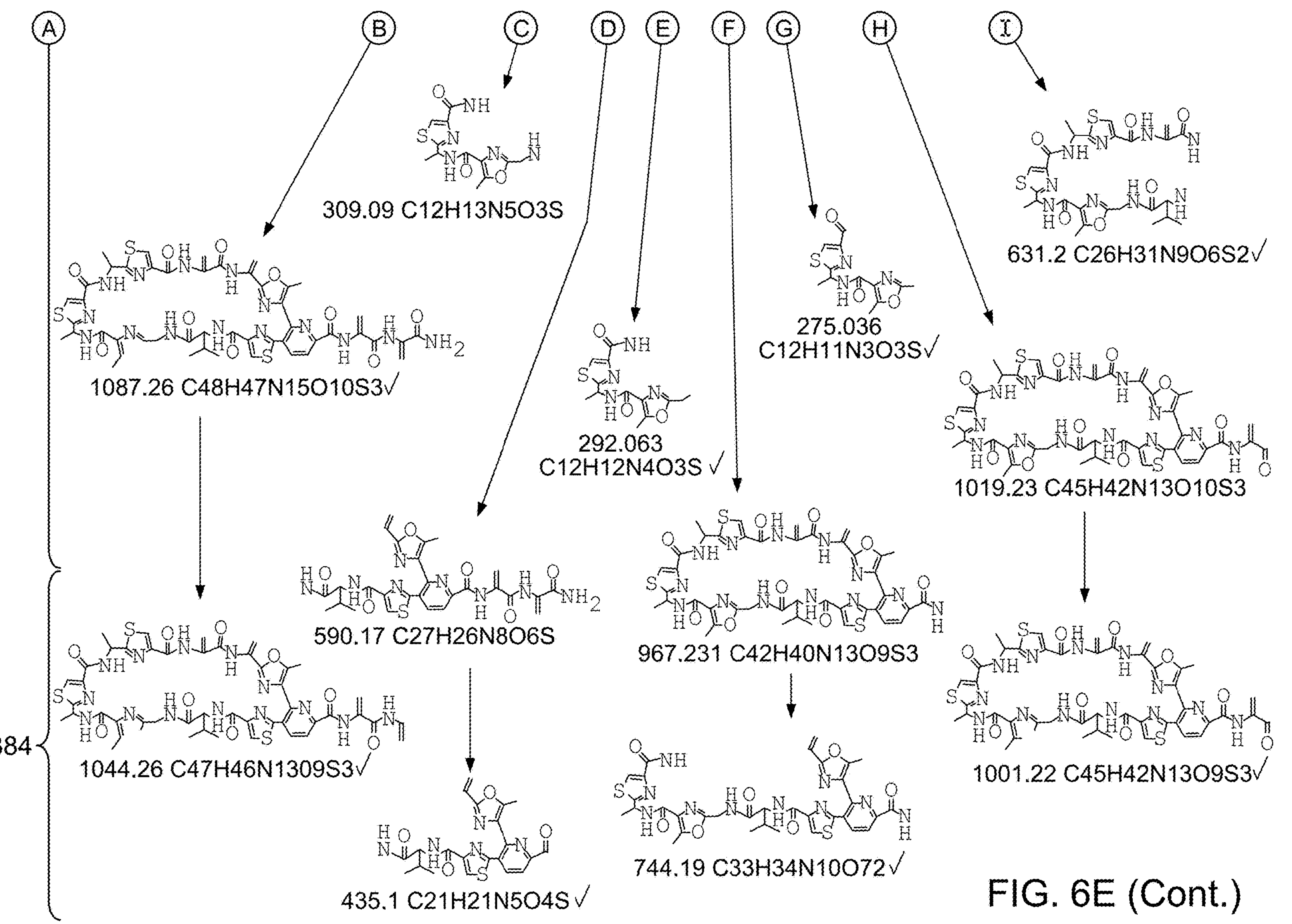
Figure 6E:
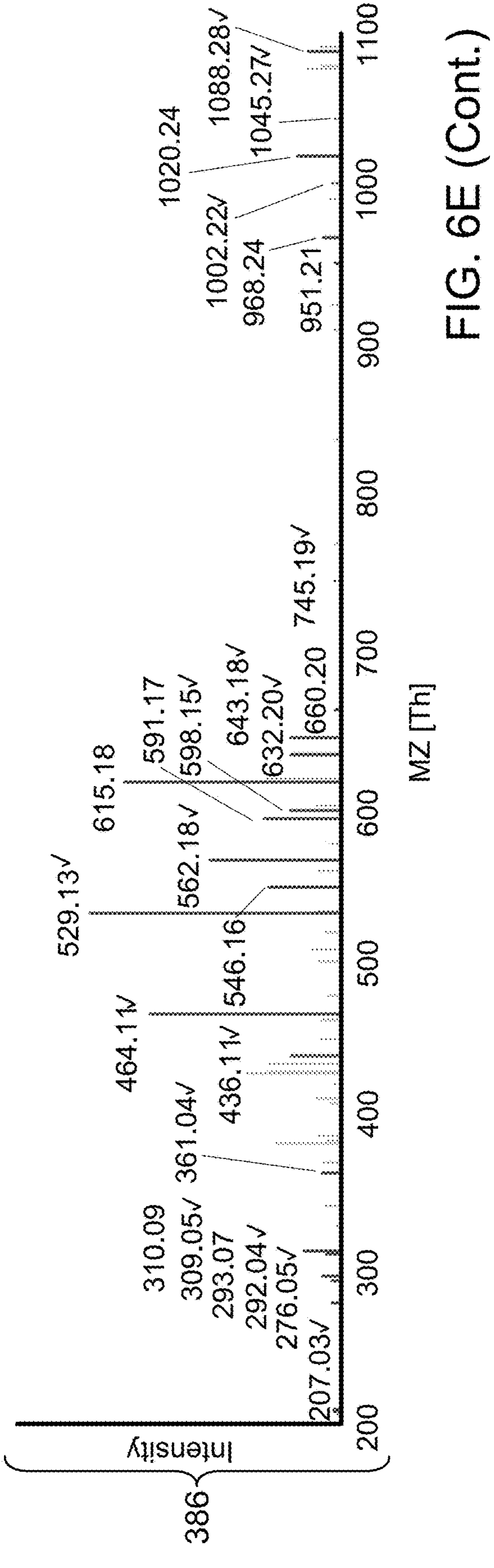
Figure 6F:
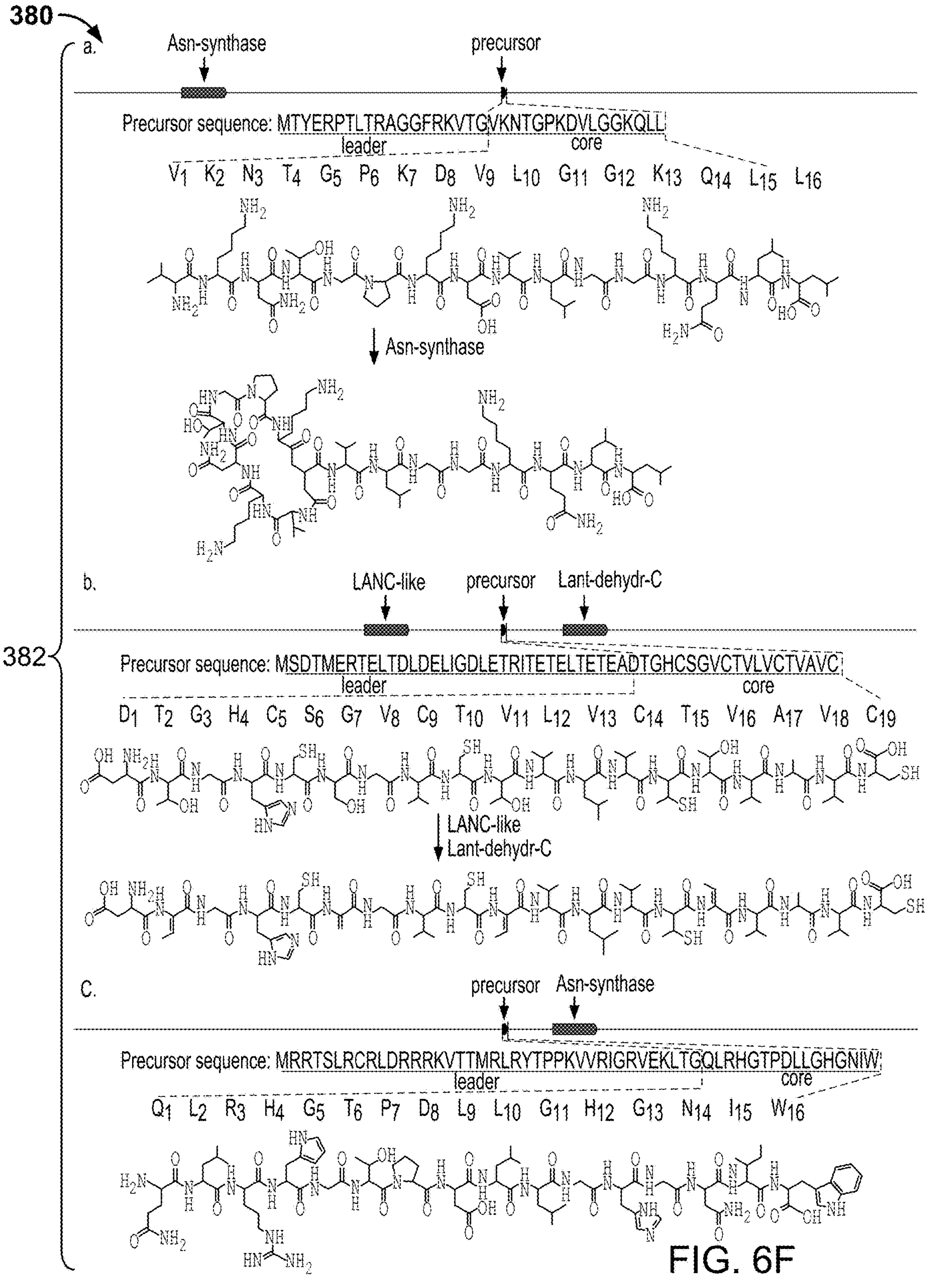
FIG. 6F (SEQ ID Nos: 30-33) shows a process.
Figure 6F:
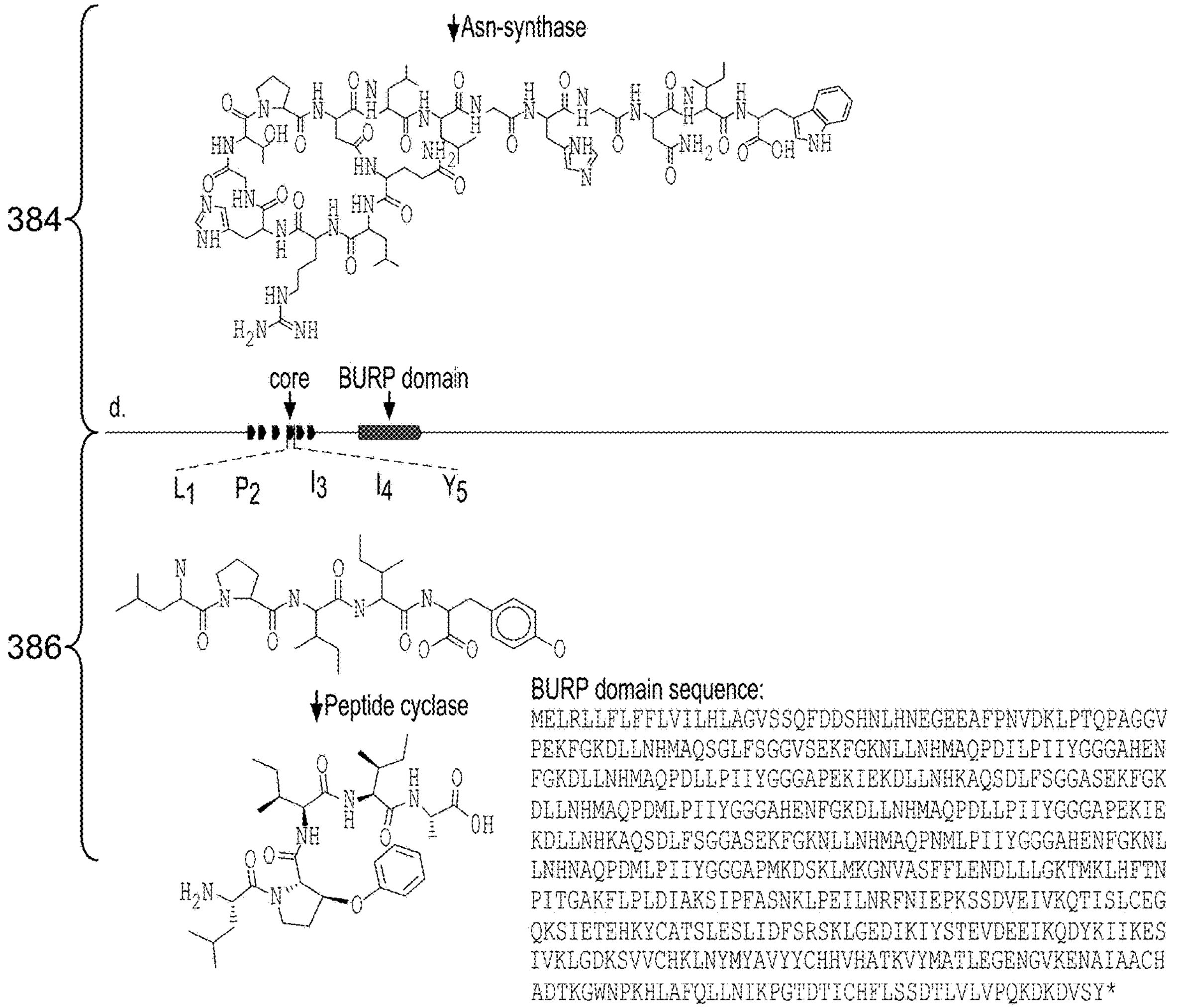

Analyzing 46 PoDP datasets with 1,036 genomes, seq2ripp predicts 17,505 BGCs, 54,605 ORFs, 118,052 cores and 30,687,610 unique RiPPs (Table 4). After searching these RiPPs against corresponding spectra with Dereplicator+, three novel RiPPs are identified, as shown in FIG. 6F.

Lasso-1648 is identified from *Streptomyces* NRRL B-2660, containing an N-terminal macro-lactam ring between N1 and D6. Based on Seq2ripp predictions, the PTM is applied by Asn-synthase (PF00733.18). Lanthi-1794 is identified from *Streptomyces* WC-3904. A dehydroalanine (Dha) located at S6, and three dehydrobutyrines (Dhb) located in T2, T10, T15 are potentially connected to one of the cysteines in the core peptide, froming lanthionine (Lan) or methyl-lanthionine (MeLan) rings. The PTM is applied by Lantibiotic dehydratase (PF05147.6 and PF04738.6). Lasso-1795 is identified from *Streptomyces* NRRL B-2660 and WC-3560, containing an N-terminal macrolactam ring between Q1 and D8. The PTM is applied by Asn-synthase (PF00733.18).

Mass spectral datasets from the PoDP database were searched against the corresponding RiPP molecules from hypoNPAtlas using Dereplicator+. At a false discovery rate (FDR) of 1% (score threshold of 15), 64 unique RiPPs (131 molecule-spectrum matches) were discovered.

Seq2ripp found 48,542 RiPP BGCs, 86,562 ORFs, and 2,159,946 cores in 2,002 *Streptomyces* draft microbial genomes (Table 4).

Benchmarking bgc2orf. Bgc2orf is compared with DeepRiPP and NeuRiPP, state-of-the-art tools for RiPP ORF identification. Since DeepRiPP and NeuRiPP are pre-trained with different datasets, two separate experiments were conducted to compare the prediction accuracy between bgc2orf and DeepRiPP/NeuRiPP on the MIBIG dataset. In the first experiment MIBIG RiPPs were discarded that were used in the DeepRiPP training data, and in the second experiment MIBIG RiPPs that were present in the NeuRiPP training data were discarded. In the first experiment bgc2orf achieved 75.0% accuracy in comparison to 70.0% for DeepRiPP, while in the second experiment bgc2orf achieved 83.3% accuracy, in comparison to 68.4% for NeuRiPP.

Orf2core generates top k cleavages for each ORF, where k is a user-adjusted parameter. Supplementary Figure S11 shows the tradeoff between accuracy and number of predicted core peptides for selecting k. Moreover, orf2core includes a repeat-finder module for identification of cores with repetitive patterns (e.g. cyanobactins and plant RiPPs). On a test dataset of 165 cores from MIBiG database (excluding training data of DeepRiPP and orf2core), orf2core correctly identified 48.48% of cores, in comparison to 35.00% for DeepRiPP. When the top 5 pairs of cleavage sites were allowed, orf2core correctly identified 63.03% of cores.

Bioactivity of novel ribosomal peptides from the human microbiota. We further tested the bioactivity of three novel N-formylated ribosomal peptides discovered by HypoNPAtlas from the human microbiota against human GPCRs. The results show that these peptides have significant agonist activity at formyl peptide receptor 1 (FPR1) by measuring the induction of β-arrestin 2 recruitment. These results demonstrates the potential of hypoNPAtlas in discovering novel bioactive ribosomal peptides.

Plant-seq2ripp is a variant of seq2ripp algorithm tuned for discovering novel BURP-domain-derived ribosomal peptides from plant species, e.g., lyciumin, legumenin, mono- and bicyclic cyclopeptide alkaloids, cercic acid and stephanotic acid.

The algorithm was applied to transcriptomic and metabolomic datasets collected on 62 plant species in order to test its potential for characterizing new RiPP chemistry from plants. Within these datasets, plant-seq2ripp correctly connected known plant RiPPs of known classes with corresponding BURP-domain precursor peptides, for example, legumenin with AhyBURP, lyciumin B with LbaLycA, cercic acid with CcaBURP1, stephanotic acid with CcaBURP2, and cyclopeptide alkaloids selanine A and B with SkrBURP. Moreover, the algorithm discovered novel plant RiPPs of known classes including four new bicyclopeptide alkaloids (cores: ILLYPSY (SEQ ID NO: 1), VLFYRSY (SEQ ID NO: 2), FLLYPY (SEQ ID NO: 3), FLLYPSY (SEQ ID NO: 4)) and one new monocyclic cyclopeptide alkaloid (core: ILLY (SEQ ID NO: 5)) derived from Selaginella kraussiana precursor SkrBURP, two lyciumins (core: QPFGVFAW (SEQ ID NO: 6), QPFGVFSW (SEQ ID NO: 7)) derived from a BURP-domain precursor of *Jeffersonia diphylla*, and a stephanotic acid (core: QLKVW (SEQ ID NO: 8)) derived from *Cercis canadensis* precursor CcaBURP2. The validation of aforementioned plant RiPPs are conducted by transient expression of the matched BURP-domain precursor gene in *N. benthamiana*. Among these, *Jeffersonia diphylla* is a member of the Berberidaceae, and in this genera no lyciumins have previously been reported. For six of the novel plant RiPPs, we conducted transient expression of the matched BURP-domain precursor gene in *N. benthamiana* via *Agrobacterium tumefaciens* LBA4404 infiltration with the pEAQ-HT expression system. After collecting LC-MS/MS, spectra corresponding to the observed ORFs were detected, confirming that the predicted spectra are indeed produced by the predicted ORFs.

Plant-seq2ripp predicted a novel BURP-domain-derived cyclic pentapeptide with a mass of 615.773 Da from *Elaeagnus pungens* with a Pro-Tyr-macrocyclization, shown in FIG. 6F. This predicted crosslink was characterized by NMR and Marfey's analysis of the purified natural product named elaeagnin. The elaeagnin PTM, a macrocyclic ether bond between the β-carbon of a proline and the phenol-hydroxy-group of a tyrosine, was previously proposed in a plant peptide derived from soybean BURP-domain precursor GLYMA 04G180400 and seq2ripp was able to discover this PTM using variable search of mass spectra, without the need to incorporate the modification. Elaeagnin was verified as a RiPP by transient expression in *N. benthamiana* and subsequent detection of elaeagnin in transgenic tobacco leaves after six days. 14 tandem mass spectra are included, where 7 of them are the spectra of six confirmed peptides and elaeagnin (on left), and another 7 are their confirmation in tobacco (on right). The discovery of elaeagnin, which belongs to a new class of BURP-domain-derived RiPPs defined by the Pro-Tyr-macrocyclization, showcases the power of seq2ripp in identifying novel classes of RiPPs.

HypoNPAtlas Server. The hypoNPAtlas webserver currently includes hypothetical RiPPs from 22,671 complete microbial genomes from RefSeq. Users can select specific strains/taxonomic clades and download the corresponding BGC, ORF, core and molecular structure data. Additionally, the hypoNPAtlas webserver supports the processing of input genomic data from users. The fragmentation of all the molecular structures are preprocessed and can be searched against mass spectral datasets using Dereplicator+.

FIG. 6D shows an example process 370 for determining a molecular structure based on genomic data. At step 372, the data processing system 102 identifies BGCs through their modification enzymes. For example, dehydration enzymes are frequently found in some classes of RiPPs. At step 374, short ORFs within 10,000 bp of these enzymes are detected by the data processing system 102 as candidate structural ORFs. At step 376, fragments of the structural ORFs with lengths between 5 to 30 amino acids are extracted by the data processing system 102 as candidate precursor peptides. The data processing system 102, depending on the tailoring enzymes in the BGC, optionally applies corresponding modifications to the precursor peptides to form hypothetical molecules FIG. 6E shows an example process 380 for mapping structures of molecules to spectra data. More specifically, FIG. 6E shows an annotation of radamycin mass spectra from GNPS actinomycete dataset MSV000078937 using a dereplicator+ model. The fragments at depth 1 are shown in bracket 382, while the fragments at depth 2 are shown in bracket 384. Fragments and peaks that are annotated by dereplicator+ but not by the string scoring method are marked with checkmarks. These can either correspond to depth two fragments or fragments resulting from non-amide bond breakage. Associated spectra 386 are shown below. By switching from a string-based model to this graph based model, the score of correct radamycin match increases from 9 to 25, and the p-value drops from 3×10-17 to 3×10-46.

The data processing system 102 derives a complete chemical structure graph of RiPPs from their BGC (rather than a precursor peptide along with modification masses). To enable this, the data processing system 102, based on precursor peptides, models tailoring enzymes as graph-modifiers. Each enzyme searches a particular chemical motif in the molecular graph of a RiPP, and whenever it finds the motif, it optionally applies the corresponding tailoring modification.

The data processing system 102 predicts hypothetical molecules by applying modifications corresponding to tailoring enzymes present in the BGC. The data processing system 102 does this by extracting all the information from the known RiPP tailoring enzymes and their corresponding modifications. Given a core sequence and a list of tailoring enzymes the data processing system 102 predicts all the hypothetical RiPP structures using the following steps. First, the chemical structure of the core sequence is represented as a graph, where each vertex is an atom with an index number and the type of atom, and each edge is a bond between two indexed atoms and the type of chemical bonds. Next, for each modification, the location of motifs are collected by subgraph isomorphism. Finally, the putative combinations of modifications are calculated and applied to the core sequence.

Breakthroughs in genome mining and mass spectrometry data collection have revolutionized the field of natural product discovery during the last decade. Development of popular genome mining tools such as antiSMASH has made it possible to quickly profile microbial genomes for detecting natural product BGCs. However, the current state-of-the-art approach for connecting BGCs to molecules is through the expression of the BGC in a heterologous host and subsequent isolation and structure elucidation of the product, which is a slow and expensive process. Therefore 99% of BGCs extracted from microbial genomes and stored in public repositories remain orphan, i.e. they are not linked to any small molecule.

On the mass spectrometry front, development of the GNPS repository along with molecular networking has made it possible to annotate known natural products and discover their novel variants. Currently, GNPS hosts more than a billion mass spectra from more than five hundred laboratories. However, only 2% of GNPS spectra has been annotated as known molecules or their analogs. It has been hypothesized that a portion of the annotated spectra from GNPS is likely to correspond to orphan BGCs from microbial genomes.

To fully utilize the power of recently developed repositories of microbial BGC and mass spectral datasets, computational techniques for high-throughput linking of BGCs to mass spectra are needed. However, in order to link mass spectral datasets to BGCs from microbial genomes, one first needs to predict the hypothetical structure of the molecular product of these BGCs. In order to fill in this gap, we present hypoNPAtlas, a public repository of hypothetical natural products predicted by mining microbial genomes. In the case of RiPP natural products, using the seq2ripp algorithm we populated this Atlas with 31,483,329 RiPPs from 22,671 complete microbial genomes available from RefSeq.

Seq2ripp identified three novel microbial RiPPs from the PoDP datasets, and ten novel plant RiPPs from 62 plant metabolomics and transcriptomic datasets. Through variable mass spectrometry, seq2ripp discovered a plant RiPP with a novel PTM from Elaeagnaceae, highlighting the power of this method for identification of novel classes of natural products that were missed by previous approaches. Bgc2orf and orf2core modules within seq2ripp are capable of identifying RiPP precursors and cores without overfitting.

Hypothetical molecules from hypoNPAtlas can be filtered to user specified taxonomic clades, and the retained molecules can be queried against mass spectral datasets using Dereplicator+, an in silico database search tool available from GNPS. Previous techniques modeled RiPPs as strings of amino acids, along with post-translational modifications. In contrast, hypoNPAtlas models RiPPs as graphs with atoms and chemical bonds, improving accuracy in representations of post-translational modifications (e.g. cyclizations). The graph model also improves the accuracy of in silico methods in predicting fragmentation of RiPPs containing nonstandard amino acids (e.g. oxazole and thiazole).

Another challenge in linking mass spectral datasets to microbial BGCs is that over 99% of spectra from GNPS are collected on strains with unknown DNA sequence from complex environments. HypoNPAtlas infrastructure supports searching mass spectral datasets against taxonomic clades, allowing for novel natural product discovery from datasets without genomic information. This often results in discovery of natural products from mass spectra of one strain against the genome of a different strain. For example, radamycin was identified by searching mass spectra of a marine *Streptomyces* against the genome of a tomato flower symbiont *Streptomyces*.

Currently, hypoNPAtlas reports on average 84 ORF, 1605 cores and 1753 molecules per RiPP BGC. Multiple RiPPs have been recorded because (i) many RiPP BGCs have multiple RiPP products, e.g. many cyanobactin and plant RiPPs have multiple cores per each ORF, and (ii) the activity of many RiPP enzymes remain ambiguous. By keeping track of multiple hypothetical RiPPs per BGC, we can increase the chance of capturing the correct RiPP. The natural drawback of this strategy is that majority of RiPPs in the Atlas will be spurious. By searching against mass spectral repositories, hypoNPAtlas enables identification of a large number of novel RiPPs, providing the training data for machine learning approaches to improve the prediction accuracy of post-translational modifications.

The pipeline for natural products discovery by hypoNPAtlas consists of the following steps. Extracting BGCs and predicting hypothetical RiPPs. BGCs are either imported from IMG-ABC, antiSMASH-DB, and BiG-SLICE, or mined from RefSeq/IMG-M. Hypothetical RiPPs are predicted from BGCs using seq2ripp. Filtering the Atlas using taxonomic information. The entire Atlas is too large for down-stream analysis. Users can filter the Atlas using specific taxa terms, and then download the entire hypothetical molecules in that clade in the SMILES format, along with corresponding BGCs, ORFs and cores. For example, the Atlas contains 20 BGCs, 48 ORFs, 273 cores and 120,701 molecules for the strain *Streptomyces globisporus* NRRL B-2709.

Predicting spectra of hypothetical molecules from the Atlas. We used Dereplicator+ to pre-calculate the fragmentation graphs for all the molecules from the Atlas. The fragmentation graphs are stored as binary files, and they are also downloadable for user-specified taxonomic clades. It is much faster to search mass spectra against pre-calculated fragmentation graphs using Dereplicator+ than it is to search against raw SMILES structures.

Mass spectral datasets can be searched against the SMILES structures/pre-calculated fragmentation graphs using Dereplicator+ from the GNPS infrastructure. HypoNPAtlas has been designed in a way that its interface is fully compatible with GNPS.

False discovery rate (FDR) based on target decoy analysis reported by Dereplicator+ are used. Molecular networking. Currently, feature-based molecular networking supports annotations from Dereplicator+, and these networks can be visualized through the GNPS infrastructure.

MetaMiner is a computational technique for discovery of novel RiPPs. The MetaMiner pipeline analyzes the paired genome/metagenome assemblies and tandem mass spectra from isolated microbes or bacterial or fungal communities. Starting from the genome assemblies, MetaMiner (i) identifies putative BGCs and their corresponding precursor peptides, (ii) constructs target and decoy putative RiPP structure databases modeling them as strings, and (iii) matches tandem mass spectra against the constructed RiPP strings using Dereplicator.

Given a microbial genome sequence in fasta format, seq2ripp predicts hypothetical RiPP molecules (in the SMILES format) in the following steps. From genome to BGCs. RiPP BGCs are identified by the genome2bgc module, using 152 hidden Markov model (HMM) profiles, corresponding to frequent RiPP tailoring enzymes for various classes of RiPPs. Alternatively, seq2ripp also supports RiPP BGC identification using antiSMASH.

From BGCs to ORFs. ORFs are extracted from BGCs by bgc2orf, a deep neural network (e.g., FIG. 6C). Additionally we also support the exhaustive strategy recruited by MetaMiner a BLAST-based strategy, and strategies from DeepRiPP and NeuRiPP In the exhaustive strategy, we all short ORFs with length longer than 10 aa are considered as feasible ORFs. While this strategy is very sensitive, it can result in a high number of false positives. In BLAST-based strategy, ORFs identified by the exhaustive search strategy are aligned against a database of 525 known RiPP ORFs with blastp, and those with e-value lower than 0.01 are retained. In bgc2orf, a sequence classification model is trained which includes a Convolutional Neural Network (CNN) and a Long Short-Term Memory (LSTM) Network, based on 2,726 amino acid sequences of known RiPP ORFs and 19,224 amino acid sequences of non-RiPP ORFs. Then for each short ORF in the BGC, whether the ORF is a structural ORF or not is predicted, and the system only considers those with high probabilities (higher than 50%) as hypothetical structural ORFs.

Bgc2orf is trained as follows: first, all input sequences are padded to a length of 200 amino acids. Each amino acid, including the padding symbol, is tokenized and embedded into a vector of size 100. The model includes two 1D CNNs. One CNN convolves the in-put sequence in terms of its topology, the other CNN convolves the tokenized vectors. The convolution on the sequence helps the model to detect the RiPP features on amino acids; the convolution on the token vector summarizes the embedded character information in high dimensional space. The outputs from the two CNNs and the input embeddings are concatenated and fed into a single layer bidirectional LSTM. The LSTM learns and summarizes the sequential features from the amino acid chain. The output of the LSTM is flattened and converted to a binary output with a flattened layer and a dense layer. The prediction loss is calculated by cross entropy loss during the training of the model. The learning rate begins with 1e-3 And decreases 10% every 40 epochs.

ORFs to cores. Core peptides are detected from ORFs by orf2core, a deep neural network. Similar to the previous step, we also support an exhaustive strategy from MetaMiner, DeepRiPP, and a BLAST-based strategy. In the exhaustive strategy, all the peptide fragments with lengths between 3 to 30 aa are considered as candidate core peptides. In the BLAST-based strategy, the ORFs are aligned with 525 known RiPP cores by blasp, and the part of ORFs aligning with the core sequence with e-value lower than 0.001 are extracted (allowing for an error of up to two bases on each sides). In orf2core, we framed the task as a phoneme discovery problem, where the input is an amino acid sequence, and the output is putative cleavage sites. The system trains a CNN-LSTM-Conditional Random Field (CRF) model on the cleavage sites information of 3169 known RiPP ORFs.

The system includes a discriminatory deep learning model to predict core and non-core frames of sequences given the amino acid sequence of an ORF as the continuous input. All input sequences are padded to a length of 200 amino acids. Each amino acid is tokenized and embedded into a vector of size 25. The model includes two 1D CNNs. One CNN convolves the input sequence in terms of its topology, and the other CNN convolves the tokenized vectors. The convolution on the sequence helps the model to detect amino acids surrounding the enzymatic cleavage site. The convolution on the token vector summarizes the embedded character information in high dimensional space. The outputs from the two CNNs, and the input embeddings are concatenated and fed into a single layer bidirectional LSTM. The LSTM learns the translation from the amino acid chain to core and non-core frames of sequences. The prediction loss is calculated by a conditional random field layer, which calculates the negative log-likelihood during the training of the model, and performs the Viterbi algorithm to optimize labels during prediction. An additional approach will be triggered when repeat patterns are observed in an ORF, by searching repeated prefix and suffix patterns in the sequence.

To use Dereplicator+ for the discovery of RiPPs, the system derives the complete chemical structure graph of RiPPs from their BGC (rather than a precursor peptide along with modification masses, required by Dereplicator). To enable this, the system starts with precursor peptides and model tailoring enzymes as graph-modifiers. Each enzyme searches a particular chemical motif in the molecular graph of a RiPP, and whenever it finds the motif, it optionally applies the corresponding tailoring modification (See FIG. 6F).

Figure 7:
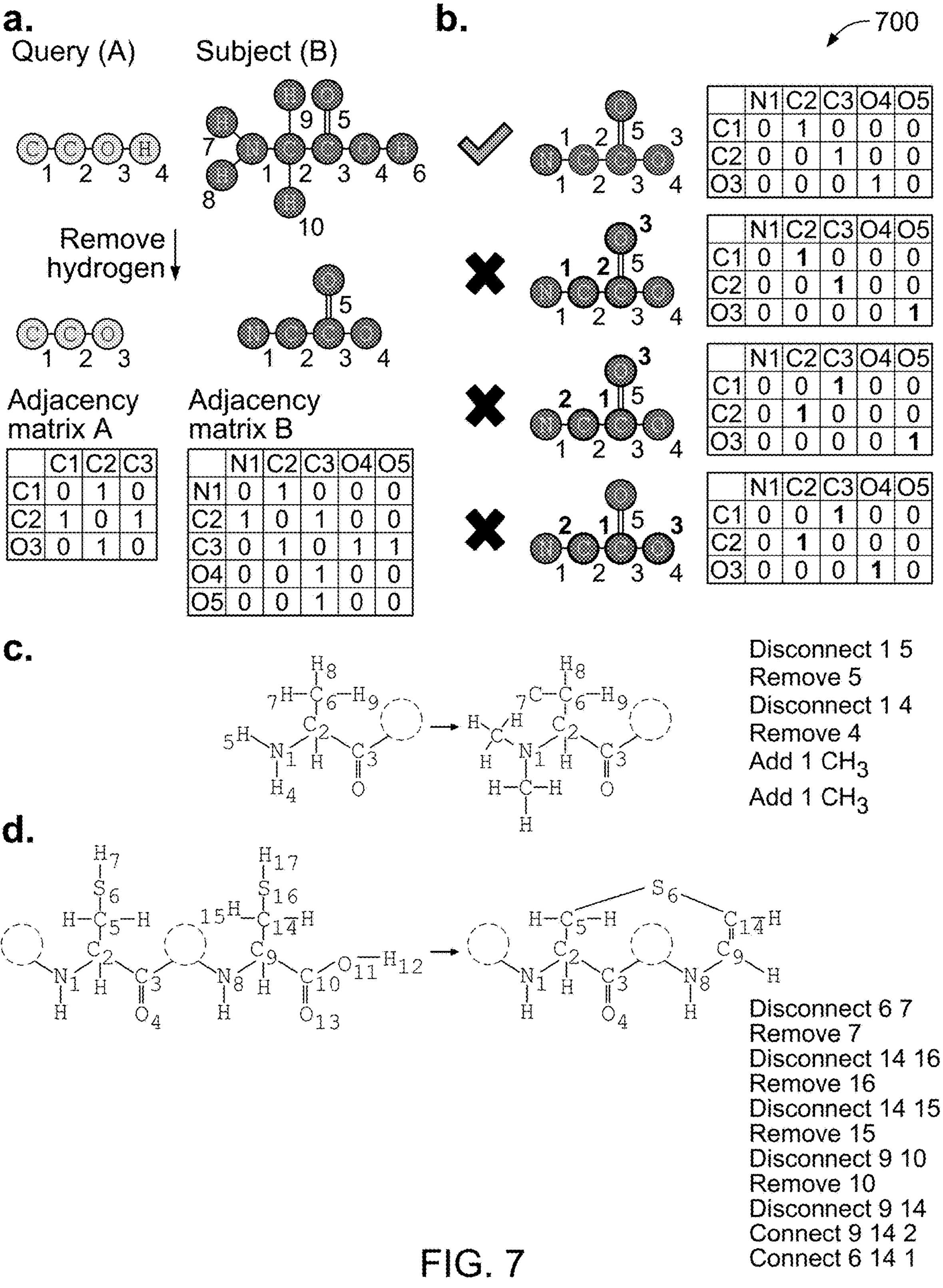
FIG. 7 shows a process.

Core2ripp predicts hypothetical molecules by applying modifications corresponding to tailoring enzymes present in the BGC. We do this by extracting all the information from the known RiPP tailoring enzymes and their corresponding modifications by literature mining and parsing them in a computer-readable format. The format includes a motif (stored as a SMILES string) along with a series of graph modifications (addition/removal of nodes and edges) that are applied to the molecular structure whenever the motif is observed, as shown in FIG. 7.

Given a core sequence and a list of tailoring enzymes, core2RiPP predicts all the hypothetical RiPP structures using the following steps. First, the chemical structure of the core sequence is represented as a graph, where each vertex is an atom with an index number and the type of atom, and each edge is a bond between two indexed atoms and the type of chemical bonds. Next, for each modification, the location of motifs are collected by subgraph isomorphism. Finally, the putative combinations of modifications will be calculated and applied to the core sequence (see details below). The final product will be stored in the SMILES format.

Finding motifs by subgraph isomorphism. The system models the problem of searching motifs in the precursor RiPP sequence as a subgraph isomorphism problem. In the subgraph isomorphism problem, given graphs A (query) and B (subject), the problem is to determine if there is a subgraph of graph B that is isomorphic to the graph A. Here, the subject is the chemical structure of the precursor peptide sequences, and the query is the chemical structure of the motifs. For both the subject and the query, vertices are atoms, and the edges are bonds. The subgraph isomorphism problem is shown to be NP-hard.

Ullman's subgraph isomorphism algorithm is updated for motif finding, which makes it three orders of magnitude faster than the original approach. Ullman's subgraph isomorphism algorithm builds an m by n binary correspondence matrix, where m is the number of nodes in the query, and n is the number of n does in the subject. The correspondence matrix has a 1 whenever the following two constraints hold: (i) the corresponding query and subject atoms have the same label (e.g. they are both carbon), and (ii) the multi-set of neighboring nodes for the query is a subset of the multiset of neighboring nodes for the subject. Then, for every row in the correspondence matrix, a single column containing a 1 is selected. This results in a mapping from query node indices to subject node indices. Then, the algorithm checks whether this mapping defines an isomorphism, i.e. all the edges in the query are present in the subject. Whenever this constraint is violated, the algorithm backtracks to select a new column with 1 from one of the rows.

The Ullman algorithm is modified by incorporating edge-level labels: the multiset of neighboring node and edge pairs for the query is a subset of the multiset for the subject, where the edge is labelled as a single/double/triple bond. We further remove the hydro-gen atoms from both query and subject to accelerate the algorithm and avoid unnecessary computations. Moreover, by constructing the query and the subject into spanning trees, we are able to enforce that in each iteration, the atom selected from the query/subject be connected to the query/subject atoms added in the previous iterations without additional computations, as shown in FIG. 7 parts a and b.

Motif-based modification. MetaMiner models RiPPs as strings of amino acids, and then modifications are applied to amino acids as mass shifts. In contrast, seq2ripp models RiPPs as graphs, and modifications are applied as graph modifications on the reaction motifs. We define modifications in a computer-readable format, using four actions: add, remove, connect, and disconnect. The add/remove actions are used for adding and removing atoms, while connect/disconnect actions are for adding and removing edges, as shown in FIG. 7 parts c and d.

Given a list of tailoring enzymes in the BGC, core2ripp predicts the hypothetical products by adding the different combinations of modifications on the core peptide. If there are 10 feasible modifications at different locations, this procedure produces 1024 possible products. These hypothetical structures are saved in SMILES format.

FIG. 7 shows a process 700. First, at (a), the hydrogens are removed from the query and the subject. Next, the atoms are labeled by a breadth first traversal of each graph from the first non-hydrogen atoms in the input file. Finally, an adjacency matrix for each graph is prepared. At (b), only the mappings that define an isomorphism are kept. Converting known enzymatic modifications of RiPPs into a computer-readable format for dimethylation of N-terminal, e.g. in cypemycin and oxidative decarboxylation, e.g. cypemycin and epidermin. In this format, commands disconnect/connect are used (for bonds) and add/remove (for chemical substructures). For example, in part (c), "disconnect 1 5" removes the bond between the nitrogen atom with index 1 and the hydrogen atom with index 5, while "remove 5" removes the hydrogen atom with index 5, and "Add 1 CH3" adds a methyl group to the nitrogen atom indexed 1 (methylation). In part (d) "connect 9 14 2" adds a double bond between atom 9 and atom 14.

Estimating the Statistical Significance of Metabolomics Annotations

In case of mass spectrometry base proteomics, modern database search strategies recruit statistical methods to evaluate the matches between peptides and spectra. Currently, the dominant technique for statistical evaluation of a set of PSMs is to estimate false discovery rate (FDR) using the Target Decoy Approach (TDA). In this approach, a database of fake (decoy) peptides are searched against mass spectra in addition to correct (target) database. Then the ratio of high score matches in the decoy database to that of target database is used as an estimate of FDR. Decoy peptides are usually generated by shuffling target peptides. Methods below are discussed to generalize this method to other natural products with more diverse structures.

In proteomics, identified PSMs are statistically evaluated through the computation of p-values. The p-value of a PSM is defined as the fraction of random peptides with a score equal to or exceeding the target PSM. To compute p-value, the data processing system 102 estimates the distribution of the score of random peptides against the spectrum.

Natural product small molecules have diverse graph structures, such as linear, cyclic, branch-cyclic, and multiple ring structures. The process now described is configured for statistical validation of metabolomics identifications by converting match scores to p-values. This process overcomes existing technical hurdles. Current methods (such as Markov Chain Monte Carlo (MCMC)) for estimating p-values do not generalize to other types of natural products since it is not clear how to generate random small molecule structures, and how to randomly modify the structure of small molecules. To overcome this, the data processing system 102 is configured to use constrained graph variational auto-encoders (CGVAE) for random generation and mutations of small molecules.

Matching Score and p-Values

A scoring function score (M, S) for a match between molecule M and spectrum S. Let M and S denote the set of all possible molecules and spectra. Molecule-based p-value for a pair of molecule and spectrum (M, S) is defined as:

$$P(\text{Score}(m,S)\geq 0) \tag{10}$$

where m is generated from a random uniform distributed on set and=Score (M, S). The probability p defined above depends on the choice of set M. Similarly, spectrum-based p-value is defined as:

$$P(\text{Score}(M,s)\geq t) \tag{11}$$

where s is generated from a random uniform distributed on set. Molecule-based p-values help in reducing bias toward molecular features, while spectrum-based p-values reduce bias toward spectral features. The data processing system 102 uses constrained graph variational auto-encoders (CG-VAE) for generating random molecules, and also generates random spectra.

Monte Carlo Approach

Monte Carlo simulation is a robust technique for simulating events and estimating their probabilities. Consider the set $$\mathcal{M}^* = \{m \in \mathcal{M}:\text{Score }(m, S) \geq t\} \tag{12}$$

$$\mathcal{S}^* = \{s \in \mathcal{S}:\text{Score }(M, s) \geq t\} \tag{13}$$

Define 1M* as an indicator function of the set M* such that 1M*(m) equals 1 if m∈M* (equivalently, Score(m)≥t) and 0 otherwise. Let m1, . . . , $m_N$ be N independent and identically distributed (iid) random variables sampled from a uniform distribution $f$ on set M. The p-value p defined in equation (10) can be written as an expectation:

$$p = \int_{\mathcal{M}} \mathbb{1}_{\mathcal{M}^*}(m) r(m) dm = \mathbb{E}_p[\mathbb{1}_{\mathcal{M}^*}] \tag{14}$$

where r is the sampling distribution over M. According to the strong law of large numbers, since m1, . . . , mN are iid samples, the probability p converges almost surely (e.g., with probability 1) to the following:

$$\hat{p}_{MC} = \frac{1}{N}\sum_{i=1}^{N} \mathbb{1}_{\mathcal{M}^*}(m_i) \tag{15}$$

$\hat{p}_{MC}$ is an unbiased and consistent estimator of p-value p. Variance of $\hat{p}_{MC}$ equals to p(1−p), which tends to 0 as N. Therefore Monte Carlo sampling is used to compute the probability p.

Importance Sampling

Importance sampling is a general Monte-Carlo approach for reducing the variance of expectations quantities. Importance sampling generates the events of interest more often by sampling from a different distribution and correcting for the bias afterward, which results in a more accurate estimate with a lower number of samples. Formally, assume $m_1$, . . . , $m_N$ are sampled from a distribution with density p. Then for a probability distribution q(m), using equation (16):

$$p = \int_{\mathcal{M}} \mathbb{1}_{\mathcal{M}^*}(m) r(m) dm = \int_{\mathcal{M}} \frac{\mathbb{1}_{\mathcal{M}^*}(m) r(m) d}{q(m)} q(m) dm = \mathbb{E}_q\left[\frac{\mathbb{1}_{\mathcal{M}^*} r}{q}\right] \tag{16}$$

The importance sampling estimator of p is defined as:

$$\hat{p}_{IS} = \frac{1}{N}\sum_{i=1}^{N}\frac{r(v_i)}{q(v_i)}\mathbb{1}_S(v_i) = \frac{1}{N}\sum_{i=1}^{N}w(v_i)\mathbb{1}_S(v_i) \quad (17)$$

where v1, . . . , vN are iid samples from q(v), called the importance sampling density, and w(vi)=p(vi) is the importance weight of sample vi.

Markov Chain Monte Carlo

The importance sampling density q has is selected in a way that relative error is minimized. The optimal density is:

$$q^*(m)\frac{\mathbb{1}_{\mathcal{M}^*}(m)r(m)}{p\varepsilon} \quad (18)$$

In this case, all generated samples fall in $U_i \in M^*$, so their importance weights are w(mi)=p, and the IS estimate $\hat{p}_{IS}$=p. In this case, just one sample (N=1) is enough to find the probability p exactly. To estimate the optimal importance sampling density, the data processing system 102 uses an iterative strategy. In the first iteration, a uniform distribution q is used, and in each iteration, the score probability distribution P(Score(m, S)=t) is estimated, and the weight and density are updated as:

$$w(t) = \frac{1}{\mathbb{P}(\text{Score}(m, S) = i)} \quad (19)$$

$$q(t) = r(t)\mathbb{P}(\text{Score}(m, S) = t) \quad (20)$$

Here, we assume density q and weight w are uniform for each score. Usually this task is approached by using the Metropolis-Hastings algorithm that allows for the usage of unnormalized densities. The data processing system 102 is configured to generate a Markov Chain having Q as an equilibrium distribution and obtain the desired sequence $\{v_n\}$ of random variables via sampling from this distribution. The ergodicity of the Markov chain ensures that as N approaches infinity, $\hat{p}_{IS}$ still converges to the target probability p.

Consider a transition kernel y(x|y) that defines a jump in M. The Metropolis Hastings algorithm realizes the desired sampling strategy as follows. Starting from a random initial point $m_0$, in each step a new point m* is samples from y(x|y). If w(m*)>w($m_i$), the transition is accepted. Otherwise the transition is accepted with probability w(m*)/w($m_i$), and rejected otherwise. If the transition is accepted, $m_i$ is set to m*, otherwise $m_i$ is set to mi−1.

Algorithm 1: Metropolis-Hastings algorithm

Input: Transition kernel γ(x | y), current state of Markov Chain $\vec{v}_i$
Output: Next state of Markov-Chain $\vec{v}_{i+1}$
Sample random variable $\vec{v}$ from conditional distribution γ (· | $\vec{v}_i$)
Sample uniform random variable r on the interval [0; 1]
Calculate the acceptance ratio $$\alpha = \min\left(\frac{q(\vec{v}_i)\gamma(\vec{v} \mid \vec{v}_i)}{q(\vec{v})\gamma(\vec{v}_i \mid \vec{v})}, 1\right)$$

-continued

Algorithm 1: Metropolis-Hastings algorithm

If r < α then
  ⌊ $\vec{v}_{i+1} \leftarrow \vec{v}$
else
  ⌊ $\vec{v}_{i+1} \leftarrow \vec{v}_i$ where the sampling from proposal density γ(•|$\vec{v}_i$) is performed as follows:

Algorithm 2: Simulation from conditional density γ (• | $\vec{v}_i$)

Input: Current state of Markov Chain $\vec{v} = (v_1, \ldots, v_{|V(G)|}) \in \mathcal{M}$
Output: Proposed state $\vec{v}$
Sample index i uniformly on {1, . . . , |E(G)|}
Consider $e_i \in E(G)$ where ($v_1$, $v_2$) are starting and ending vertices
Sample δ uniformly on [−m ($v_1$) ; m ($v_2$)]
set $\vec{v}_{v_1}$ based on δ (Details need to be added here)
Gathering all the parts of the proposed method together we end with the following algorithm to compute $\hat{p}_{IS}$.

Algorithm 3: Importance Sampling estimator for p

Input: A molecule MP and spectrum S
Output: An estimate $\hat{p}_{IS}$ of statistical significance p and confidence interval $C_N$
Construct a random molecule m based on CGVAE model
let Score(m) = Score(S, m)
Determine the set of weights w(m) using Wang-Landau algorithm (Details need to be added here)
while Stopping criterion is not satisfied do
  | Simulate next state $\vec{v}_N$ using Metropolis-Hastings algorithm (see algorithm 1)
  ⌊ update the stopping criterion
Calculate $\hat{p}_{IS}$ based on Equation 9

There are two ways for computing the statistical significance of a molecule spectrum match. A first method fixes the molecule and computes the ratio of random spectra getting a score higher than the target match (spectrum-based p-value). A second method fixes the spectrum and computes the ratio of random molecules getting a score higher than the target match (molecule-based p-value). In case of spectrum-based p-values, the data processing system 102 generates (and modifies) random spectra based on the statistics of peaks/intensities learned from the GNPS library. In the case of molecule-based p-values, the data processing system 102 uses constrained graph variational autoencoders (CGVAE) for random generation and modification of molecular structures.

Generating Random Spectra

The data processing system 102 determines a statistical significance for generated molecule structures by producing a target-decoy database of random MS/MS spectra for small molecules. For this part the set M includes of generated spectra in order to calculate equation (10) for each pair of (molecule, spectrum). Two strategies are used to create the decoy MS/MS database.

A first method to create the decoy MS/MS database is the naïve method. For the naive decoy spectral library, all possible fragment ions from the reference library of spectra are used. The data processing system 102 randomly adds these ions to the decoy spectral library until each decoy spectrum reaches the desired number of fragment ions that mimics the corresponding library spectrum. This method is presented as a baseline evaluation of the other, more intricate method.

The spectrum-based method is similar to the naive method, as the data processing system 102 generates a decoy spectral library through choosing fragment ions that co-appear in the spectra from the target spectral library. In this spectrum-based approach, the data processing system 102 starts with an empty set of fragment ion candidates. First, the data processing system 102 randomly selects the precursor fragment ion of the target spectrum. For each fragment ion added to the decoy spectrum, the data processing system 102 chooses all spectra from the target spectral library which contain this fragment ion, within a threshold (=5 p.p.m). From these spectra, the data processing system 102 uniformly draws (all fragment ions have the same probability to be drawn) five fragment ions that are added to the fragment ion candidate set. The data processing system 102 draws a fragment ion from the fragment ion candidate set and add it to the decoy spectrum, then proceed as described above until we reach the desired number of fragment ions that mimics the corresponding library spectrum. The two-step process of first drawing candidates, then drawing the actual decoy spectrum is introduced to better mimic fragmentation cascades and dependencies between fragments. Furthermore, it prevents that fragment-rich spectra dominate the process.

Generating Random Molecules

A CGVAE model is used by the data processing system 102 to generate random molecules. The process is seeded with N vectors that together form a latent specification for the graph to be generated (N is an upper bound on the number of nodes in the final graph). The model uses a variational autoencoder to design molecules that are close to the real molecules in the nature.

Fast Mass Spectrometry Searches of Untargeted Metabolomics Data Using MASST+

The throughput rate of mass spectrometers and the size of publicly available metabolomics data is growing rapidly. Illuminating the molecules present in untargeted mass spectrometry data that cannot be identified by existing approaches. MASST is configured to search a query spectrum against a database and cluster families of related molecules in untargeted mass spectrometry data. MASST+ is configured to scale to searching and clustering billions of mass spectral data in large metabolomics repositories, e.g. the global natural product social (GNPS) molecular networking infrastructure. By utilizing the strategy to preprocess and sort peaks in mass spectra described in this section of the specification, MASST+ searches a query spectrum against billions of spectra in less than an hour and Networking+ maps the chemical diversity of the entirety of billions of spectra in the entire GNPS in less than a week on a single compute node.

MASST and molecular networking are based on a naive approach for scoring two spectra. MASST compares the query spectrum against all of the reference spectra one by one and computes a similarity score based on the relative intensities of shared and shifted peaks. Therefore, the runtime of MASST grows linearly with the repository size. Molecular networking first uses MS-Clustering28 to cluster identical spectra by calculating the dot-product score (see FIG. 8 part a) between the spectra. Then Spectral Networking29 is used to calculate a dot product score that accounts for peaks that are shared or shifted (see FIG. 8 part b) between all pairs of clusters. This latter procedure grows quadratically with the number of clusters. Current trends show that the size of public mass spectral repositories doubles every two to three years. Therefore, the current implementations of MASST and Molecular Networking will not be able to scale with the growth of future repositories. A MASST search for a single spectrum against the clustered global natural product social (GNPS) database (83 million spectra) currently takes about an hour on a single thread and a MASST search against the entire GNPS (717 million spectra) does not complete after being run for three days. A molecular networking job on a million spectra finishes in about 1.5 hours, while a molecular networking job on 20 million spectra does not yield results after running for a month. Similar to computational genomics, handling the exponential growth of repositories requires the development of more efficient and scalable search algorithms.

To overcome these inefficiencies, MASST+ and Networking+, scalable methods are used for querying and clustering billions of spectra that are two to three orders of magnitude more efficient than existing methods. MASST+ and Networking+ preprocess all the peaks in all the spectral datasets and construct an indexing table that for each pair of masses M and p, records all the spectra with precursor m/z M that contains peak with m/z p. Then, given each query spectrum, the ExactScore/ShiftedScore against spectra in all datasets can be computed by iterating through each query peak and using the indexing table to efficiently retrieve spectra with similar peaks (FIG. 2). Since mass spectra are sparse, only a small fraction of spectra/peaks are retrieved for each query, making these approaches two to three orders of magnitude more efficient than the state of the art. Moreover, these approaches support insertion of new spectra into the table without the need for recalculating from scratch. MASST+ is currently available as a web service from https://masst.ucsd.edu/masstplus/. GNPS supports stand-alone MASST+ and integration with molecular networking.

Figure 8:
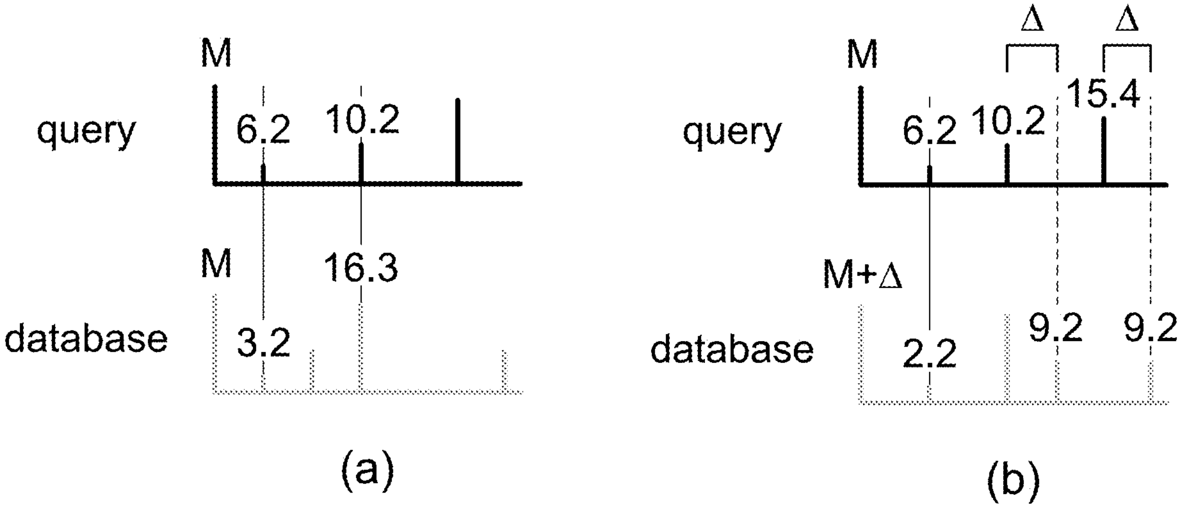
FIG. 8 shows a similarity score process.

FIG. 8 shows a similarity score process. For part a, in a case of exact search, MASST searches a query spectrum against all database spectra with similar precursor masses, and computes ExactScore as the sum of multiplications between peaks shared by the query and database spectrum (shown in solid grey). In this case the score is 6.2*3.2+10.2*16.3=186.1. For part b, in a case of analog search, MASST searches the query spectrum against all database spectra within a specific precursor mass range (e.g. 300 Da) and computes the ShiftedScore as the sum of multiplications between peaks that are shared and A-shifted between query and database spectrum. Here there is one shared (solid grey) and two A-shifted (dashed grey) peaks, yielding a total score of 6.2*2.2+10.2*9.2+15.4*9.2=249.16. A denotes the precursor mass difference between query and database spectra.

Figure 9:
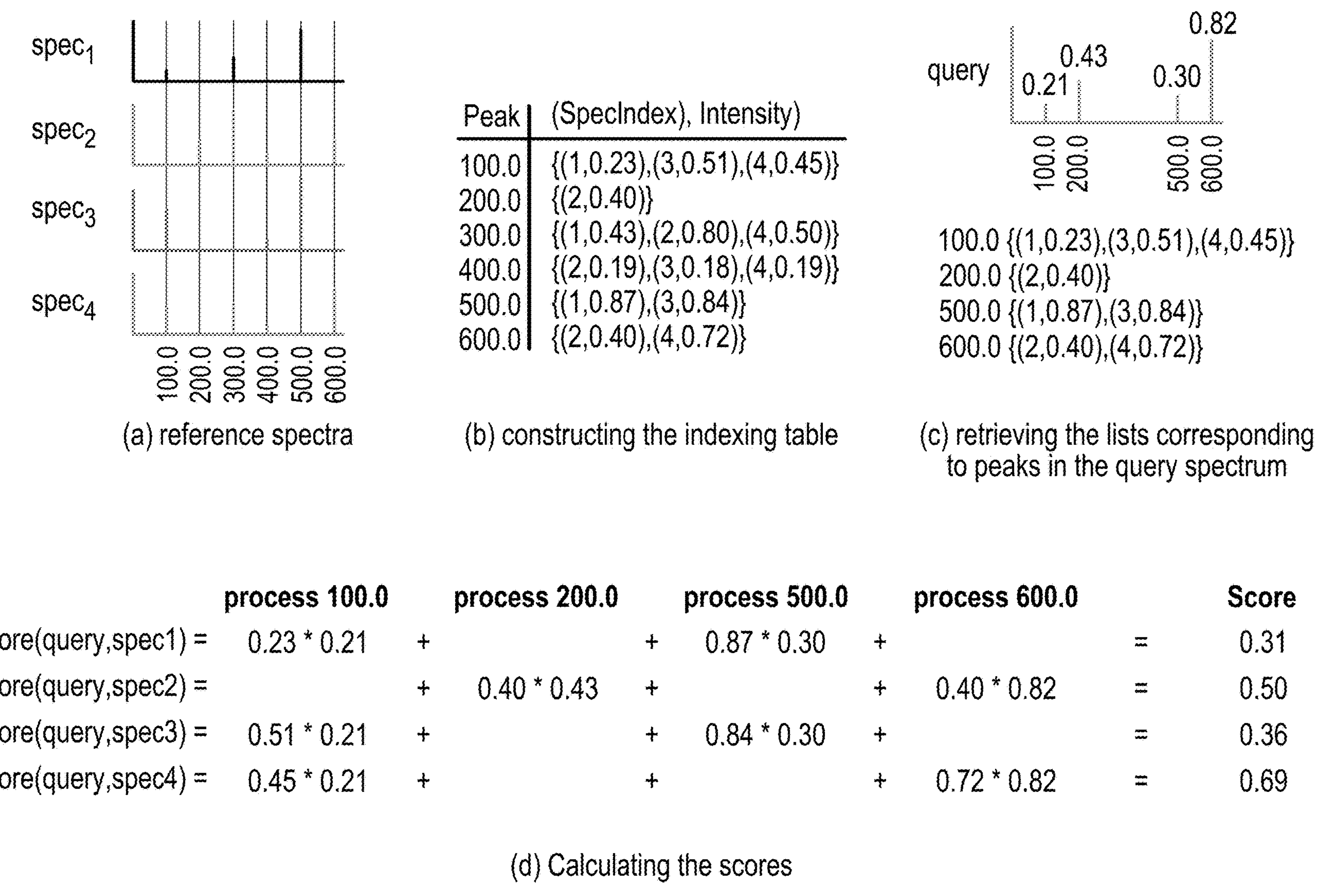
FIG. 9 shows a MASST+ Exact Search.

FIG. 9 shows a MASST+ Exact Search. At step (a), given a database of spectra MASST+ starts with (b) constructing an indexing table, where each row corresponds to a fragment peak mass, and contains a list of tuples of spectra indices that contain the peak, along with the intensity of the peak in these spectra. At step (c), given a query spectrum, MASST+ retrieves all lists corresponding to peaks present in the query. Then, at step (d) MASST+ iterates over each list, and for each tuple in the list, adds the product of the intensity of the query and database peaks to the total ExactScore of query and database spectra.

Given a query spectrum, MASST+ searches a database of reference spectra to find similar entries by creation of an indexing table—a data structure which allows rapid retrieval of similar spectra based on the peaks present in the query spectrum. For each precursor mass M and each peak mass p, a list of indices of spectra with precursor M and peak p are stored, along with the intensity of the peaks. In case of exact search, MASST+ iterates through the peaks in query spectrum, and retrieves the lists corresponding to the peaks and precursor masses, within a tolerance threshold (e. g. 0.02 Da in case of high-resolution data). The ExactScore is calculating by multiplying and adding up the intensity of each peak in query spectrum and reference spectra, shown in FIG. 9. In case of analog search, MASST+ uses a much larger precursor mass tolerance (e. g. 300 Da) and computes ShiftedScore that takes into account both shared and A-shifted peaks (peaks in reference spectra that are A Da larger than peaks in query), where A is the mass difference between the precursor of query and reference spectra, shown in FIG. 8.

Networking+ algorithm clusters spectral datasets into families of related molecules by first putting spectra from identical molecules into the same clusters (Clustering+), then forming the centers of each cluster by taking their consensus, and then connecting the clusters that are predicted to be generated from related molecules (Pairing+). Clustering+ iterates over all spectra, and puts each spectrum in the cluster that is most similar. It uses a strategy similar to MASST+ exact search for efficiently calculating the SharedScore between the spectrum and each cluster center. Pairing+ uses a shared and Δ-shifted dot-product as similarity measure for identifying related spectra. It uses a strategy similar to MASST+ analog search to find all pairs of clusters with high ShiftedScore.

Figure 10:
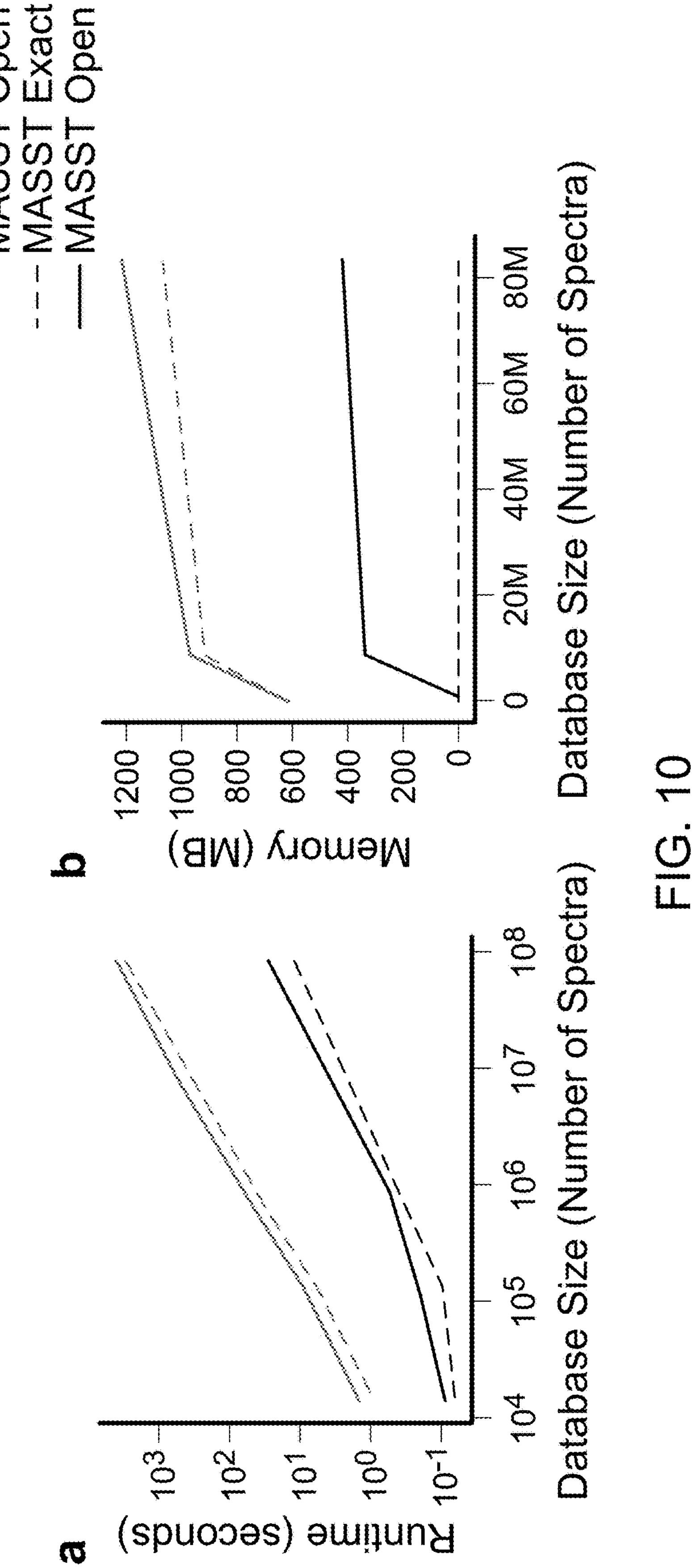
FIG. 10 illustrates the runtime and memory consumption of MASST+.

FIG. 10 illustrates the runtime and memory consumption of MASST+ in exact and analog mode for various subsets of the clustered GNPS. Indexing time and memory consumption grows linearly with the size of datasets. MASST+ takes eight hours of compute time and eight gigabytes of memory to index ~83.1 million spectra from the clustered GNPS. MASST+ is used for annotation of mass spectral datasets containing unknown molecules by searching them against 140M annotated spectra in ReDU repository.

FIG. 10 shows graphs. Graph (a) shows MASST+ is two orders of magnitudes faster than MASST in exact and analog search for various database sizes. Graph (b) shows MASST+ outperforms MASST in memory efficiency.

Figure 11:
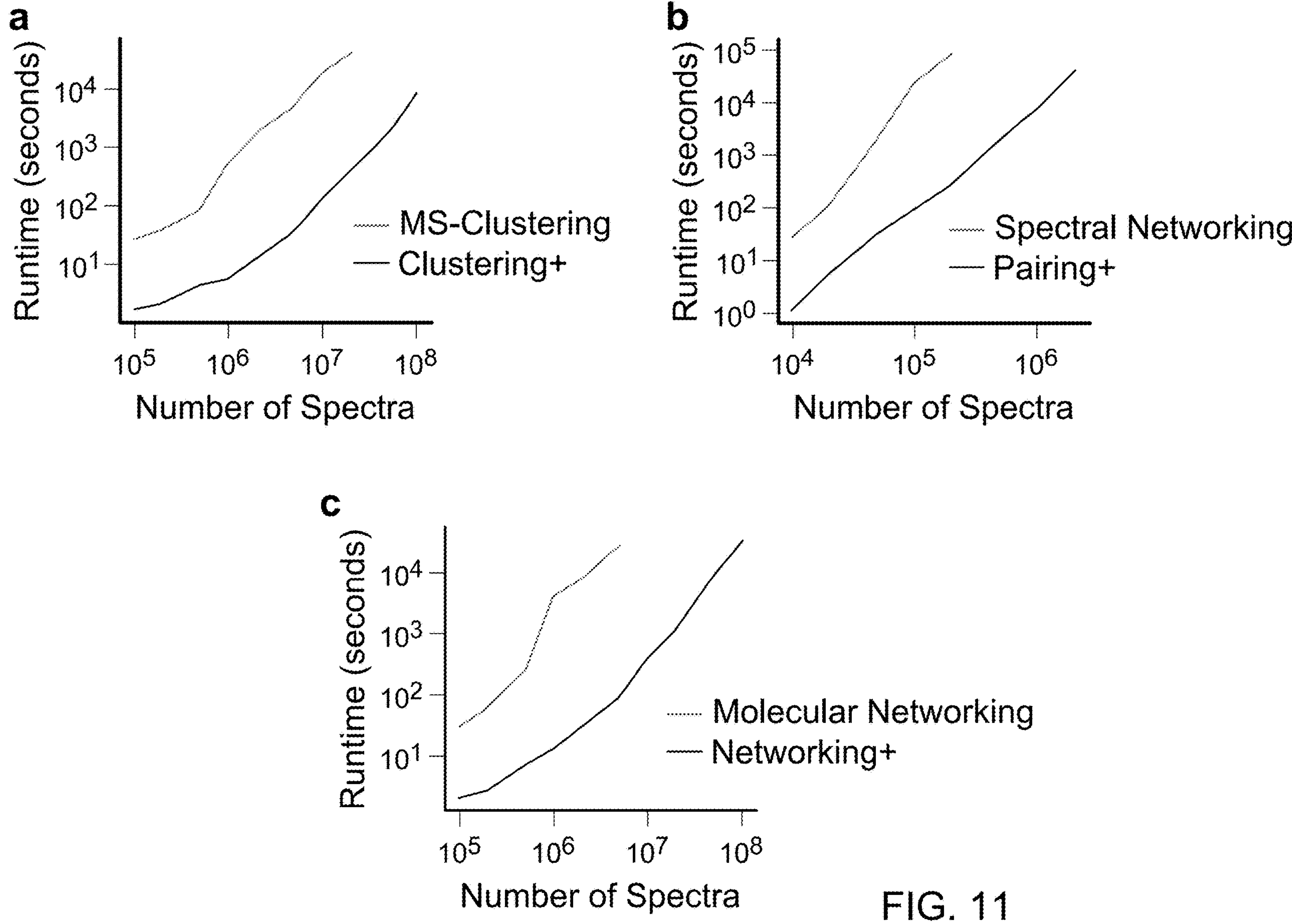
FIG. 11 shows graphs.

FIG. 11 shows graphs. Graph a) shows clustering+ is over two orders of magnitude faster than MS-Clustering. Graph b) shows pairing+ is over two magnitudes faster than Spectral and Networking. Graph c) shows networking+ is over two magnitudes faster than Molecular Networking.

Lanthipeptides are a biologically important class of natural products that include antibiotics30, antifungals31, antivirals32, and antinociceptives33. Lanthipeptides are structurally defined by the thioether amino acids lanthionine, methyllanthionine and labionin. Lanthionine and methyllanthionine are introduced by dehydration of a serine or threonine to generate a dehydroalanine or dehydrobutyrine and addition of a cysteine thiol, catalyzed by a dehydratase and a cyclase, respectively34. During lanthipeptide biosynthesis,

TABLE 5

Benchmarking MASST+ search.

| Method | Mode | # Queries | Dataset | DB Size | Search Time (s)* | Search Memory (kb)* | # IDs** |
|---|---|---|---|---|---|---|---|
| MASST | exact | 10 | MSV000078787 | 5,433 | 0.41 (0.15) | 50,517 (151,552) | 10 |
| MASST+ | exact | 10 | MSV000078787 | 5,433 | 0.13 (0.08) | 0 (0) | 10 |
| MASST | analog | 10 | MSV000078787 | 5,433 | 0.61 (0.22) | 40,604 (121,811) | 16 |
| MASST+ | analog | 10 | MSV000078787 | 5,433 | 0.14 (0.04) | 0 (0) | 16 |
| MASST | exact | 10 | Clustered GNPS | 83,131,248 | 2,090 (582) | 952,692 (88,013) | 49 |
| MASST+ | exact | 10 | Clustered GNPS | 83,131,248 | 8.6 (2.6) | 24,259 (72,778) | 49 |
| MASST | analog | 10 | Clustered GNPS | 83,131,248 | 2,949 (722) | 1,180,383 (47,687) | 2,175 |
| MASST+ | analog | 10 | Clustered GNPS | 83,131,248 | 15 (7) | 159,102 (215,971) | 2,175 |
| MASST | exact | 10 | Entire GNPS | 717,395,473 | N/A | N/A | N/A |
| MASST+ | exact | 10 | Entire GNPS | 717,395,473 | 2,589 (846) | 21,297,193 (6,127,544) | 171 |
| MASST | analog | 10 | Entire GNPS | 717,395,473 | N/A | N/A | N/A |

For all queries, MSV000078787 (5.4k spectra), clustered GNPS (83.1M spectra), or entire GNPS (717.4M spectra) are used as the reference database. Search time, search memory consumption, and number of identifications are shown. For MSV000078787, clustered GNPS, and entire GNPS, MASST+ is two orders of magnitude faster than MASST while achieving the same or better memory consumption. MASST search did not yield results for entire in a reasonable time frame (three days threshold). In other cases, MASST+ reports are identical to MASST.

MASST+ is benchmarked on various GNPS datasets including the dataset MSV000078787 collected on *Streptomyces* cultures (5,433 spectra), clustered GNPS (83,131,248 spectra), and entire GNPS (717,395,473 spectra). While MASST and MASST+ report identical hits, MASST+ is two orders of magnitude faster and as memory efficient (Table 5). In case of the clustered GNPS, MASST+ performs analog search in 54 seconds while MASST takes over one hour. In case of entire GNPS, MASST+ performed analog search in under two hours on average, while MASST search did not finish after three days.

a precursor gene lanA is translated by the ribosome to yield a precursor peptide LanA that consists of a N-terminal leader peptide and a C-terminal core peptide sequence. The core peptide is post-translationally modified by the lanthionine biosynthetic machinery and other enzymes, proteolytically cleaved from the leader peptide to yield the mature lanthipeptide and exported out of the cell by transporters.

Currently methods for high-throughput discovery of lanthipeptides through computational analysis of genomics and metabolomics data suffer from various limitations. Lanthipeptides usually possess specific network motifs that enables mining them in spectral networks. These motifs include mass shifts of −18.01 Da (H2O mass) that corresponds to alternative number of dehydrations, and mass shifts equal to amino acid masses that corresponds to promiscuity in N-terminal leader processing. The system clustered the entire GNPS (717 million scans) using Clustering+, and formed the network using Pairing+. This resulted in 8.5 million clusters, and Y connected components with a total of 17 million edges. In order to mine this network for lanthipeptides, we focused on edges from a subset of 500 *Strepto-*

*myces* cultures with known genomes (Supplementary Table S4). 9,410,802 scans clustered into 354,401 nodes, 6,032 connected components, and 1,265,311 edges. 29,639 nodes are retained that possess the network motif (connected to an edge with mass difference equal to a loss of H2O, NH3, or an amino acid mass). The system mined for nodes with long amino acid sequence tags of length 1235. There are a total of 2,353 nodes with sequence tags of length 12 or longer, and 285 of these nodes are connected to an edge with mass difference equal to H2O or an amino acid loss. The system inspected these nodes using our in-house software algorithm, Seq2RiPP which given a lanthipeptide precursor, generates all the possible candidate molecules considering different cores and various modifications, and then search the candidate molecular structures against mass spectra using Dereplicator36. This strategy identified three known and 14 novel lanthipeptides with p-values below 1e-15 (Table 6).

Table 6 (SEQ ID Nos: 9-25) shows novel and known lanthipeptides discovered by network motif mining. The producer organism, name, sequence, Dereplicator score and p-value, mass and references are shown.

| Organism | name | Sequence | score | p-value | Mass |
|---|---|---|---|---|---|
| *Streptomyces rimosus* NRRL WC-3904 | CHM-1793 | DT-18GHCS-18GVCT-18VLVCT-18VAVC | 21 | 2.50E-36 | 1793.77 |
| *Streptomyces albus* NRRL F-5917 | CHM-1731 | YS-18QVCS-18IVVCNT-18VVICG | 19 | 5.80E-33 | 1731.81 |
| *Streptomyces lavenduligriseus* NRRL ISP-5487 | SapT | YT-18QGCS-18GLCT-18IVICAT-18VVICG | 18 | 1.40E-32 | 2030.95 |
| *Streptomyces* species NBRL S-340 | CHM-1911 | S-18TAGCS-18GLCT-18IIVCAT-18VVICA | 17 | 5.20E-31 | 1911.91 |
| *Streptomyces pathocidini* NRBL B-24287 | CHM-2168 | IT-18S-18IS-18YCT-18PGCT-18SDGGGS-18GCS-18HCC | 16 | 1.60E-26 | 2168.76 |
| *Streptomyces moroccanus* NRRL B-24548 | CHM-2182 | IT-18S-18IS-18YCT-18PGCT-18SEGGGS-18GCS-18HCC | 15 | 2.00E-25 | 2182.78 |
| *Streptomyces cinerochromogenes* NBRC 13822 | CHM-1974 | YT-18EGCS-18GLCT-18ILVCAT-18VVIC | 13 | 9.10E-24 | 1974.91 |
| *Streptomyces hygroscopicus* NRRL ISP-5087 | CHM-1354 | MT-18QVCPVT-18SWHC | 13 | 3.60E-23 | 1354.56 |
| *Streptomyces rimosus* NRRL WC-3874 | CHM-1831 | PSRSSSPGSFPPGST-18PS-18APS-18 | 14 | 1.60E-21 | 1831.85 |
| *Streptomyces albus* NBRC 13041 | CHM-1775 | YS-18QVCS-18IVICNT-18VVICS | 11 | 5.50E-20 | 1775.84 |
| *Streptomyces kanamyceticus* NBRC 13414 | CHM-1748 | IS-18GEES-18CFRT-18CT-18TCS-18LC | 12 | 3.40E-19 | 1748.68 |
| *Streptomyces sulphureus* NRRL B-2195 | CHM-2229 | TEGGGGDS-18SGCS-18GVCT 18IVVCT-18VIVC | 9 | 1.10E-17 | 2229.95 |
| *Streptomyces anulatus* NBRC 12853 | AmfS | T-18GS-18QVS-18LLVCEYSS-18LSVVLCTP | 11 | 2.10E-17 | 2212.09 |

-continued

| Organism | name | Sequence | score | p-value | Mass |
|---|---|---|---|---|---|
| *Streptomyces anulatus* NBRC 13369 | CHM-1669 | C-34LPEPFP + 16TATT-18RVGCD | 11 | 9.50E-17 | 1669.78 |
| *Streptomyces paludis* JCM 33019 | CHM-1635 | S-18GEES 18CFRT-18CT-18T-18CSLC | 11 | 2.30E-16 | 1635.59 |
| *Streptomyces anulatus* NBRC 12861 | CHM-2433 | CRPPSASLCIT-18SDRS-18S-18TGRYLSM | 11 | 3.10E-18 | 2433.14 |
| *Streptomyces brasiliensis* NBRC 101283 | Amfs analog | TGS-18QVS-18VLVCEYS-18S-18LSVVLCTP | 11 | 7.10E-16 | 2198.08 |

Figure 12:
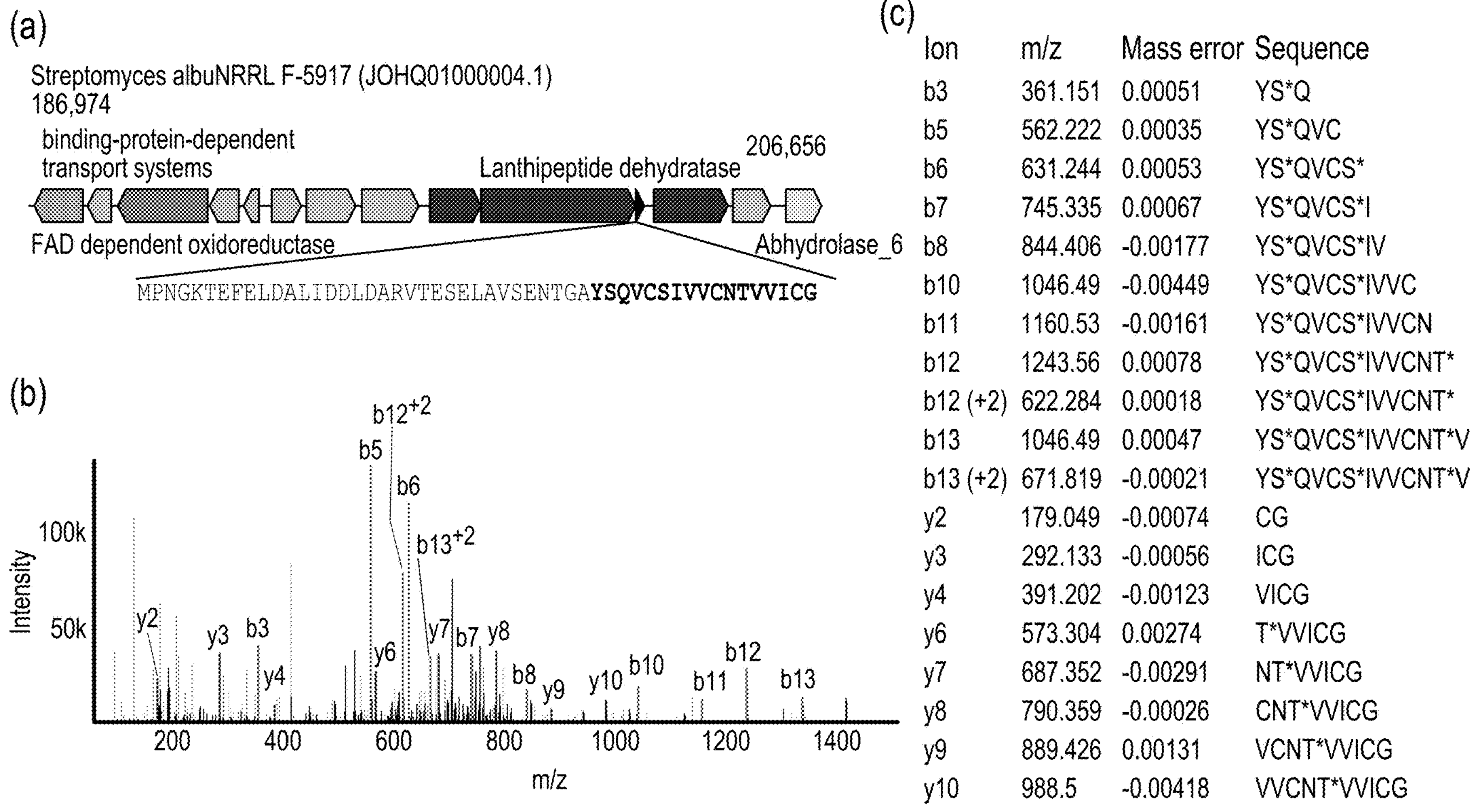
FIG. 12 (SEQ ID NO: 34 and 36-49) shows peptides.

FIG. 12 shows one of the peptides (CHM-1731 from *Streptomyces albus*). Part (a) shows a biosynthetic gene cluster of CHM-1731. Part (b) shows an annotation of peaks in mass spectra of CHM-1731. B-ions (prefix fragmentations) are shown, and γ-ions (suffix fragmentations) are shown. Part (c) shows a mass accuracy of annotations are shown in parts per million (ppm). Stars stand for dehydrated serine/threonine.

An overview of MASST algorithm is now described. In an exact search mode, MASST performs exact search by retrieving the spectra in the database that have the same precursor mass as the query and computing SharedScore between each retrieved spectrum and the query. Analog search is conducted by retrieving all spectra using a large precursor mass tolerance (e.g. 300 Da), and computing the ShiftedScore. To compute these scores, MASST iterates over all the peaks in the query spectrum, and for each peak it explores whether a peak with similar or shifted m/z is present in each database spectrum. Whenever such a peak is present, MASST increments the score between the query and the database spectrum by the product of the intensity of peaks in the query and database spectrum.

MASST+ exact search. Given a query spectrum, MASST+ efficiently searches a database of reference spectra to find similar spectra by creation of an indexing table a data structure which allows rapid retrieval of similar spectra based on the peaks present in the query spectrum. For each precursor mass M and each peak mass p, a list of indices of spectra with precursor M and peak p are stored, along with the intensity of the peaks. In case of exact search, MASST+ iterates through the peaks in the query spectrum, and retrieves the lists corresponding to the peaks and precursor masses within a tolerance threshold of query (e. g. 0.02 Da in case of high-resolution data). The SharedScore is calculated by multiplying and adding up the intensity of each peak in query spectrum and reference spectra.

MASST+ analog search. In case of analog search, MASST+ use a much larger precursor mass tolerance (e. g. 300 Da) and computes ShiftedScore. ShiftedScore takes into account both shared and A-shifted peaks, where A is the mass difference between the query and reference spectra. In analog mode, MASST+ iterates through each peak p in the query spectra with precursor mass M, and scans lists (M', p') where either p=p' (shared scenario) or M−p=M'−p' (shifted scenario). The ShiftedScore is calculated by multiplying and adding up the intensity of shared and shifted peaks in query spectrum and reference spectra (Supplementary Figure S8).

To find structurally related families of small molecules, molecular networking first clusters spectra from identical molecules using MS-Clustering29, and then connects clusters of related molecules using spectral networking28. MS-Clustering puts two spectra in the same cluster if their precursor mass difference is below a threshold (usually 2 Da) and their cosine dot product (a normalized SharedScore) is above a certain threshold (usually 0.7). Then for each cluster, a consensus spectrum is constructed. In spectral networking, two consensus spectra are connected to each other if the shared-shifted cosine score (a normalized ShiftedScore) is above a threshold (usually 0.7).

Networking+ includes two modules, Clustering+ and Pairing+. Clustering+ is implemented using a greedy procedure, wherein each iteration the similarity score between each spectrum and all the existing cluster centers are calculated (initially there are no clusters). To efficiently calculate the similarity score between the spectrum and all clusters, an indexing table similar to MASST+ exact search is constructed and iteratively updated. The indexing table stores the list of all clusters with a specific precursor mass M and peak mass p. Whenever, the highest score between the spectrum and clusters is greater than a threshold, the spectrum is added to the maximal cluster, and its center is updated. If the highest score is below the threshold, then a new cluster is created consisting of the current spectrum (set as the center). This procedure continues till all the spectra are processed.

Pairing+ computes a score similar to MASST+ analog search (Supplementary Figure S8) that accounts for A-shifted and shared peaks for all pairs of input spectra (e.g. cluster centers from clustering+). To do this, it constructs an indexing table similar to MASST+ analog search. Then the table is used to efficiently compute the score between all pairs of spectra.

Figure 13:
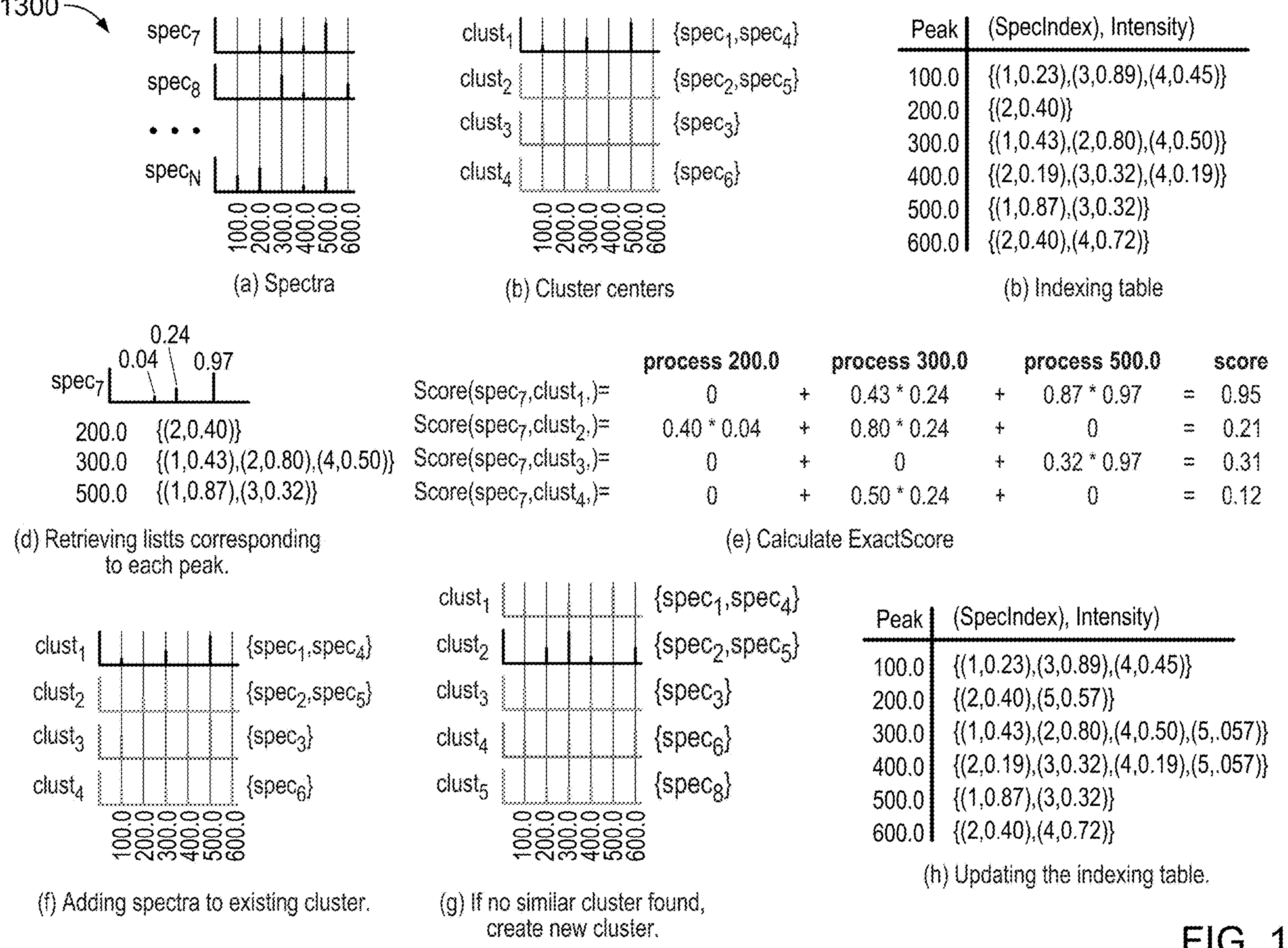
FIG. 13 shows a process.

FIG. 13 shows process 1300. At step (a), given a spectral dataset, Clustering+ performs the following steps. Starting from (b) the existing cluster centers, (c) an indexing table is constructed. Then, (d) lists corresponding to each peak in the spectrum are retrieved from the indexing table, and (e) the ExactScore between query spectra and each cluster is calculated by adding up the product of intensity of peaks in query and the cluster. (f) If the maximum score is higher than a threshold, the spectra is added to the maximal cluster. (g) Otherwise, a new cluster is created, with the spectra as its center, and then (h) the indexing table is updated.

FIG. 14 shows a process 1400. Starting from (a) reference spectra, Pairing+ first (b) constructs the indexing table. Then (c) lists corresponding to each peak are retrieved from the indexing table, and (d) pairwise ShiftedScore between each pair of spectra are calculated. Here, only shared peaks are highlighted for the simplicity. Then (e) a similarity matrix is formed between all pairs of spectra, and (f) molecular network is formed by retaining all the pairs with Shifted-Score exceeding a threshold (e. g. 0.7).

Figure 15:
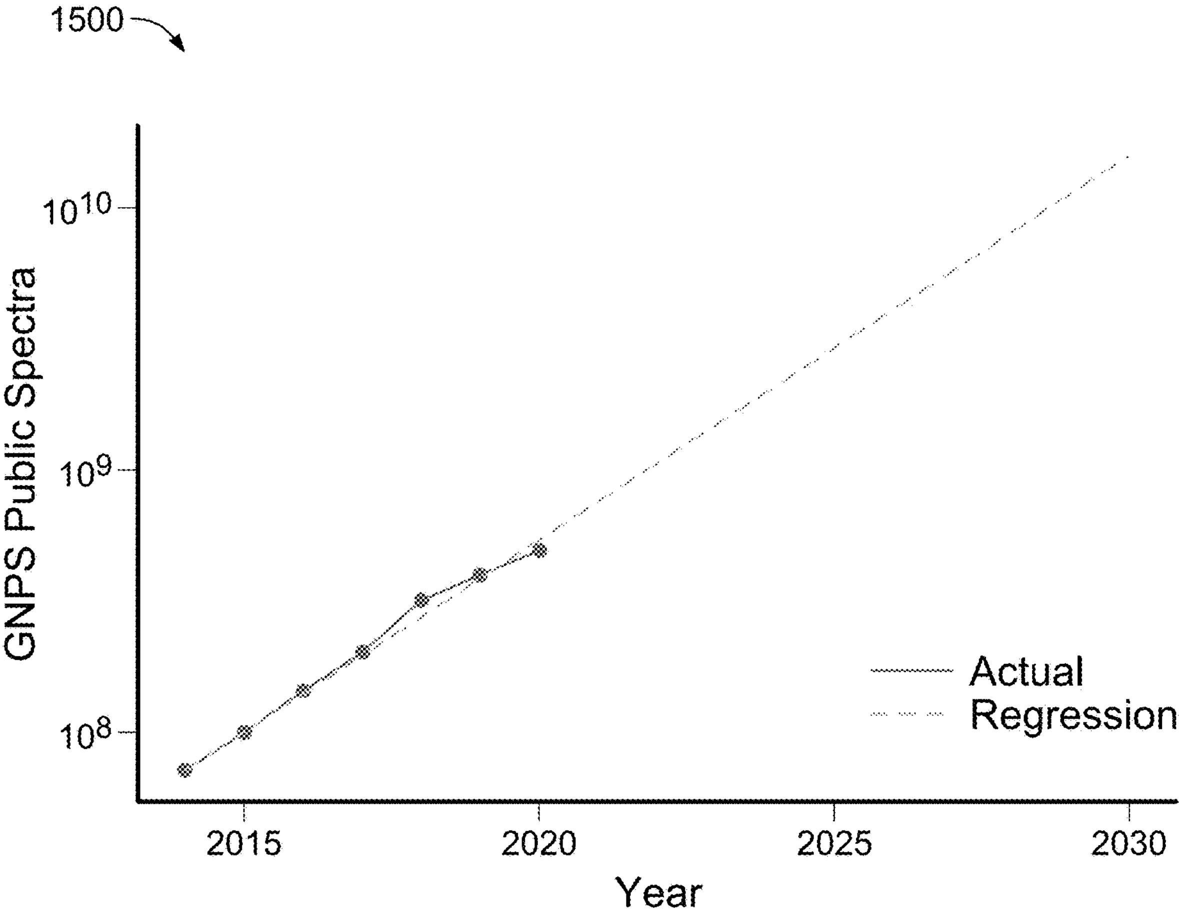
FIG. 15 shows a graph

FIG. 15 shows a graph 1500 showing a growth of the GNPS database size since 2015. The size of the public GNPS database is projected to contain a billion spectra by the year 2026.

Figure 16:
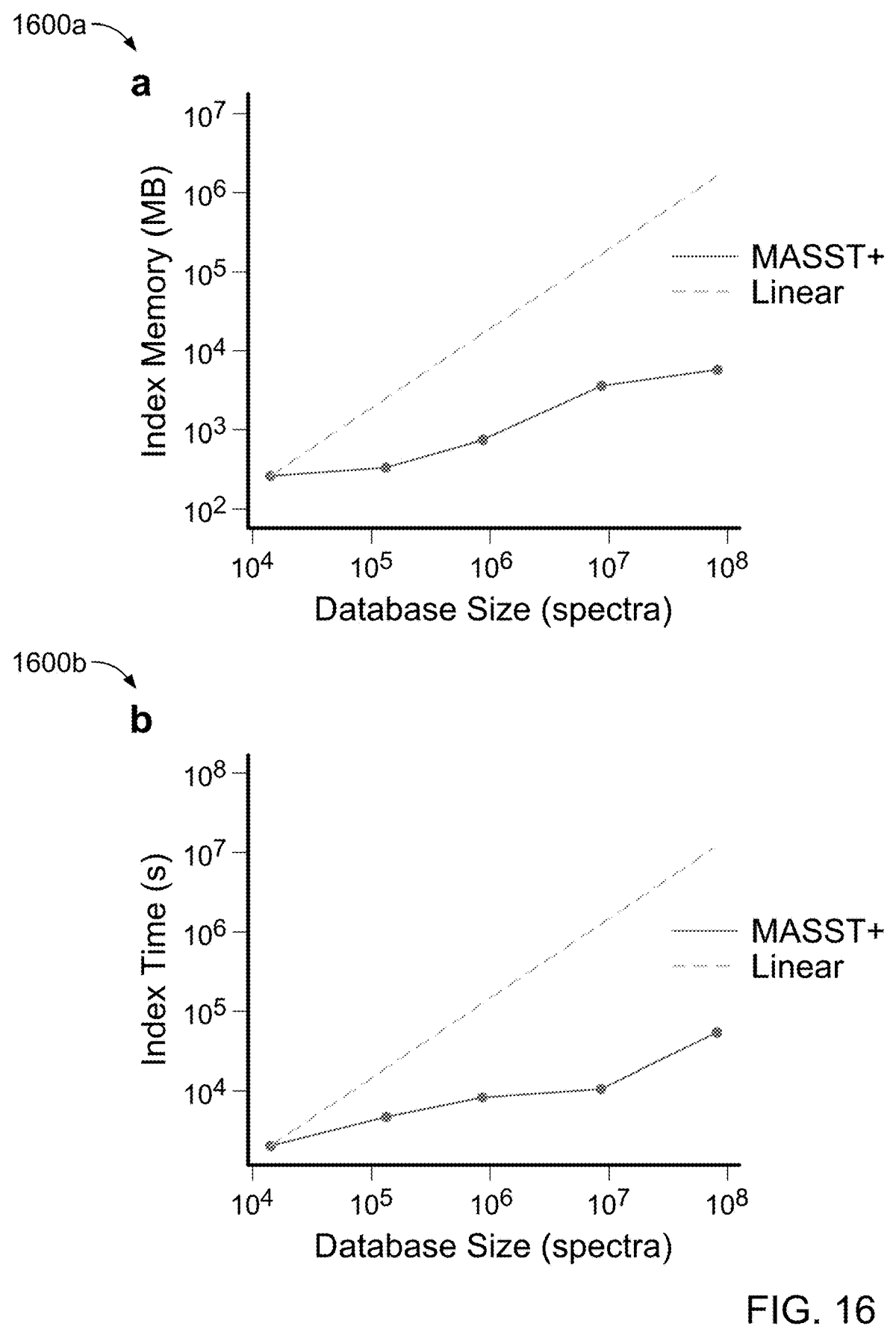

FIG. 16 shows graphs **1600*a* and 1600*b*. MASST+ indexing memory is at graph 1600*a*. Run time is shown at graph 1600*b*** as database size grows. Both runtime and memory grow sub-linearly (linear growth shown on dashed line). On the clustered GNPS, MASST+ requires eight hours of and eight gigabytes of memory. Note that indexing need only be performed once for each database.

Figure 17:
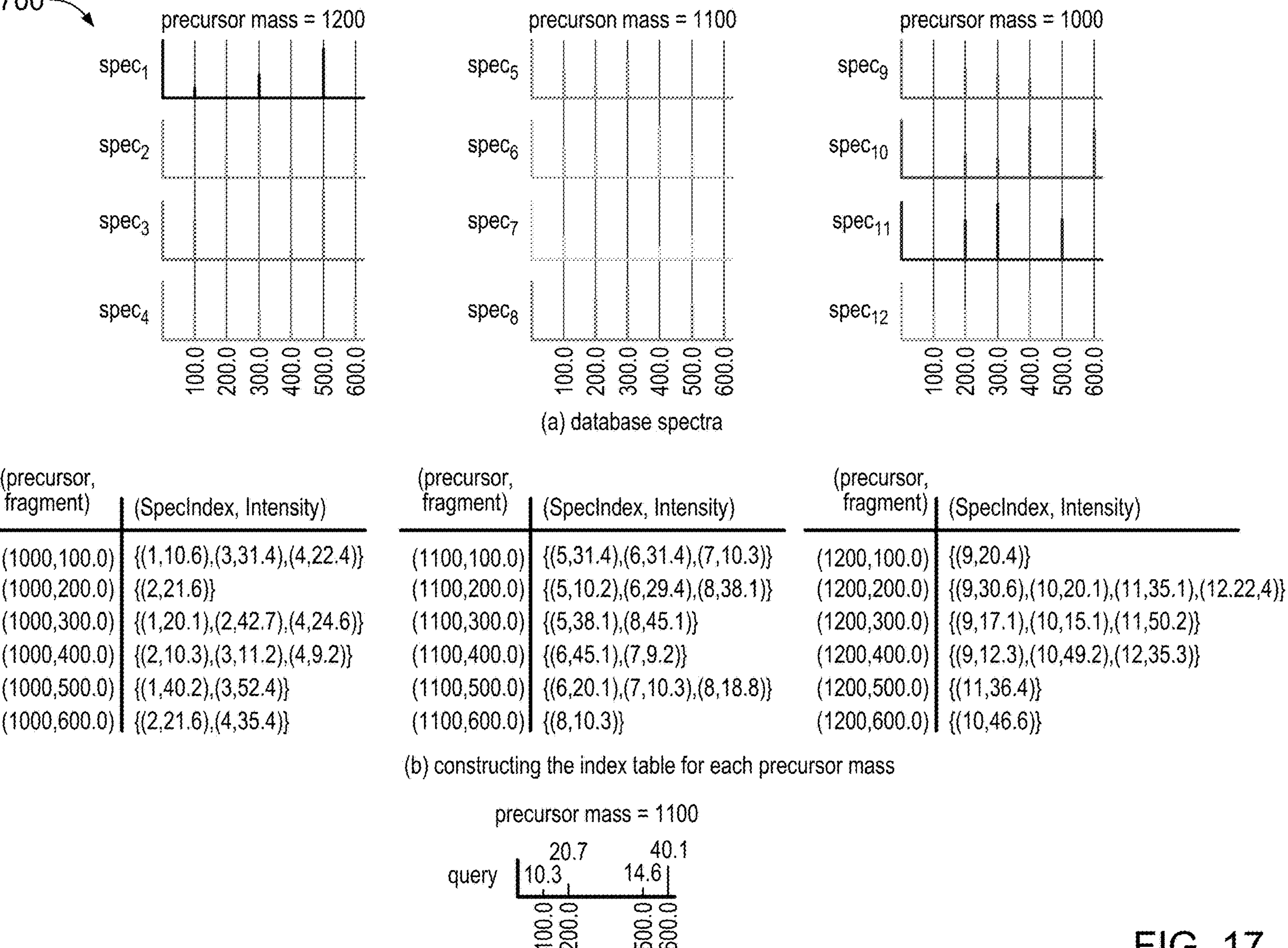
FIG. 17 shows a process for MASST+ analog search.

FIG. 17 shows a process 1700 for MASST+ analog search. At step (a) given a reference mass spectral database, MASST+ (b) constructs multiple indexing tables, each corresponding to spectra of a certain precursor mass. Each indexing table contains rows corresponding to a specific precursor mass, and each row contains a list of spectra in which a specific fragment peak is present, along with the intensity of the fragment peak in those spectra. Then (c) given a query spectrum, MASST+ iterates through each indexing table, and retrieves rows correspond to query peaks and A-shifted version of query peaks, where A is the precursor mass difference between the query spectrum and the indexing table. Then (d) MASST+ computes the ShiftedScore by adding up the product of the intensity of query peaks and database peaks.

Figure 18:
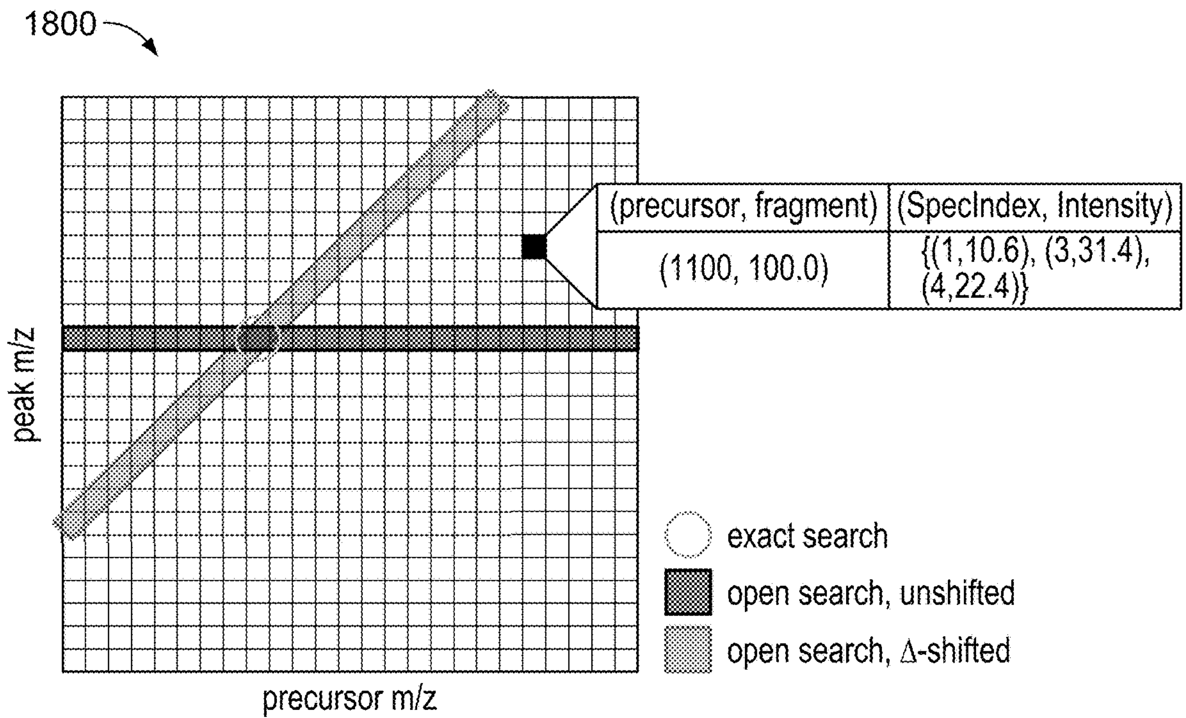
FIG. 18 shows an image of MASST+ Index Visualization.

FIG. 18 shows an image 1800 of MASST+ Index Visualization. The MASST+ indexing table corresponds a two-dimensional grid, with precursor mass on the x-axis and peak mass on the y-axis. Each database peak is inserted into a list corresponding to a specific location in the grid, determined by the peak mass and the precursor mass. In exact search, for each query peak only the list in a single cell will be retrieved (highlighted with green circle). For analog search, red cells (corresponding the shared peaks) and blue cells (corresponding to A-shifted peaks) are retrieved.

Table 7 shows data for Benchmarking Clustering+ and MS-Clustering runtimes for various sizes of spectral datasets (runtimes are shown in seconds). The cases where the search did not yield results within 24 hours are shown with N/A.

| Dataset size | Clustering+ | MS-Clustering |
|---|---|---|
| 100,000 | 1.7 | 27 |
| 200,000 | 2.2 | 40 |
| 500,00 | 4.4 | 86 |
| 1,000,000 | 5.7 | 529 |
| 2,000,000 | 13.1 | 1818 |
| 5,000,000 | 36.9 | 3077 |
| 10,000,000 | 133.6 | 19696 |
| 20,000,000 | 376.0 | 41074 |
| 50,000,000 | 1791.7 | N/A |
| 100,000,000 | | N/A |

Table 8 shows data for Benchmarking Pairing+ and Spectral Networking runtimes for various sizes of spectral datasets (runtimes are shown in seconds). The cases where the search did not yield results within 24 hours are shown with N/A.

| Dataset size | Pairing+ | Spectral Networking |
|---|---|---|
| 10,000 | 1.14 | 27 |
| 20,000 | 5.62 | 111 |
| 30,000 | 32.3 | 2072 |
| 100,000 | 91.8 | 23808 |
| 200,000 | 278.3 | 83101 |
| 500,000 | 2018.8 | N/A |
| 1,000,000 | 7900.2 | N/A |
| 2,000,000 | 39737 | N/A |

Table 9 shows a comparison of Molecular Networking and Molecular Networking+ runtimes for various sizes of spectral datasets (runtimes are shown in seconds). The cases where the search did not yield results within 24 hours are shown with N/A.

| Dataset size | Networking+ | Molecular Networking |
|---|---|---|
| 100,000 | 2.075523 | 30 |
| 200,000 | 2.793048 | 62 |
| 500,00 | 7.23322 | 247 |
| 1,000,000 | 13.24785 | 4041 |
| 2,000,000 | 31.0602 | 8067 |
| 5,000,000 | 93.5747 | 28117 |
| 10,000,000 | 387.022 | N/A |
| 20,000,000 | 1156.634 | N/A |
| 50,000,000 | 8718.59 | N/A |
| 100,000,000 | | N/A |

Table 10 shows a List of MassIVE datasets mined for lanthipeptides.

| MassIVE ID | # strain | media |
|---|---|---|
| MSV000090476 | 60 | ISP 2 |
| MISV000090473 | 60 | ISF-4 |
| MISV000090472 | 60 | NSG |
| ISV000090471 | 60 | TSA |
| MSV000090457 | 60 | Czapek |
| MSV000089818 | 264 | ISP-4 |
| MSV000089817 | 264 | TSA |
| MSV000089816 | 264 | Czapek |
| MSV000089813 | 264 | NSG |
| MSV000089813 | 264 | ISP-2 |
| MSV000088816 | 176 | ISP-4 |
| MSV000088801 | 176 | TSA |
| MSV000088800 | 176 | Czapek |
| MSV000088764 | 176 | NSG |
| MSV000088763 | 176 | ISP-2 |

Table 11 shows a number of nodes for different tag lengths in the network of microbial datasets with known genomes from GNPS. The second column shows the total number of nodes, while the third columns show the nodes that possess the network motif.

| Tag length | # nodes | overlap |
|---|---|---|
| 6 | 32449 | 4008 |
| 7 | 20474 | 2472 |
| 8 | 12957 | 1544 |
| 9 | 8337 | 1013 |
| 10 | 5400 | 647 |
| 11 | 3607 | 441 |
| 12 | 2353 | 285 |

-continued

| Tag length | # nodes | overlap |
|---|---|---|
| 13 | 1580 | 193 |
| 14 | 1077 | 135 |
| 15 | 717 | 86 |
| 16 | 506 | 60 |
| 17 | 344 | 39 |

Pathogen-Oriented Platform for Large-Scale Discovery of Drug-Like Natural Products Discovers Novel Antifungal Targeting Urgent-Threat Drug-Resistant Candidiasis.

More than half of all drugs approved by the Food and Drug Administration are derived from bioactive natural products. Natural products are produced through complex biosynthetic pathways that are optimized through millions of years of natural selection that lead to a vast structural diversity. Due to their massive chemical and functional diversity, natural products are especially an excellent source for finding new treatments for orphan and drug-resistant pathogens. However, their complex biosynthesis and structure present a significant challenge for the discovery efforts in this field and curbed the pace of natural product discovery in the past decades. The urgent demand for new drugs targeting the orphan cancer types and the emerging drug-resistant bacterial, viral, and fungal infections, highlights the need for new discovery platforms that can target such pathogens. In this study we focused on non-ribosomal peptides (NRPs) that include many FDA-approved anti-infective and anti-cancer drugs.

Natural products discovery in omics era. High-throughput omics technologies revolutionized the state of natural product analyses and created new opportunities for drug discovery. Tandem mass spectrometry (high-throughput metabolomics) proved itself as an inexpensive, scalable, and sensitive technology to rapidly analyze small molecules in microbial isolates and (environmental/host-oriented) communities. Currently, public repositories such as Global Natural Product Social (GNPS) molecular networking contain tens of thousands of datasets representing thousands of unknown microbial natural products. On the other hand, advances in (meta) genome sequencing enabled the sequencing of thousands of natural-product-producing biosynthetic gene clusters (BGCs, the chromosomally adjacent set of genes synthesizing microbial natural products), which are available through National Center for Biotechnology Information (NCBI) and the Joint Genome Institute (JGI) repositories. However, only 640 out of 500,000 BGCs in public genome assemblies are connected to their small molecules. Therefore, there exists a large gap between the number of sequenced BGCs and the number of BGCs with characterized natural product molecules that represent a goldmine for discovering novel bioactive molecules.

Challenges of genome mining methods for discovering novel natural products. Currently, several end-to-end discovery platforms exist that acquire genomics data for discovering novel natural product molecules. These technologies all tend to first leverage genomic data rather than analytical chemistry to identify BGCs. Genome mining methods use information from known BGCs with already characterized molecules, to predict the structure of the molecules encoded by novel BGCs. Currently, various methods exist for identifying the BGCs from genomic data and predicting the potential structures of their encoding NRPs. However, the existing genome mining methods are plagued by low accuracy and resulted in less than 4% accuracy for NRP prediction (using Tanimoto coefficient threshold >90% between true and predicted structures). Additionally, large-scale genome mining experiments often identify thousands of BGCs where each BGC can encode various biosynthesis pathways, leading to millions of potential hypothetical molecules. Since only a very small portion of these potential molecules are the bioactive NRPs that are secreted by the organisms, additional analyses are necessary to find the needle in this haystack. Therefore, methods that only rely on genomics data often recruit wet-lab-intensive, cumbersome, costly, and one-off methods that usually are time- and labor-intensive8. In the past decade, several end-to-end platforms have been introduced for discovered novel NRP molecules that are secreted by the organism.

Discovering novel peptides using peptide synthesis. Multiple methods use genome mining for finding BGCs with no tailoring modifications and then synthesizing the peptides predicted by genome mining. This approach is especially useful in the case of BGCs that remain silent in laboratory conditions. However, it requires perfect prediction of the final NRPs from the genomic data therefore cannot be applied to NRPs with unknown tailoring modifications or novel chemistry that cannot be predicted from the genome.

Discovering novel natural products using heterologous expression. In the past few years, several end-to-end discovery platforms have been introduced for characterizing the secreted novel molecules using heterologous expression techniques. These platforms start by selecting a small pool of sequenced BGCs and then expressing them in a host organisms using synthetic biology, followed by isolation and nuclear magnetic resonance (NMR) spectroscopy. While this method allows one to discover novel molecules even when the genome-driven predictions are not perfect, but it faces multiple challenges that hinder its utility for large-scale novel discovery. Although many efforts have been made to develop optimized heterologous hosts for BGC expression, there is still no host that can work for molecules from various producers. Hence, the optimal host for each BGC should be explored using trial and error. Additionally, many unknown BGCs are still silent in heterologous hosts, requiring extensive genetic engineering efforts for their activation. Furthermore, due to large sizes of NRP BGCs spanning 10-200 kb, cloning them is often a technically challenging and time-consuming process, thus forming a major bottleneck in the overall process of heterologous expression. Due to these challenges, heterologous expression for natural product discovery is currently not suitable for large scale discovery of novel molecules.

Existing metabolomics-based methods for NRP discovery. Some of the existing approaches leverage metabolomics data from microbial samples to characterize novel molecules. Goering et al introduced a discovery platform that focuses on analyzing the co-occurrence of isolated microbes and molecules. However, this approach does not leverage the structural information provided by the biosynthetic gene clusters in an automated fashion and is limited to cases when the encoding BGC and molecules co-occur in multiple organisms.

Limitations of NRPminer. In addition to the methods focusing on correlations, metabolomics data can be used to directly characterize the novel molecules by searching the spectral datasets against the genome-driven hypothetical structures. NRPminer4, the only existing method for scalable NRP characterization uses metabolomics data. NRPminer suffers from several limitations and cannot deliver pathogen-specific drug-lead discovery. Firstly, NRPminer relies on antiSMASH for genome mining, leading to low accuracy (<1% accuracy in predicting NRP structures with Tanimoto similarity threshold %90 between true and predicted structures). Moreover, NRPminer models NRPs as strings of amino acids (aa's), significantly limiting its power in handling more complex fragmentation patterns beyond amide bonds in mass spectrometry and reducing sensitivity. Furthermore, while many drug-like NRPs are extensively modified, NRPminer does not support post-assembly modifications. Additionally, NRPminer cannot predict the bioactivity of the identified molecules. Finally, NRPminer is currently slow and cannot search billions of spectra that are present in public datasets or are often generated in large-scale microbial projects. Due to these challenges, NRPminer was not able to find any novel molecules active against any human pathogens.

In silico prediction of natural products' bioactivity from BGCs. Finding molecules active against certain pathogens is an urgent need. Therefore, assessing bioactivity of the identified molecules is an essential step in discovery efforts. However, since the experimental assessment of the bioactivity of the natural products encoded by all sequenced BGCs is infeasible, methods for predicting the activity of natural products from BGCs are necessary. Existing machine learning methods rely on genomic data and the list of enzymes on a given BGC. These methods use BGCs with already characterized molecules as training data. However, since there is a limited number of natural products that are connected to their BGCs, relying only on genomic features result in poor performance (<1% true positives at 10% false positive rate across broad antifungal, antibiotic, and anti-cancer outcomes). Furthermore, these methods cannot predict bioactivity at pathogen-level, rendering them ineffective for finding molecules active against specific pathogens of interest. Finally, these approaches cannot predict the potential mode of action (MOA), and it is currently not possible to identify the molecules with known mode of actions, to clear the way for focusing on novel MOAs.

NPDiscover platform for discovering bioactive NRPs. To address these challenges, we developed a new platform to identify novel bioactive NRPs. NPDiscover uses novel algorithms to accurately predict the hypothetical structures of mature NRPs, improving the state-of-the-art by three folds. NPDiscover is the first scalable method that can incorporate tailoring enzymes present in the BGCs. NPDiscover uses a novel clustering approach to combinatorically apply the identified tailoring modifications and efficiently predicts possible mature structures. Additionally, NPDiscover is the first tool that can identify active NRPs with a novel chemistry (for example a novel monomer or a novel tailoring modification) by rapidly analyzing mass shifts in the spectral matches across billions of spectra, using a variable search strategy. Afterwards, NPDiscover uses a new Markov Chain Monte Carlo strategy to efficiently calculate statistical significance of the identified NRP-spectrum matches. It then uses a machine learning method that utilizes structural features of statistically significant predictions to predict their potential bioactivity and MOA. After these computational analyses, NPDiscover provides detailed information for each identified NRP, including molecular mass, retention time, structural and activity predictions, predicted MOA, and genomic loci. This information allows the investigators to directly isolate and purify the molecules of interest from using a mass-guided HPLC-purification approach.

Discovery of novel antifungal NRP that is active against urgent-thread multidrug-resistant fungal pathogens. The system demonstrated the power of NPDiscover in identifying novel NRPs that are active against drug-resistant and orphan pathogens, we searched datasets from 119 Actinobacteria strains. Our downstream experimental analyses confirmed the structure and bioactivity against drug-resistant *Candida auris* predicted by NPDiscover. Moreover, as predicted by NPDiscover, the molecule showed no toxicity against healthy human cells. *Candida auris* is an urgent drug-resistant fungal threat due to its rapid global emergence, high mortality, and persistent transmissions. Infection with *Candida auris* is associated with high mortality rates, and it is often resistant to multiple classes of antifungal drugs, currently leaving patients with only highly toxic treatment options such as amphotericin. Despite this rapid global spread and resistance, no new antifungal agent has been introduced for this disease since its emergence. These findings signify NPDiscover as a large-scale screening and discovery NRP discovery platform of drug-leads for urgent-threat pathogens and/or orphan diseases.

Figure 19:
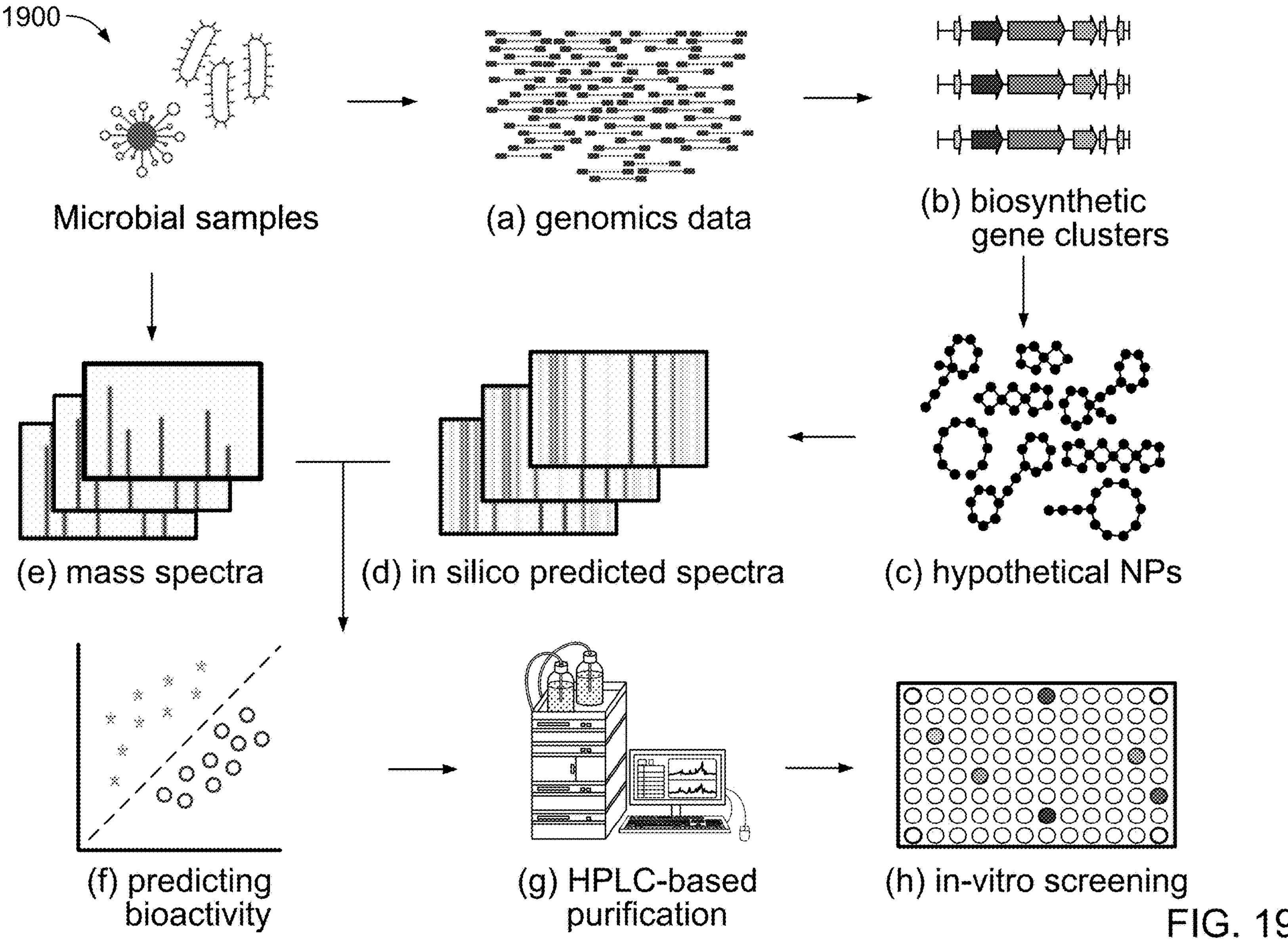
FIG. 19 shows a process for a NPDiscover pipeline.

A machine-learning-empowered platform NPDiscover is generated for discovering novel NRP molecules active against a given set of pathogens of interest. As shown in FIG. 19, a process for a NPDiscover pipeline starts from microbial samples, first, (a) genomic DNA is sequenced, and (b) natural product BGCs are extracted. Then (c) Hypothetical chemical structures produced by BGCs are predicted, and (d) their fragmentation pattern in mass spectrometry is predicted. (e) Mass spectra are collected from crude extracts of microbial cultures, and (f) mass spectra are searched against predicted spectra to identify correct structure of natural products. Then the bioactivities of these natural products are predicted. (g) Bioactive molecules with novel chemistries are purified using HPLC-based methods, and (h) their bioactivities and toxicities are characterized.

NPDiscover accurately predicts the hypothetical 2D structure of mature NRPs from their BGCs. NPDiscover starts by automatically annotating the BGCs. It then finds the core NRP products using novel machine learning methods that predict the specificity of amino acids based on identified domains on the BGCs. It then applies enzymatic tailoring modifications (post-assembly modifications) upon the reconstructed core NRPs. We conducted literature mining for 570 NRPs with known gene clusters reported in the MIBiG database30. For each such modification, we aligned all the homologous enzymes (from different gene clusters) that were predicted to be responsible for that modification and constructed a Hidden Markov Model profile. We further stored each such modification in a computer-readable format that includes a chemical motif where the modification occurs (i.e. reaction sites), along with a series of node and bond alterations that tailor the motif to its mature structure.

Using the collected modifications, NPDiscover starts by (i) finding all the graph isomorphisms between the motif of modifications for which the corresponding enzymes are present in the BGC and the generated core NRPs using Ullman algorithm31. Since, NRP BGCs with tailoring enzymes and promiscuous amino can lead to many biosynthesis pathways, NPDiscover uses a novel clustering algorithm to efficiently predict the final structures. After finding the modification enzymes, NPDiscover it clusters the modifications based on the position of the motif on the core NRPs. For each cluster, we use a representative motif to curb the total number of potential molecules without any accuracy, (iii) after this selection, the system iteratively goes through each of these motif sites and consider whether they are altered or not. To evaluate the performance of this novel clustering-based approach in NPDiscover, NRP BGCs in MiBIG database are analyzed using NPDiscover.

Figure 22:
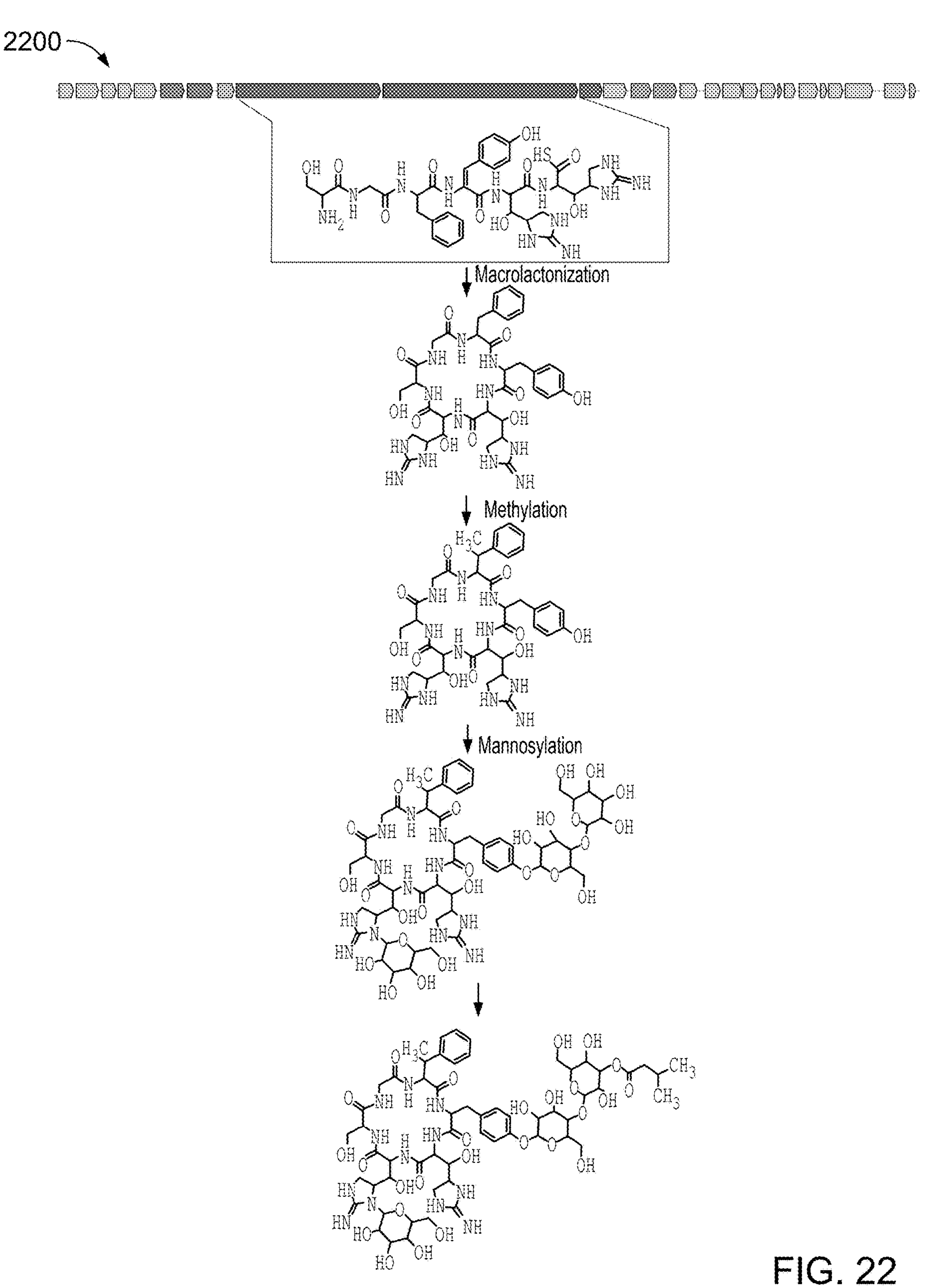
Figure 22:
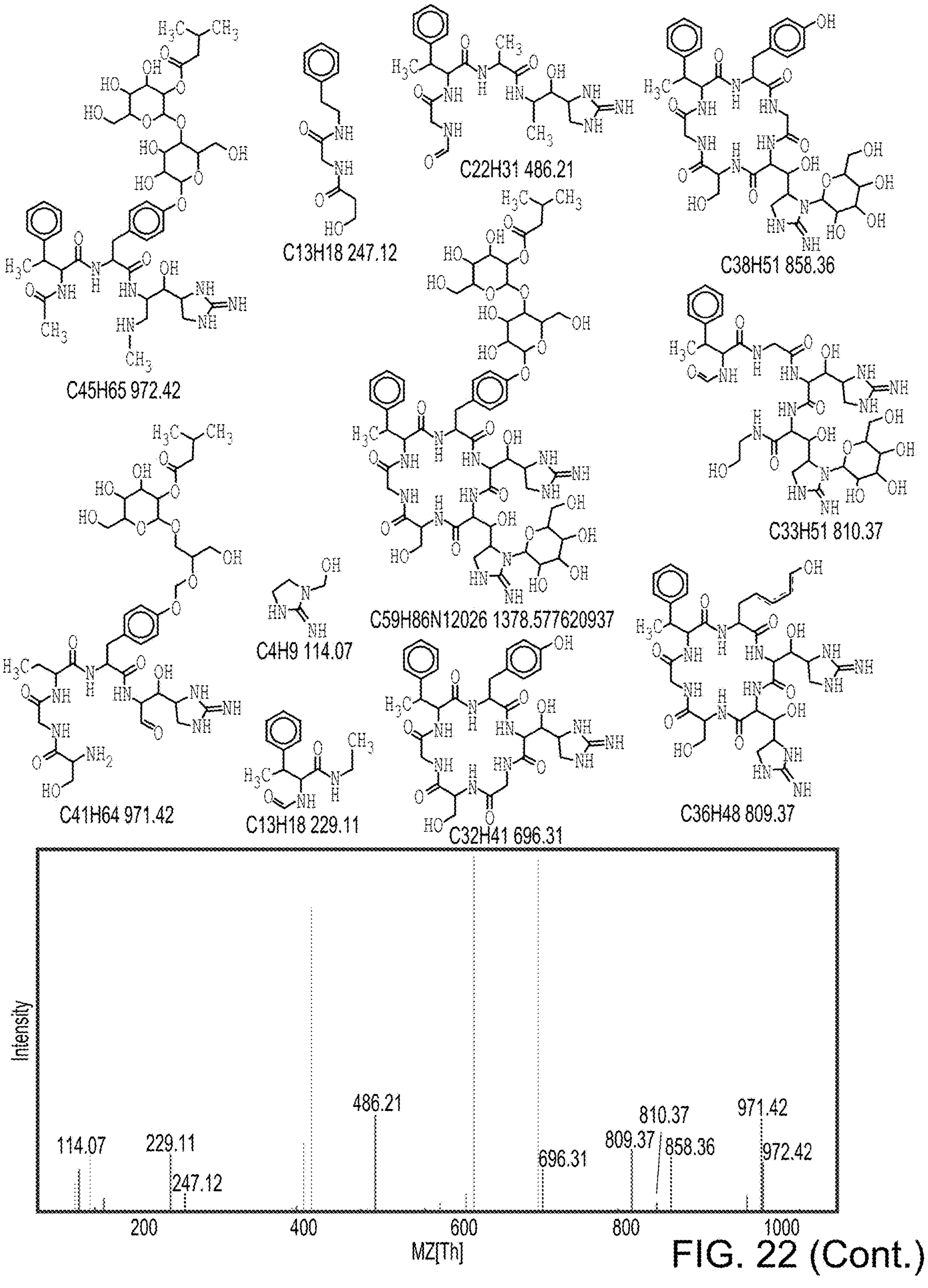

To evaluate the performance of NPDiscover for predicting hypothetical NRP structures from NRP BGCs, its genome mining module is compared against antiSMASH and PRISM methods using all NRP BGCs in MiBIG database that resulted in at least one structural prediction by all three programs. Then, for each BGC in this database, we calculated the maximum Tanimoto similarity coefficient between the true and predicted structures. FIG. 22 shows the number of NRP structures predicted by each method at different Tanimoto similarity coefficients. NPDiscover was able to reconstruct 18 molecules out of 145 with Tanimoto coefficient above 90%. In contrast, the PRISM only predicted six NRPs and antiSMASH failed to predict any NRPs, at this threshold.

Figure 20:
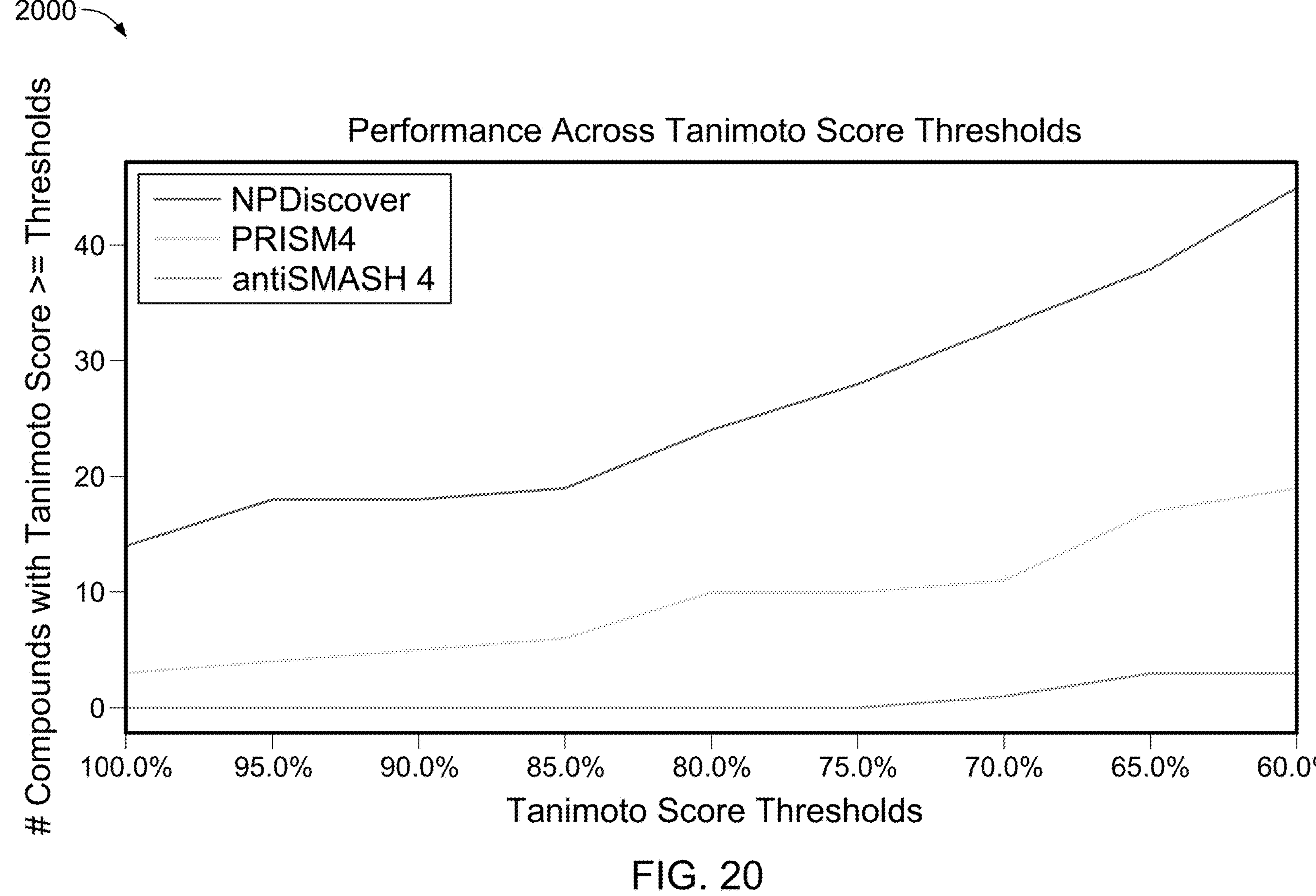
FIG. 20 shows a graph comparing accuracy levels in predicting of NRP structure from NRP BGCs by NPDiscover, PRISM, and antiSMASH.

FIG. 20 shows a graph 2000 comparing accuracy levels in predicting of NRP structure from NRP BGCs by NPDiscover, PRISM, and antiSMASH. The plot shows the distribution of the Tanimoto similarity coefficients between true and predicted structures for the subset of MiBIG NRP BGCs with at least one predicted structure by all three programs (total 145 BGCs). At each point x on X-axis, the Y-axis shows the total number of NRP BGCs for which the maximum Tanimoto coefficient between true and predicted structure exceeds x. NPDiscover shows a three-fold improvement in the number of 2D structures compared to the state-of-the-art (PRISM4) at Tanimoto coefficient threshold 90%.

NPDiscover accurately identifies the mature NRP metabolites with the scalable search of metabolomics data against predicted 2D structures.

NPDiscover's performance is evaluated for matching spectral and genomic data for NRP identification against NRPminer on a dataset of 509 Actinobacteria strains (referred to as Actinobacteria dataset) whose genomics and metabolomics data were available via NCBI and GNPS, respectively. Table 12 shows the list of all known NRP families identified in the metabolomics dataset using the molDiscovery search against PubChem in which BGCs were also identified by antiSMASH analysis against MiBIG BGCs. This table shows that out of six known NRP-BGC pairs in this dataset, NPDiscover, identified five of them correctly without any prior knowledge of them using P-value threshold $10^{-15}$. NPDiscover failed to identify any of the molecules in Actinomycin NRP family due to its failure in identifying one of the tailoring modifications necessary for predicting its structure (the enzyme involved in this modification was not present in our list of HMM profiles). In contrast, aside from surugamide, NRPminer failed to predict any of the remaining five molecules due to its inability to predict the tailoring modifications.

Table 12 shows six NRP families identified in Actinobacteria dataset. For each NRP family, the identified producer organism and the MiBIG BGC ID is listed. Column "P-value" shows the lowest P-value generated by NPDiscover among all NRP-spectrum matches for that family (without any prior knowledge of them) and "Charge" shows the charge of the spectrum resulting in the listed P-value. Column "Tanimoto" shows the Tanimoto similarity coefficient between the true and the NPDiscover-predicted structure that resulted in the listed P-value. NPDiscover failed to identify any of the NRPs in Actinomycin family.

| NRP family | Identified Organism | BGC ID | Tanimoto | Charge | P-value |
|---|---|---|---|---|---|
| Mannopeptomycin | Sueptomyces lydicus ISP-5461 | BGC0000388 | 1 | 2 | $1.4 \times 10^{-17}$ |
| CDA | Streptomyces coelescens B-12348 | BGC0000315 | 1 | 1 | $1.2 \times 10^{-20}$ |
| Cyclomaria | Streptomyces speibonne B-24240 | BGC0000333 | 1 | 1 | $2.0 \times 10^{-29}$ |
| Surgsmaide | Streptomyces diastaticus NBRC 13412 | BGC0001792 | 1 | 1 | $2.1 \times 10^{-68}$ |
| griseobactin | Streptomyces sp. NRRL WC3703 | BGC0000368 | 0.97 | 2 | $2.4 \times 10^{-28}$ |
| echinomycia | Streptomyces sp. NRRL B-3362 | BGC0000296 | — | — | — |

Figure 21:
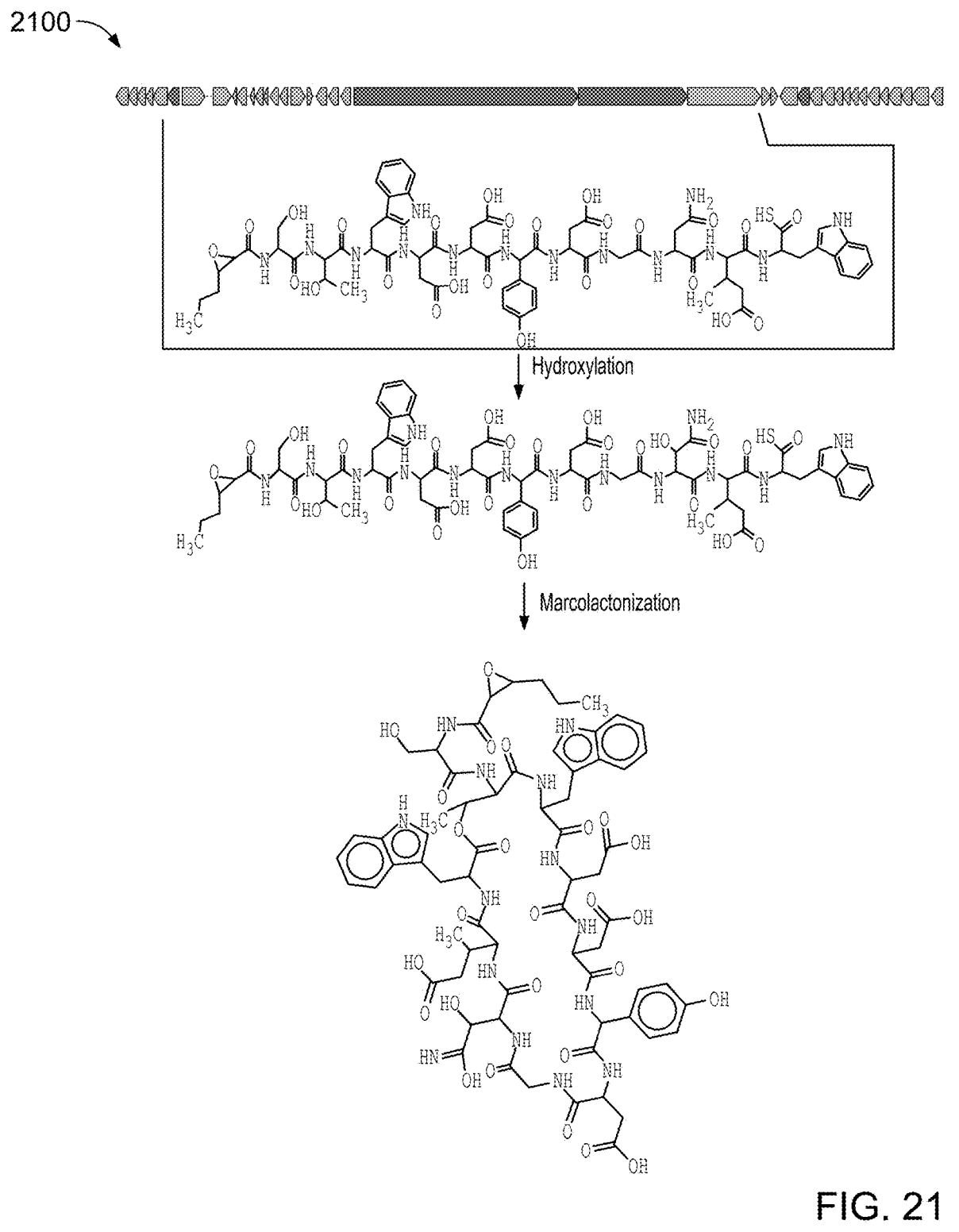
Figure 23:
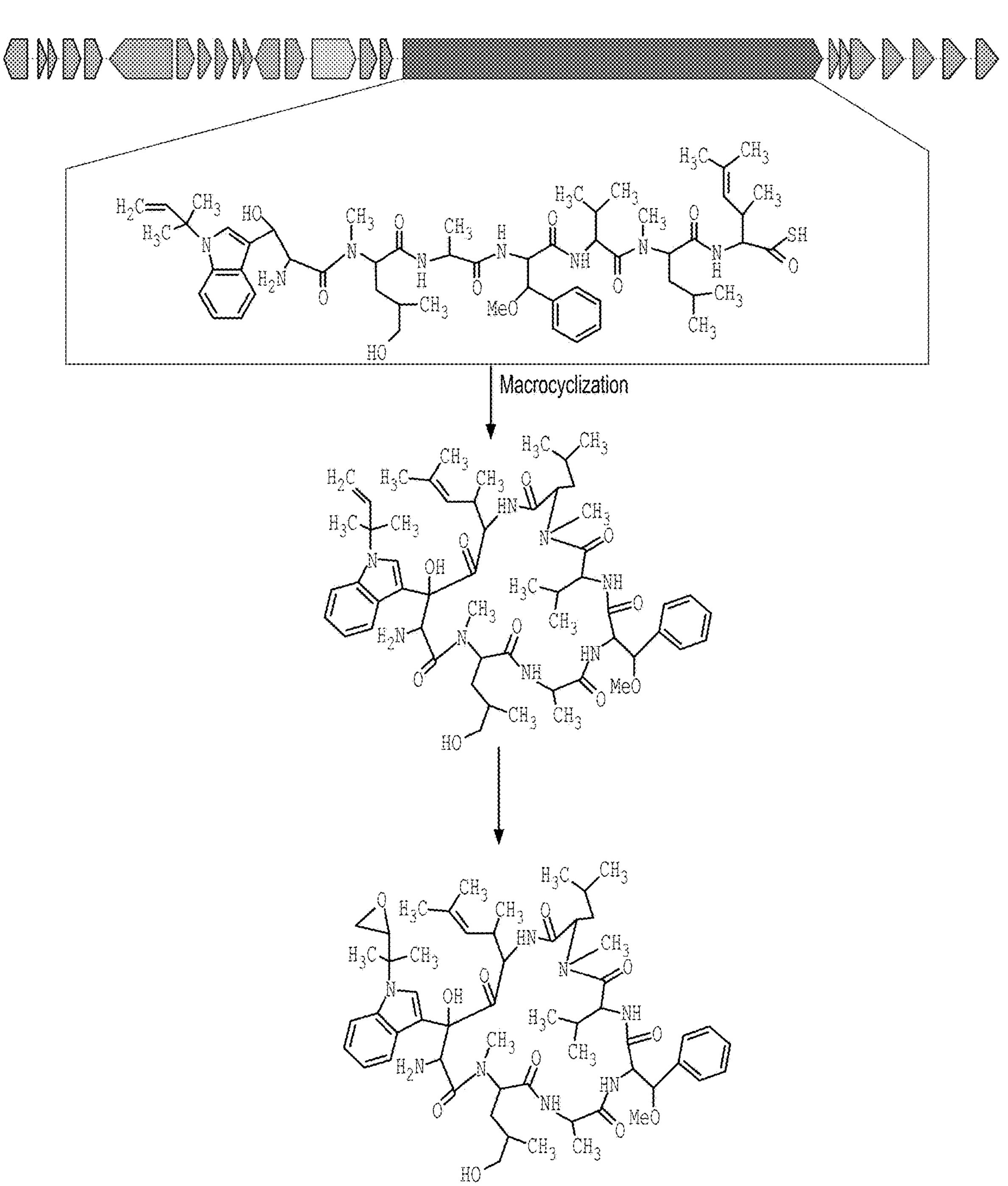
Figure 23:
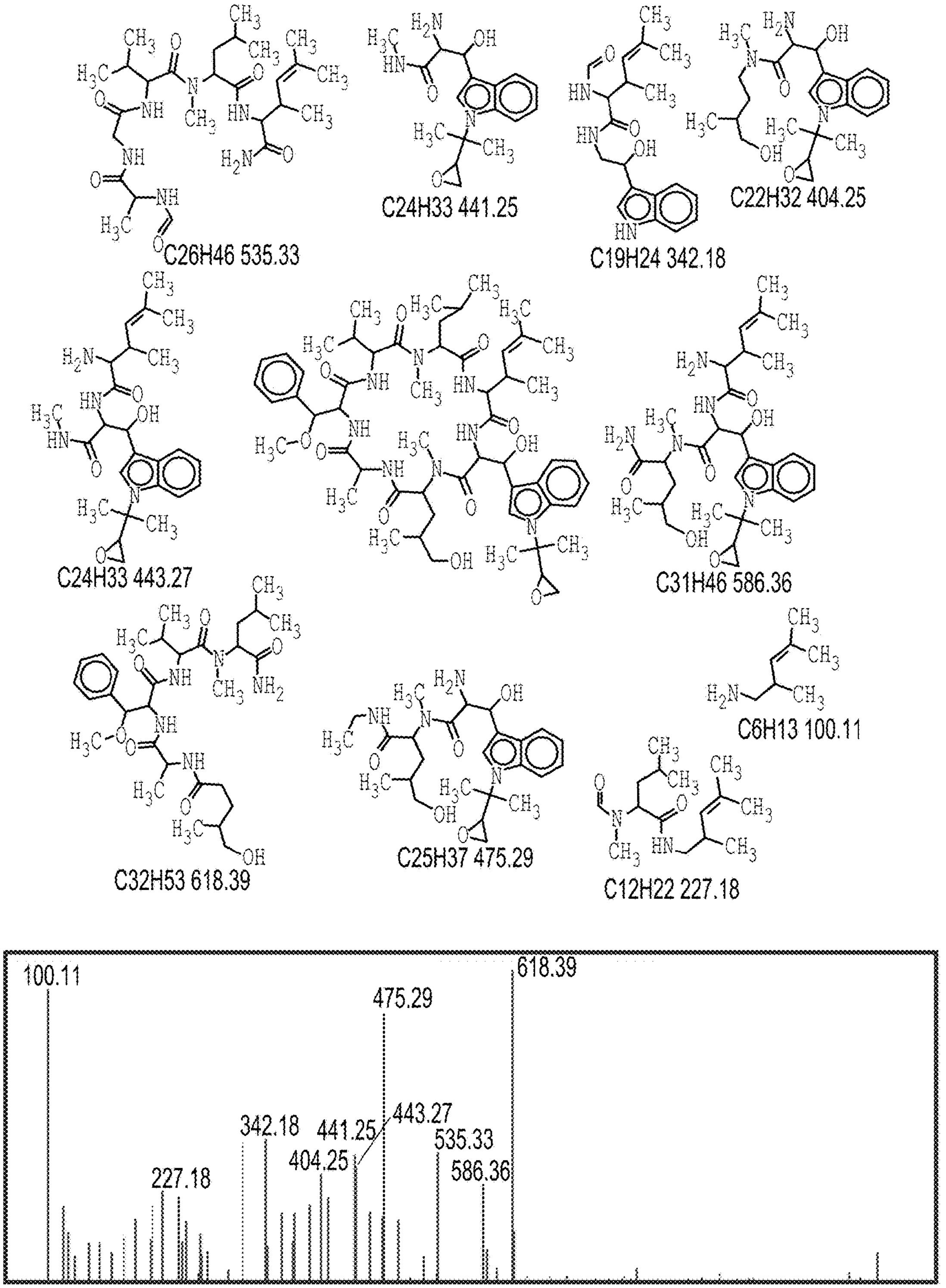

FIGS. 21, 22 and 23 illustrate the NPDiscover processes 2100, 2200, and 2300 for identifying lipopeptide CDA, glycopeptide Mannopeptimycin, and Cyclomarin NRP families, respectively. FIG. 21 shows process 2100 for identification of CDA in Actinobacteria dataset. (a) CDA BGC annotated by NPDiscover is shown on the top. In additional to the main biosynthesis genes, NPDiscover identified tailoring enzymes corresponding to hydroxylation and macrolactonization in this BGC without any prior knowledge of them. The chemical structures below the BGC track, show how NPDiscover applies the tailoring modifications step-by-step for predicting the final mature CDA molecule. (b) The spectrum matched to the mature CDA structure by NPDiscover. The top ten most intense peaks are shown with their masses. The CDA fragments identified by NPDiscover that are matching these peaks are shown above the spectrum.

FIG. 22 shows process 200 for identification of Mannopeptimycin in Actinobacteria dataset. (left) Mannopeptimycin BGC annotated by NPDiscover is shown at the top. In addition to the main biosynthesis genes, NPDiscover identified genes corresponding to four tailoring enzymes including macrolactonization, methylation, and mannosylation in this BGC. The chemical structures below the BGC track show how NPDiscover applies the tailoring modifications step-by-step for predicting the final mature Mannopeptimycin molecule. (right) Annotation of the spectrum matched to the mature Mannopeptimycin structure by NPDiscover is shown at the bottom. The top ten most intense peaks are shown with their masses. The Mannopeptimycin fragments identified by NPDiscover that are matching these peaks are shown above the spectrum.

FIG. 23 shows a process 2300 for identification of Cyclomarin in Actinobacteria dataset. (left) Cyclomarin BGC annotated by NPDiscover is shown on the top. In addition to the main biosynthesis genes, NPDiscover identified a tailoring enzymes on this BGC shown without any prior knowledge of them. The chemical structures below the BGC track show how NPDiscover applies the tailoring modifications step-by-step for predicting the final mature Cyclomarin molecule. (right) Annotation of the spectrum matched to the mature Cyclomarin structure by NPDiscover. The top ten most intense peaks are shown with their masses. The Cyclomarin fragments identified by NPDiscover that are matching these peaks are shown above the spectrum.

Discovery of novel antifungal natural product CHM-752 active against drug-resistant *Candida aureus* is performed using the end-to-end platform NPDiscover. In addition to the known NRPs, NPDiscover identified a novel NRP families in *Streptomyces* sp. NRRL F-2202 in silico search of Actinobacteria metabolomics datasets against 2D structures predicted from novel BGCs in in their paired genomes, with lowest reported P-value $3.1\times10^{-15}$ across the family. NPDiscover further analyzed the identified NRPs to find those with potential activity against seven microbial pathogens of interest. To do so a database of minimum inhibitory concentration (MIC) levels is collected across 4,803 small molecules against seven bacterial and fungal pathogens, which include *Staphylococcus aureus, Pseudomonas aeruginosa, Acinetobacter baumannii, Candida albicans, Klebsiella pneumoniae, Cryptococcus neoformans*, and *Escheria coli* by from various sources37,38. NPDiscover identified one of the predicted structures as potentially active against the *Candida* pathogen. It identified 13 moieties in this NRP, including one 2,3-dihydroxybenzoyl, three L-Gly, two L-Thr, one D-Ser, one D-Leu, one L-Val, one D-His, one D-Tyr, one D-hydroxy-formyl-ornithine, and one cyclic hydroxy ornithine. Additionally, NPDiscover predicted a blind modification (not predictable from BGC) in this structure with mass 57.02 Da. NPDiscover's machine-learning-based MOA prediction showed that CHM-752 does not represent any of the essential substructures appearing in the known molecules active against *Candida*, potentially suggesting a novel MOA.

Figure 24:
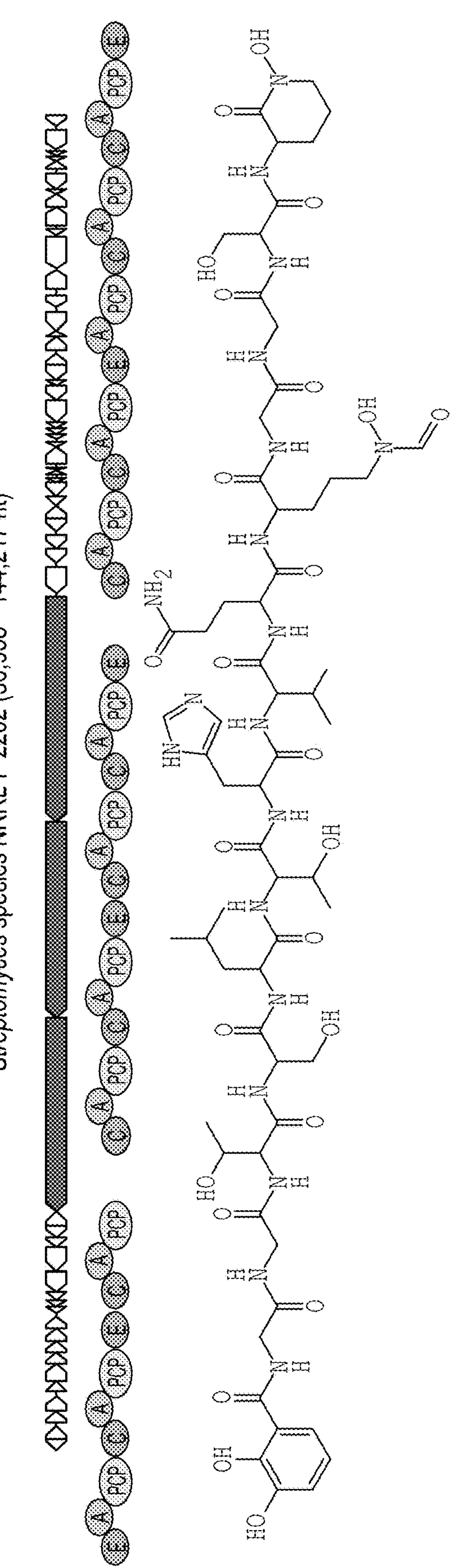
FIG. 24 shows the structure elucidated by NMR experiments.

As part of the platform, the m/z and retention time of the matched spectrum are used as reported by NPDiscover to directly isolate and purify the identified molecule. 12 mg of CHM-752 is isolated. NMR structure elucidation confirmed that NPDiscover predicted all monomers aside from a single amino acid that was out of 13 moieties (Tyr instead of Gln). FIG. 24 shows the structure elucidated by NMR experiments. The NMR experiments confirmed presence of an additional Gly in the final structure of the molecule compared to the structure predicted by NPDiscover which matched the addition of 57.02 at the modification site predicted by NPDiscover. We hypothesize that one of the Gly-specific adenylation domains is responsible for the activation of two consecutive Gly units in the final mature NRP accounting for the 57.02 mass shift predicted by NPDiscover, suggesting an iterative use of the Gly-incorporating module (similar to stuttering observed in polyketide synthases.

Direct bioactivity screening experiments of CHM-752 are performed against *Candida* pathogens (Table 13). These experiments showed that CHM-752 exhibits strong antifungal activity against multidrug-resistant *Candida* pathogens while no toxicity was observed against healthy human cell lines at concentrations up to 64 μg/ml.

Table 13 shows minimum inhibitory concentration (MIC) of CHM-752 against a panel of *Candida* pathogens (ug/ml). CHM-752 is capable of inhibiting *Candida* strains that are resistant against Azoles, Echinocandins, and Amphotericin B. CH, CAS, ANI, MCF, FLC, VRC and AMP represent CHM-752, Caspofungin, Anidulafungin, Micafungin, Fluconazole, Voriconazole and Amphotericin B. CHM-752 showed no toxicity against human cell lines at concentrations up to 64 ug/ml.

| Strain | CH | CAS | ANI | MF | FLC | VRC | AMP |
|---|---|---|---|---|---|---|---|
| *C. albicans* ATCC 90028 | 2 | 0.5 | 0.01 | 0.02 | 0.25 | 0.01 | 0.13 |
| *C. albicans* MYA-574 | 1 | 0.5 | N.R. | 0.06 | 64 | 0.25 | 0.13 |

-continued

| Strain | CH | CAS | ANI | MF | FLC | VRC | AMP |
|---|---|---|---|---|---|---|---|
| *C. auris* CDC #0381 | 0.5 | 0.13 | 0.25 | 0.13 | 4 | 0.03 | 0.13 |
| *C. auris* CDC #0383 | 1 | 0.25 | 1 | 1 | 128 | 4 | 0.38 |
| *C. auris* CDC #0384 | 1 | 16 | 2 | 2 | 128 | 1 | 0.5 |
| *C. auris* CDC #0385 | 0.5 | 0.5 | 1 | 0.5 | >256 | 16 | 0.5 |
| *C. auris* CDC #0387 | 0.5 | 0.25 | 0.5 | 0.5 | 8 | 0.06 | 0.75 |
| *C. auris* CDC #0389 | 1 | 0.5 | 1 | 0.25 | 256 | 0.4 | 4 |
| *C. auris* CDC #0390 | 1 | 0.5 | 1 | 0.25 | >256 | 8 | 4 |
| *C. glabrata* ATCC 36583 | 0.5 | 0.5 | N.R. | N.R. | 8 | 0.5 | 0.13 |
| C. glabrata CDC #0315 | 0.5 | 16 | 2 | 4 | 4 | 0.25 | 0.38 |
| *C. glabrata* CDC #0318 | 1 | 16 | 4 | 4 | 32 | 1 | 0.19 |
| *C. glabrata* CDC #0321 | 1 | 4 | 2 | 1 | 64 | 2 | 0.09 |
| *C. glabrata* CDC #0325 | 0.5 | >16 | 4 | 4 | 128 | 16 | 0.25 |

An Interpretable Machine Learning Approach to Identify Mechanism of Action of Antibiotics With hundreds of millions of known molecular structures available in molecular libraries, methods for prediction of bioactivity solely based on chemical structure can aid in selecting promising molecules active against targets of interest for downstream bioactivity testing.

One of the main bottlenecks of the existing approaches is that they usually report hundreds/thousands of molecules, where the majority of them possess known mechanisms of action. Overcoming antibiotic resistant pathogens crucially depends on finding small molecules with novel mechanism of action, and currently determining the mechanism of action for small molecules remains an expensive and time-consuming effort. Therefore, it is crucial to develop computational methods for determining molecules with known mechanisms of action and prioritize molecules with novel mechanisms.

Mechanism of action of small molecules are usually linked to their bioactive moieties. One way to extract these moieties would be to find features of the molecule graph that correlate to bioactivity. Methods such as recursive feature elimination, boruta, and lasso have been developed for this purpose, but they are limited to cases where a feature set is available.

Another method to find bioactive moieties is to determine the portion of a molecular graph that a D-MPNN uses to make a prediction. Several heuristic approaches have been developed in order to interpret graph neural networks. One approach is to take the gradient of neural networks with respect to the atoms in the molecular graph and to attribute atoms with more importance if the gradient value for an atom is large. The set of atoms determined to be important by this approach, however, are not necessarily biologically relevant as often a large portion of the molecular graph is flagged as important. Furthermore although gradient methods have had some empirical success, the gradient only represents how the model changes with small perturbations, and high gradient values for atoms do not necessarily mean those atoms are important for classification by a neural network. Another approach for interpreting graph neural networks is to exhaustively search all subgraphs of a molecular graph and find those subgraphs that are either subsets of important nodes as determined by the gradient method or those that do not change the output of the neural network significantly. These methods again often fail in capturing reasonable bioactive moieties as they highlight subgraphs that are common in the molecular space.

Interpreting which substructures are responsible for bioactivity is a challenging problem for the existing algorithms, as there are an exponential number of substructures of molecular graphs, and it is impossible to correctly infer which of these millions of substructures are responsible for activity from a few thousand training points. One way to overcome this issue is to limit the candidate substructures to those that are biologically important, including simple ring structures and functional groups. This knowledge however has rarely been integrated in machine learning methods for drug discovery.

This section of the specification describes an interpretable machine learning model by first identifying the simple ring structures and functional groups in the training data and using them to create binary feature vectors for each molecule where zeros and ones indicate absence/presence of rings and functional groups. Using simple rings and structures as features is advantageous since it is easier to interpret the correlations between these features and mechanism of action in the downstream analysis. Then a logistic regression or extra trees model is trained with balanced scoring on these features in order to create a low complexity model that accounts for imbalanced data. The machine learning model clusters molecules based on their mechanism of action. Moreover, the method can associate a bioactive molecule with its bioactive moiety, providing a strategy for prioritizing molecules with novel mechanism of action. Application of our method to the Community for Open Antimicrobial Drug Discovery (CO-ADD) and a FDA-approved dataset of antibacterial and antifungal bioactivities of several thousand molecules assigned five known mechanism of actions to their moieties.

FIG. 25 shows a process for predicting bioactivity of small molecules. Given (a) a collection of molecules (b) all unique simple ring structures and functional groups are extracted into binary vectors where 0/1 indicates absence/presence of a substructure. Then, (c) extra trees/logistic regression classifier with l1 regularization is trained on the extracted binary features using balanced scoring. Given (d) a query molecule, (e) binary features are extracted, and (f) the trained model is used for predicting bioactivity.

Figure 26:
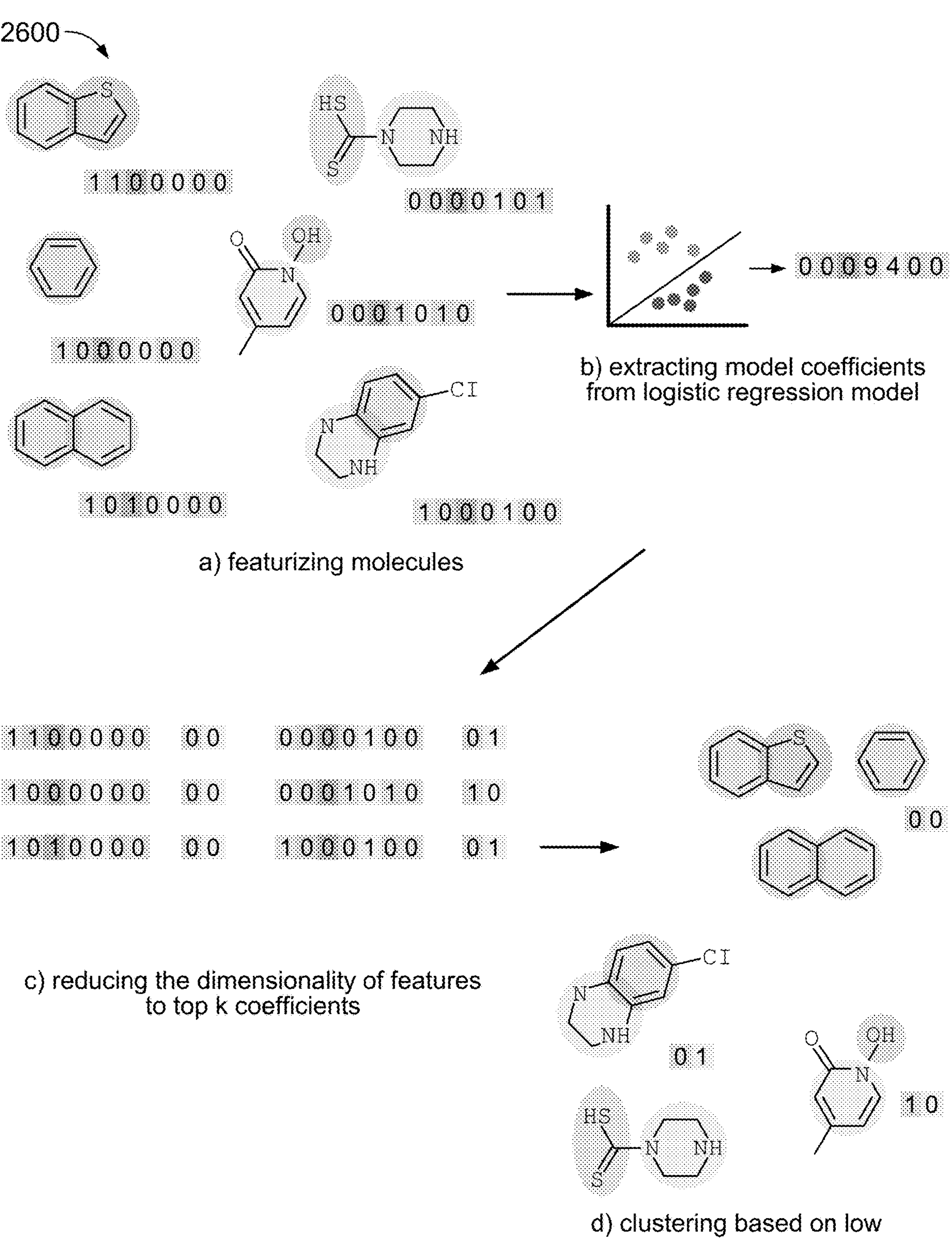
FIG. 26 shows a process 2600 for grouping molecules with similar mechanism of action (MOA).

FIG. 26 shows a process 2600 for grouping molecules with similar mechanism of action (MOA) in the following steps. Given (a) a collection of molecules, MOACluster extracts their binary features. Then a logistic regression classifier with l1 regularization and balanced scoring is trained to predict bioactivity, and the model parameters are extracted. (c) MOACluster finds the indices of the top k coefficients and reduces molecule binary features to those k indices. (d) The molecules are clustered according to the reduced binary features.

The machine learning model is trained on two datasets. The first dataset contains molecules from a US Food and Drug (FDA)-approved library, along with 800 natural products isolated from plant, animal, and microbial sources (total of 2335 unique compounds). Data on growth inhibition against *Escherichia coli* is available for all the molecules. The corresponding test data contains growth inhibition of 162 molecules from the Drug Repurposing Hub. Each molecule in the test data is annotated with a mechanism of action by which it fights the disease it was originally purposed for. The second data set, CO-ADD, contains bio-activity data from 4,803 molecules against seven bacterial and fungal pathogens, which include *Staphylococcus aureus, Pseudomonas aeruginosa, Acinetobacter baumannii, Candida albicans, Klebsiella pneumoniae, Cryptococcus neoformans*, and *Escheria coli*. For this dataset, 80% of the molecules are randomly selected for training and the rest are allocated for testing.

Figure 27:
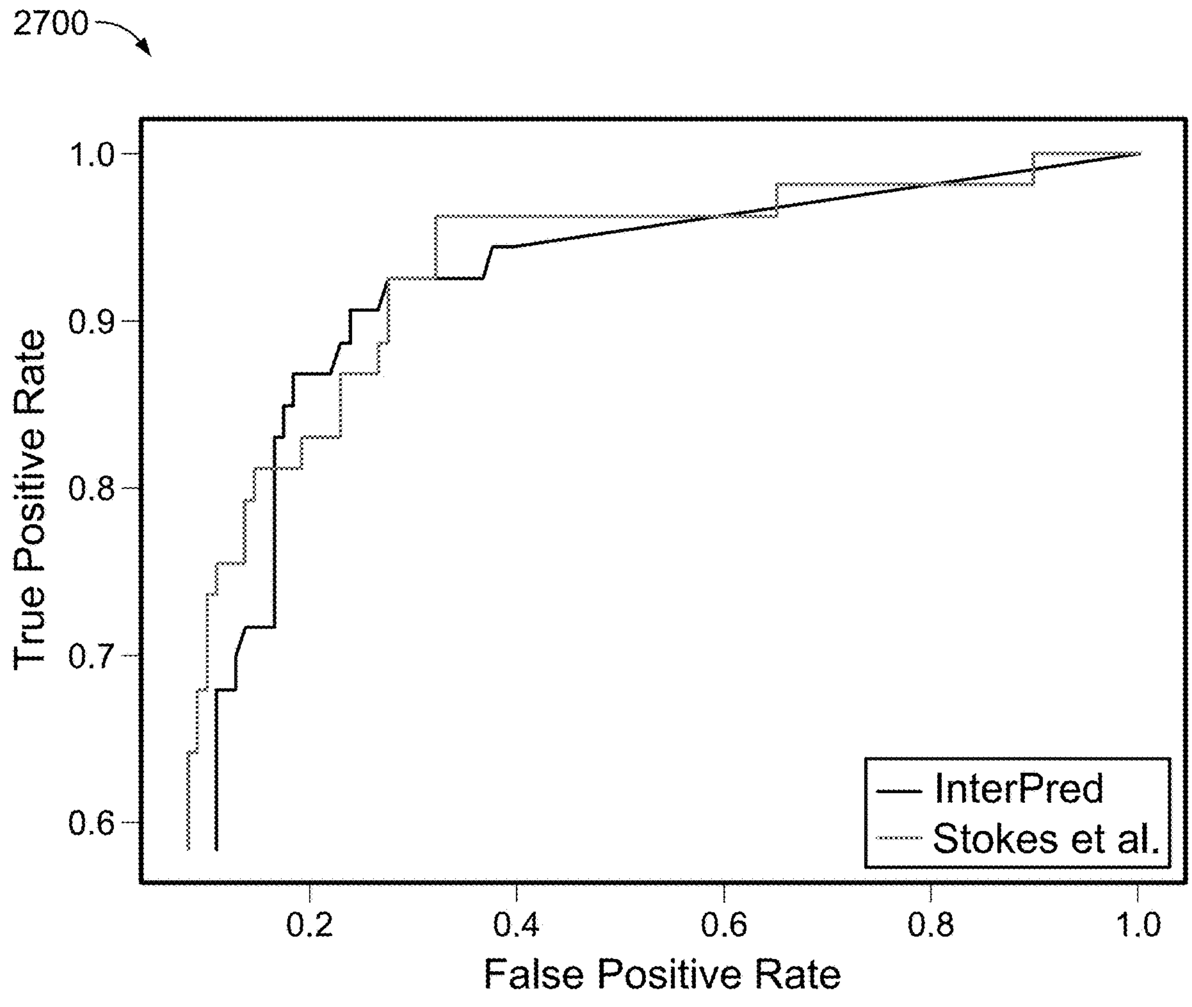
FIG. 27 illustrates a graph showing a receiver operating characteristic (ROC) curve.

FIG. 27 illustrates a graph 2700 showing a receiver operating characteristic (ROC) curve compared to the approach from Stokes et al. on predicting activity against *E. coli*. Here 2335 molecules have been used for training, 162 molecules have been used for testing. These test molecules correspond to the portion of the Drug Repurposing Hub for which screening data against *E. coli* is available (Stokes et al.). The ROC curve is for neural network model from Stokes et al. and InterPred. For false positive rates greater than 0.3, the models have nearly identical true positive rate.

Figure 28:
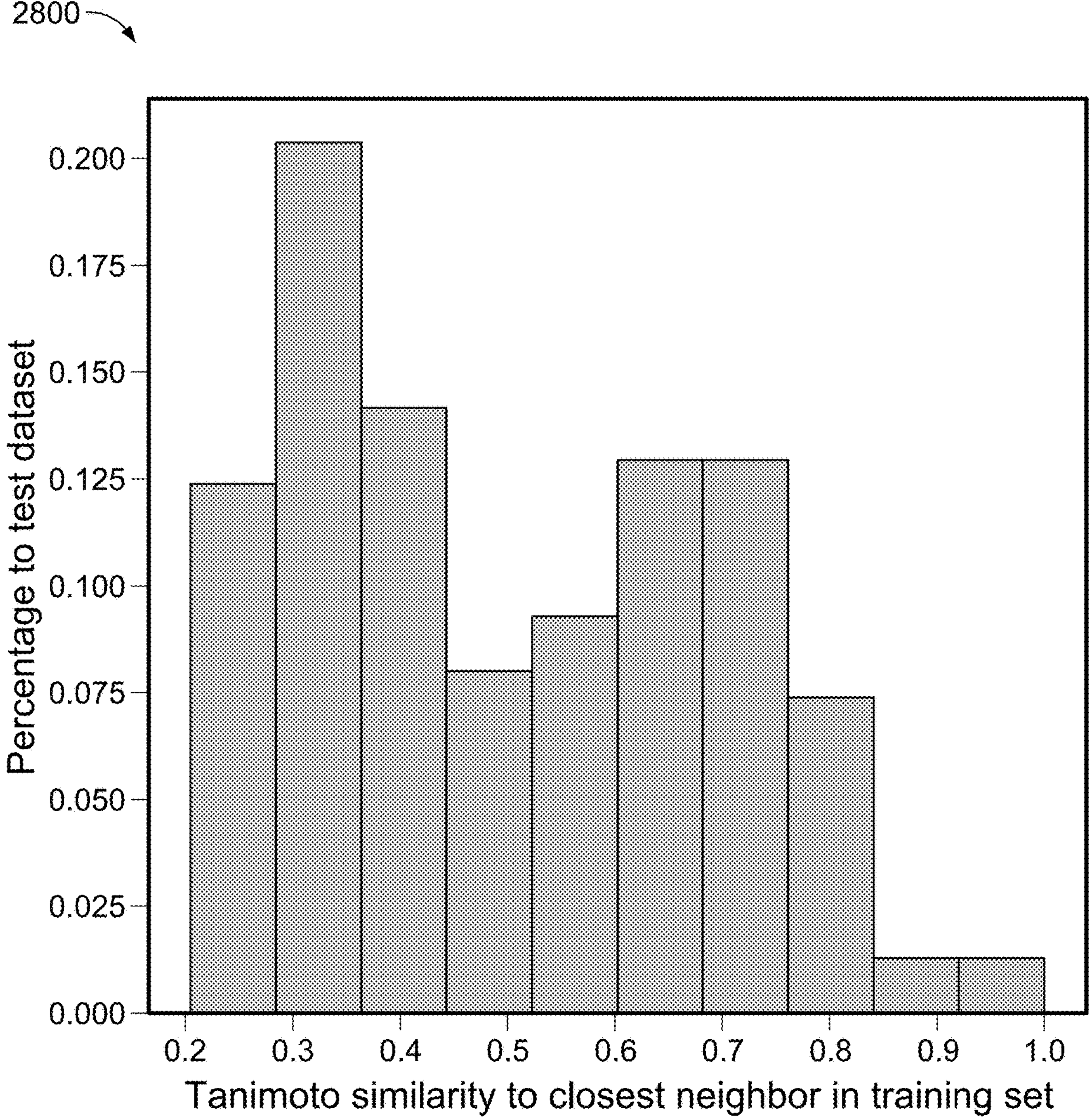
FIG. 28 shows a chart representing a distribution of the tanimoto similarity between each test data point and their closest neighbor.

FIG. 28 shows a chart 2800 representing a distribution of the tanimoto similarity between each test data point and their closest neighbor in the training dataset. InterPred achieves nearly the same accuracy as Stokes et al. The area under the curve (AUC) for InterPred is 0.87 while the AUC for Stokes et al. is 0.88. Unlike Stokes et al., InterPred uses fully interpretable features. The average tanimoto similarity between test data points and their closest neighbors is 0.5035 and the standard deviation is 0.18. Only 1.2% of test data points are more than 90% similar to a training data point.

Figure 29:
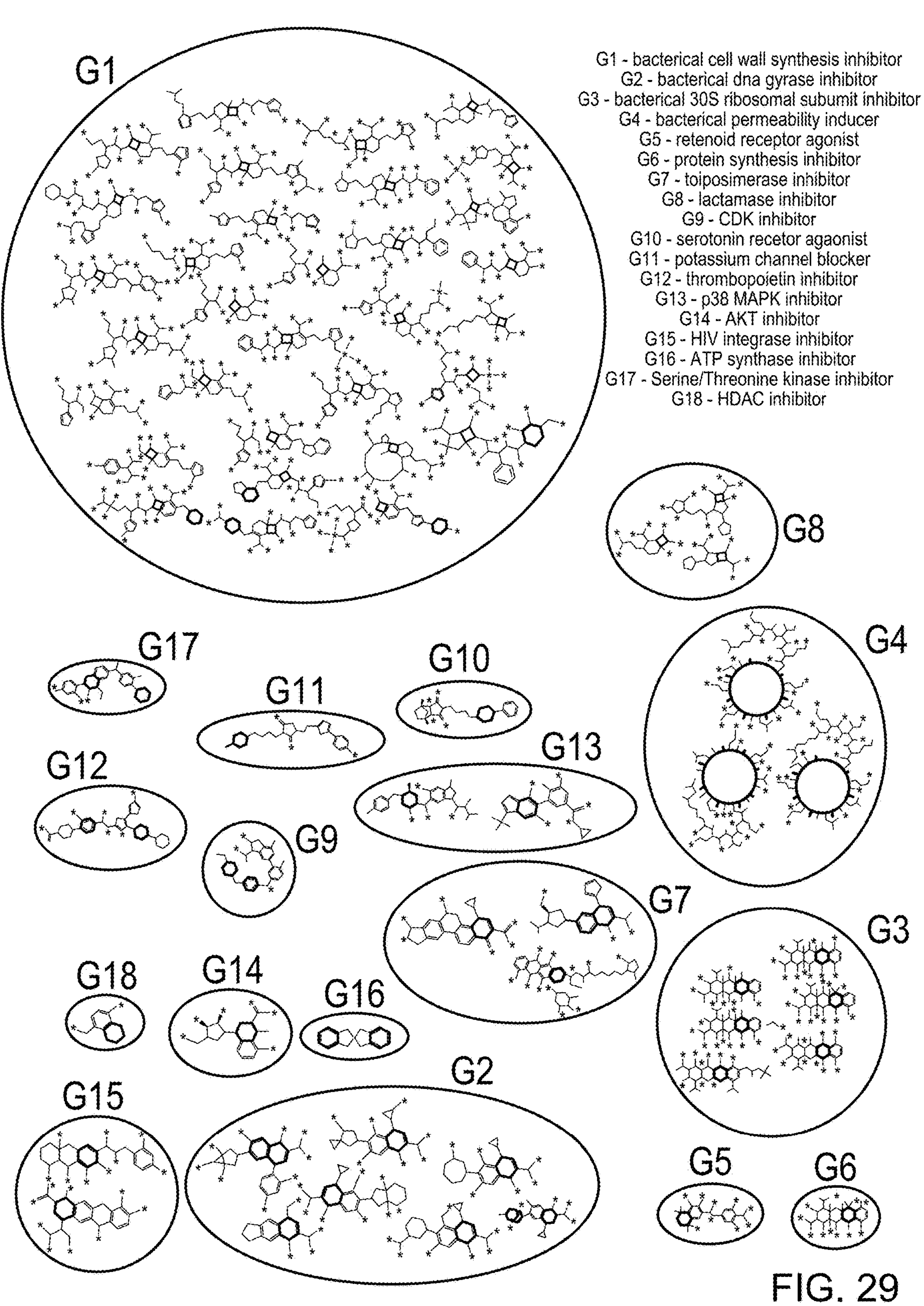
FIG. 29 shows the mechanism of action of molecules including at least one of the five most important simple rings according to the logistic regression model.

FIG. 29 shows the mechanism of action of molecules including at least one of the five most important simple rings according to the logistic regression model. For the majority of molecules with similar bioactive moiety, the mode of action is the same. For example beta-lactam rings (shown in blue), are present in antibiotics such as penicillin and cephalosporin, and they have been reported to prevent cell wall synthesis. The majority of the molecules with this ring are mapped to the cell wall inhibition (G1) mechanism of action. In cases when molecules with the same moiety are mapped to multiple mechanisms of action, those mechanisms of action are usually similar. For example, for cyclohexane (shown in purple) associated mechanisms of action are bacterial 30S ribosomal subunit inhibitor (G3) and protein synthesis inhibitor (G6), both related to inhibiting protein synthesis. For moiety 4-quinolone (shown in green), the associated modes of action are HDAC inhibitor (G18), DNA gyrase inhibitor (G2), and topoisomerase inhibitor (G7), which are all related to inhibition of bacterial nucleic acid synthesis. Molecules containing 4-quinolone are known to inhibit bacterial nucleic acid synthesis by disrupting the enzymes topoisomerase IV and DNA gyrase27. In cases where two molecules contain distinct bioactive moieties, they usually have distinct mechanisms of action. The only exceptions G13 and G17 can be explained by the fact that MAP kinases are a subset of Serine/Threonine Kinases28. Among all the pairs of molecules with the same mechanism of action, 76% are clustered together by MOACluster, and among all the pairs of molecules clustered together by MOACluster, 67.6% have identical and 71% have similar mechanisms of action Mechanism of action of molecules containing at least one of the five most important simple rings according to the logistic regression model. Each of the five rings are highlighted with a different color. Molecules sharing the same mechanism of action, as reported in the Drug Repurposing Hub, are further circled together. For the majority of molecules with similar bioactive moiety, the mode of action is the same.

Figure 30:
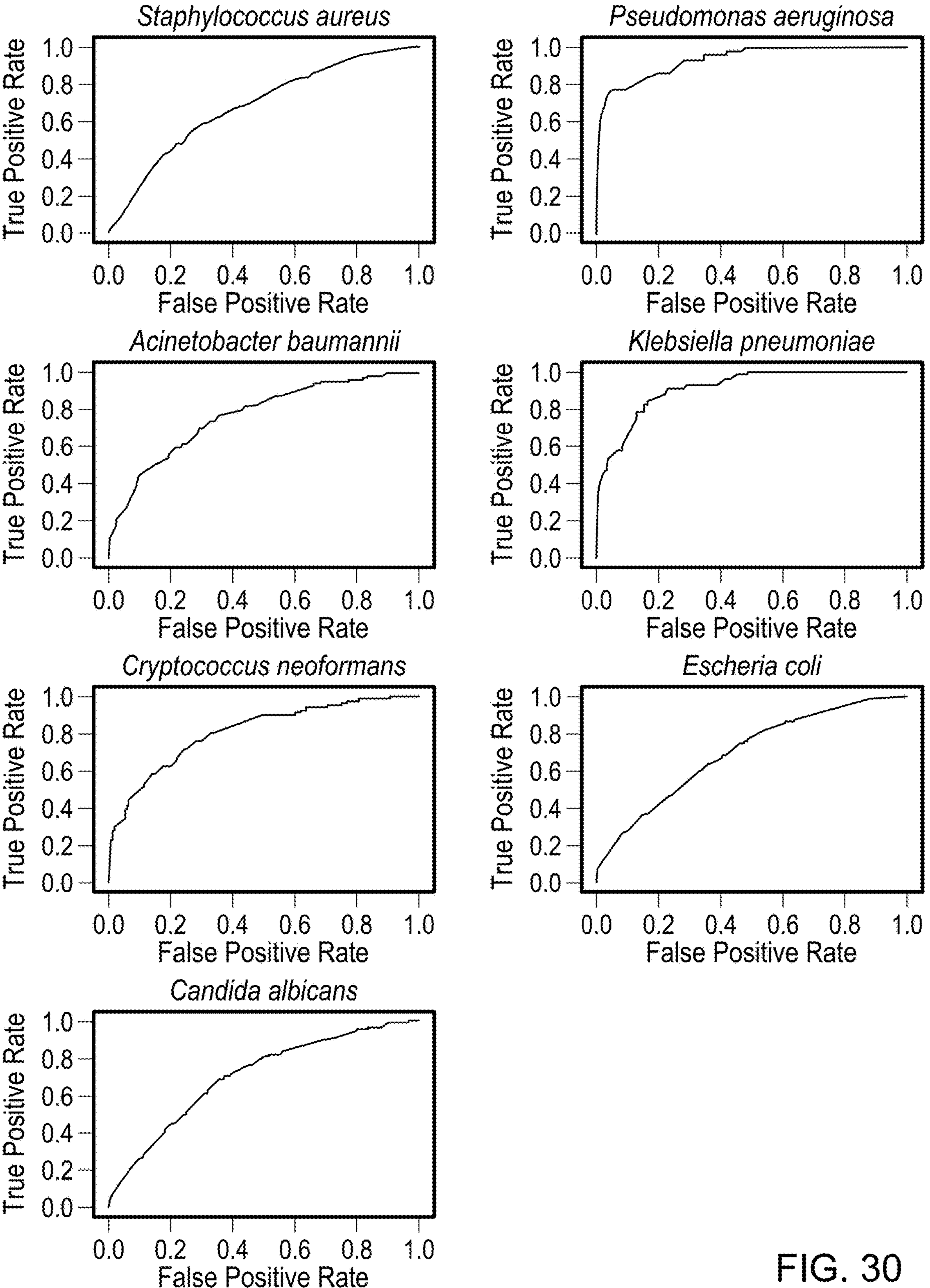
FIG. 30 shows ROC curves of InterPred for prediction of growth inhibition.

FIG. 30 shows ROC curves of InterPred for prediction of growth inhibition for 7 different bacteria in the CO-ADD dataset.

FIG. 31 shows the top 31 ring/functional group features predicted to govern the mechanism of action of molecules along with pathogens they inhibit. The pathogens that are predicted to be inhibited by each moiety are also shown. It has been reported that guanadine and nitro are the bioactive moiety in various antibacterial molecules. Moreover hydrazone/hydrazine have been reported to be potent against *S. aureus, A. baumannii*, and *C. albicans*.

InterPred is an interpretable machine learning algorithm for prediction of bioactivity, functional groups responsible for bioactivity, and mechanism of action by training on data. Below we describe various steps of the InterPred algorithm.

Extracting molecular features. Presence of simple rings are extracted using open source package rdkits by finding symmetrized smallest set of smallest rings. Additionally the presence 32 functional groups are extracted by checking whether each molecule has a graph substructure matching the functional group using the descriptors module in RDKit. These substructures are de-duplicated using kekulized canonical SMILES36. Since small molecules have only a few simple rings, feature vectors for each molecules usually only have a few non-zero entries.

Training. Both the extra trees ensemble classifier and logistic regression model with l1 norm regularization are trained on training data and hyper-parameters are optimized via five-fold cross validation. The number of trees in the extra trees model was cross-validated for the numbers 10, 40, 70, 100, 130, and 160. The lambda parameter for l1-regularized logistic regression was cross-validated for values $$\frac{1}{.01}, \frac{1}{.05}, \frac{1}{.1}, \frac{1}{.15}, \text{ and } \frac{1}{.2}.$$

In logistic regression and extra trees, the loss function is of the form $$\min \sum_{t=1}^{T} L(f(x^t), y^t)$$

where t is used as an index for each training point, $y^t$ represents the true label of each molecule in the training dataset, $x^t$ represents the features of each molecule, f is a function with range [0,1], and L refers to a loss function that is low when $f(x^t)$ is close to $y^t$ and high otherwise. $y^t$ takes on value 1 if molecule t inhibits bacterial growth and 0 otherwise. In logistic regression, $f(x^t)=\text{Sigmoid}((c^T x^t))$. c is the coefficient vector of logistic regression and $$\text{Sigmoid}(z) = \frac{1}{1+\exp(-z)} L(f(x^t), y^t) = CrossEntropy(f(x^t), y^t) + \lambda \frac{|c|_1}{T},$$

where $\text{CrossEntropy}(y,\hat{\gamma})=-\gamma\log(\hat{\gamma})-(1-y)\log(1-y)$ and $\lambda$ is a regularization parameter optimized via cross validation. In extra trees $f(x^t)$ is either 0 or 1 and is determined the by the majority label produced by all the trees in the extra trees ensemble. $L(f(x^t), y^t)$ is 0 if $f(x^t)$ and $y^t$ are not the same and 1 otherwise. In the training set introduced by Stokes et al., nearly 95% of the molecules do not have antibacterial activity. Such an imbalance could result in misclassification of bioactive molecules as inactive. To avoid this, a "balanced" approach is used. The objective function in (1) is modified to the following:

$$\min \sum_{t=1}^{T} \frac{L(f(x^t), y^t)}{b^t}$$

Where bt is the number of training points with label $y^t$. This way bioactive and inactive molecules will contribute to the training nearly equally.

Identifying bioactive moieties. Substructures corresponding to largest positive coefficients of the logistic regression model are reported as bioactive moieties.

Clustering mechanism of action. Since the logistic regression model is trained with l1 regularization, only a few coefficients are non-zero in the model. InterPred algorithm first reduces the feature vector for each molecule to these non-zero features, and then molecules with identical reduced feature vectors are assigned to the same cluster.

Seq2Saccharide: Discovering Novel Saccharide Natural Products by Integrating Computational Mass Spectrometry and Microbial Genome Mining.

Figure 32:
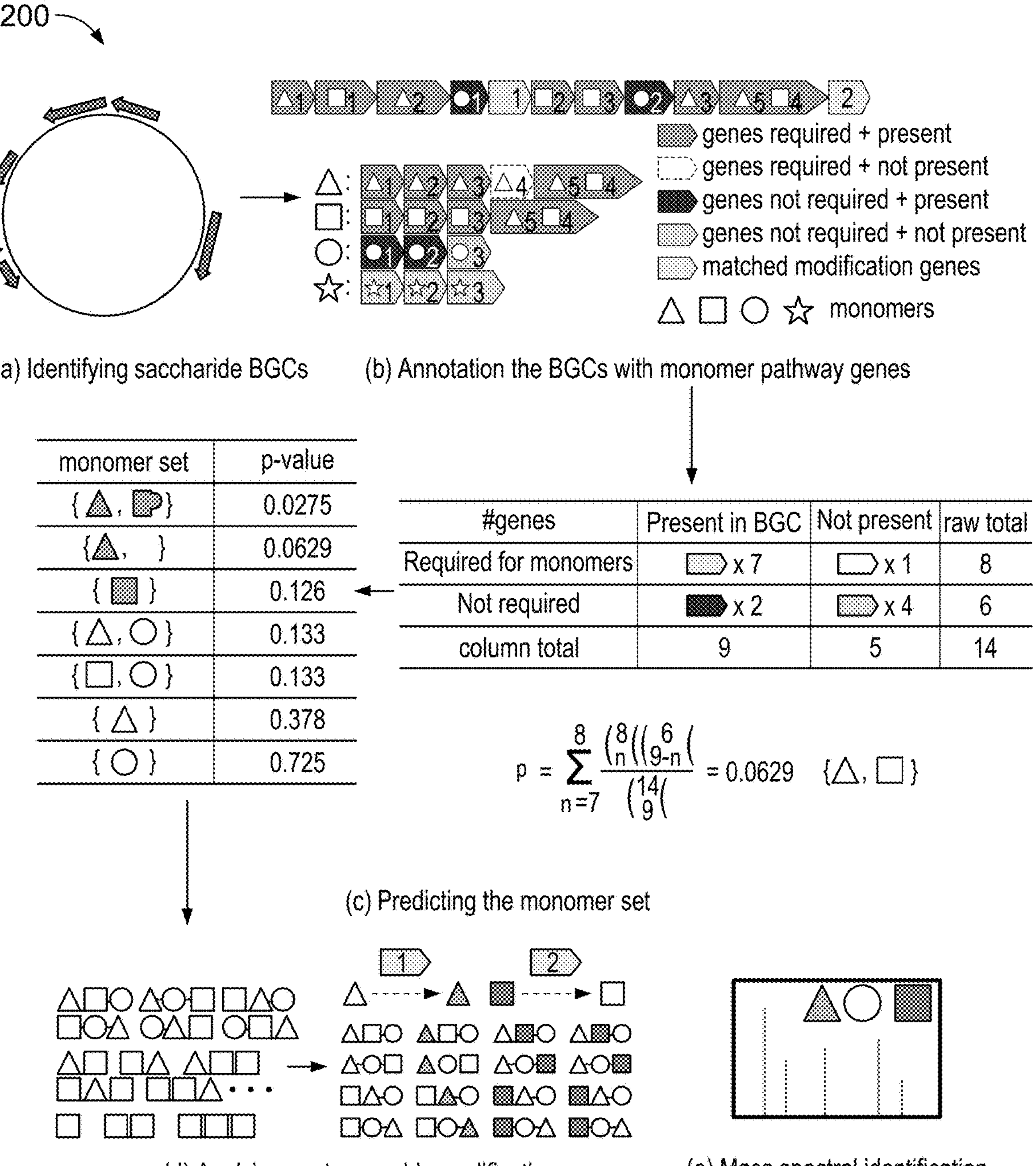
FIG. 32 shows a process 2300 for predicting the structure of candidate saccharides from their biosynthetic gene clusters.

FIG. 32 shows a process 2300 for predicting the structure of candidate saccharides from their biosynthetic gene clusters. (a) DNA sequences are mined to find saccharide encoding BGCs. (b) A database of enzymes required for the biosynthesis of each monomer (monomer pathway) is created. Each monomer is represented with a different shape (tringle, square, circle, or star). Furthermore, the tailoring modification enzymes are identified. The list of all genes required for biosynthesis of each monomer is formed. Various monomer sets (combinations of monomers) are considered per BGC. To test whether monomers in each set are likely to be present in the molecular product of the BGC, the overlap between the required genes and the genes present in that BGC are calculated. (c) A statistical significance score is assigned to each monomer set and its corresponding BGC, and (d) the most likely monomer sets are reported as candidate backbones for each BGC. (e) These backbones are further modified based on the modification enzymes present in the BGC.

Figure 33:
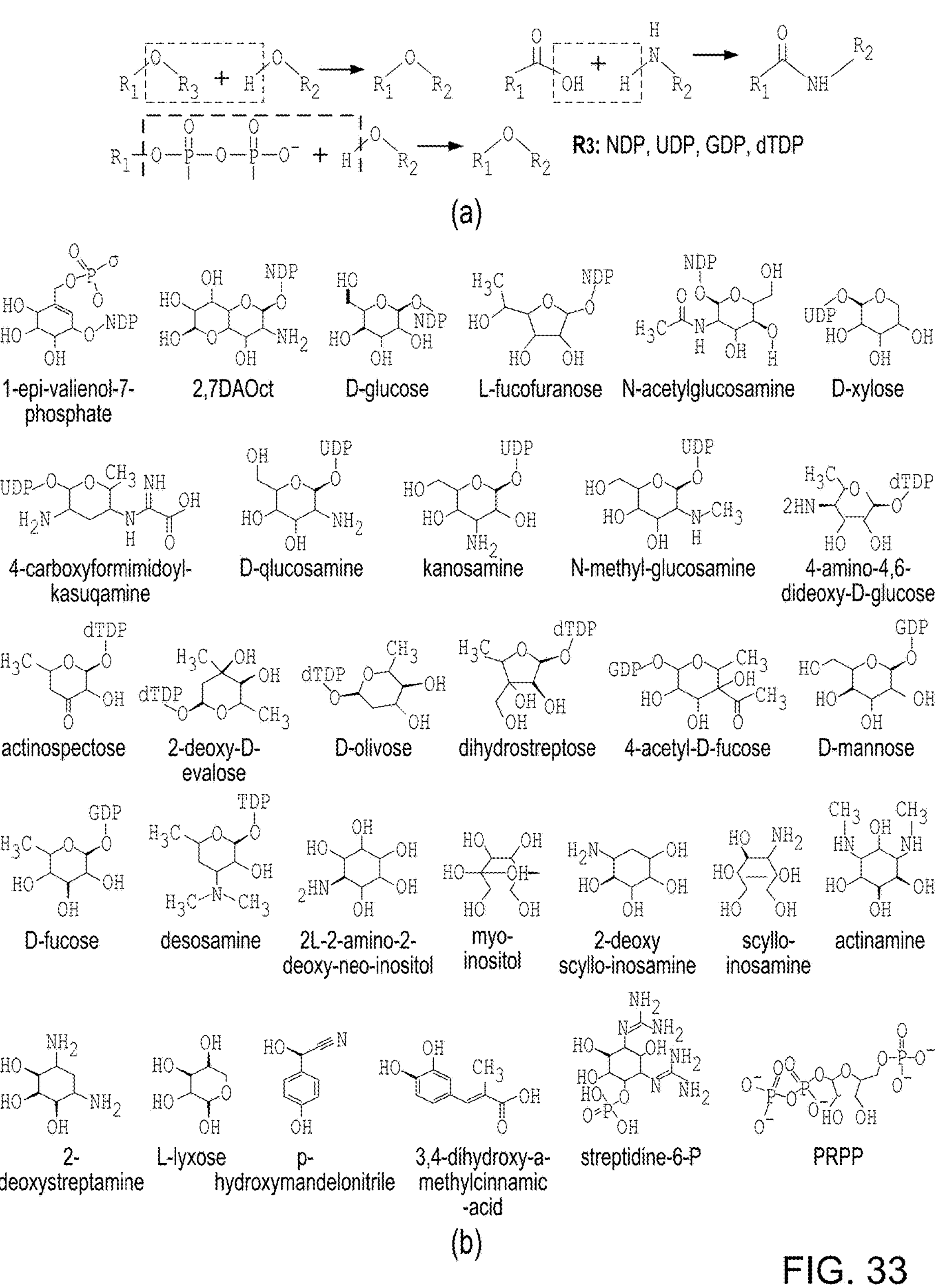
FIG. 33 shows a monomer database for Seq2Saccharide.

FIG. 33 shows a monomer database for Seq2Saccharide. (a) The bond formation mechanisms between monomers, wherein the first reaction, R3 group represents NDP, GDP, UDP, and dTDP; (b) Various monomers with their reaction groups defined in the database are illustrated. For each monomer the reaction sites are highlighted with different colors based on the bond formation mechanism they follow as shown in part a.

Figure 34:
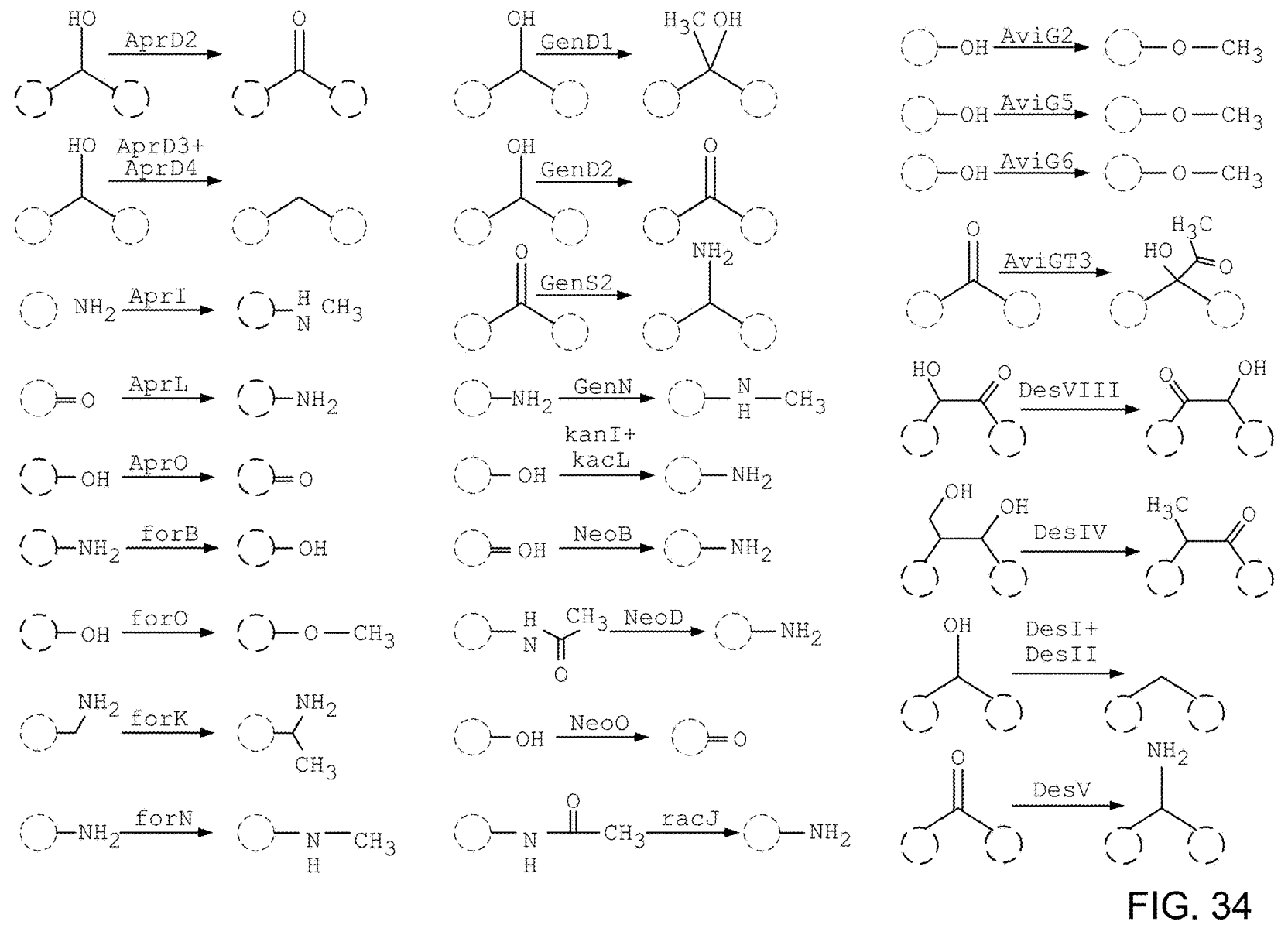
Figure 34:
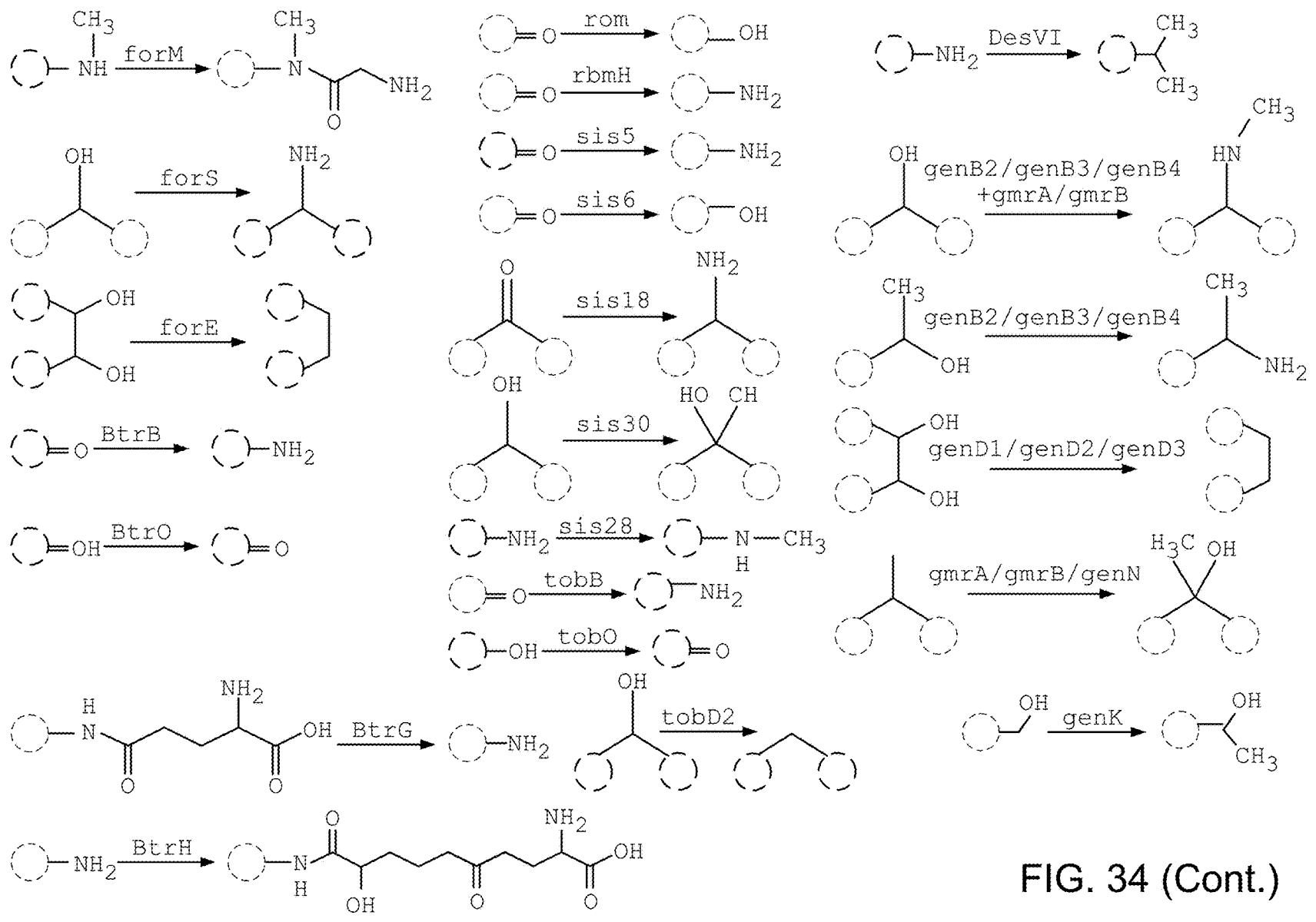

FIG. 34 shows a list of saccharide post-assembly modifications collected from known saccharide BGCs from the MIBiG database. The modification sites and reactions are highlighted in red. In each case, the enzyme responsible for the modification is also shown. Modifications requiring more than one enzyme are noted with a plus sign between the enzymes.

FIG. 35 shows enzymatic modifications are stored in a computer readable format for a) aminotransferase enzyme (sisomicin) and (b) dehydratase enzyme (desosamine). Commands disconnect/connect are used (for bonds) and add/remove (for chemical substructures). For example, in part (a), "Disconnect 1 2" removes the double bond between the carbon atom with index 1 and an oxygen atom with index 2. "Remove 2" removes an oxygen atom with index 2, while "add 3 N: 4 H: 5H", followed by "Connect 3 4 1" and "Connect 3 5 1" adds an amine group NH2. Finally, "Connect 1 3 1" connects the carbon atom with index 1 with nitrogen atom with index 3 in a single bond. Similarly, in part (b), command "Connect 1 4 2" forms a double bond between the carbon atom with index 1 and oxygen atom with index 4.

Figure 36:
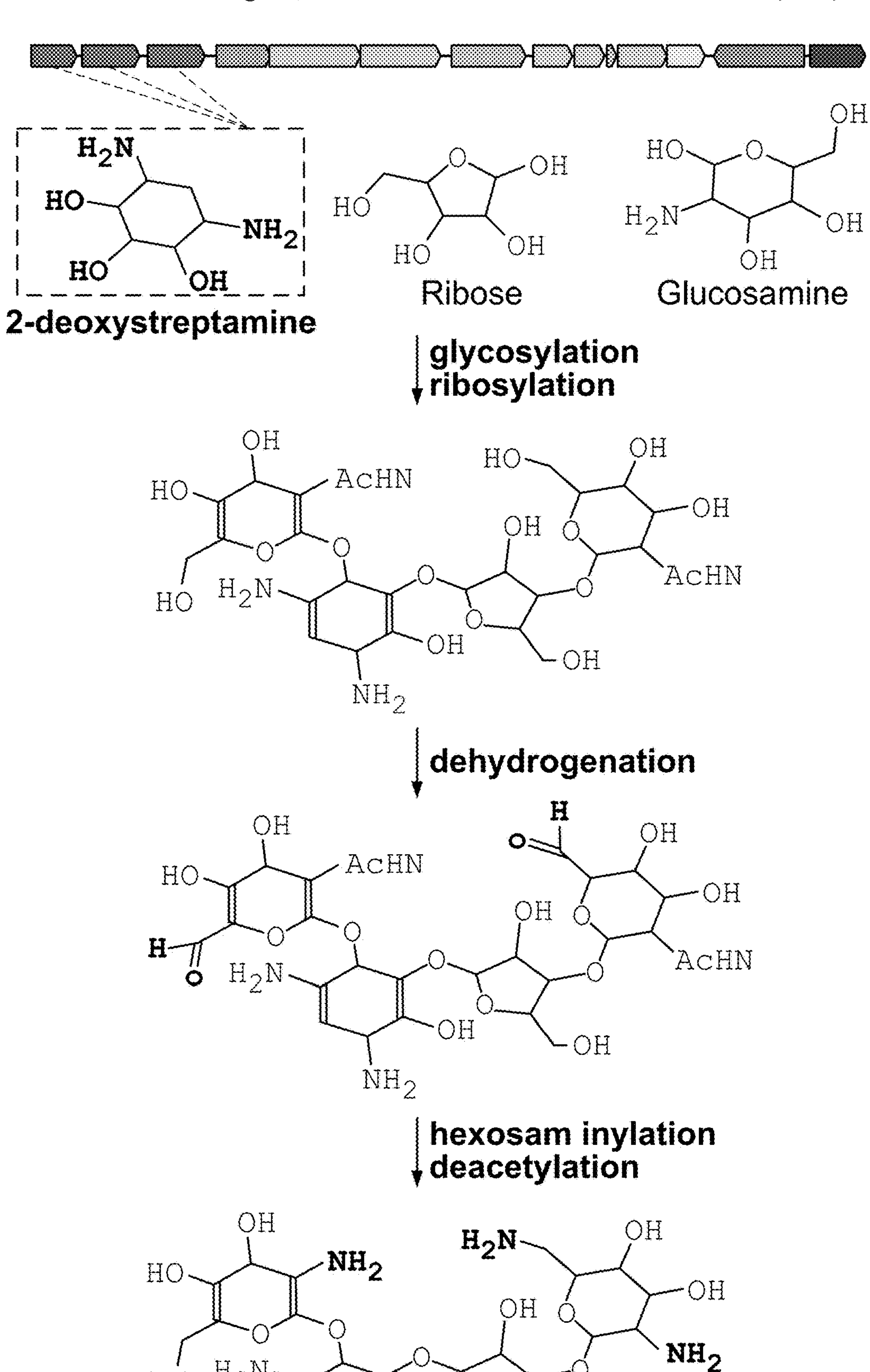
FIG. 36 shows predicting neomcyin structure.

FIG. 36 shows predicting neomcyin structure. Seq2Saccharide predicts the correct structure of neomycin by mining the genome of *Streptomyces* sp. ISP-5003, without any prior knowledge of it. Seq2Saccharide identifies three potential enzymes that are involved in the synthesis of 2-deoxystreptamine. In addition to the enzymatic monomers, Seq2Saccharide also considers two enzyme-independent metabolites, glucosamine and ribose which cannot be predicted from the BGC sequences. All possible combinations of these three monomers are considered as the potential backbones for neomycin. Furthermore, Seq2Saccharide identified the tailoring enzymes involved in glycosylation, ribosylation, dehydrogenation, hexosaminylation and deacetylation of neomycin backbone.

Figure 37:
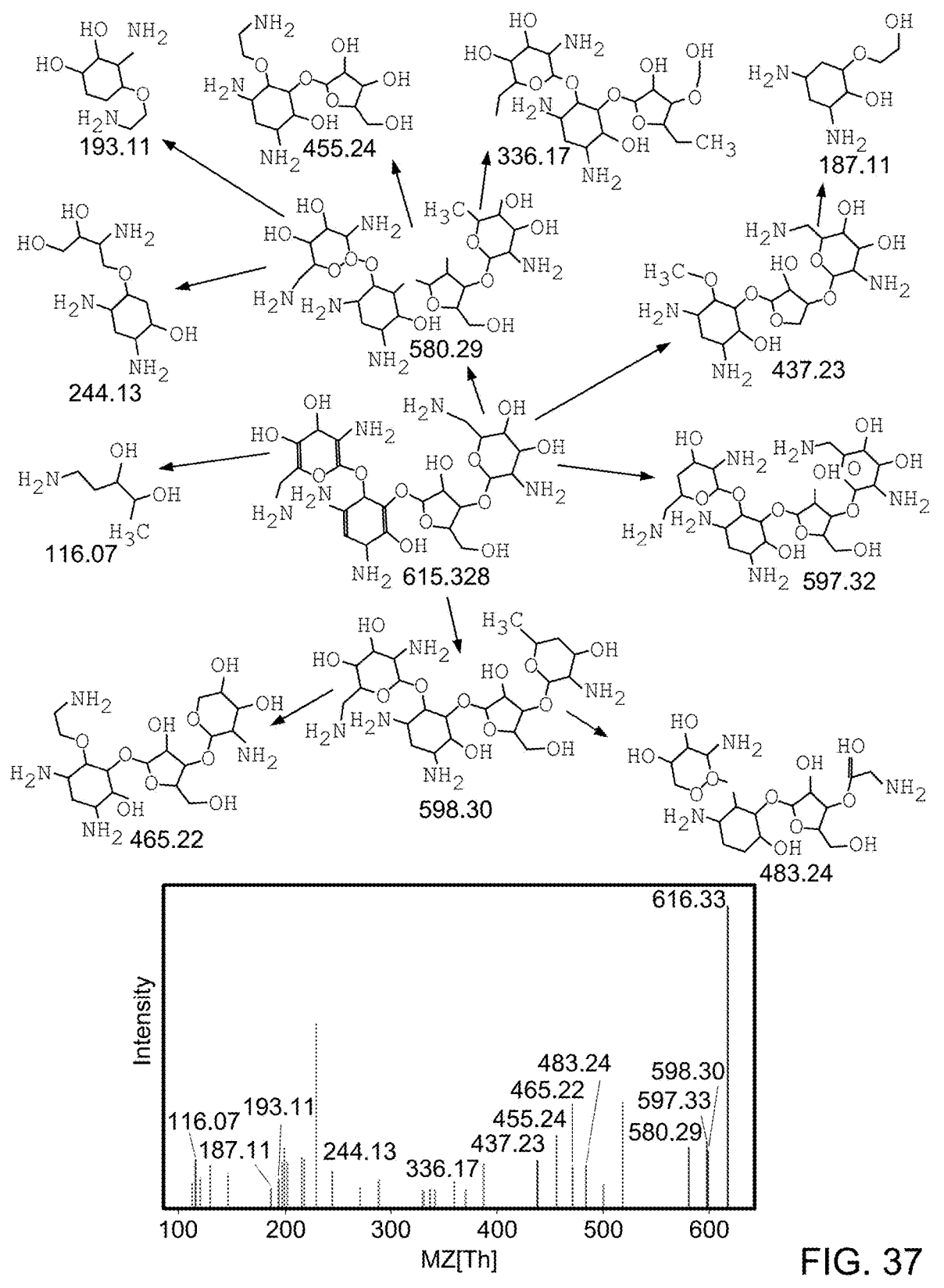

FIG. 37 shows identifying neomcyin by searching the spectral dataset generated from the extracts of *Streptomyces* sp. ISP-5003 against all the hypothetical structures predicted from each saccharide BGC. The fragments matching a peak in the neomcyin spectrum are shown at the top and the matched spectrum identified by Seq2Saccharide is illustrated at the bottom. Fragments are generated either by removing one bond (depth 1) or two bonds (depth 2) from the original structure. The red (green) structures and peaks correspond to neomycin fragments generated at depth 1 (2).

Figure 38:
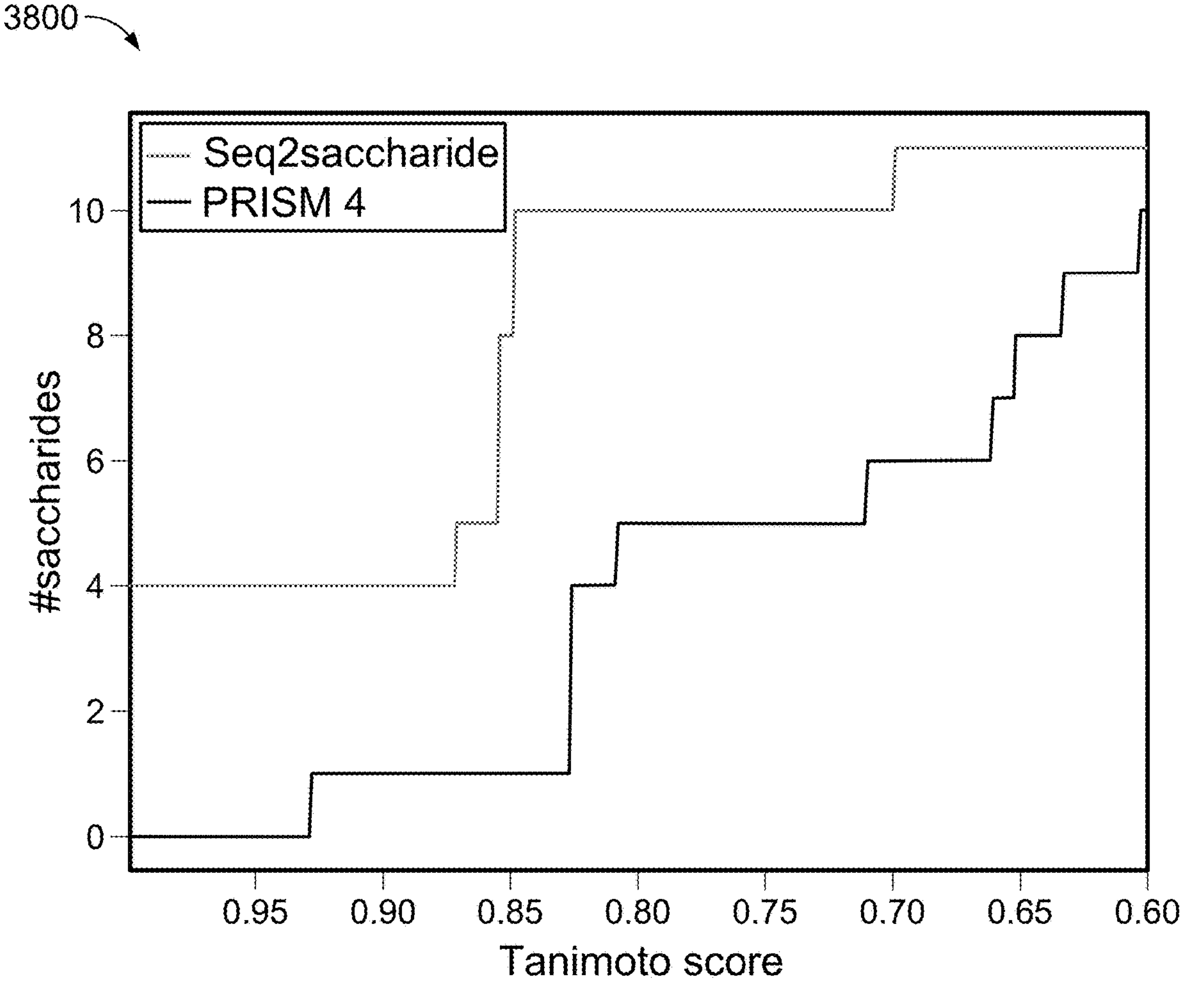
FIG. 38 shows a graph 3800 benchmarking Seq2saccharide algorithm

FIG. 38 shows a graph 3800 benchmarking Seq2saccharide algorithm against Prism4 on 36 known saccharides from the MiBIG dataset. At Tanimoto threshold of 95%, Seq2saccharide correctly constructs four out of 42 known saccharides, while Prims4 cannot correctly identify any. At Tanimoto threshold of 80%, Seq2saccharide correctly predicts 10 out of 42 known saccharides, while Prims4 predicts five.

Seq2Saccharide algorithm including the following steps detailed below (FIG. 32): (a) identifying saccharide BGCs, (b) annotating the BGCs with monomer pathways genes and finding modification enzymes, (c) predicting the monomer set, (d) predicting the hypothetical structure of saccharides by applying post-assembly modifications to the backbone based on identified enzymes, and (e) identifying novel saccharide by error-tolerant search of mass spectra against the genomic-driven hypothetical structures. Identifying saccharide BGCs. Saccharide BGCs are identified using Minowa and antiSMASH.

Annotating the BGCs with monomer pathways genes. A database of 30 saccharide monomers have been constructed by literature mining. Using this database, three general enzymatic mechanisms for bond formation in Saccharide were identified (FIG. 33). Moreover, a database of enzymes required for the biosynthesis of each monomer (monomer pathway) has been constructed, in the Hidden Markov Model profile format. Each BGC is annotated by all the genes present in these monomer pathways (FIG. 32) predicting the monomer sets. To test whether a set of monomers are likely present in a molecular product, Seq2Saccharide uses an approach similar to the gene set enrichment analysis. For each possible set of monomers, list of all genes required for the synthesis of the monomers in that set are formed. Then the hypothesis that these required genes significantly overlap with the genes present in the BGC is tested. A statistical significance score is assigned to each pair of monomer sets and BGCs, and the most likely monomer sets are reported as candidate backbones (FIG. 32).

Applying the post-assembly modifications. A database of 51 unique post-assembly modifications was mined from the gene clusters of 36 saccharides reported in the MIBiG database (FIG. 34). For each unique modification, Seq2Saccharide finds all the homologous enzymes that were predicted to drive that modification, to construct a Hidden Markov Model profile. Each modification is stored in a computer-readable format that includes a chemical motif where the modification happens, along with a series of node and bond alterations that tailor the motif to its mature structure (FIG. 35). Using the database of tailoring enzymes/modifications Seq2saccharide predicts all the hypothetical mature molecules through the following steps (FIG. 32): (i) annotating the modification enzymes in the BGC, and (ii) finding all the graph isomorphisms between the motifs corresponding to enzymes present in the BGCs and the backbone structures, using Ullman algorithm. Then, (iii) iteratively selecting each of these motifs and considering whether they are altered or not (a total of 2! hypothetical mature molecules, where m is the number of motifs present in the backbone structure).

Figure 39:
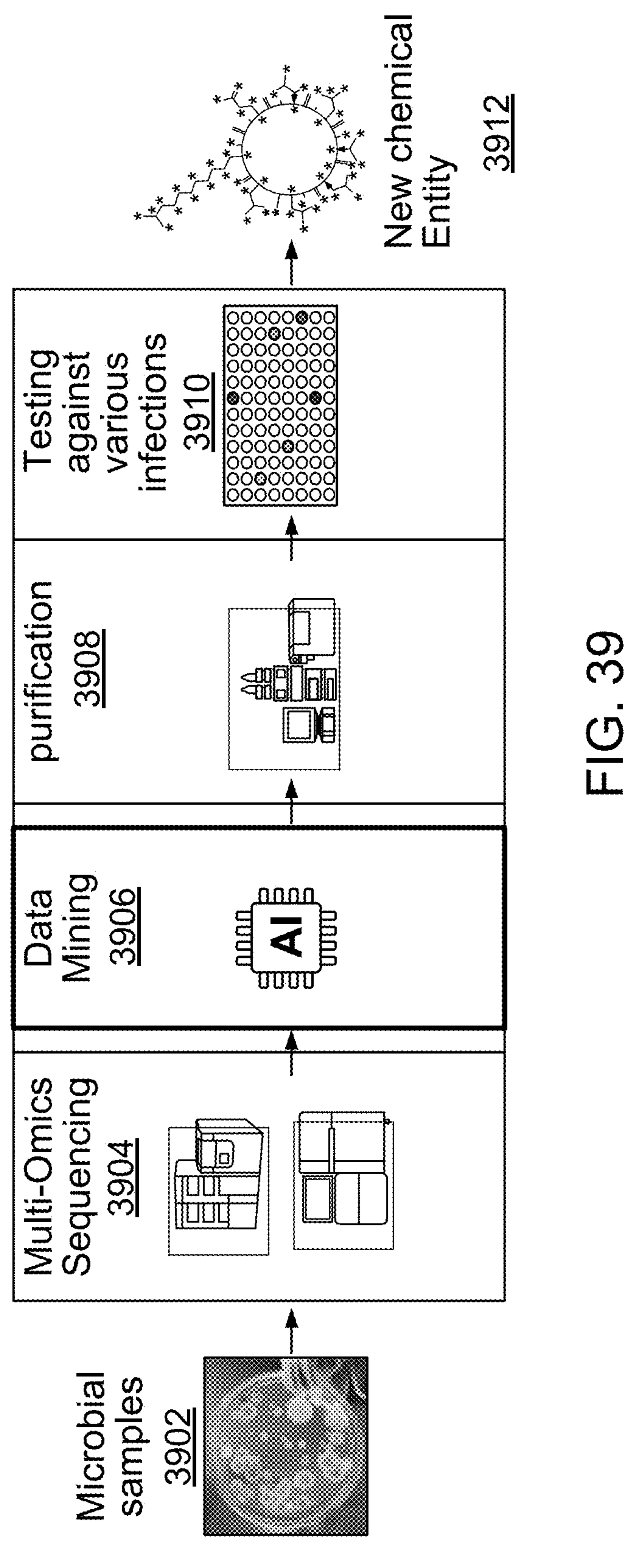
FIG. 39 shows an example process for identifying a natural product drug from microbial samples.

FIG. 39 shows an example process 3900 for identifying a natural product drug from microbial samples. Process 3900 shows natural product identification in the context of drug discovery. For example, microbial samples are collected (3902). To identify natural products from these microbial samples, the samples are sequenced with multi-omics (3904) processes. These processes generate genomic data including sequencing information and/or mass spectra of the samples. The sequences and mass spectra of the microbial samples are input into the data processing system 102. The data processing system 102 at step 3906 is configured to determine the structures of the small molecules represented in the mass spectra based on the processes described above. Candidate structures can be purified (3908) and tested (3910) against various infections. A resulting drug can be determined as an output (3912).

Figure 40:
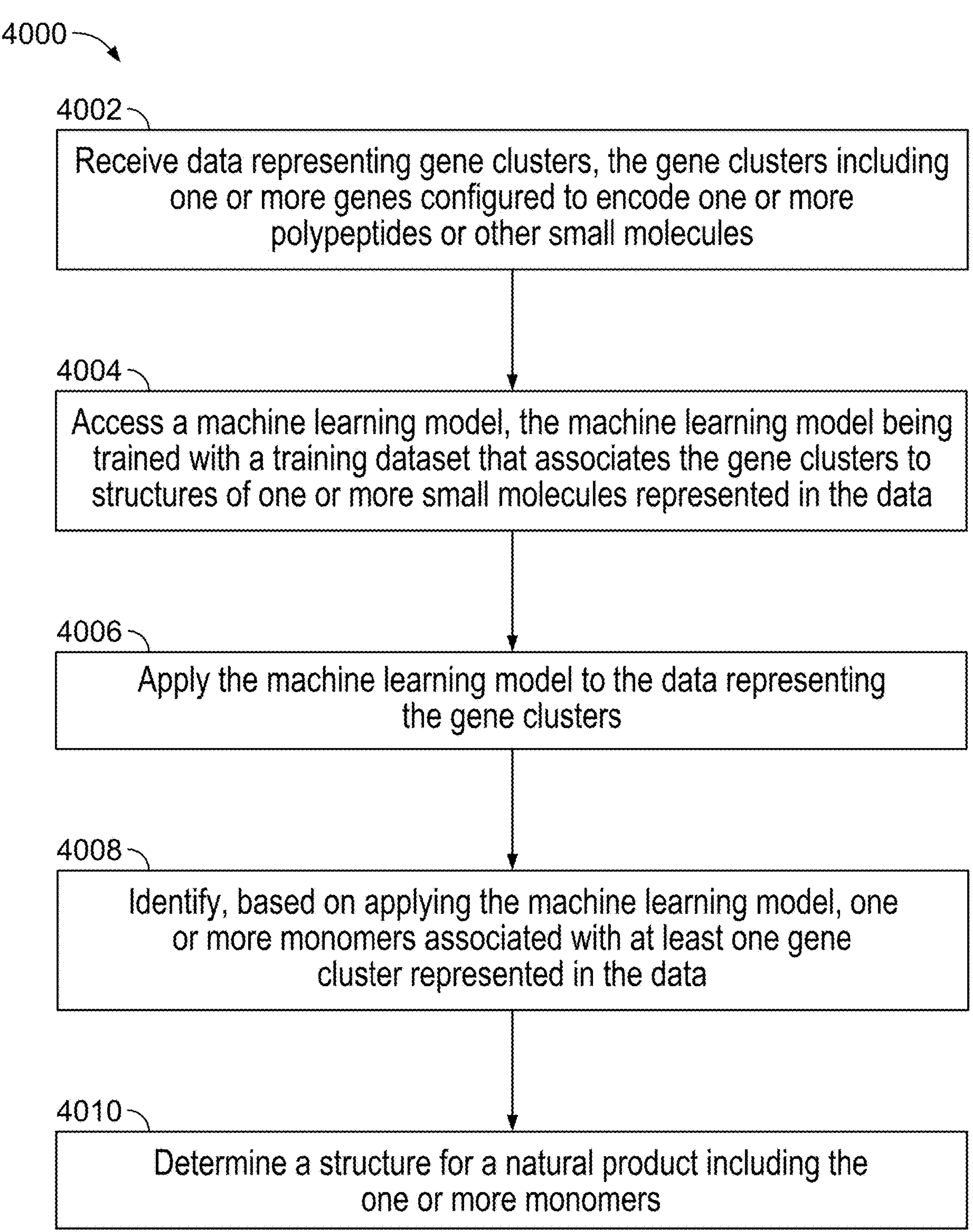
FIG. 40 shows a flow diagram representing a process for identifying the structures of molecular compounds from mass spectrometry data.

FIG. 40 shows a flow diagram representing a process 4000 for identifying the structures of molecular compounds from mass spectrometry data. The process 4000 can be executed by a computing system, such as the computing system described in relation to FIG. 41. The process 4000 includes receiving (4002) data representing gene clusters, the gene clusters including one or more genes configured to encode one or more polypeptides or other small molecules. The process 4000 includes accessing (4004) a machine learning model, the machine learning model being trained with a training dataset that associates the gene clusters to structures of one or more small molecules represented in the data. The process 4000 includes applying (4006) the machine learning model to the data representing the gene clusters. The process 4000 includes identifying (4008), based on applying the machine learning model, one or more monomers associated with at least one gene cluster represented in the data. The process 4000 includes determining (4010) a structure for a natural product including the one or more monomers.

In some implementations, the machine learning model is trained by performing operations comprising: accessing a set of hypothetical structures for natural products including the structure for the natural product; generating a set of random structures of molecules, the random structures including small molecules; testing, using mass spectrometry data representing known structures and the set of random structures, the set of hypothetical structures for the natural products including the structure for the natural product; generating a score for the structure, the score indicating a match between the structure and a known structure represented in the mass spectrometry data; filtering, based on the score, one or more hypothetical structures from the set of hypothetical structures to generate a filtered set of hypothetical structures that includes the structure for the natural product; and generating the training dataset for training the machine learning model, the training dataset including the filtered set of hypothetical structures.

In some implementations, the process 4000 includes determining a class associated with the gene clusters; and accessing, based on the class, a set of training data that is specific to the class associated with the gene clusters.

In some implementations, the process 4000 includes predicting a biological activity of an identified natural product based on the machine learning model that is trained with the training dataset. In some implementations, the process 4000 includes generating, based on predicting the activity, a data library comprising data that associates a gene cluster with a respective biological activity. In some implementations, the process 4000 includes purifying the natural product based on the determined structure.

In some implementations, determining the structure for the natural product including the one or more monomers comprises: predicting, based on the one or more monomers that are identified, a core molecule that is assembled by combining a group of monomers; determining one or more particular gene clusters represented in the data that cause a change of a structure of the core molecule; and identifying an enzyme associated with one or more particular gene clusters that cause the change to the structure of the core molecule.

In some implementations, the core molecule includes a peptide, and wherein the change comprises an addition of an amino acid.

In some implementations, the change comprises an addition of a lipid tail to the core molecule.

In some implementations, the change comprises an addition of a monomer to the core molecule.

In some implementations, the data representing the gene clusters comprises one or more data signatures, wherein data signatures comprise a location of a gene cluster with respect to one or more other gene clusters; and wherein determining the structure for a natural product including the one or more monomers is based on the data signatures.

In some implementations, the core molecule includes a peptide, and wherein the change comprises an addition of an amino acid.

In some implementations, the core molecule includes a non-ribosomal peptide.

In some implementations, the core molecule includes a ribosomally synthesized and post-translationally modified peptide.

In some implementations, the core molecule includes a polyketide.

In some implementations, the core molecule includes a saccharide or aminoglycoside.

In some implementations, the change comprises an addition of a lipid tail to the core molecule.

In some implementations, the core molecule includes a hybrid of non-ribosomal peptide and/or ribosomally synthesized and post-translationally modified peptide and/or a polyketide and/or a saccharide or aminoglycoside, and wherein the change comprises an addition of a monomer.

In some implementations, the data representing the gene clusters comprises one or more data signatures, wherein data signatures comprise a location of a gene cluster with respect to one or more other gene clusters; and wherein determining the structure for a natural product including the one or more monomers is based on the data signatures.

In some implementations, structures of predicted molecules are stored in a computer format that allows for accelerated search against mass spectra.

Figure 41:
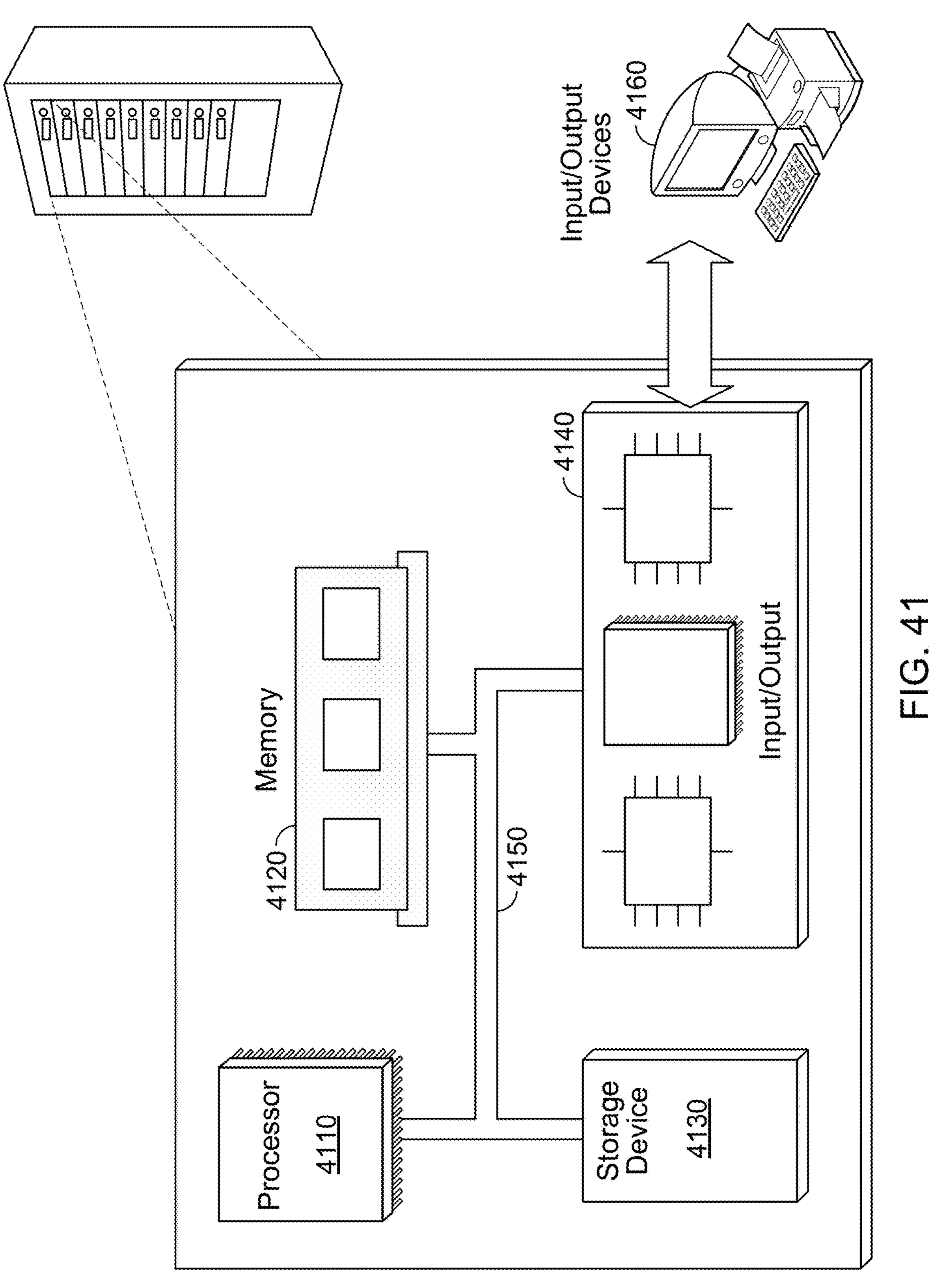
FIG. 41 shows an example of a computing system.

FIG. 41 shows an example computer system 4100 that includes a processor 4100, a memory 4120, a storage device 4130 and an input/output device 4140. Each of the components 4100, 4120, 4130 and 4140 can be interconnected, for example, by a system bus 4150. The processor 4110 is capable of processing instructions for execution within the system 4100. In some implementations, the processor 4100 is a single-threaded processor, a multi-threaded processor, or another type of processor. The processor 4100 is capable of processing instructions stored in the memory 4120 or on the storage device 4130. The memory 4120 and the storage device 4130 can store information within the system 4100.

The input/output device 4140 provides input/output operations for the system 4100. In some implementations, the input/output device 4140 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 4160. In some implementations, mobile computing devices, mobile communication devices, and other devices can be used.

While this specification includes many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the scope of the present disclosure.

What is claimed is:

1. A method comprising:

receiving data representing gene clusters, the gene clusters including one or more genes configured to encode one or more polypeptides or other small molecules;

accessing a machine learning model, the machine learning model being trained with a training dataset that associates the gene clusters to structures of one or more small molecules represented in the data;

wherein the machine learning model is trained by performing operations comprising:

accessing a set of hypothetical structures for natural products including the structure for the natural product;

generating a set of random structures of molecules, the random structures including small molecules;

testing, using mass spectrometry data representing known structures and the set of random structures, the set of hypothetical structures for the natural products including the structure for the natural product;

generating a score for the structure, the score indicating a match between the structure and a known structure represented in the mass spectrometry data;

filtering, based on the score, one or more hypothetical structures from the set of hypothetical structures to generate a filtered set of hypothetical structures that includes the structure for the natural product; and generating the training dataset for training the machine learning model, the training dataset including the filtered set of hypothetical structures;

applying the machine learning model to the data representing the gene clusters;

identifying, based on applying the machine learning model, one or more monomers associated with at least one gene cluster represented in the data; and determining a structure for a natural product including the one or more monomers.

2. The method of claim 1, further comprising:

determining a class associated with the gene clusters; and accessing, based on the class, a set of training data that is specific to the class associated with the gene clusters.

3. The method of claim 1, further comprising predicting a biological activity of an identified natural product based on the machine learning model that is trained with the training dataset.

4. The method of claim 3, further comprising generating, based on predicting the activity, a data library comprising data that associates a gene cluster with a respective biological activity.

5. The method of claim 1, further comprising purifying the natural product based on the determined structure.

6. The method of claim 1, wherein determining the structure for the natural product including the one or more monomers comprises:

predicting, based on the one or more monomers that are identified, a core molecule that is assembled by combining a group of monomers;

determining one or more particular gene clusters represented in the data that cause a change of a structure of the core molecule; and identifying an enzyme associated with one or more particular gene clusters that cause the change to the structure of the core molecule.

7. The method of claim 6, wherein the core molecule includes a peptide, and wherein the change comprises an addition of an amino acid.

8. The method of claim 6, wherein the change comprises an addition of a lipid tail to the core molecule.

9. The method of claim 6, wherein the change comprises an addition of a monomer to the core molecule.

10. The method of claim 1, wherein the data representing the gene clusters comprises one or more data signatures, wherein data signatures comprise a location of a gene cluster with respect to one or more other gene clusters; and wherein determining the structure for a natural product including the one or more monomers is based on the data signatures.

11. A system for searching a database to identify structures of molecular compounds from mass spectrometry data, the system comprising:

at least one processor; and a memory storing instructions that, when executed by the at least one processor, cause the at least one processor to perform operations comprising:

receiving data representing gene clusters, the gene clusters including one or more genes configured to encode one or more polypeptides or proteins;

accessing a machine learning model, the machine learning model being trained with a training dataset that associates structures of small molecules to one or more of the gene clusters represented in the data;

wherein the machine learning model is trained by performing operations comprising:

accessing a set of hypothetical structures for natural products including the structure for the natural product;

generating a set of random structures of molecules, the random structures including small molecules;

testing, using mass spectrometry data representing known structures and the set of random structures, the set of hypothetical structures for the natural products including the structure for the natural product;

generating a score for the structure, the score indicating a match between the structure and a known structure represented in the mass spectrometry data;

filtering, based on the score, one or more hypothetical structures from the set of hypothetical structures to generate a filtered set of hypothetical structures that includes the structure for the natural product; and generating the training dataset for training the machine learning model, the training dataset including the filtered set of hypothetical structures;

applying the machine learning model to the data representing the gene clusters;

identifying, based on applying the machine learning model, one or more monomers associated with at least one gene cluster represented in the data; and determining a structure for a natural product including the one or more monomers.

12. The system of claim 11, the operations further comprising:

determining a class associated with the gene clusters; and accessing, based on the class, a set of training data that is specific to the class associated with the gene clusters.

13. The system of claim 11, the operations further comprising predicting a biological activity of an identified natural product based on the machine learning model that is trained with the training dataset.

14. The system of claim 13, the operations further comprising generating, based on predicting the activity, a data library comprising data that associates a gene cluster with a respective biological activity.

15. The system of claim 11, the operations further comprising purifying the natural product based on the determined structure.

16. The system of claim 11, wherein determining the structure for the natural product including the one or more monomers comprises:

predicting, based on the one or more monomers that are identified, a core molecule that is assembled by combining a group of monomers;

determining one or more particular gene clusters represented in the data that cause a change of a structure of the core molecule; and identifying an enzyme associated with one or more particular gene clusters that cause the change to the structure of the core molecule.

17. The system of claim 16, wherein the core molecule includes a peptide, and wherein the change comprises an addition of an amino acid.

18. The system of claim 16, wherein the core molecule includes a non-ribosomal peptide.

19. The system of claim 16, wherein the core molecule includes a ribosomally synthesized and post-translationally modified peptide.

20. The system of claim 16, wherein the core molecule includes a polyketide.

21. The system of claim 16, wherein the core molecule includes a saccharide or aminoglycoside.

22. The system of claim 16, wherein the change comprises an addition of a lipid tail to the core molecule.

23. The system of claim 16, wherein the core molecule includes a hybrid of non-ribosomal peptide and/or ribosomally synthesized and post-translationally modified peptide and/or a polyketide and/or a saccharide or aminoglycoside, and wherein the change comprises an addition of a monomer.

24. The system of claim 16, wherein the data representing the gene clusters comprises one or more data signatures, wherein data signatures comprise a location of a gene cluster with respect to one or more other gene clusters; and wherein determining the structure for a natural product including the one or more monomers is based on the data signatures.

25. The system of claim 16, wherein structures of predicted molecules are stored in a computer format that allows for accelerated search against mass spectra.

* * * * *